(12) United States Patent
Clackson et al.

(10) Patent No.: US 6,506,379 B1
(45) Date of Patent: Jan. 14, 2003

(54) INTRAMUSCULAR DELIVERY OF RECOMBINANT AAV

(75) Inventors: Timothy P. Clackson, Cambridge, MA (US); Michael Gilman, Newton, MA (US); Dennis Holt, Royersford, PA (US)

(73) Assignee: Ariad Gene Therapeutics, Inc., Cambridge, MA (US)

(*) Notice: Subject to any disclaimer, the term of this patent is extended or adjusted under 35 U.S.C. 154(b) by 0 days.

(21) Appl. No.: 09/481,620

(22) Filed: Jan. 12, 2000

Related U.S. Application Data

(63) Continuation-in-part of application No. 08/791,044, filed on Jan. 28, 1997, now abandoned, which is a continuation-in-part of application No. 08/481,941, filed on Jun. 7, 1995, now abandoned.

(60) Provisional application No. 60/015,502, filed on Feb. 9, 1996, now abandoned.

(51) Int. Cl.$^7$ .................. A61K 48/00; A61K 35/00; C12N 15/63

(52) U.S. Cl. ................ 424/93.21; 424/93.21; 435/320.1

(58) Field of Search .............. 514/44; 424/93.2, 424/93.21; 435/320.1

(56) References Cited

U.S. PATENT DOCUMENTS

| | | | |
|---|---|---|---|
| 5,139,941 A | 8/1992 | Muzyczka et al. | |
| 5,658,565 A | 8/1997 | Billiar et al. | |
| 5,658,785 A | 8/1997 | Johnson | |
| 5,780,447 A | * 7/1998 | Nienhuis | 514/44 |
| 5,797,870 A | 8/1998 | March et al. | |
| 5,834,266 A | 11/1998 | Crabtree et al. | |
| 5,846,528 A | * 12/1998 | Podsakoff et al. | 424/93.2 |
| 5,858,351 A | * 1/1999 | Podsakoff et al. | 424/93.2 |
| 5,869,337 A | 2/1999 | Crabtree et al. | |
| 5,962,424 A | 10/1999 | Hallahan et al. | |
| 6,103,226 A | 8/2000 | Kang et al. | |
| 6,127,521 A | 10/2000 | Berlin et al. | |
| 6,150,137 A | 11/2000 | Berlin et al. | |
| 6,162,796 A | 12/2000 | Kaplitt et al. | |
| 6,187,757 B1 | 2/2001 | Clackson et al. | |

FOREIGN PATENT DOCUMENTS

| | | |
|---|---|---|
| WO | WO 95/06743 | 3/1995 |
| WO | WO 95/06744 | 3/1995 |
| WO | WO 95/13365 | 5/1995 |
| WO | WO 95/13374 | 5/1995 |
| WO | WO 95/13376 | 5/1995 |
| WO | WO 96/06111 | 2/1996 |
| WO | WO 96/41865 | 12/1996 |

OTHER PUBLICATIONS

IM Verma et al., "Gene therapy–promises, problems and prosoects,"Sep. 1997, vol. 389, pp. 239–242.*
N Miller et al., FASEB Journal, "Targeted vectors for gene therapy," Reviews, Feb. 1995, vol. 9, 190–199.*

(List continued on next page.)

*Primary Examiner*—James Ketter
*Assistant Examiner*—Janice Li
(74) *Attorney, Agent, or Firm*—David L. Berstein

(57) ABSTRACT

This invention concerns new configurations for biological switches and provides new methods and materials useful for regulating biological events in animal cells. The invention involves recombinant DNA constructs comprising DNA sequences derived from sequences encoding the proteins FRAP, Tor1, Tor2 and other proteins capable of binding to FKBP:rapamycin, other recombinant DNA constructs comprising DNA sequences encoding part or all of an FKBP protein, the proteins encoded by those constructs, cells (especially animal cells) transformed with one or more of the constructs, small molecules (multivalent multimerizing agents) which bind to and are capable of inducing multimerization of the chimeric proteins, and methods for preparing and using the foregoing, including methods involving the intramuscular delivery of such recombinant DNA constructs in AAV virus particles.

10 Claims, 15 Drawing Sheets

OTHER PUBLICATIONS

SL Eck et al., The Pharmacological Basis of Therapeutics, "Gene–Based Therapy," 1995, 9th Ed., Chap. 5, pp. 77–101.*

SH Orkin et al., Report and Recommendations of the Panel to Assess the NIH Investment in Research on Gene Therapy, Dec. 1995, pp. 1–41.*

Kunz et al, "Target of rapamycin in yeast, TOR2, is an essential phosphatidylinositol kinase homolog required for G1 progression." —(1993) Cell 73: 585–596.

Chiu et al., "RAPT1, a mammalian homolog of yeast Tor, interacts with the FKBP12/rapamycin complex." —(1994) Proc Natl Acad Sci USA 91: 12574–12578.

Brown et al, "A mammalian protein targeted by G1–arresting rapamycin–receptor complex." —(1994) Nature 369: 756–758.

Helliwell et al, "TOR1 and TOR2 are structurally and functionally similar but not identical phosphatidylinositol kinase homologues in yeast." —(1994) Mol Biol Cell 5: 105–118.

Sabatini et al., "RAFT1: a mammalian protein that binds to FKBP12 in a rapamycin–dependent fashion and is homologous to yeast TORs." —(1994) Cell, 78; 35–43.

Pomerantz, et al., "Structure–based design of transcription factors." —(1995) Science, 267: 93–96.

Chen et al, "Identification of an 11–kDa FKBP12–rapamycin–binding domain within the 289–kDa FKBP12–rapamycin–associated protein and characterization of a critical serine residue." —(1995) Proc Natl Acad Sci USA 92: 4947–4951.

Ho et al., "Dimeric ligands define a role for transcriptional activation domains in reinitiation." —(1996) Nature, 382: 822–826.

Rivera, et al., "A humanized system for pharmacologic control of gene expression." —(1996) Nature Medicine, 2(9): 1028–1032.

Graef et al., "Proximity and orientation underlie signaling by the non–receptor tyrosine kinase ZAP70."—(1997) EMBO J. 16: 5618–5628.

Amara et al., "A versatile synthetic dimerizer for the regulation of protein–protein interactions." —(1997) Proc Natl Acad Sci USA 94: 10618–10623.

Liberles et al., "Inducible gene expression and protein translocation using nontoxic ligands identified by a mammalian three–hybrid screen." —(1997) Proc Natl Acad Sci USA 94: 7825–7830.

Rivera et al., "Long–term regulated expression of growth hormone in mice after intramuscular gene transfer." —(1999) Proc Natl Acad Sci USA 96: 8657–8662.

Ye et al., "Regulated delivery of therapeutic proteins after in vivo somatic cell gene transfer." —(1999) Science 283: 88–91.

Castellano et al., "Inducible recruitment of Cdc42 or WASP to a cell–surface receptor triggers actin polymerization and filopodium formation." —(1999) Current Biology 9: 351–360.

Kourtis et al., Cardiac gene therapy with adeno–associated virus as a means of achieving graft–specific immuno–suppression. (1995) Modern Pathology, vol. 8(1): 33A, Abstract #178.

Xiao et al., Efficient long–term transfer into muscle tissue of immunocompetent mice by adeno–associated virus vector. (1996) J Virology, 70(11): 8098–108.

Podsakoff et al., Long–term in vivo gene expression in muscle using AAV. (1995) Blood, vol. 83(10), Suppl 10 Pg. 1004a, Abstract #4004.

Alexander et al., Effects of gamma irradiation on the transduction of dividing and non–dividing cells in the brain and muscle of rats by adeno–associated virus vectors. (1996) Human Gene Therapy, vol. 7: 841–850.

Kessler et al., Gene delivery to skeletal muscle results in sustained expression and systemic delivery of a therapeutic protein. (1996) PNAS, vol. 93: 14082–14087.

Kaplitt et al., Long–term gene transfer in porcine myocardium after coronary infusion of an adeno–associated virus vector. (1996) Ann Thoracic Surg; 62(6): 1669–76.

Ali et al., The use of DNA viruses as vectors for gene therapy. (1994) Gene Therapy, 1: 367–84.

Srivastava, Parvovirus Based Vectors for Human Gene Therapy (1994) Blood Cells 20:531–538.

Kremer & Perricaudet, Adenovirus and adeno–associated virus mediated gene transfer. (1995) Br Med Bull. 51: 31–44.

Flotte & Carter, Adeno–associted virus vectors for gene therapy. (1995) Gene Therapy, 2: 357–362.

During & Leone, Adeno–associated virus vectors for gene therapy of neurodegenerative disorders. (1996) Clinical Neuroscience, 3: 292–300.

McKeon & Samulski, Meeting Report: NIDDK Workshop on AAV Vectors: Gene transfer into Quiescent cells. (1996) Human Gene Therapy, 7: 1615–1619.

Carter, The promise of adeno–associated virus vectors. (1996) Nature Biotechnology, 14; 1725–1726.

NHLBI AIDS related research, FY 1994 http://www.nhlbi.nih.gov/resources.aids/fy94.htm.

Pilot studies on gene therapy vectors for metabolic diseases. (1996) NIH GUIDE, vol. 25, No. 35, Oct. 18, 1996 http://grants/nih.gov/grants/guide/pa–files/PAR–91–002.html.

Samulski et al., A recombinant plasmid from which an infectious adeno–associated virus genome can be excised in vitro and its use to study viral replication. (1987) J Virology, 61(10): 3096–3101.

McLaughlin et al., Adeno–associated virus general transduction vectors: Analysis of proviral structures. (1988) 62(6): 1963–1973.

Samulski et al, Helper–free stocks of recombinant adeno–associated viruses: Normal integration does not require viral gene expression. (1989) J Virology, 63(9): 3822–3828.

Hong et al., In vitro replication of adeno–associated virus DNA. (1992) PNAS 89: 4673–4677.

Goodman et al., Recombinant adeno–associated virus mediated gene transfer into hematopoietic progenitor cells. (1994) Blood, 84(5): 1492–1500.

Podsakoff et al., Efficient gene transfer into nondividing cells by adeno–associated virus based vectors. J Virology, 1994, 68(9): 5656–5666.

Flotte et al., Stable in vivo expression of the cystic fibrosis transmembrane conductance regulator with an adeno–associated virus vector. (1993) PNAS 90: 10613–10617.

* cited by examiner

SEQUENCE LISTING

```
<160> NUMBER OF SEQ ID NOS: 132

<210> SEQ ID NO 1
<211> LENGTH: 14
<212> TYPE: PRT
<213> ORGANISM: Artificial Sequence
<220> FEATURE:
<223> OTHER INFORMATION: lipid binding domain
<221> NAME/KEY: LIPID
<222> LOCATION: (1)..(14)

<400> SEQUENCE: 1

Met Gly Ser Ser Lys Ser Lys Pro Lys Asp Pro Ser Gln Arg
1               5                   10

<210> SEQ ID NO 2
<211> LENGTH: 4
<212> TYPE: PRT
<213> ORGANISM: Artificial Sequence
<220> FEATURE:
<223> OTHER INFORMATION: organelle targeting domain
<221> NAME/KEY: BINDING
<222> LOCATION: (1)..(4)

<400> SEQUENCE: 2

Lys Asp Glu Leu
1

<210> SEQ ID NO 3
```

-continued

```
<211> LENGTH: 4
<212> TYPE: PRT
<213> ORGANISM: Artificial Sequence
<220> FEATURE:
<223> OTHER INFORMATION: organelle targeting domain
<221> NAME/KEY: BINDING
<222> LOCATION: (1)..(4)

<400> SEQUENCE: 3

His Asp Glu Leu
1

<210> SEQ ID NO 4
<211> LENGTH: 31
<212> TYPE: DNA
<213> ORGANISM: Artificial Sequence
<220> FEATURE:
<223> OTHER INFORMATION: cloning primer
<221> NAME/KEY: misc_feature
<222> LOCATION: (1)..(31)

<400> SEQUENCE: 4
atgctctaga gaacgcccat atgcttgccc t                              31

<210> SEQ ID NO 5
<211> LENGTH: 34
<212> TYPE: DNA
<213> ORGANISM: Artificial Sequence
<220> FEATURE:
<223> OTHER INFORMATION: cloning primer
<221> NAME/KEY: misc_feature
<222> LOCATION: (1)..(34)

<400> SEQUENCE: 5
atgcgcggcc gccgcctgtg tgggtgcgga tgtg                           34

<210> SEQ ID NO 6
<211> LENGTH: 33
<212> TYPE: DNA
<213> ORGANISM: Artificial Sequence
<220> FEATURE:
<223> OTHER INFORMATION: cloning primer
<221> NAME/KEY: misc_feature
<222> LOCATION: (1)..(33)

<400> SEQUENCE: 6
atgcgcggcc gcaggaggaa gaaacgcacc agc                            33

<210> SEQ ID NO 7
<211> LENGTH: 49
<212> TYPE: DNA
<213> ORGANISM: Artificial Sequence
<220> FEATURE:
<223> OTHER INFORMATION: cloning primer
<221> NAME/KEY: misc_feature
<222> LOCATION: (1)..(49)

<400> SEQUENCE: 7
gcatggatcc gattcaacta gtgttgattc tttttctttt ctggcggcg           49

<210> SEQ ID NO 8
<211> LENGTH: 306
<212> TYPE: DNA
<213> ORGANISM: Homo sapiens
<220> FEATURE:
<221> NAME/KEY: misc_structure
<222> LOCATION: (1)..(306)
<223> OTHER INFORMATION: p65 transcription activation domain
```

```
<400> SEQUENCE: 8
ctgggggcct tgcttggcaa cagcacagac ccagctgtgt tcacagacct ggcatccgtc      60
gacaactccg agtttcagca gctgctgaac cagggcatac ctgtggcccc ccacacaact    120
gagcccatgc tgatggagta ccctgaggct ataactcgcc tagtgacagg ggcccagagg    180
ccccccgacc cagctcctgc tccactgggg gccccgggc tccccaatgg cctcctttca    240
ggagatgaag acttctcctc cattgcggac atggacttct cagccctgct gagtcagatc    300
agctcc                                                                306

<210> SEQ ID NO 9
<211> LENGTH: 573
<212> TYPE: DNA
<213> ORGANISM: Homo sapiens
<220> FEATURE:
<221> NAME/KEY: misc_structure
<222> LOCATION: (1)..(573)
<223> OTHER INFORMATION: extended p65 transcription activation domain

<400> SEQUENCE: 9
gatgagtttc ccaccatggt gtttccttct gggcagatca gccaggcctc ggccttggcc      60
ccggcccctc cccaagtcct gccccaggct ccagcccctg ccctgctcc agccatggta    120 tcagctctgg cccaggcccc agcccctgtc ccagtcctag cccaggccc tcctcaggct    180 gtggccccac ctgcccccaa gcccacccag gctggggaag aacgctgtc agaggccctg    240 ctgcagctgc agtttgatga tgaagacctg ggggccttgc ttggcaacag cacagaccca    300
gctgtgttca cagacctggc atccgtcgac aactccgagt ttcagcagct gctgaaccag    360
ggcatacctg tggcccccca cacaactgag cccatgctga tggagtaccc tgaggctata    420
actcgcctag tgacagccca gaggcccccc gacccagctc ctgctccact gggggccccg    480 gggctccccca atggcctcct ttcaggagat gaagacttct cctccattgc ggacatggac    540
ttctcagccc tgctgagtca gatcagctcc taa                                  573

<210> SEQ ID NO 10
<211> LENGTH: 36
<212> TYPE: DNA
<213> ORGANISM: Artificial Sequence
<220> FEATURE:
<223> OTHER INFORMATION: cloning primer
<221> NAME/KEY: misc_feature
<222> LOCATION: (1)..(36)

<400> SEQUENCE: 10
gcatgtctag agagatgtgg catgaaggcc tggaag                                36

<210> SEQ ID NO 11
<211> LENGTH: 35
<212> TYPE: DNA
<213> ORGANISM: Artificial Sequence
<220> FEATURE:
<223> OTHER INFORMATION: cloning primer
<221> NAME/KEY: misc_feature
<222> LOCATION: (1)..(35)

<400> SEQUENCE: 11
gcatcactag tctttgagat tcgtcggaac acatg                                 35

<210> SEQ ID NO 12
<211> LENGTH: 33
<212> TYPE: DNA
<213> ORGANISM: Artificial Sequence
```

```
<220> FEATURE:
<223> OTHER INFORMATION: cloning primer
<221> NAME/KEY: misc_feature
<222> LOCATION: (1)..(33)

<400> SEQUENCE: 12
gcacattcta gaattgatac gcccagaccc ttg                              33

<210> SEQ ID NO 13
<211> LENGTH: 33
<212> TYPE: DNA
<213> ORGANISM: Artificial Sequence
<220> FEATURE:
<223> OTHER INFORMATION: cloning primer
<221> NAME/KEY: misc_feature
<222> LOCATION: (1)..(33)

<400> SEQUENCE: 13
cgatcaacta gtaagtgtca atttccgggg cct                              33

<210> SEQ ID NO 14
<211> LENGTH: 36
<212> TYPE: DNA
<213> ORGANISM: Artificial Sequence
<220> FEATURE:
<223> OTHER INFORMATION: cloning primer
<221> NAME/KEY: misc_feature
<222> LOCATION: (1)..(36)

<400> SEQUENCE: 14
gcactatcta gactgaagaa catgtgtgag cacagc                           36

<210> SEQ ID NO 15
<211> LENGTH: 36
<212> TYPE: DNA
<213> ORGANISM: Artificial Sequence
<220> FEATURE:
<223> OTHER INFORMATION: cloning primer
<221> NAME/KEY: misc_feature
<222> LOCATION: (1)..(36)

<400> SEQUENCE: 15
gcactatcta gagtgagcga ggagctgatc cgagtg                           36

<210> SEQ ID NO 16
<211> LENGTH: 36
<212> TYPE: DNA
<213> ORGANISM: Artificial Sequence
<220> FEATURE:
<223> OTHER INFORMATION: cloning primer
<221> NAME/KEY: misc_feature
<222> LOCATION: (1)..(36)

<400> SEQUENCE: 16
cgatcaacta gtggaaacat attgcagctc taagga                           36

<210> SEQ ID NO 17
<211> LENGTH: 36
<212> TYPE: DNA
<213> ORGANISM: Artificial Sequence
<220> FEATURE:
<223> OTHER INFORMATION: cloning primer
<221> NAME/KEY: misc_feature
<222> LOCATION: (1)..(36)

<400> SEQUENCE: 17
cgatcaacta gttggcacag ccaattcaag gtcccg                           36
```

<210> SEQ ID NO 18
<211> LENGTH: 31
<212> TYPE: DNA
<213> ORGANISM: Artificial Sequence
<220> FEATURE:
<223> OTHER INFORMATION: cloning primer
<221> NAME/KEY: misc_feature
<222> LOCATION: (1)..(31)

<400> SEQUENCE: 18
atgctctaga ctgggggcct tgcttggcaa c                            31

<210> SEQ ID NO 19
<211> LENGTH: 31
<212> TYPE: DNA
<213> ORGANISM: Artificial Sequence
<220> FEATURE:
<223> OTHER INFORMATION: cloning primer
<221> NAME/KEY: misc_feature
<222> LOCATION: (1)..(31)

<400> SEQUENCE: 19
atgctctaga gatgagtttc ccaccatggt g                            31

<210> SEQ ID NO 20
<211> LENGTH: 39
<212> TYPE: DNA
<213> ORGANISM: Artificial Sequence
<220> FEATURE:
<223> OTHER INFORMATION: cloning primer
<221> NAME/KEY: misc_feature
<222> LOCATION: (1)..(39)

<400> SEQUENCE: 20
gcatggatcc gctcaactag tggagctgat ctgactcag                    39

<210> SEQ ID NO 21
<211> LENGTH: 31
<212> TYPE: DNA
<213> ORGANISM: Artificial Sequence
<220> FEATURE:
<223> OTHER INFORMATION: cloning primer
<221> NAME/KEY: misc_feature
<222> LOCATION: (1)..(31)

<400> SEQUENCE: 21
atgctctaga cttggaaccg gacctgccgc c                            31

<210> SEQ ID NO 22
<211> LENGTH: 34
<212> TYPE: DNA
<213> ORGANISM: Artificial Sequence
<220> FEATURE:
<223> OTHER INFORMATION: cloning primer
<221> NAME/KEY: misc_feature
<222> LOCATION: (1)..(34)

<400> SEQUENCE: 22
gcatcactag tccagaaagg gcaccagcca atat                         34

<210> SEQ ID NO 23
<211> LENGTH: 134
<212> TYPE: DNA
<213> ORGANISM: Artificial Sequence
<220> FEATURE:
<223> OTHER INFORMATION: 12CA5epitope--SV40NLS--ZFHD5'
<221> NAME/KEY: misc_structure
<222> LOCATION: (1)..(134)

```
<400> SEQUENCE: 23
gtagaagcgc gtatggcttc tagctatcct tatgacgtgc ctgactatgc cagcctggga      60
ggaccttcta gtcctaagaa gaagagaaag gtgtctagag aacgcccata tgcttgccct     120
gtcgagtcct gcga                                                        134

<210> SEQ ID NO 24
<211> LENGTH: 41
<212> TYPE: PRT
<213> ORGANISM: Artificial Sequence
<220> FEATURE:
<223> OTHER INFORMATION: 12CA5epitope--SV40NLS--ZFHD5'
<221> NAME/KEY: PEPTIDE
<222> LOCATION: (1)..(41)

<400> SEQUENCE: 24

Met Ala Ser Ser Tyr Pro Tyr Asp Val Pro Asp Tyr Ala Ser Leu Gly
1               5                   10                  15

Gly Pro Ser Ser Pro Lys Lys Lys Arg Lys Val Ser Arg Glu Arg Pro
            20                  25                  30

Tyr Ala Cys Pro Val Glu Ser Cys Asp
        35                  40

<210> SEQ ID NO 25
<211> LENGTH: 41
<212> TYPE: DNA
<213> ORGANISM: Artificial Sequence
<220> FEATURE:
<223> OTHER INFORMATION: ZFHD1.3'--FRB.5'
<221> NAME/KEY: misc_structure
<222> LOCATION: (1)..(41)

<400> SEQUENCE: 25
agaatcaaca ctagagagat gtggcatgaa ggcctggaag a                          41

<210> SEQ ID NO 26
<211> LENGTH: 14
<212> TYPE: PRT
<213> ORGANISM: Artificial Sequence
<220> FEATURE:
<223> OTHER INFORMATION: ZFHD1.3'--FRB.5'
<221> NAME/KEY: PEPTIDE
<222> LOCATION: (1)..(14)

<400> SEQUENCE: 26

Arg Ile Asn Thr Arg Glu Met Trp His Glu Gly Leu Glu Glu
1               5                   10

<210> SEQ ID NO 27
<211> LENGTH: 34
<212> TYPE: DNA
<213> ORGANISM: Artificial Sequence
<220> FEATURE:
<223> OTHER INFORMATION: FRB.3'
<221> NAME/KEY: misc_structure
<222> LOCATION: (1)..(34)

<400> SEQUENCE: 27
cgaatctcaa agactagtta ttagggatcc tgag                                  34

<210> SEQ ID NO 28
<211> LENGTH: 8
<212> TYPE: PRT
<213> ORGANISM: Artificial Sequence
<220> FEATURE:
```

```
<223> OTHER INFORMATION: FRB.c terminus
<221> NAME/KEY: PEPTIDE
<222> LOCATION: (1)..(8)
<223> OTHER INFORMATION: X represents a stop codon

<400> SEQUENCE: 28

Arg Ile Ser Lys Thr Ser Tyr Xaa
1               5

<210> SEQ ID NO 29
<211> LENGTH: 30
<212> TYPE: DNA
<213> ORGANISM: Artificial Sequence
<220> FEATURE:
<223> OTHER INFORMATION: cloning primer
<221> NAME/KEY: misc_feature
<222> LOCATION: (1)..(30)

<400> SEQUENCE: 29
gaattcctag aagcgaccat ggcttctagc                                      30

<210> SEQ ID NO 30
<211> LENGTH: 31
<212> TYPE: DNA
<213> ORGANISM: Artificial Sequence
<220> FEATURE:
<223> OTHER INFORMATION: cloning primer
<221> NAME/KEY: misc_feature
<222> LOCATION: (1)..(31)

<400> SEQUENCE: 30
gaagagaaag gtggctagcg aacgcccata t                                    31

<210> SEQ ID NO 31
<211> LENGTH: 25
<212> TYPE: DNA
<213> ORGANISM: Artificial Sequence
<220> FEATURE:
<223> OTHER INFORMATION: cloning primer
<221> NAME/KEY: misc_feature
<222> LOCATION: (1)..(25)

<400> SEQUENCE: 31
gccatggtgg ctagcctata gtgag                                           25

<210> SEQ ID NO 32
<211> LENGTH: 25
<212> TYPE: DNA
<213> ORGANISM: Artificial Sequence
<220> FEATURE:
<223> OTHER INFORMATION: cloning primer
<221> NAME/KEY: misc_feature
<222> LOCATION: (1)..(25)

<400> SEQUENCE: 32
ggcggtgttg gctagcgtcg gtcag                                           25

<210> SEQ ID NO 33
<211> LENGTH: 123
<212> TYPE: DNA
<213> ORGANISM: Artificial Sequence
<220> FEATURE:
<223> OTHER INFORMATION: 12CA5epitope--SV40NLS
<221> NAME/KEY: misc_structure
<222> LOCATION: (1)..(123)

<400> SEQUENCE: 33
gaattccaga agcgcgtatg gcttctagct atccttatga cgtgcctgac tatgccagcc     60
```

```
tgggaggacc ttctagtcct aagaagaaga gaaaggtgtc tagatatcga ggatcccaag    120
ctt                                                                  123
```

<210> SEQ ID NO 34
<211> LENGTH: 26
<212> TYPE: PRT
<213> ORGANISM: Artificial Sequence
<220> FEATURE:
<223> OTHER INFORMATION: 12CA5epitope--SV40NLS
<221> NAME/KEY: PEPTIDE
<222> LOCATION: (1)..(26)

<400> SEQUENCE: 34

```
Met Ala Ser Ser Tyr Pro Tyr Asp Val Pro Asp Tyr Ala Ser Leu Gly
1               5                   10                  15

Gly Pro Ser Ser Pro Lys Lys Lys Arg Lys
            20                  25
```

<210> SEQ ID NO 35
<211> LENGTH: 222
<212> TYPE: DNA
<213> ORGANISM: Artificial Sequence
<220> FEATURE:
<223> OTHER INFORMATION: 12 ZFHD1 binding sites
<221> NAME/KEY: misc_structure
<222> LOCATION: (1)..(222)

<400> SEQUENCE: 35

```
gctagctaat gatgggcgct cgagtaatga tgggcggtcg actaatgatg ggcgctcgag    60
taatgatggg cgtctagcta atgatgggcg ctcgagtaat gatgggcggt cgactaatga   120
tgggcgctcg agtaatgatg ggcgtctagc taatgatggg cgctcgagta atgatgggcg   180
gtcgactaat gatgggcgct cgagtaatga tgggcgtcta ga                      222
```

<210> SEQ ID NO 36
<211> LENGTH: 121
<212> TYPE: DNA
<213> ORGANISM: Artificial Sequence
<220> FEATURE:
<223> OTHER INFORMATION: CMV promoter
<221> NAME/KEY: promoter
<222> LOCATION: (1)..(121)

<400> SEQUENCE: 36

```
tctagaacgc gaattccggt aggcgtgtac ggtgggaggt ctatataagc agagctcgtt    60
tagtgaaccg tcagatcgcc tggagacgcc atccacgctg ttttgacctc catagaagct   120
t                                                                   121
```

<210> SEQ ID NO 37
<211> LENGTH: 141
<212> TYPE: DNA
<213> ORGANISM: Homo sapiens
<220> FEATURE:
<221> NAME/KEY: promoter
<222> LOCATION: (1)..(141)

<400> SEQUENCE: 37

```
tctagaacgc gaattcaaca ttttgacacc cccataatat ttttccagaa ttaacagtat    60
aaattgcatc tcttgttcaa gagttcccta tcactctctt taatcactac tcacagtaac   120
ctcaactcct gccacaagct t                                             141
```

```
<210> SEQ ID NO 38
<211> LENGTH: 304
<212> TYPE: DNA
<213> ORGANISM: Artificial Sequence
<220> FEATURE:
<223> OTHER INFORMATION: IL-2/Gal4 chimeric promoter
<221> NAME/KEY: promoter
<222> LOCATION: (1)..(304)

<400> SEQUENCE: 38
atcgatgttt tctgagttac ttttgtatcc ccaccccccc tcgagcttgc atgcctgcag      60
gtcggagtac tgtcctccga gcggagtact gtcctccgag cggagtactg tcctccgagc    120
ggagtactgt cctccgagcg gagtactgtc ctccgagcgc agactctaga ggatccgaga    180
acattttgac accccataa tattttttcca gaattaacag tataaattgc atctcttgtt    240
caagagttcc ctatcactct ctttaatcac tactcacagt aacctcaact cctgccacaa    300
gctt                                                                  304

<210> SEQ ID NO 39
<211> LENGTH: 24
<212> TYPE: DNA
<213> ORGANISM: Artificial Sequence
<220> FEATURE:
<223> OTHER INFORMATION: cloning primer
<221> NAME/KEY: misc_feature
<222> LOCATION: (1)..(24)

<400> SEQUENCE: 39
cccgtggtcc cgcgttgctt cgat                                             24

<210> SEQ ID NO 40
<211> LENGTH: 127
<212> TYPE: PRT
<213> ORGANISM: Artificial Sequence
<220> FEATURE:
<223> OTHER INFORMATION: hexahistidine Tag--12CA5epitope--FKBP
<221> NAME/KEY: PEPTIDE
<222> LOCATION: (1)..(127)

<400> SEQUENCE: 40

Met His His His His His His Asp Tyr Lys Asp Asp Asp Lys Ala
1               5                   10                  15

Met Ala His Met Gly Val Gln Val Glu Thr Ile Ser Pro Gly Asp Gly
            20                  25                  30

Arg Thr Phe Pro Lys Arg Gly Gln Thr Cys Val Val His Tyr Thr Gly
        35                  40                  45

Met Leu Glu Asp Gly Lys Lys Phe Asp Ser Ser Arg Asp Arg Asn Lys
    50                  55                  60

Pro Phe Lys Phe Met Leu Gly Lys Gln Glu Val Ile Arg Gly Trp Glu
65                  70                  75                  80

Glu Gly Val Ala Gln Met Ser Val Gly Gln Arg Ala Lys Leu Thr Ile
                85                  90                  95

Ser Pro Asp Tyr Ala Tyr Gly Ala Thr Gly His Pro Gly Ile Ile Pro
            100                 105                 110

Pro His Ala Thr Leu Val Phe Asp Val Glu Leu Leu Lys Leu Glu
        115                 120                 125

<210> SEQ ID NO 41
<211> LENGTH: 27
<212> TYPE: DNA
<213> ORGANISM: Artificial Sequence
<220> FEATURE:
```

```
<223> OTHER INFORMATION: cloning primer
<221> NAME/KEY: misc_feature
<222> LOCATION: (1)..(27)

<400> SEQUENCE: 41
agcataaact tatggggctt gtttctg                                          27

<210> SEQ ID NO 42
<211> LENGTH: 27
<212> TYPE: DNA
<213> ORGANISM: Artificial Sequence
<220> FEATURE:
<223> OTHER INFORMATION: cloning primer
<221> NAME/KEY: misc_feature
<222> LOCATION: (1)..(27)

<400> SEQUENCE: 42
agcataaact ttagggctt gtttctg                                           27

<210> SEQ ID NO 43
<211> LENGTH: 27
<212> TYPE: DNA
<213> ORGANISM: Artificial Sequence
<220> FEATURE:
<223> OTHER INFORMATION: cloning primer
<221> NAME/KEY: misc_feature
<222> LOCATION: (1)..(27)

<400> SEQUENCE: 43
agcataaact ttagggctt gtttctg                                           27

<210> SEQ ID NO 44
<211> LENGTH: 27
<212> TYPE: DNA
<213> ORGANISM: Artificial Sequence
<220> FEATURE:
<223> OTHER INFORMATION: cloning primer
<221> NAME/KEY: misc_feature
<222> LOCATION: (1)..(27)

<400> SEQUENCE: 44
ttgcctagca tatgcttaaa gggcttg                                          27

<210> SEQ ID NO 45
<211> LENGTH: 27
<212> TYPE: DNA
<213> ORGANISM: Artificial Sequence
<220> FEATURE:
<223> OTHER INFORMATION: cloning primer
<221> NAME/KEY: misc_feature
<222> LOCATION: (1)..(27)

<400> SEQUENCE: 45
ttgcctagca ttaacttaaa gggcttg                                          27

<210> SEQ ID NO 46
<211> LENGTH: 27
<212> TYPE: DNA
<213> ORGANISM: Artificial Sequence
<220> FEATURE:
<223> OTHER INFORMATION: cloning primer
<221> NAME/KEY: misc_feature
<222> LOCATION: (1)..(27)

<400> SEQUENCE: 46
ttgcctagca tagccttaaa gggcttg                                          27
```

```
<210> SEQ ID NO 47
<211> LENGTH: 26
<212> TYPE: DNA
<213> ORGANISM: Artificial Sequence
<220> FEATURE:
<223> OTHER INFORMATION: cloning primer
<221> NAME/KEY: misc_feature
<222> LOCATION: (1)..(26)

<400> SEQUENCE: 47
cctcggatca ccgcctgctt gcctag                                              26

<210> SEQ ID NO 48
<211> LENGTH: 26
<212> TYPE: DNA
<213> ORGANISM: Artificial Sequence
<220> FEATURE:
<223> OTHER INFORMATION: cloning primer
<221> NAME/KEY: misc_feature
<222> LOCATION: (1)..(26)

<400> SEQUENCE: 48
cagcctcgga tcgcctcctg cttgcc                                              26

<210> SEQ ID NO 49
<211> LENGTH: 30
<212> TYPE: DNA
<213> ORGANISM: Artificial Sequence
<220> FEATURE:
<223> OTHER INFORMATION: cloning primer
<221> NAME/KEY: misc_feature
<222> LOCATION: (1)..(30)

<400> SEQUENCE: 49
ccgggaggaa tcggctttct ttccatcttc                                          30

<210> SEQ ID NO 50
<211> LENGTH: 30
<212> TYPE: DNA
<213> ORGANISM: Artificial Sequence
<220> FEATURE:
<223> OTHER INFORMATION: cloning primer
<221> NAME/KEY: misc_feature
<222> LOCATION: (1)..(30)

<400> SEQUENCE: 50
ccgggaggaa tcgactttct ttccatcttc                                          30

<210> SEQ ID NO 51
<211> LENGTH: 30
<212> TYPE: DNA
<213> ORGANISM: Artificial Sequence
<220> FEATURE:
<223> OTHER INFORMATION: cloning primer
<221> NAME/KEY: misc_feature
<222> LOCATION: (1)..(30)

<400> SEQUENCE: 51
ccgggaggaa tcagatttct ttccatcttc                                          30

<210> SEQ ID NO 52
<211> LENGTH: 30
<212> TYPE: DNA
<213> ORGANISM: Artificial Sequence
<220> FEATURE:
<223> OTHER INFORMATION: cloning primer
<221> NAME/KEY: misc_feature
<222> LOCATION: (1)..(30)
```

-continued

```
<400> SEQUENCE: 52
ccgggaggaa tccattttct ttccatcttc                                        30

<210> SEQ ID NO 53
<211> LENGTH: 27
<212> TYPE: DNA
<213> ORGANISM: Artificial Sequence
<220> FEATURE:
<223> OTHER INFORMATION: cloning primer
<221> NAME/KEY: misc_feature
<222> LOCATION: (1)..(27)

<400> SEQUENCE: 53
aagctccaca tcggcgacga gagtggc                                           27

<210> SEQ ID NO 54
<211> LENGTH: 27
<212> TYPE: DNA
<213> ORGANISM: Artificial Sequence
<220> FEATURE:
<223> OTHER INFORMATION: cloning primer
<221> NAME/KEY: misc_feature
<222> LOCATION: (1)..(27)

<400> SEQUENCE: 54
aagctccaca tcgccgacga gagtggc                                           27

<210> SEQ ID NO 55
<211> LENGTH: 29
<212> TYPE: DNA
<213> ORGANISM: Artificial Sequence
<220> FEATURE:
<223> OTHER INFORMATION: cloning primer
<221> NAME/KEY: misc_feature
<222> LOCATION: (1)..(29)

<400> SEQUENCE: 55
caagcatccc ggtggcgtgc accacgcag                                         29

<210> SEQ ID NO 56
<211> LENGTH: 29
<212> TYPE: DNA
<213> ORGANISM: Artificial Sequence
<220> FEATURE:
<223> OTHER INFORMATION: cloning primer
<221> NAME/KEY: misc_feature
<222> LOCATION: (1)..(29)

<400> SEQUENCE: 56
tcccgggagg aagcaaattt ctttccatc                                         29

<210> SEQ ID NO 57
<211> LENGTH: 26
<212> TYPE: DNA
<213> ORGANISM: Artificial Sequence
<220> FEATURE:
<223> OTHER INFORMATION: cloning primer
<221> NAME/KEY: misc_feature
<222> LOCATION: (1)..(26)

<400> SEQUENCE: 57
cctcggatca ccgcctgctt gcctag                                            26

<210> SEQ ID NO 58
<211> LENGTH: 27
<212> TYPE: DNA
<213> ORGANISM: Artificial Sequence
```

```
<220> FEATURE:
<223> OTHER INFORMATION: cloning primer
<221> NAME/KEY: misc_feature
<222> LOCATION: (1)..(27)

<400> SEQUENCE: 58
cctttcccca aagtgcaaac gagatgc                                          27

<210> SEQ ID NO 59
<211> LENGTH: 27
<212> TYPE: DNA
<213> ORGANISM: Artificial Sequence
<220> FEATURE:
<223> OTHER INFORMATION: cloning primer
<221> NAME/KEY: misc_feature
<222> LOCATION: (1)..(27)

<400> SEQUENCE: 59
cctttcccca aagagcaaac gagatgc                                          27

<210> SEQ ID NO 60
<211> LENGTH: 27
<212> TYPE: DNA
<213> ORGANISM: Artificial Sequence
<220> FEATURE:
<223> OTHER INFORMATION: cloning primer
<221> NAME/KEY: misc_feature
<222> LOCATION: (1)..(27)

<400> SEQUENCE: 60
cctttcccca aaggccaaac gagatgc                                          27

<210> SEQ ID NO 61
<211> LENGTH: 29
<212> TYPE: DNA
<213> ORGANISM: Artificial Sequence
<220> FEATURE:
<223> OTHER INFORMATION: cloning primer
<221> NAME/KEY: misc_feature
<222> LOCATION: (1)..(29)

<400> SEQUENCE: 61
gttcctttcc ccatggtaca aacgagatg                                        29

<210> SEQ ID NO 62
<211> LENGTH: 29
<212> TYPE: DNA
<213> ORGANISM: Artificial Sequence
<220> FEATURE:
<223> OTHER INFORMATION: cloning primer
<221> NAME/KEY: misc_feature
<222> LOCATION: (1)..(29)

<400> SEQUENCE: 62
gttcctttcc cctaagtaca aacgagatg                                        29

<210> SEQ ID NO 63
<211> LENGTH: 29
<212> TYPE: DNA
<213> ORGANISM: Artificial Sequence
<220> FEATURE:
<223> OTHER INFORMATION: cloning primer
<221> NAME/KEY: misc_feature
<222> LOCATION: (1)..(29)

<400> SEQUENCE: 63
gttcctttcc ccagcgtaca aacgagatg                                        29
```

<210> SEQ ID NO 64
<211> LENGTH: 27
<212> TYPE: DNA
<213> ORGANISM: Artificial Sequence
<220> FEATURE:
<223> OTHER INFORMATION: cloning oligo
<221> NAME/KEY: misc_feature
<222> LOCATION: (1)..(27)

<400> SEQUENCE: 64
gtcccaggct tgggcgaggt ccttgac                                27

<210> SEQ ID NO 65
<211> LENGTH: 40
<212> TYPE: DNA
<213> ORGANISM: Artificial Sequence
<220> FEATURE:
<223> OTHER INFORMATION: cloning primer
<221> NAME/KEY: misc_feature
<222> LOCATION: (1)..(40)

<400> SEQUENCE: 65
gtcccaggct tggttgaggt tcgagacatt ccctgatttc                  40

<210> SEQ ID NO 66
<211> LENGTH: 27
<212> TYPE: DNA
<213> ORGANISM: Artificial Sequence
<220> FEATURE:
<223> OTHER INFORMATION: cloning primer
<221> NAME/KEY: misc_feature
<222> LOCATION: (1)..(27)

<400> SEQUENCE: 66
gtcccaggct tggttgaggt ccttgac                                27

<210> SEQ ID NO 67
<211> LENGTH: 29
<212> TYPE: DNA
<213> ORGANISM: Artificial Sequence
<220> FEATURE:
<223> OTHER INFORMATION: cloning primers
<221> NAME/KEY: misc_feature
<222> LOCATION: (1)..(29)

<400> SEQUENCE: 67
catgataata gagggcccag gcttgggtg                              29

<210> SEQ ID NO 68
<211> LENGTH: 50
<212> TYPE: DNA
<213> ORGANISM: Artificial Sequence
<220> FEATURE:
<223> OTHER INFORMATION: cloning primer
<221> NAME/KEY: misc_feature
<222> LOCATION: (1)..(50)

<400> SEQUENCE: 68
gcatcccatg gcaatcctct ggcatgagat gtggcatgaa ggcctggaag       50

<210> SEQ ID NO 69
<211> LENGTH: 34
<212> TYPE: DNA
<213> ORGANISM: Artificial Sequence
<220> FEATURE:
<223> OTHER INFORMATION: cloning primer
<221> NAME/KEY: misc_feature
<222> LOCATION: (1)..(34)

<400> SEQUENCE: 69
cgtgaggatc ctactttgag attcgtcgga acac                                34

<210> SEQ ID NO 70
<211> LENGTH: 48
<212> TYPE: DNA
<213> ORGANISM: Artificial Sequence
<220> FEATURE:
<223> OTHER INFORMATION: cloning primer
<221> NAME/KEY: misc_feature
<222> LOCATION: (1)..(48)

<400> SEQUENCE: 70
gcatctctag aatcctctgg catgagatgt ggcatgaagg cctggaag                 48

<210> SEQ ID NO 71
<211> LENGTH: 47
<212> TYPE: DNA
<213> ORGANISM: Artificial Sequence
<220> FEATURE:
<223> OTHER INFORMATION: cloning primer
<221> NAME/KEY: misc_feature
<222> LOCATION: (1)..(47)

<400> SEQUENCE: 71
ggtctggatc cctaataact agtctttgag attcgtcgga acacatg                  47

<210> SEQ ID NO 72
<211> LENGTH: 127
<212> TYPE: PRT
<213> ORGANISM: Artificial Sequence
<220> FEATURE:
<223> OTHER INFORMATION: hexahistidine tag--12CA5epitope--FKBP
<221> NAME/KEY: PEPTIDE
<222> LOCATION: (1)..(127)

<400> SEQUENCE: 72

Met His His His His His His Asp Tyr Lys Asp Asp Asp Lys Ala
1               5                   10                  15

Met Ala His Met Gly Val Gln Val Glu Thr Ile Ser Pro Gly Asp Gly
            20                  25                  30

Arg Thr Phe Pro Lys Arg Gly Gln Thr Cys Val Val His Tyr Thr Gly
        35                  40                  45

Met Leu Glu Asp Gly Lys Lys Phe Asp Ser Ser Arg Asp Arg Asn Lys
    50                  55                  60

Pro Phe Lys Phe Met Leu Gly Lys Gln Glu Val Ile Arg Gly Trp Glu
65                  70                  75                  80

Glu Gly Val Ala Gln Met Ser Val Gly Gln Arg Ala Lys Leu Thr Ile
                85                  90                  95

Ser Pro Asp Tyr Ala Tyr Gly Ala Thr Gly His Pro Gly Ile Ile Pro
            100                 105                 110

Pro His Ala Thr Leu Val Phe Asp Val Glu Leu Leu Lys Leu Glu
        115                 120                 125

<210> SEQ ID NO 73
<211> LENGTH: 26
<212> TYPE: DNA
<213> ORGANISM: Artificial Sequence
<220> FEATURE:
<223> OTHER INFORMATION: cloning primer
<221> NAME/KEY: misc_feature
<222> LOCATION: (1)..(26)

-continued

```
<400> SEQUENCE: 73
ccttgatatt cataaacgaa tggatc                                          26

<210> SEQ ID NO 74
<211> LENGTH: 24
<212> TYPE: DNA
<213> ORGANISM: Artificial Sequence
<220> FEATURE:
<223> OTHER INFORMATION: cloning primer
<221> NAME/KEY: misc_feature
<222> LOCATION: (1)..(24)

<400> SEQUENCE: 74
catggcgact agttaagcac gtag                                            24

<210> SEQ ID NO 75
<211> LENGTH: 24
<212> TYPE: DNA
<213> ORGANISM: Artificial Sequence
<220> FEATURE:
<223> OTHER INFORMATION: cloning primer
<221> NAME/KEY: misc_feature
<222> LOCATION: (1)..(24)

<400> SEQUENCE: 75
gatcctacgt gcttaactag tcgc                                            24

<210> SEQ ID NO 76
<211> LENGTH: 37
<212> TYPE: DNA
<213> ORGANISM: Artificial Sequence
<220> FEATURE:
<223> OTHER INFORMATION: cloning primer
<221> NAME/KEY: misc_feature
<222> LOCATION: (1)..(37)

<400> SEQUENCE: 76
gcatcccatg gccgctgagc tgatccgagt ggccatc                              37

<210> SEQ ID NO 77
<211> LENGTH: 37
<212> TYPE: DNA
<213> ORGANISM: Artificial Sequence
<220> FEATURE:
<223> OTHER INFORMATION: cloning primer
<221> NAME/KEY: misc_feature
<222> LOCATION: (1)..(37)

<400> SEQUENCE: 77
cgtgaggatc ctactgcttt gagattcgtc ggaacac                              37

<210> SEQ ID NO 78
<211> LENGTH: 388
<212> TYPE: DNA
<213> ORGANISM: Artificial Sequence
<220> FEATURE:
<223> OTHER INFORMATION: pCANTAB--AP--FRAP--
<221> NAME/KEY: misc_structure
<222> LOCATION: (1)..(388)

<400> SEQUENCE: 78
gtgaaaaaat tattattcgc aattccttta gttgttcctt tctatgcggc ccagccggcc     60
atggccgctg agctgatccg agtggccatc tctggcatg agatgtgca tgaaggcctg      120 gaagaggcat ctcgtttgta ctttggggaa aggaacgtga aaggcatgtt tgaggtgctg    180
gagcccttgc atgctatgat ggaacggggc ccccagactc tgaaggaaac atcctttaat    240
```
caggcctatg gtcgagattt aatggaggcc caagagtggt gcaggaagta catgaaatca    300
gggaatgtca aggacctcac ccaagcctgg gacctctatt atcatgtgtt ccgacgaatc    360
tcaaagcagt aggatccatt cgtttatg    388

<210> SEQ ID NO 79
<211> LENGTH: 129
<212> TYPE: PRT
<213> ORGANISM: Artificial Sequence
<220> FEATURE:
<223> OTHER INFORMATION: pCANTAB--AP--FRAP--
<221> NAME/KEY: PEPTIDE
<222> LOCATION: (1)..(128)
<223> OTHER INFORMATION: X represents a stop codon

<400> SEQUENCE: 79

Met Lys Lys Leu Leu Phe Ala Ile Pro Leu Val Val Pro Phe Tyr Ala
1               5                   10                  15

Ala Gln Pro Ala Met Ala Ala Glu Leu Ile Arg Val Ala Ile Leu Trp
            20                  25                  30

His Glu Met Trp His Glu Gly Leu Glu Glu Ala Ser Arg Leu Tyr Phe
        35                  40                  45

Gly Glu Arg Asn Val Lys Gly Met Phe Glu Val Leu Glu Pro Leu His
    50                  55                  60

Ala Met Met Glu Arg Gly Pro Gln Thr Leu Lys Glu Thr Ser Phe Asn
65                  70                  75                  80

Gln Ala Tyr Gly Arg Asp Leu Met Glu Ala Gln Glu Trp Cys Arg Lys
                85                  90                  95

Tyr Met Lys Ser Gly Asn Val Lys Asp Leu Thr Gln Ala Trp Asp Leu
            100                 105                 110

Tyr Tyr His Val Phe Arg Arg Ile Ser Lys Gln Xaa Asp Pro Phe Val
        115                 120                 125

Tyr

<210> SEQ ID NO 80
<211> LENGTH: 34
<212> TYPE: DNA
<213> ORGANISM: Artificial Sequence
<220> FEATURE:
<223> OTHER INFORMATION: cloning primer
<221> NAME/KEY: misc_feature
<222> LOCATION: (1)..(34)

<400> SEQUENCE: 80
ccataccatg gccgcaggag tgcaggtgga gact    34

<210> SEQ ID NO 81
<211> LENGTH: 31
<212> TYPE: DNA
<213> ORGANISM: Artificial Sequence
<220> FEATURE:
<223> OTHER INFORMATION: cloning primer
<221> NAME/KEY: misc_feature
<222> LOCATION: (1)..(31)

<400> SEQUENCE: 81
gcatgggatc ctattccagt tttagaagct c    31

<210> SEQ ID NO 82
<211> LENGTH: 81
<212> TYPE: DNA
<213> ORGANISM: Artificial Sequence -continued

```
<220> FEATURE:
<223> OTHER INFORMATION: cloning primer
<221> NAME/KEY: misc_feature
<222> LOCATION: (1)..(81)

<400> SEQUENCE: 82
gccctgaatg tgcacaccgg gatgcttgaa gatggaaaga atcctcccg ggacaacaag      60 cccttttaagt ttatgctagg c                                              81

<210> SEQ ID NO 83
<211> LENGTH: 68
<212> TYPE: DNA
<213> ORGANISM: Artificial Sequence
<220> FEATURE:
<223> OTHER INFORMATION: cloning primer
<221> NAME/KEY: misc_feature
<222> LOCATION: (1)..(68)

<400> SEQUENCE: 83
gcgaactacg gatcctattc cagttttaga agctccacat cgacgagagt ggcatgtggt     60
gggatgat                                                              68

<210> SEQ ID NO 84
<211> LENGTH: 411
<212> TYPE: DNA
<213> ORGANISM: Artificial Sequence
<220> FEATURE:
<223> OTHER INFORMATION: pCANTAB--AP--FKBP--
<221> NAME/KEY: misc_structure
<222> LOCATION: (1)..(411)

<400> SEQUENCE: 84
gtgaaaaaat tattattcgc aattccttta gttgttcctt tctatgcggc ccagccggcc     60
atggccgcag gagtgcaggt ggagactatc tccccaggag acgggcgcac cttccccaag    120
cgcggccaga cctgcgtggt gcactacacc gggatgcttg aagatggaaa gaaatttgat    180
tcctcccggg acagaaacaa gccctttaag tttatgctag gcaagcagga ggtgatccga    240
ggctgggaag aagggggttgc ccagatgagt gtgggtcaga gagccaaact gactatatct    300
ccagattatg cctatggtgc cactgggcac ccaggcatca tcccaccaca tgccactctc    360
gtcttcgatg tggagcttct aaaactggaa taggatccat tcgtttatga a             411

<210> SEQ ID NO 85
<211> LENGTH: 137
<212> TYPE: PRT
<213> ORGANISM: Artificial Sequence
<220> FEATURE:
<223> OTHER INFORMATION: pCANTAB--AP--FKBP--
<221> NAME/KEY: PEPTIDE
<222> LOCATION: (1)..(136)
<223> OTHER INFORMATION: X represents a stop codon

<400> SEQUENCE: 85

Val Lys Lys Leu Leu Phe Ala Ile Pro Leu Val Val Pro Phe Tyr Ala
1               5                   10                  15

Ala Gln Pro Ala Met Ala Ala Gly Val Gln Val Glu Thr Ile Ser Pro
                20                  25                  30

Gly Asp Gly Arg Thr Phe Pro Lys Arg Gly Gln Thr Cys Val Val His
            35                  40                  45

Tyr Thr Gly Met Leu Glu Asp Gly Lys Lys Phe Asp Ser Ser Arg Asp
        50                  55                  60

Arg Asn Lys Pro Phe Lys Phe Met Leu Gly Lys Gln Glu Val Ile Arg
```

```
                65                  70                  75                  80
        Gly Trp Glu Glu Gly Val Ala Gln Met Ser Val Gly Gln Arg Ala Lys
                            85                  90                  95

Leu Thr Ile Ser Pro Asp Tyr Ala Tyr Gly Ala Thr Gly His Pro Gly
                        100                 105                 110

Ile Ile Pro Pro His Ala Thr Leu Val Phe Asp Val Glu Leu Leu Lys
                    115                 120                 125

Leu Glu Xaa Asp Pro Phe Val Tyr Glu
                130                 135

<210> SEQ ID NO 86
<211> LENGTH: 8
<212> TYPE: PRT
<213> ORGANISM: Artificial Sequence
<220> FEATURE:
<223> OTHER INFORMATION: Flag epitope
<221> NAME/KEY: PEPTIDE
<222> LOCATION: (1)..(8)

<400> SEQUENCE: 86

Asp Tyr Lys Asp Asp Asp Asp Tyr
1               5

<210> SEQ ID NO 87
<211> LENGTH: 85
<212> TYPE: DNA
<213> ORGANISM: Artificial Sequence
<220> FEATURE:
<223> OTHER INFORMATION: oligo sequence
<221> NAME/KEY: misc_feature
<222> LOCATION: (1)..(85)

<400> SEQUENCE: 87
catgtctaga gggagtagca agagcaagcc taaggacccc agccagcgca ctagttaaga      60
attctgatga tcagcggatc ctagc                                           85

<210> SEQ ID NO 88
<211> LENGTH: 85
<212> TYPE: DNA
<213> ORGANISM: Artificial Sequence
<220> FEATURE:
<223> OTHER INFORMATION: oligo sequence
<221> NAME/KEY: misc_feature
<222> LOCATION: (1)..(85)

<400> SEQUENCE: 88
gctaggatcc gctgatcatc agaattctta actagtgcgc tggctgggt ccttaggctt      60 gctcttgcta ctccctctag acatg                                           85

<210> SEQ ID NO 89
<211> LENGTH: 37
<212> TYPE: DNA
<213> ORGANISM: Artificial Sequence
<220> FEATURE:
<223> OTHER INFORMATION: oligo sequence
<221> NAME/KEY: misc_feature
<222> LOCATION: (1)..(37)

<400> SEQUENCE: 89
cgccttgtag aattcgcgcg tatggggagt agcaaga                              37

<210> SEQ ID NO 90
<211> LENGTH: 30
<212> TYPE: DNA
```

```
<213> ORGANISM: Artificial Sequence
<220> FEATURE:
<223> OTHER INFORMATION: oligo sequence
<221> NAME/KEY: misc_feature
<222> LOCATION: (1)..(30)

<400> SEQUENCE: 90
cccagccagc gctctagata agaattctga                              30

<210> SEQ ID NO 91
<211> LENGTH: 18
<212> TYPE: DNA
<213> ORGANISM: Artificial Sequence
<220> FEATURE:
<223> OTHER INFORMATION: oligo sequence
<221> NAME/KEY: misc_feature
<222> LOCATION: (1)..(18)

<400> SEQUENCE: 91
aagggtcccc aaactcac                                           18

<210> SEQ ID NO 92
<211> LENGTH: 61
<212> TYPE: DNA
<213> ORGANISM: Artificial Sequence
<220> FEATURE:
<223> OTHER INFORMATION: oligo sequence
<221> NAME/KEY: misc_feature
<222> LOCATION: (1)..(61)

<400> SEQUENCE: 92
gcatgactag ttatccgtac gacgtaccag actacgcata agaaaagtga ggatcctacg    60
g                                                             61

<210> SEQ ID NO 93
<211> LENGTH: 61
<212> TYPE: DNA
<213> ORGANISM: Artificial Sequence
<220> FEATURE:
<223> OTHER INFORMATION: oligo sequence
<221> NAME/KEY: misc_feature
<222> LOCATION: (1)..(61)

<400> SEQUENCE: 93
ccgtaggatc ctcacttttc ttatgcgtag tctggtacgt cgtacggata actagtcatg    60
g                                                             61

<210> SEQ ID NO 94
<211> LENGTH: 58
<212> TYPE: DNA
<213> ORGANISM: Artificial Sequence
<220> FEATURE:
<223> OTHER INFORMATION: oligo sequence
<221> NAME/KEY: misc_feature
<222> LOCATION: (1)..(58)

<400> SEQUENCE: 94
ccgtaggatc ctcacttttc ttaataatcg tcatcgtctt tgtagtcact agtcatgc      58

<210> SEQ ID NO 95
<211> LENGTH: 58
<212> TYPE: DNA
<213> ORGANISM: Artificial Sequence
<220> FEATURE:
<223> OTHER INFORMATION: oligo sequence
<221> NAME/KEY: misc_feature
<222> LOCATION: (1)..(58)
```

```
<400> SEQUENCE: 95
gcatgactag tgactacaaa gacgatgacg attattaaga aaagtgagga tcctacgg        58

<210> SEQ ID NO 96
<211> LENGTH: 103
<212> TYPE: DNA
<213> ORGANISM: Artificial Sequence
<220> FEATURE:
<223> OTHER INFORMATION: cloning vector sequence
<221> NAME/KEY: misc_feature
<222> LOCATION: (1)..(103)

<400> SEQUENCE: 96
cgccttgtag aattcgcgcg tatggggagt agcaagagca agcctaagga ccccagccag      60
cgctctagat aagaattctg atgatcagcg gatcctgaga act                       103

<210> SEQ ID NO 97
<211> LENGTH: 20
<212> TYPE: PRT
<213> ORGANISM: Artificial Sequence
<220> FEATURE:
<223> OTHER INFORMATION: 5' FRB/FKBP construct
<221> NAME/KEY: PEPTIDE
<222> LOCATION: (1)..(19)
<223> OTHER INFORMATION: X represents a stop codon

<400> SEQUENCE: 97

Met Gly Ser Ser Lys Ser Lys Pro Lys Asp Pro Ser Gln Arg Ser Arg
1               5                   10                  15

Xaa Glu Phe Xaa
            20

<210> SEQ ID NO 98
<211> LENGTH: 36
<212> TYPE: DNA
<213> ORGANISM: Artificial Sequence
<220> FEATURE:
<223> OTHER INFORMATION: cloning primer
<221> NAME/KEY: misc_feature
<222> LOCATION: (1)..(36)

<400> SEQUENCE: 98
gcactatcta gactgaagaa catgtgtgag cacagc                                36

<210> SEQ ID NO 99
<211> LENGTH: 34
<212> TYPE: DNA
<213> ORGANISM: Artificial Sequence
<220> FEATURE:
<223> OTHER INFORMATION: cloning primer
<221> NAME/KEY: misc_feature
<222> LOCATION: (1)..(34)

<400> SEQUENCE: 99
gcattctaga acagcccggc acaatgcagc caac                                  34

<210> SEQ ID NO 100
<211> LENGTH: 34
<212> TYPE: DNA
<213> ORGANISM: Artificial Sequence
<220> FEATURE:
<223> OTHER INFORMATION: cloning primer
<221> NAME/KEY: misc_feature
<222> LOCATION: (1)..(34)

<400> SEQUENCE: 100
```

```
gcattctaga ctggtccagc aggccatgat ggtg                              34

<210> SEQ ID NO 101
<211> LENGTH: 42
<212> TYPE: DNA
<213> ORGANISM: Artificial Sequence
<220> FEATURE:
<223> OTHER INFORMATION: cloning primer
<221> NAME/KEY: misc_feature
<222> LOCATION: (1)..(42)

<400> SEQUENCE: 101
cgaatctcaa agcagctgcc tggagtgcag gtggagacta tc                     42

<210> SEQ ID NO 102
<211> LENGTH: 42
<212> TYPE: DNA
<213> ORGANISM: Artificial Sequence
<220> FEATURE:
<223> OTHER INFORMATION: cloning primer
<221> NAME/KEY: misc_feature
<222> LOCATION: (1)..(42)

<400> SEQUENCE: 102
aagcagctgc ctcagctcac aggagtgcag gtggagacta tc                     42

<210> SEQ ID NO 103
<211> LENGTH: 42
<212> TYPE: DNA
<213> ORGANISM: Artificial Sequence
<220> FEATURE:
<223> OTHER INFORMATION: cloning primer
<221> NAME/KEY: misc_feature
<222> LOCATION: (1)..(42)

<400> SEQUENCE: 103
cctcagctca catccttaga gggagtgcag gtggagacta tc                     42

<210> SEQ ID NO 104
<211> LENGTH: 44
<212> TYPE: DNA
<213> ORGANISM: Artificial Sequence
<220> FEATURE:
<223> OTHER INFORMATION: cloning primer
<221> NAME/KEY: misc_feature
<222> LOCATION: (1)..(44)

<400> SEQUENCE: 104
gccaaggatc cctaataact agtttccagt tttagaagct ccac                   44

<210> SEQ ID NO 105
<211> LENGTH: 31
<212> TYPE: DNA
<213> ORGANISM: Artificial Sequence
<220> FEATURE:
<223> OTHER INFORMATION: cloning primer
<221> NAME/KEY: misc_feature
<222> LOCATION: (1)..(31)

<400> SEQUENCE: 105
gcattctaga ggagtgcagg tggagactat c                                 31

<210> SEQ ID NO 106
<211> LENGTH: 42
<212> TYPE: DNA
<213> ORGANISM: Artificial Sequence
<220> FEATURE:
```

```
<223> OTHER INFORMATION: cloning primer
<221> NAME/KEY: misc_feature
<222> LOCATION: (1)..(42)

<400> SEQUENCE: 106
gtggagcttc taaaactgga agaggagctg atccgagtgg cc                42

<210> SEQ ID NO 107
<211> LENGTH: 42
<212> TYPE: DNA
<213> ORGANISM: Artificial Sequence
<220> FEATURE:
<223> OTHER INFORMATION: cloning primer
<221> NAME/KEY: misc_feature
<222> LOCATION: (1)..(42)

<400> SEQUENCE: 107
gtggagcttc taaaactgga acgagtggcc atcctctggc at                42

<210> SEQ ID NO 108
<211> LENGTH: 42
<212> TYPE: DNA
<213> ORGANISM: Artificial Sequence
<220> FEATURE:
<223> OTHER INFORMATION: cloning primer
<221> NAME/KEY: misc_feature
<222> LOCATION: (1)..(42)

<400> SEQUENCE: 108
gtggagcttc taaaactgga aatcctctgg catgagatgt gg                42

<210> SEQ ID NO 109
<211> LENGTH: 44
<212> TYPE: DNA
<213> ORGANISM: Artificial Sequence
<220> FEATURE:
<223> OTHER INFORMATION: cloning primer
<221> NAME/KEY: misc_feature
<222> LOCATION: (1)..(44)

<400> SEQUENCE: 109
cgtcaggatc cctaataact agtctgcttt gagattcgtc ggaa              44

<210> SEQ ID NO 110
<211> LENGTH: 690
<212> TYPE: DNA
<213> ORGANISM: Artificial Sequence
<220> FEATURE:
<223> OTHER INFORMATION: FRAP--FKBP Fusion
<221> NAME/KEY: misc_structure
<222> LOCATION: (1)..(690)

<400> SEQUENCE: 110
tctagactgg tccagcaggc catgatggtg agcgaggagc tgatccgagt ggccatcctc    60
tggcatgaga tgtggcatga aggcctggaa gaggcatctc gtttgtactt tggggaaagg   120
aacgtgaaag gcatgtttga ggtgctggag cccttgcatg ctatgatgga acgggcccc    180
cagactctga aggaaacatc ctttaatcag gcctatggtc gagatttaat ggaggcccaa   240
gagtggtgca ggaagtacat gaaatcaggg aatgtcaagg acctcaccca agcctgggac   300
ctctattatc atgtgttccg acgaatctca aagcagctgc ctcagctcac aggagtgcag   360
gtggagacta tctccccagg agacgggcgc accttcccca gcgcggcca gacctgcgtg   420
gtgcactaca ccgggatgct tgaagatgga agaaatttg attcctcccg ggacagaaac   480
aagccctta agtttatgct aggcaagcag gaggtgatcc gaggctggga agaagggggtt   540
```

```
gcccagatga gtgtgggtca gagagccaaa ctgactatat ctccagatta tgcctatggt      600
gccactgggc acccaggcat catcccacca catgccactc tcgtcttcga tgtggagctt      660
ctaaaactgg aaactagtta ttagggatcc                                       690
```

```
<210> SEQ ID NO 111
<211> LENGTH: 230
<212> TYPE: PRT
<213> ORGANISM: Artificial Sequence
<220> FEATURE:
<223> OTHER INFORMATION: FRAP/FKBP Fusion
<221> NAME/KEY: PEPTIDE
<222> LOCATION: (1)..(229)
<223> OTHER INFORMATION: X represents a stop codon

<400> SEQUENCE: 111
```

Ser Arg Leu Val Gln Gln Ala Met Met Val Ser Glu Glu Leu Ile Arg
1               5                  10                  15

Val Ala Ile Leu Trp His Glu Met Trp His Glu Gly Leu Glu Glu Ala
            20                  25                  30

Ser Arg Leu Tyr Phe Gly Glu Arg Asn Val Lys Gly Met Phe Glu Val
        35                  40                  45

Leu Glu Pro Leu His Ala Met Met Glu Arg Gly Pro Gln Thr Leu Lys
    50                  55                  60

Glu Thr Ser Phe Asn Gln Ala Tyr Gly Arg Asp Leu Met Glu Ala Gln
65                  70                  75                  80

Glu Trp Cys Arg Lys Tyr Met Lys Ser Gly Asn Val Lys Asp Leu Thr
                85                  90                  95

Gln Ala Trp Asp Leu Tyr Tyr His Val Phe Arg Arg Ile Ser Lys Gln
            100                 105                 110

Leu Pro Gln Leu Thr Gly Val Gln Val Glu Thr Ile Ser Pro Gly Asp
        115                 120                 125

Gly Arg Thr Phe Pro Lys Arg Gly Gln Thr Cys Val Val His Tyr Thr
    130                 135                 140

Gly Met Leu Glu Asp Gly Lys Lys Phe Asp Ser Ser Arg Asp Arg Asn
145                 150                 155                 160

Lys Pro Phe Lys Phe Met Leu Gly Lys Gln Glu Val Ile Arg Gly Trp
                165                 170                 175

Glu Glu Gly Val Ala Gln Met Ser Val Gly Gln Arg Ala Lys Leu Thr
            180                 185                 190

Ile Ser Pro Asp Tyr Ala Tyr Gly Ala Thr Gly His Pro Gly Ile Ile
        195                 200                 205

Pro Pro His Ala Thr Leu Val Phe Asp Val Glu Leu Leu Lys Leu Glu
    210                 215                 220

Thr Ser Tyr Xaa Gly Ser
225             230

```
<210> SEQ ID NO 112
<211> LENGTH: 38
<212> TYPE: DNA
<213> ORGANISM: Artificial Sequence
<220> FEATURE:
<223> OTHER INFORMATION: HindIII--EcoRI--Kozak--p75
<221> NAME/KEY: misc_feature
<222> LOCATION: (1)..(38)

<400> SEQUENCE: 112
ggcccaagct tgaattccgg gcgatggggg caggtgcc                              38
```

```
<210> SEQ ID NO 113
<211> LENGTH: 5
<212> TYPE: PRT
<213> ORGANISM: Artificial Sequence
<220> FEATURE:
<223> OTHER INFORMATION: p75
<221> NAME/KEY: PEPTIDE
<222> LOCATION: (1)..(5)

<400> SEQUENCE: 113

Met Gly Ala Gly Ala
1               5

<210> SEQ ID NO 114
<211> LENGTH: 30
<212> TYPE: DNA
<213> ORGANISM: Artificial Sequence
<220> FEATURE:
<223> OTHER INFORMATION: transmembrane domain--XbaI
<221> NAME/KEY: misc_feature
<222> LOCATION: (1)..(30)

<400> SEQUENCE: 114
gcctacatag ccttcaagag gtctagaccg                              30

<210> SEQ ID NO 115
<211> LENGTH: 9
<212> TYPE: PRT
<213> ORGANISM: Artificial Sequence
<220> FEATURE:
<223> OTHER INFORMATION: transmembrane doamin
<221> NAME/KEY: PEPTIDE
<222> LOCATION: (1)..(9)

<400> SEQUENCE: 115

Ala Tyr Ile Ala Phe Lys Arg Ser Arg
1               5

<210> SEQ ID NO 116
<211> LENGTH: 30
<212> TYPE: DNA
<213> ORGANISM: Artificial Sequence
<220> FEATURE:
<223> OTHER INFORMATION: XbaI--intracellular--FAS
<221> NAME/KEY: misc_feature
<222> LOCATION: (1)..(30)

<400> SEQUENCE: 116
ggctctagaa agagaaagga agtacagaaa                              30

<210> SEQ ID NO 117
<211> LENGTH: 9
<212> TYPE: PRT
<213> ORGANISM: Artificial Sequence
<220> FEATURE:
<223> OTHER INFORMATION: intracellular FAS
<221> NAME/KEY: PEPTIDE
<222> LOCATION: (1)..(9)

<400> SEQUENCE: 117

Ser Arg Lys Arg Lys Glu Val Gln Lys
1               5

<210> SEQ ID NO 118
<211> LENGTH: 57
<212> TYPE: DNA
<213> ORGANISM: Artificial Sequence
<220> FEATURE:
```

```
<223> OTHER INFORMATION: SpeI mutation
<221> NAME/KEY: misc_feature
<222> LOCATION: (1)..(57)

<400> SEQUENCE: 118
actagcgact cagaaaattc aaacttcaga atgaaatcc aaagcttggt cactagt        57

<210> SEQ ID NO 119
<211> LENGTH: 19
<212> TYPE: PRT
<213> ORGANISM: Artificial Sequence
<220> FEATURE:
<223> OTHER INFORMATION: SpeI mutation in FAS
<221> NAME/KEY: PEPTIDE
<222> LOCATION: (1)..(19)

<400> SEQUENCE: 119

Thr Ser Asp Ser Glu Asn Ser Asn Phe Arg Asn Glu Ile Gln Ser Leu
1               5                   10                  15

Val Thr Ser

<210> SEQ ID NO 120
<211> LENGTH: 24
<212> TYPE: DNA
<213> ORGANISM: Artificial Sequence
<220> FEATURE:
<223> OTHER INFORMATION: FAS construct
<221> NAME/KEY: misc_feature
<222> LOCATION: (1)..(24)

<400> SEQUENCE: 120
atcatcctca aggacattac tagt                                           24

<210> SEQ ID NO 121
<211> LENGTH: 8
<212> TYPE: PRT
<213> ORGANISM: Artificial Sequence
<220> FEATURE:
<223> OTHER INFORMATION: FAS construct fragment
<221> NAME/KEY: PEPTIDE
<222> LOCATION: (1)..(8)

<400> SEQUENCE: 121

Ile Ile Leu Lys Asp Ile Thr Ser
1               5

<210> SEQ ID NO 122
<211> LENGTH: 38
<212> TYPE: DNA
<213> ORGANISM: Artificial Sequence
<220> FEATURE:
<223> OTHER INFORMATION: cloning oligo
<221> NAME/KEY: misc_feature
<222> LOCATION: (1)..(38)

<400> SEQUENCE: 122
ggcccaagct tgaattccgg gcgatggggg caggtgcc                            38

<210> SEQ ID NO 123
<211> LENGTH: 30
<212> TYPE: DNA
<213> ORGANISM: Artificial Sequence
<220> FEATURE:
<223> OTHER INFORMATION: cloning oligo
<221> NAME/KEY: misc_feature
<222> LOCATION: (1)..(30)

<400> SEQUENCE: 123
```

```
cggtctagac ctcttgaagg ctatgtaggc                                    30

<210> SEQ ID NO 124
<211> LENGTH: 30
<212> TYPE: DNA
<213> ORGANISM: Artificial Sequence
<220> FEATURE:
<223> OTHER INFORMATION: cloning oligo
<221> NAME/KEY: misc_feature
<222> LOCATION: (1)..(30)

<400> SEQUENCE: 124
ggctctagaa agagaaagga agtacagaaa                                    30

<210> SEQ ID NO 125
<211> LENGTH: 60
<212> TYPE: DNA
<213> ORGANISM: Artificial Sequence
<220> FEATURE:
<223> OTHER INFORMATION: cloning oligo
<221> NAME/KEY: misc_feature
<222> LOCATION: (1)..(60)

<400> SEQUENCE: 125
gcactagtga ccaagctttg gatttcattt ctgaagtttg aattttctga gtcgctagta   60

<210> SEQ ID NO 126
<211> LENGTH: 33
<212> TYPE: DNA
<213> ORGANISM: Artificial Sequence
<220> FEATURE:
<223> OTHER INFORMATION: cloning oligo
<221> NAME/KEY: misc_feature
<222> LOCATION: (1)..(33)

<400> SEQUENCE: 126
ttagccctcg agctagacca agctttggat ttc                                33

<210> SEQ ID NO 127
<211> LENGTH: 38
<212> TYPE: DNA
<213> ORGANISM: Artificial Sequence
<220> FEATURE:
<223> OTHER INFORMATION: LexCon probe/Lex A binding site
<221> NAME/KEY: misc_feature
<222> LOCATION: (1)..(38)

<400> SEQUENCE: 127
gatcctctag atactgtata tatatacagt aagatctc                           38

<210> SEQ ID NO 128
<211> LENGTH: 38
<212> TYPE: DNA
<213> ORGANISM: Artificial Sequence
<220> FEATURE:
<223> OTHER INFORMATION: LexCon probe/LexA binding site
<221> NAME/KEY: misc_feature
<222> LOCATION: (1)..(38)

<400> SEQUENCE: 128
gagatctatg acatatatat atgtcattct agagagct                           38

<210> SEQ ID NO 129
<211> LENGTH: 31
<212> TYPE: DNA
<213> ORGANISM: Artificial Sequence
<220> FEATURE:
```

-continued

```
<223> OTHER INFORMATION: LexA--XbaI
<221> NAME/KEY: misc_feature
<222> LOCATION: (1)..(31)

<400> SEQUENCE: 129
atgctctaga aaagcgttaa cggccaggca a                              31

<210> SEQ ID NO 130
<211> LENGTH: 43
<212> TYPE: DNA
<213> ORGANISM: Artificial Sequence
<220> FEATURE:
<223> OTHER INFORMATION: LexA87Spe/Bam
<221> NAME/KEY: misc_feature
<222> LOCATION: (1)..(43)

<400> SEQUENCE: 130
cgtaggatcc ttactaacta gttggttcac cggcagccac acg                 43

<210> SEQ ID NO 131
<211> LENGTH: 54
<212> TYPE: DNA
<213> ORGANISM: Artificial Sequence
<220> FEATURE:
<223> OTHER INFORMATION: XG6FKBP fragment
<221> NAME/KEY: misc_feature
<222> LOCATION: (1)..(54)

<400> SEQUENCE: 131
tcagtctaga ggaggcggtg gaggtggagc tagcggagtg caggtggaaa ccat      54

<210> SEQ ID NO 132
<211> LENGTH: 40
<212> TYPE: DNA
<213> ORGANISM: Artificial Sequence
<220> FEATURE:
<223> OTHER INFORMATION: FKBPSpe/Bam
<221> NAME/KEY: misc_feature
<222> LOCATION: (1)..(40)

<400> SEQUENCE: 132
tcagggatcc tcaataacta gtttccagtt ttagaagctc                     40
```

INTRAMUSCULAR DELIVERY OF RECOMBINANT AAV

This application is a continuation-in-part of each of the following applications: U.S. Ser. No. 60/015,502 filed Feb. 9, 1996 (now abandoned); U.S. Ser. No. 08/481,941 filed Jun. 7, 1995 (now abandoned); U.S. Ser. No. 08/791,044 filed Jan. 28, 1997 (now abandoned).

BACKGROUND OF THE INVENTION

Rapamycin (I) is a natural product which binds to a FK506-bining protein, FKBP, with high affinity to form a rapamycin:FKBP complex. Reported Kd values for that interaction are as low as 200 pM. The rapamycin:FKBP complex binds with high affinity to the large cellular protein FRAP to form a tripartite, [FKBP:rapamycin]:[FRAP], complex. In this tripartite complex rapamycin acts as a dimerizer or adapter to join FKBP to FRAP. The portion of the FRAP protein which interacts with the FKBP:rapamycin complex is referred to as the FRB domain, which is discussed in detail below. The rapamycin-dependent association of FKBP12 and a large mammalian protein termed FRAP, RAFT1 or RAPT1 and its yeast homologs DRR and TOR have been described by several research groups. See e.g., Brown et al, 1994, Nature 369:756–758; Sabatini et al, 1994, Cell 78:35–43; Chiu et al, 1994, Proc. Natl. Acad. Sci. USA 91:12574–12578; Chen et al, 1994, Biochem. Biophys. Res. Comm. 203:1–7; Kunz et al, 1993 Cell 73:585–596; and Cafferkey et al, 1993 Mol. Cell. Biol. 13:6012–6023. Chiu et al, supra, and Stan et al, 1994, J. Biol. Chem. 269:32027–32030 describe the rapamycin-dependent binding of FKBP12 to smaller subunits of FRAP containing the FRB domain. FRAP, RAFT, RAPT and the TOR proteins each contain homologous FRB domains and are considered FRAP proteins for the purpose of this document.

(I)

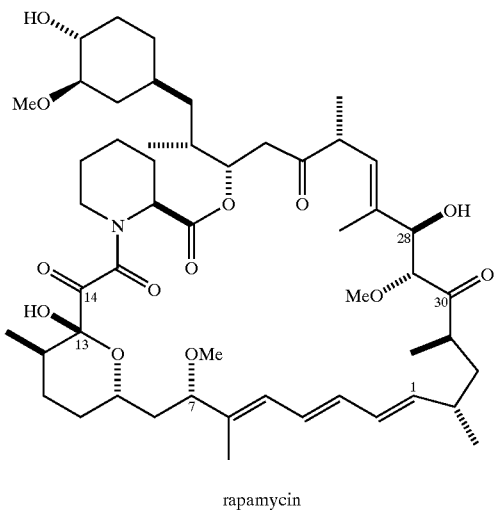

rapamycin

Numerous naturally occurring FK506 binding proteins (FKBPs) are known. See e.g. Kay, 1996, Biochem. J. 314:361–385 (review). FKBP proteins have been used for their ligand-binding properties in biological switches based on ligand-mediated multimerization of immunophilin-based recombinant proteins as disclosed e.g. in Spencer et al, 1993, Science 262:1019–1024 and in PCT/US94/01617. While the potent immunosuppressive activity of FK506 would limit its utility as a dimerizer, especially in animals, dimers of FK506 (and related compounds) lack such immunosuppressive activity and have been shown to be effective for dimerizing chimeric proteins containing ligand binding domains derived from FKBP.

While rapamycin, like FK506, is a natural dimerizer of proteins, and is capable of dimerizing appropriately designed chimeric proteins, its significant biological activities, including potent immunosuppressive activity, rather severely limit its use in engineered biological switches, particularly for use in animals. This invention harnesses the dimerizing potential of rapamycin (and related compounds) while avoiding its profound, inherent limitations.

SUMMARY OF THE INVENTION

This invention concerns new configurations for biological switches and provides new methods and materials for regulating biological events, particularly in animal cells. Those biological events include, for example, gene transcription, activation of an intracellular signal transduction pathway leading for example to gene expression or apoptotic cell death, gene knock-out, blockade of expression of a gene, and inhibition of the function of a gene product. The invention relies upon two types of chimeric proteins which when complexed through mutual binding to a common ligand, are capable of actuating, directly or indirectly, the desired event.

This invention encompasses recombinant DNA constructs encoding those chimeric proteins; DNA vectors containing one or more of those constructs; the fusion proteins encoded by the foregoing constructs; cells, especially animal cells, transformed with (i.e., containing and capable of expressing) one or more of the DNA constructs described herein; small molecules (bivalent or multivalent multimerizing agents) which bind to and are capable of inducing multimerization of the chimeric protein molecules; and, methods for preparing and using the foregoing.

More specifically, this invention provides methods and materials for making and using genetically engineered cells which are responsive to the presence of rapamycin or to the presence of an analog, mimic or derivative of rapamycin (a "rapalog"). The invention relies upon the introduction into cells of recombinant DNAs encoding a set of fusion proteins which are capable of complexing with each other in the presence of rapamycin or a rapalog. Contacting such genetically engineered cells with rapamycin or a suitable rapalog results in complexation of the fusion proteins and the initiation of a biological response. One of the fusion proteins contains one or more copies of an EKBP:rapamycin binding (FRB) domain and at least one heterologous protein domain. The second fusion protein contains one or more copies of a domain derived from an FKBP protein which is capable of binding to rapamycin or a rapalog and forming a complex with an FRB-containing protein. The second fusion protein also contains at least one heterologous domain which may be the same or different from a heterologous domain of the first fusion protein. FRB and FKBP domains for use in fusion proteins of this invention may be selected from naturally occurring proteins and may be variously modified, as is discussed in detail below. While FRB, FKBP and heterologous domains derived from various species may be used, human peptide sequences or variants thereof are preferred for human gene therapy applications. Operationally, the FRB and FKBP domains serve as receptor (or "ligand-binding") domains and direct the complexation of the fusion proteins under the mediation of rapamycin or rapalog molecules. The nature of the biological response triggered by rapamycin- or rapalog-mediated complexation is determined by the heterologous domains of the fusion proteins. The heterologous domains are therefore also referred to as "action" domains.

Various heterologous protein domains may be used in these fusion proteins. In one aspect of the invention, the two fusion proteins (one of which contains at least one FRB domain, the other contains at least one FKBP domain) each contain at least one different heterologous domain, i.e., a heterologous domain not contained in the other fusion protein. For example, in certain embodiments, one of the fusion proteins contains at least one DNA binding domain and the other fusion protein contains at least one transcription activation domain. Ligand-mediated association of the fusion proteins represents the formation of a transcription factor complex and leads to initiation of transcription of a target gene linked to a DNA sequence recognized by (i.e., capable of binding with) a DNA-binding domain on one of the fusion proteins. In other embodiments, one of the fusion proteins contains at least one domain capable of directing the fusion protein to a particular cellular location such as the cell membrane, nucleus, etc. Localization domains which target the cell membrane include domains such as a myristoylation site or a transmembrane region of a receptor protein or other membrane-spanning protein. The other fusion protein contains a signalling domain capable, upon membrane localization and/or clustering, of activating a cellular signal transduction pathway. Examples of signalling domains include an intracellular domain of a growth factor or cytokine receptor, an apoptosis triggering domain such as the intracellular domain of FAS or TNF-R1, and domains derived from other intracellular signalling proteins such as SOS, Raf, Ick, ZAP-70, etc. A number of signalling proteins are disclosed in PCT/US94/01617 (see e.g. pages 23–26). In still other embodiments, each of the fusion proteins contains at least one FRB domain and at least one FKBP domain, as well as one or more heterologous domains. Such fusion proteins are capable of homodimerization in the presence of rapamycin or a rapalog. In general, domains containing peptide sequence endogenous to the host cell are preferred. Thus, for human gene therapy applications, domains of human origin are of particular interest Recombinant DNA molecules encoding the fusion proteins are also provided, as are vectors capable of directing their expression, particularly in eukaryotic cells, of which yeast and animal cells are of particular interest. In view of the constituent components of the fusion proteins, the recombinant DNA molecules which encode them are capable of selectively hybridizing (a) to a DNA molecule encoding a given fusion protein's ligand-binding domain (FRB domain or FKBP domain) or a protein containing such a domain and (b) to a DNA molecule encoding the heterologous domain or a protein from which the heterologous protein domain was derived. DNAs are also encompassed which would be capable of so hybridizing but for the degeneracy of the genetic code.

Using DNA sequences encoding the chimeric proteins of this invention, and vectors capable of directing their expression in eukaryotic cells, one may genetically engineer cells for a number of important uses. To do so, one first provides an expression vector or DNA construct for directing the expression in a eukaryotic (preferably animal) cell of the desired chimeric protein and then introduces the recombinant DNA into the cells in a manner permitting DNA uptake and expression of the introduced DNA in at least a portion of the cells. One may use any of the various methods and materials for introducing DNA into cells for heterologous gene expression, a variety of which are well known and/or commercially available.

One object of this invention is thus to provide an animal cell containing recombinant DNAs encoding two fusion proteins as described herein. One of the fusion proteins is capable of binding to rapamycin or a rapalog and contains at least one FKBP domain and at least one domain heterologous thereto. The second fusion protein contains at least one FRB domain and at least one domain heterologous thereto and is capable of forming a tripartite complex with the first fusion protein and one or more molecules of rapamycin or a rapalog. In some embodiments one or more of the heterologous domains present on one of the fusion proteins are also present on the other fusion protein, i.e., the two fusion proteins have one or more common heterologous domains. In other embodiments, each fusion protein contains one or more different heterologous domains.

A specific object of this invention is to provide animal cells engineered such that contacting the cells with rapamycin or a rapalog leads to transcription of a target gene. Such cells contain, in addition to recombinant DNAs encoding the two fusion proteins, a target gene construct which comprises a target gene operably linked to a DNA sequence which is responsive to the presence of a complex of the fusion proteins with rapamycin or a rapalog. In certain embodiments the cells are responsive to contact with a rapalog which binds to the FKBP fusion protein and FRB fusion protein with a detectable preference over binding to endogenous FKBP or FRB-containing proteins of the host cell.

Another specific object of this invention is to provide animal cells engineered such that contacting the cells with rapamycin or a rapalog leads to the initiation of cell death. In such cells, at least one of the heterologous domains on at least one of the fusion proteins is a domain such as the intracellular domain of FAS or TNF-R1, which, upon clustering, triggers apoptosis of the cell.

Another specific object of this invention is to provide animal cells engineered such that contacting the cells with rapamycin or a rapalog stimulates cell growth, differentiation or proliferation. In such cells, at least one of the heterologous domains on at least one of the fusion proteins is a domain such as the intracellular domain of a receptor for a hormone which mediates cell growth, differentiation or proliferation. Cell growth, differentiation and/or proliferation follow clustering of the receptor intracellular signalling domains. Such clustering occurs in nature following hormone binding, and in engineered cells of this invention following contact with rapamycin or a rapalog.

Cells of human origin are preferred for. human gene therapy applications, although cell types of various origins (human or other species) may be used, and may, if desired, be encapsulated within a biocompatible material for use in human subjects.

Another object of the invention is to provide materials and methods for producing the foregoing engineered cells. This object is met by providing recombinant DNAs encoding the fusion proteins, together with any ancillary recombinant DNAs such as a target gene construct, and introducing the recombinant DNAs into the host cells under conditions permitting DNA uptake by cells. Such transfection may be effected ex vivo, using host cells maintained in culture. Cells that are engineered in culture may subsequently be introduced into a host organism, e.g. in ex vivo gene therapy applications. Doing so thus constitutes a method for providing a host organism, preferably a human or non-human mammal, which is responsive (as described herein) to the presence of rapamycin or a rapalog. Alternatively transfection may be effected in vivo, using host cells present in a human or non-human host organism In such cases, the DNA molecules are introduced directly into the host organism under conditions permitting uptake of the DNA by one or more of the host organism's cells. This approach thus constitutes an alternative method for providing a host organism, preferably a human or non-human mammal, which is responsive (as described herein) to the presence of rapamycin or a rapalog. Various materials and methods for the introduction of DNA into cells in culture or in whole organisms are known in the art and may be adapted for use in practicing this invention.

Other objects are achieved using the engineered cells described herein. For instance, a method is provided for multimerizing the fusion proteins of this invention by contacting cells engineered as described herein with an effective amount of rapamycin or a suitable rapalog permitting the rapamycin or rapalog to form a complex with the fusion proteins. In embodiments in which multimerization of the fusion proteins triggers transcription of a target gene, this constitutes a method for activating the expression of the target gene. In embodiments in which the fusion proteins contain one or more signalling domains, this constitutes a method for activating a cellular signal transduction pathway. In embodiments in which the fusion proteins contain one or more domains capable upon clustering of triggering apoptotic cell death, this constitutes a method for actuating cell death. These methods may be carried out in cell culture or in whole organisms, including human patients. In the former case, the rapamycin or rapalog is added to the culture medium. In the latter case, the rapamycin or rapalog (which may be in the form of a pharmaceutical or veterinary composition) is administered to the whole organism, e.g., orally, parenterally, etc. Preferably, the dose or rapamycin or rapalog administered to an animal is below the dosage level that would cause undue immunosuppression in the recipient.

A further object of this invention is to provide kits for use in the genetic engineering of cells or human or non-human animals as described herein. One such kit contains recombinant DNA constructs encoding a pair of fusion proteins of this invention. The recombinant DNA constructs will generally be in the form of eukaryotic expression vectors suitable for introduction into animal cells and capable of directing the expression of the fusion proteins therein. The kit may also contain a sample of rapamycin or a rapalog capable of forming a complex with the encoded fusion proteins. The kit may further contain a multimerization antagonist such as FK506 or some other compound capable of binding to one of the fusion proteins but incapable of forming a complex with both. In certain embodiments, the recombinant DNA constructs encoding the fusion proteins will contain a cloning site in place of DNA encoding one or more of the heterologous domains, thus permitting the practitioner to introduce DNA encoding a heterologous domain of choice. In some embodiments the kit may also contain a target gene construct containing a target gene or cloning site linked to a DNA sequence responsive to the presence of the complexed fusion proteins, as described in more detail elsewhere.

BRIEF DESCRIPTION OF THE FIGURES

FIG. 12 depicts illustrative examples of configurations useful for rapamycin-dependent control of signal transduction processes.

DETAILED DESCRIPTION OF THE INVENTION

Figure 1A:
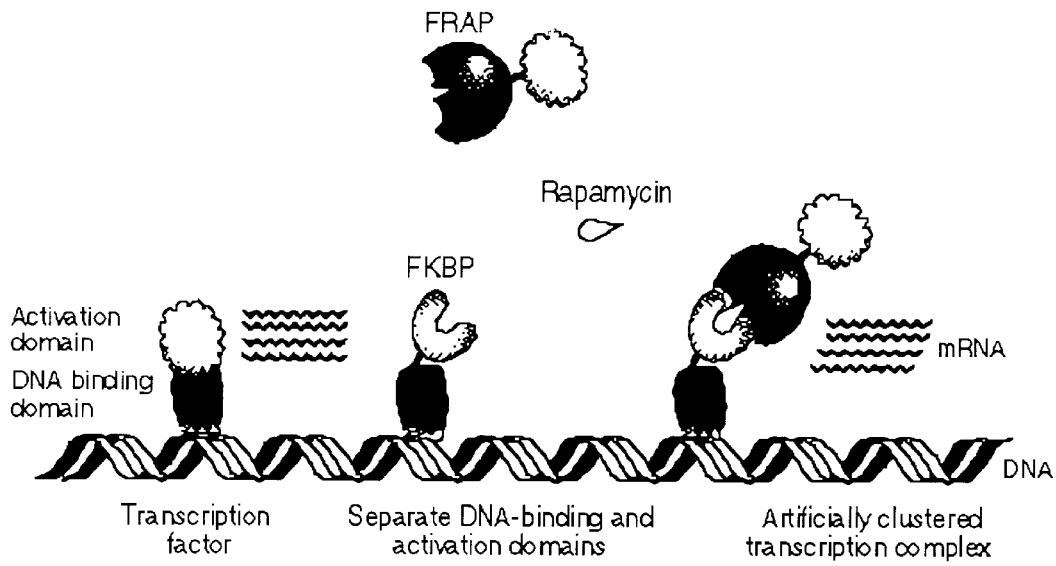
FIG. 1. (A) Rapamycin-dependent dimerization of a FKBP chimera containing a DNA-binding domain with a FRAP chimera containing a transcription activation domain is depicted. (B) Schematic diagrams of representative plasmids used in some of the experimental examples. Transcription factor fusion proteins were produced under the control of the human cytomegalovirus (hCMV) immediate early promoter and enhancer. "E" represents an epitope tag and "N" represents the SV40 T antigen nuclear localization sequence, both fused to the N-termini of the the transcription factors. The reporter genes consisted of a minimal hCMV promoter devoid of enhancer sequences flanked by 12 tandemly reiterated binding sites for ZFHD1.

The definitions and orienting information below will be helpful for a full understanding of the present disclosure.

FRB domains are polypeptide regions (protein "domains"), typically of at least about 89 amino acid residues, which are capable of forming a tripartite complex with an FKBP protein and rapamycin (or a rapalog). FRB domains are present in a number of naturally occurring proteins, including FRAP proteins (also referred to in the literature as "RAPT1" or "RAFT") from human and other species; yeast proteins including Tor1 and Tor2; and a Candida FRAP homolog. Information concerning the nucleotide sequences, cloning, and other aspects of these proteins is already known in the art, permitting the synthesis or cloning of DNA encoding the desired FRB peptide sequence, e.g., using well known methods and PCR primers based on published sequences.

| protein source | reference/sequence accession numbers |
|---|---|
| human FRAP | Brown et al, 1994, Nature 369, 756–758; GenBank accession # L34075, NCBI Seq ID 508481; Chiu et al, 1994, PNAS USA 91, 12574 12578; Chen et al, 1995, PNAS USA 92, 4947 4951 |
| murine RAPT1 | Chiu et al, supra. |
| yeast Tor1 | Helliwell et al, 1994, Mol Cell Biol 5, 105–118; EMBL Accession #X74857 NCBI Se Id #468738 |
| yeast Tor2 | Kunz et al, 1993, Cell 73, 585–596; EMBL Accession #X71416, NCBI Seq ID 298027 |
| Candida homolog | WO95/33052 |

FRB domains for use in this invention generally contain at least about 89–100 amino acid residues. FIG. 2 of Chiu et al, supra, displays a 160-amino acid span of human FRAP, murine FRAP, S. cerevisiae TOR1 and S. cerevisiae TOR2 encompassing the conserved FRB region. Typically the FRB sequence selected for use in fusion proteins of this invention will span at least the 89-amino acid sequence Glu-39 through Lys/Arg-127, as the sequence is numbered in that figure. For reference, using the numbering of Chen et al or Sabitin et al, the 89-amino acid sequence is numbered Glu-2025 through Lys-2113 in the case of human FRAP, Glu-1965 through Lys-2053 in the case of Tor2, and Glu-1,962 through Arg-2050 in the case of Tor1. An FRB peptide sequence for use in fusion proteins of this invention will be capable of binding to a complex of an FKBP protein bound to rapamycin or a rapalog (as may be determined by any means, direct or indirect, for detecting such binding), and may comprise a naturally occurring pep tide sequence spanning the indicated 89-amino acid region of the proteins noted above or corresponding regions of homologous proteins; may contain up to about ten (preferably 1–5) amino acid substitutions, insertions or deletions within that region relative to the naturally occurring sequence; may be a peptide sequence encoded by a DNA sequence capable of selectively hybridizing to a DNA molecule encoding a naturally occurring FRB region; or may be encoded by a DNA sequence which would be capable, but for the degeneracy of the genetic code, of selectively hybridizing to a DNA molecule encoding a naturally occurring FRB region.

FKBPs (FK506 binding proteins) are the cytosolic receptors for macrolides such as FK506, FK520 and rapamycin and are highly conserved across species lines. For the purpose of this disclosure, FKBPs are proteins or protein domains which are capable of binding to rapamycin or to a rapalog of this invention and further forming a tripartite complex with an FRB-containing protein. Information concerning the nucleotide sequences, cloning, and other aspects of various FKBP species is already known in the art, permitting the synthesis or cloning of DNA encoding the desired FKBP peptide sequence, e.g., using well known methods and PCR primers based on published sequences. See e.g. Staendart et al, 1990, Nature 346, 671–674 (human FKBP12); Kay, 1996, Biochem. J. 314, 361–385 (review). Homologous FKBP proteins in other mammalian species, in yeast, and in other organsims are also known in the art and may be used in the fusion proteins disclosed herein. See e.g. Kay, 1996, Biochem. J. 314, 361–385 (review). The size of FKBP domains for use in this invention varies, depending on which FKBP protein is employed. An FKBP peptide sequence for use in fusion proteins of this invention will be capable of binding to rapamycin or a rapalog and participating in a tripartite complex with a FRB-containing protein (as may be determined by any means, direct or indirect, for detecting such binding), and may comprise a naturally occurring peptide sequence derived from the human FKBP12 protein (exemplified below) or a peptide sequence derived from another human FKBP, from a murine or other mammalian FKBP, or from some other animal, yeast or fungal FKBP; may contain up to about ten (preferably 1–5) amino acid substitutions, insertions or deletions within that region relative to the naturally occurring sequence; may be a peptide sequence encoded by a DNA sequence capable of selectively hybridizing to a DNA molecule encoding a naturally occurring FKBP or may be encoded by a DNA sequence which would be capable, but for the degeneracy of the genetic code, of selectively hybridizing to a DNA molecule encoding a naturally occurring FKBP.

"Capable of selectively hybridizing" as that phrase is used herein means that two DNA molecules are susceptible to hybridization with one another, despite the presence of other DNA molecules, under hybridization conditions which can be chosen or readily determined empirically by the practitioner of ordinary skill in this art. Such treatments include conditions of high stringency such as washing extensively with buffers containing 0.2 to 6×SSC, and/or containing 0.1% to 1% SDS, at temperatures ranging from room temperature to 65–75° C. See for example F. M. Ausubel et al., Eds, Short Protocols in Molecular Biology, Units 6.3 and 6.4 (John Wiley and Sons, New York, 3d Edition, 1995).

"Recombinant", "chimeric" and "fusion", as those terms are used herein, indicate that the various component domains or sequences are mutually heterologous in the sense that they do not occur together in the same arrangement in nature. More specifically, the component portions are not found in the same continuous polypeptide or nucleotide sequence or molecule in nature, at least not in the same order or orientation or with the same spacing present in the chimeric protein or recombinant DNA molecule of this invention.

"Dimerization", "oligomerization" and "multimerization" refer to the association of two or more proteins, mediated, in the practice of this invention, by the binding of each such protein to a common ligand. The formation of a tripartite complex comprising a protein containing an FRB domain, a protein containing an FKBP domain and a molecule of rapamycin is an example of dimerization. In certain embodiments of this invention, fusion proteins contain multiple copies of FRAP and/or FRB domains. Complexes of such proteins may contain more than one molecule of rapamycin or the rapalog and more than one copy of one or more of the constituent proteins. Such multimeric complexes are still referred to herein as tripartite complexes to indicate the presence of the three types of constituent molecules, even if one or more are represented by multiple copies.

Rapalogs are compounds other than rapamycin, preferably of molecular weight below 5 kD, more preferably below 2.5 kD, which are capable of binding with an FKBP fusion protein and of forming a complex with an FKBP fusion protein and an FRB fusion protein. Rapalogs of particular interest include compounds, other than rapamycin itself, of the formula:

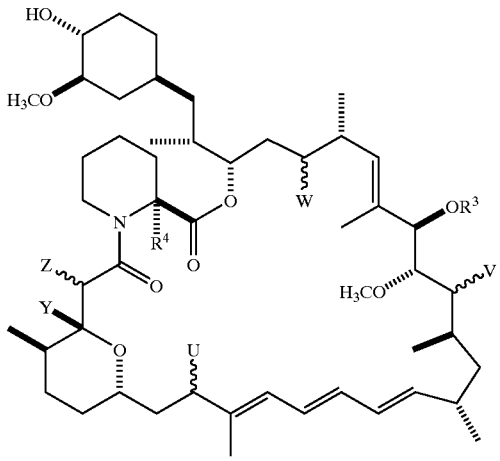

wherein U is —H, —OR¹, —OC(O)R¹, —OC(O)NHR¹, —SR¹, —NHR¹, —NHC(O)R¹, —NH—SO₂—R¹ or —R²; V is —OR³ or (=O); W is =O, =NR⁴=NOR⁴, =NNHR⁴, —NHOR⁴, —NHNHR⁴, —OR⁴, —OC(O)R⁴, —OC(O)NR⁴, or —H; Y is —OR⁵, —OC(O)R⁵ or —OC(O)NHR⁵; Z is =O, —OR⁶, —NR⁶, —H, —NC(O)R⁶, —OC(O)R⁶ or —OC(O)NR⁶; R² is substituted aryl or allyl or alkylaryl (e.g. benzyl or substituted benzyl); R³ is H, —R⁷, —C(O)R⁷, —C(O)NHR⁷ or C-28/C-30 cyclic carbonate; and R¹, R⁴, R⁵, R⁶ and R⁷ are independently selected from H, alkyl, alkylaryl or aryl, including the individual resolved stereoisomers as well as mixtures thereof. Rapalogs of special interest form complexes with proteins comprising naturally occurring human FKBP and FRB domains with measurably lower affinity than with proteins containing corresponding FKBP and FRAP domains in which one or both of the receptor domains contain at least one amino acid replacement, deletion or addition, as described herein.

As mentioned above, the chimeric proteins contain at least one "receptor" or "ligand binding" domain comprising peptide sequence derived from a FRAP or FKBP protein and at least one "action" domain, heterologous with respect to the receptor domain, but capable, upon oligomerization of the chimeric protein molecules, of triggering a cellular or biological response. The action domains of the chimeric proteins may be selected from a broad variety of protein domains capable of effecting a desired biological result upon oligomerization or clustering of the chimeric proteins. For instance, one action domain may comprise a localization domain capable of directing the chimeric protein to a particular cellular location (membrane, nucleus, other organelle, etc.), or a signalling domain, e.g. derived from an intracellular domain of a growth factor receptor or cytokine receptor and capable, upon clustering or multimerization, of initiating an intracellular signal transduction pathway leading to cell growth or proliferation, to the transcription of a desired gene, to cell death or to some other desired result. For example, clustering of chimeric proteins containing an action domain derived from the intracellular portion of the T cell receptor CD3 zeta domain triggers transcription of a gene under the transcriptional control of the IL-2 promoter or derivatives thereof. In other embodiments, the action domain comprises a domain derived from proteins such as the FAS antigen or TNF-alpha receptor (TNFalpha-R1), which are capable, upon oligomerization, of triggering apoptosis of the cell. In still other embodiments, the action domains comprise a DNA-binding domain such as GAL4 and a transcription activation domain such as VP16, paired such that oligomerization of the chimeric proteins represents assembly of a transcription factor complex which triggers transcription of a gene linked to a DNA sequence recognized by (capable of specific binding interaction with) the DNA binding domain.

DNA constructs which encode the expression of these chimeric proteins (and accessory constructs such as DNA constructs encoding target genes) are provided for use in the genetic engineering of the host cells. To produce genetically engineered cells of this invention one introduces into host cells recombinant DNA molecules which comprise the foregoing DNA constructs and are capable of directing the expression of the desired chimeras. Any desired accessory constructs are also introduced. This may be accomplished using conventional methods and materials, various examples of which are commercially available. If desired, the modified cells may then be selected, separated from other cells and cultured, again by conventional methods. Engineered cells of this invention contain and are capable of expressing at least one DNA construct encoding such a chimeric protein. In some embodiments the cells contain and are capable of expressing DNA constructs encoding a pair of chimeric proteins of this invention which are capable of multimerizing in the presence of an appropriate ligand. In still other embodiments, the cells further contain a target gene construct containing a target gene under the expression control of a DNA element-responsive to the multimerized chimeric proteins. The engineered cells may be transiently transfected or stably transformed with one or more of the introduced DNA molecules.

Useful multimerizing ligands include rapamycin and rapalogs which are capable of dimerizing FRB and FKBP domains of this invention. Such compounds are bivalent ligands, i.e., are capable of binding to, and thus multimerizing, two or more of the chimeric protein molecules containing FRAP and FRB domains, respectively.

Many embodiments of this invention involve two recombinant DNA molecules (or at least two recombinant DNA sequences within the same DNA molecule) encoding a pair of different chimeric proteins. The first recombinant DNA molecule encodes a chimeric protein comprising (i) at least one FKBP domain capable of binding to rapamycin or a rapalog and (ii) at least one protein ("action") domain heterologous with respect to at least one of such FKBP domain. Such chimeric proteins, which are referred to simply as "FKBP chimeras", are capable of binding to rapamycin or a rapalog to form a complex, analogous to the complex formed by the binding of naturally occurring FKBP proteins such as FKBP12 to rapamycin. The second recombinant DNA molecule encodes a chimeric protein containing (i) at least one FRB domain capable of binding to the complex formed by the first chimeric protein and rapamycin or a rapalog and (ii) a protein ("action") domain heterologous with respect to at least one of such FRB domain. These chimeric proteins are referred to simply as "FRAP chimeras". Pairs of FKBP chimeras and FRAP chimeras are capable of forming a tripartite complex with rapamycin or a rapalog, as can be detected by a variety of means, including e.g. coimmunoprecipitation. Embodiments involving multiple FKBP and/or FRB domains per chimera are capable of forming higher order multimers in the presence of rapamycin or the rapalog. Some embodiments involve a recombinant DNA molecule encoding a "mixed" chimeric protein containing one or more FKBP domains, one or more FRB domains and one or more action domains heterologous with respect to at least one of the receptor domains. Mixed chimeras are capable of forming protein homodimers or homomultimers via mutual binding of mixed chimeric protein molecules to rapamycin or to a rapalog.

Chimeric proteins containing one or more ligand-binding (i.e., receptor) domains and one or more action domains, e.g. for activation of transcription of a target gene, triggering cell death or other signal transduction pathway, cellular localization, etc., are disclosed in PCT/US94/01617, PCT/US94/08008 and Spencer et al, supra. The design and use of such chimeric proteins for ligand-mediated gene-knock out and for ligand-mediated blockade of gene expression or inhibition of gene product function are disclosed in PCT/US95/10591. Novel DNA binding domains and DNA sequences to which they bind which are useful in embodiments involving regulated transcription of a target gene are disclosed, e.g., in Pomeranz et al, 1995, Science 267:93–96. Those references provide substantial information, guidance and examples relating to the design, construction and use of DNA constructs encoding analogous chimeras, target gene constructs, multivalent ligands, and other aspects which may also be useful to the practitioner of the subject invention. See also PCT/US95/06722 (Mitotix, Inc.). The full contents of the foregoing documents are incorporated herein by reference.

By appropriate choice of chimeric proteins, this invention permits one to activate the transcription of a desired gene, actuate apoptosis, or trigger other biological events in engineered cells in a rapamycin- or rapalog-dependent manner analogous to the systems described in PCT/US94/01617 and PCT/US94/08008 and other references cited above. The engineered cells, preferably animal cells, may be growing or maintained in culture or may be present within whole organisms, as in the case of human gene therapy, transgenic animals, and other such applications. The rapamycin or rapalog multimerizing agent is administered to the cell culture or to the organism containing the engineered cells, as the case may be, in an amount effective to multimerize chimeric proteins containing the corresponding ligand-binding domains (as may be observed indirectly by monitoring target gene transcription, apoptosis or other biological process so triggered). In the case of administration to whole organisms, the rapamycin or rapalog may be administered in a composition containing the multimerizing agent and one or more acceptable verterinary or pharmaceutical diluents and/or excipients.

A compound which binds to one of the chimeric proteins but does not form tripartite complexes with both chimeric proteins may be used as a multimerization antagonist. As such it may be administered to the engineered cells, or to organisms containing them (preferably in a composition as described above in the case of administration to whole animals), in an amount effective for blocking or reversing the effect of the multimerizing agent, i.e. for preventing, inhibiting or disrupting multimerization of the chimeras. For instance, in cases in which rapamycin can serve as the multimerizing agent, FK506, FK520 or any of the many synthetic FKBP ligands which do not form tripartite complexes with FKBP and FRAP may be used as an antagonist.

Figure 1B:
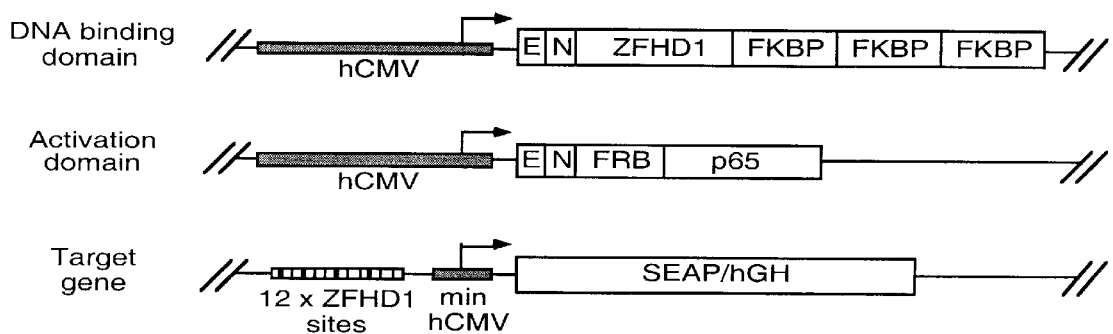

One aspect of this invention provides materials and methods for ligand-dependent, direct activation of transcription of a desired gene. In one such embodiment, a set of two or more different chimeric proteins, and corresponding DNA constructs capable of directing their expression, is provided. One such chimeric protein contains as its action domain(s) one or more transcriptional activation domains. The other chimeric protein contains as its action domain(s) one or more DNA-binding domains (FIG. 1). Rapamycin or a rapalog of this invention is capable of binding to both chimeras to form a dimeric or multimeric complex thus containing at least one DNA binding domain and at least one transcriptional activating domain. Formation of such complexes leads to activation of transcription of a target gene linked to, and under the transcriptional control of, a DNA sequence to which the DNA-binding domain is capable of binding, as can be observed by monitoring directly or indirectly the presence or concentration of the target gene product.

Preferably the DNA binding domain, and a chimera containing it, binds to its recognized DNA sequence with sufficient selectivity so that binding to the selected DNA sequence can be observed (directly or indirectly) despite the presence of other, often numerous other, DNA sequences. Preferably, binding of the chimera comprising the DNA-binding domain to the selected DNA sequence is at least two, more preferably three and even more preferably more than four orders of magnitude greater than binding to any one alternative. DNA sequence, as measured by in vitro binding studies or by measuring relative rates or levels of transcription of genes associated with the selected DNA sequence as compared with any alternative DNA sequences.

Cells which have been genetically engineered to contain such a set of constructs, together with any desired accessory constructs may be, used in applications involving ligand-mediated, regulated actuation of the desired biological event, be it regulated transcription of a desired gene, regulated triggering of a signal transduction pathway such as the triggering of apoptosis, or another event. Cells engineered for regulatable expression of a target gene, for instance, can be used for regulated production of a desired protein (or other gene product) encoded by the target gene. Such cells may be grown in culture by conventional means. Addition of the ligand to the culture medium containing the cells leads to expression of the target gene by the cells and production of the protein encoded by that gene. Expression of the gene and production of the protein can be turned off by withholding further multimerization agent from the media, by removing residual multimerization agent from the media, or by adding to the medium a multimerization antagonist reagent.

Engineered cells of this invention can also be produced and/or used in vivo, to modify whole organisms, preferably animals, especially humans, e.g. such that the cells produce a desired protein or other result within the animal containing them. Such uses include gene therapy applications.

Embodiments involving regulatable actuation of apoptosis provide engineered cells susceptible to ligand-inducible cell death. Such engineered cells can be eliminated from a cell culture or host organism after they have served their intended purposed (e.g. production of a desired protein or other product), if they have or develop unwanted properties, or if they are no longer useful, safe or desired. Elimination is effected by adding the rapamycin or rapalog to the medium or administering it to the host organism. In such cases, the action domains of the chimeras are protein domains such as the intracellular domains of the FAS antigen or TNF-R1 which upon oligomerization trigger apoptosis.

This invention thus provides materials and methods for achieving a biological effect in cells in response to the addition of a multimerizing ligand. The method involves providing cells engineered as described herein and exposing the cells to the ligand.

For example, this invention provides a method for activating transcription of a target gene in cells. The method involves providing cells containing (a) DNA constructs encoding a set of chimeric proteins of this invention capable upon ligand-mediated multimerization of initiating transcription of a target gene and (b) a target gene linked to an associated cognate DNA sequence responsive to the multimerization event (e.g. a DNA sequence recognized, i.e., capable of binding with, a DNA-binding domain of a foregoing chimeric protein. The method involves exposing the cells to a multimerization ligand capable of binding to the chimeric proteins in an amount effective to result in expression of the target gene. In cases in which the cells are growing in culture, exposing the cells to the ligand may be effected by adding the ligand to the culture medium. In cases in which the cells are present within a host organism, exposing them to the ligand is effected by administering the ligand to the host organism. For instance, in cases in which the host organism is a human or non-human, the ligand may be administered to the host organism by oral, bucal, sublingual, transdermal, subcutaneous, intramuscular, intravenous, intra-joint or inhalation administration in an appropriate vehicle therefor. Again, depending on the design of the constructs for the chimeric proteins and of any accessory constructs, the ligand-mediated biological event may be activation of a cellular function such as signal transduction leading to cell growth, cell proliferation, gene transcription, or apoptosis; deletion of a gene of interest, blockade of expression of a gene of interest, or inhibition of function of a gene product of interest; direct transcription of a gene of interest; etc.

This invention further encompasses a pharmaceutical composition comprising rapamycin or a rapalog of this invention in admixture with a pharmaceutically acceptable carrier and optionally with one or more pharmaceutically acceptable excipients. Such pharmaceutical compositions can be used to promote multimerization of chimeras of this invention in engineered cells in whole animals, e.g. in human gene therapy applications to achieve any of the objectives disclosed herein.

Said differently, this invention provides a method for achieving any of those objectives, e.g. activation of transcription of a target gene (typically a heterologous gene for a therapeutic protein), cell growth or proliferation, cell death or some other selected biological event, in an animal, preferably a human patient, in need thereof and containing engineered cells of this invention. That method involves administering to the animal a pharmaceutical composition containing the rapamycin or rapalog by a route of administration and in an amount effective to cause multimerization of the chimeric proteins in at least a portion of the engineered cells. Multimerization may be detected indirectly by detecting the occurrence of target gene expression; cell growth, proliferation or death; or other objective for which the chimeras were designed and the cells genetically engineered.

This invention further encompasses a pharmaceutical composition comprising a multimerization antagonist of this invention in admixture with a pharmaceutically acceptable carrier and optionally with one or more pharmaceutically acceptable excipients for inhibiting or otherwise reducing, in whole or part, the extent of multimerization of chimeric proteins in engineered cells of this invention in a subject, and thus for de-activating the transcription of a target gene, for example, or turning off another biological result of this invention. Thus, the use of the multimerization reagents and of the multimerization antagonist reagents to prepare pharmaceutical compositions and achieve their pharmacologic results is encompassed by this invention.

This invention also offers a method for providing a host organism, preferably an animal, typically a non-human mammal or a human subject, responsive to a multimerization ligand of this invention. The method involves introducing into the organism cells which have been engineered in accordance with this invention, i.e. containing one or more DNA constructs encoding the chimeric proteins, and so forth. The engineered cells may be encapsulated using any of a variety of materials and methods before being introduced into the host organism. Alternatively, one can introduce the DNA constructs of this invention into a host organism, e.g. a mammal, under conditions permitting incorporation of the DNA into one or more cells of the host mammal, e.g. using viral vectors, introduction of DNA by injection or via catheter, etc.

Also provided are kits for producing cells responsive to rapamycin or a rapalog of this invention. One such kit contains one or more DNA constructs encoding and capable of directing the expression of chimeras which, upon ligand-mediated oligomerization, trigger the desired .biological response. The kit may contain a quantity of an oligomerizing ligand (rapamycin or a rapalog) capable of multimerizing the chimeric protein molecules encoded by the DNA construct(s) of the kit, and may contain in addition a quantity of a multimerization antagonist. The kit may further contain a DNA construct encoding a target gene (or cloning site) linked to a cognate DNA sequence which is recognized by the dimerized chimeric proteins permitting transcription of a gene linked to that cognate DNA sequence in the presence of multimerized chimeric protein molecules. The DNA constructs will preferably be associated with one or more selection markers for convenient selection of transfectants, as well as other conventional vector elements useful for replication in prokaryotes, for expression in eukaryotes, and the like. The selection markers may be the same or different for each different DNA construct, permitting the selection of cells which contain each such DNA construct(s).

The accessory construct for introducing into cells a target gene in association with a cognate DNA sequence may contain a cloning site in place of a target gene. A kit constaining such a construct permits the engineering of cells for regulatable expression of a gene to be provided by the practitioner.

Other kits of this invention may contain one or two (or more) DNA constructs for chimeric proteins in which one or more contain a cloning site in place of the transcriptional activator or DNA binding protein, permitting the user to insert whichever such domain s/he wishes. Such a kit may optionally include other elements as described above, e.g. DNA construct for a target gene with or without a cognate DNA sequence for a pre-selected DNA binding domain.

Any of the kits may also contain positive control cells which were stably transformed with constructs of this invention such that they express a reporter gene (for CAT, beta-galactosidase or any conveniently detectable gene product) in response to exposure of the cells to the ligand. Reagents for detecting and/or quantifying the expression of the reporter gene may also be provided.

FKBP Chimeras

The FKBP chimeric protein comprises at least one ligand-binding domain containing all or part of the peptide sequence of an FKBP and at least one heterologous action domain. This chimeric protein must be capable of binding to rapamycin or a rapalog, preferably with a Kd value below about 100 nM, more preferably below about 10 nM and even more preferably below about 1 nM, as measured by direct binding measurement (e.g. fluorescence quenching), competition binding measurement (e.g. versus FK506), inhibition of FKBP enzyme activity (rotamase), or other assay methodology. Typically the chimeric protein will contain one or more protein domains comprising peptide sequence corresponding to that of FKBP12, e.g. as described in International Patent Application PCT/US94/01617. That peptide sequence may be modified to adjust the binding specificity, usually with replacement, insertion or deletion of 10 or fewer, preferably 5 or fewer, amino acid residues. Such modifications are elected in certain embodiments to yield one or both of the following binding profiles: (a) binding of a rapalog to the modified FKBP domain, or chimera containing it, preferably at least one, and more preferably at least two, and even more preferably three or four or more, orders of magnitude better (by any measure) than to FKBP12 or the FKBP endogenous to the host cells to be engineered; and (b) binding of the complex formed by the FKBP chimera with rapamycin or a rapalog to the second chimera (which, as discussed below, contains at least one FRB domain) preferably at least one, and more preferably at least two, and even more preferably at least three, orders of magnitude better (by any measure) than to the FRAP or other FRB-containing protein endogenous to the host cell to be engineered.

The FKBP chimera also contains at least one heterologous action domain, i.e., a protein domain containing non-FKBP peptide sequence. The action domain may be a DNA-binding domain, transcription activation domain, cellular localization domain, intracellular signal transduction domain, e.g. as described elsewhere herein or in PCT/US94/01617 or the other cited references. Generally speaking, the action domain is capable of directing the chimeric protein to a selected cellular location or of initiating a biological effect upon association or aggregation with another action domain, for instance, upon multimerization of proteins containing the same or different action domains.

A recombinant DNA encoding such a protein will be capable of selectively hybridizing to a DNA encoding the parent FKBP protein, e.g. human FKBP12, or would be capable of such hybridization but for the degeneracy of the genetic code. Since these chimeric proteins contain an action domain derived from another protein; e.g. Gal4, VP16, FAS, CD3 zeta chain, etc., the recombinant DNA encoding the chimeric protein will also be capable of selectively hybridizing to a DNA encoding that other protein, or would be capable of such hybridization but for the degeneracy of the genetic code.

FKBP chimeric proteins of this invention, as well as FRAP chimeric proteins discussed in further detail below, may contain one or more copies of one or more different ligand binding domains and one or more copies of one or more action domains. The ligand binding domain(s) may be N-terminal, C-terminal, or interspersed with respect to the action domain(s). Embodiments involving multiple copies of a receptor domain usually have 2, 3 or 4 such copies. For example, an FKBP chimera may contain 2, 3 or 4 FKBP domains. The various domains of the FKBP chimeras (and of the FRAP chimeras discussed below) are optionally separated by linking peptide regions which may be derived from one of the adjacent domains or may be heterologous.

Illustrative examples of FKBP chimeras useful in the practice of this invention include the FKBP fusion proteins disclosed in PCT/US94/01617 (Stanford & Harvard), PCT/US94/08008 (Stanford & Harvard), Spencer et al (supra), PCT/US95/10591 (ARIAD) and PCT/US95/06722 (Mitotix, Inc.); the FKBP fusion proteins disclosed in the examples which follow; variants of any of the foregoing FKBP fusion proteins which contain up to 10 (preferably 1–5) amino acid insertions, deletions or substitutions in one or more of the FKBP domains and which are still capable of binding to rapamycin or to a rapalog; variants of any of the foregoing FKBP fusion proteins which contain one or more copies of an FKBP domain which is encoded by a DNA sequence capable of selectively hybridizing to a DNA sequence encoding a naturally occurring FKBP domain and which are still capable of binding to rapamycin or to a rapalog; variants of any of the foregoing in which one or more heterologous action domains are deleted, replaced or supplemented with a different heterologous action domain; variants of any of the foregoing FKBP fusion proteins which are capable of binding to rapamycin or a rapalog and which contain an FKBP domain derived from a non-human source; and variants of any of the foregoing FKBP fusion proteins which contain one or more amino acid residues corresponding to Tyr26, Phe36, Asp37, Arg42, Phe46, Phe48, Glu54, Val55, or Phe99 of human FKBP12 in which one or more of those amino acid residues is replaced by a different amino acid, the variant being capable of binding to rapamycin or a rapalog.

For instance, in a number of cases the FKBP fusion proteins comprise multiple copies of an FKBP domain containing amino acids 1–107 of human FKBP12, separated by the 2-amino acid linker Thr-Arg encoded by ACTAGA, the ligation product of DNAs digested respectively with the restriction endonucleases SpeI and XbaI. The following table provides illustrative subsets of mutant FKBP domains based on the foregoing FKBP12 sequence:

| Illustrative Mutant FKBPs | | | |
|---|---|---|---|
| F36A | Y26A | F48H | F36V/F99A |
| F36V | Y26V | F48L | F36V/F99G |
| F36M | Y26S | F48A | F36M/F99A |
| F36S | D37A | E54A | F36M/F99G |
| F99A | I90A | E54K | |
| F99G | I91A | V55A | |
| | F46H | W59A | |
| | F46L | H87W | |
| | F46A | H87R | | note:
Entries identify the native amino acid by single letter code and sequence position, followed by the replacement amino acid in the mutant. Thus, F36V designates a human FKBP12 sequence in which phenylalanine at position 36 is replaced by valine. F36V/F99A indicates a double mutation in which phenylalanine at positions 36 and 99 are replaced by valine and alanine, respectively.

FRAP Chimeric Protein

The second type of chimeric protein, referred to as the "FRAP chimeric protein", comprises at least one FRB domain (which may comprise all or part of the peptide sequence of a FRAP protein or a variant thereof, as described elsewhere) and at least one heterologous protein ("action") domain.

Generally speaking, the FRB domain, or a chimeric protein encompassing it, is encoded by a DNA molecule capable of hybridizing selectively to a DNA molecule encoding a protein comprising a naturally occurring FRB domain, e.g. a DNA molecule encoding a human or other mammalian FRAP protein or one of yeast proteins, Tor-1 or Tor-2 or the previously mentioned Candida FRB-containing protein. FRB domains of this invention include those which are capable of binding to a complex of an FKBP protein and rapamycin or a rapalog. As disclosed in greater detail herein, rapalogs include compounds of the formula

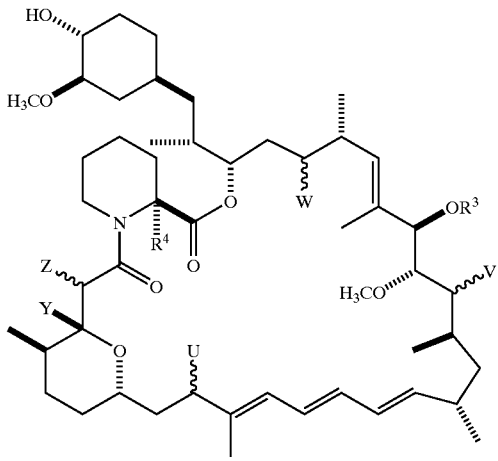

wherein U is —H or —OR$^1$, —OC(O)R$^1$ or OC(O)NHR$^1$, —SR$^1$, —NHR$^1$, —NHC(O)R$^1$, —NH—SO$_2$—R$^1$ or —R$^2$, where R$^2$=substituted aryl or allyl or alkylaryl (e.g. benzyl or substituted benzyl); V is —OR$^3$ or (=O); W is =O, =NR$^4$=NOR$^4$ or =NNHR$^4$, —NHOR$^4$ or —NHNHR$^4$, OR$^4$, —OC(O)R$^4$ or OC(O)NR$^4$, or —H; Y is —OR$^5$, —OC(O)R$^5$ or —OC(O)NHR$^5$; Z is =O, —OR$^6$, —NR$^6$, —H, —NC(O)R$^6$, or —OC(O)R$^6$ or —OC(O)NR$^6$; wherein, R$^3$ is H, —R$^7$, —C(O)R$^7$ or —C(O)NHR$^7$ or C-28/C-30 cyclic carbonate, R$^4$ is H or alkyl, and R$^1$, R$^4$, R$^5$, R$^6$ and R$^7$ are independently selected from H, alkyl, alkylaryl or aryl.

The FRAP chimeric protein must be capable of binding to the complex formed by the FKBP chimera with rapamycin or a rapalog. Preferably, the FRAP chimera binds to that complex with a Kd value below 200 μM, more preferably below 10 μM, as measured by conventional methods. The FRB domain will be of sufficient length and composition to maintain high affinity for a complex of rapamycin or a rapalog with the FKBP chimera. In some embodiments the FRB domain spans fewer than about 150 amino acids in length, and in some cases fewer than about 100 amino acids. One such region comprises a 133 amino acid region of human FRAP extending from Val$^{2012}$ through Tyr$^{2144}$. See Chiu et al, 1994, Proc. Natl. Acad. Sci. USA 91:12574–12578. An FRB region of particular interest spans Glu$^{2025}$ through Gln$^{2114}$ of human FRAP and retains affinity for FKBP12-rapamycin. In some embodiments Q2214 is removed from the 90-amino acid sequence rendering this an 89-amino acid FRB domain. The FRB peptide sequence may be modified to adjust the binding specificity, usually with replacement, insertion or deletion, of 10 or fewer, preferably 5 or fewer, amino acids. Such modifications are elected in certain embodiments to achieve a preference towards formation of the complex comprising one or more molecules of the FKBP chimera, FRAP chimera and rapamycin or a rapalog over formation of complexes of endogenous FKBP and FRAP proteins with the rapamycin/rapalog. Preferably that preference is at least one, and more preferably at least two, and even more preferably three, orders of magnitude (by any measure).

A recombinant DNA encoding such a protein will be capable of selectively hybridizing to a DNA encoding a FRAP species, or would be capable of such hybridization but for the degeneracy of the genetic code. Again, since these chimeric proteins contain an action domain derived from another protein, e.g. Gal4, VP16, Fas, CD3 zeta chain, etc., the recombinant DNA encoding the chimeric protein will be capable of selectively hybridizing to a DNA encoding that other protein, or would be capable of such hybridization but for the degeneracy of the genetic code.

Illustrative examples of FRB chimeras useful in the practice of this invention include those disclosed in the examples which follow, variants thereof in which one or more of the heterologous domains are replaced with alternative heterologous domains or supplemented with one or more additional heterologous domains, variants in which one or more of the FRB domains is a domain of non-human peptide sequence origin (such as Tor 2 or Candida for example), and variants in which the FRB domain is modified by amino acid substitution, replacement or insertion as described herein, so long as the chimera is capable of binding to a complex formed by an FKBP protein and rapamycin or a rapalog. An illustrative FRB fusion protein contains one or more 89-amino acid FRBs containing residues 2025–2113 of human FRAP, separated by the linker Thr-Arg formed by ligation of SpeI-XbaI sites as mentioned previously. It should be appreciated that such restriction sites or linkers in any of the fusion proteins of this invention may be deleted, replaced or extended using conventional techniques such as site-directed mutagenesis.

Mixed Chimeric Proteins

A third type of chimeric protein comprises one or more FKBP-derived ligand-binding (i.e., "receptor") domains and one or more heterologous action domains, but further contains one or more FRB domains as described for the FRAP chimeras.

Mixed chimeric protein molecules are capable of forming homodimeric or homomultimeric protein complexes in the presence of rapamycin or a rapalog to which they bind. Embodiments involving mixed chimeras have the advantage of requiring the introduction into cells of a single recombinant DNA construct in place of two recombinant DNA constructs otherwise required to direct the expression of both an FKBP chimera and a FRAP chimera.

A recombinant DNA encoding a mixed chimeric protein will be capable of selectively hybridizing to a DNA encoding an FKBP protein, a DNA encoding FRAP, and a heterologous DNA sequence encoding the protein from which one or more action domains is derived (e.g. Gal4, VP16, Fas, CD3 zeta chain, etc.), or would be capable of such hybridization but for the degeneracy of the genetic code.

Heterologous Domains

As mentioned above, the heterologous action domains of the FKBP and FRAP chimeras are protein domains which, upon mutual association of the chimeric proteins bearing them, are capable of triggering (or inhibiting) DNA-binding and/or transcription of a target gene; actuating cell growth, differentiation, proliferation or apoptosis; directing proteins to a particular cellular location; or actuating other biological events.

Embodiments involving regulatable gene transcription involve the use of target gene constructs which comprise a target gene (which encodes a polypeptide, antisense RNA, ribozyme, etc. of interest) under the transcriptional control of a DNA element responsive to the association or multimerization of the heterologous domains of the 1st and 2d chimeric proteins.

In embodiments of the invention involving direct activation of transcription, the heterologous domains of the 1st and 2d chimeric proteins comprise a DNA binding domain such as Gal4 or a chimeric DNA binding domain such as ZFHD1, discussed below, and a transcriptional activating domain such as those derived from VP16 or p65, respectively. The multimerization of a chimeric protein containing such a transcriptional activating domain to a chimeric protein containing a DNA binding domain targets the transcriptional activator to the promoter element to which the DNA binding domain binds, and thus activates the transcription of a target gene linked to that promoter element. Foregoing the transcription activation domain or substituting a repressor domain (see PCT/US94/01617) in place of a transcription activation domain provides an analogous chimera useful for inhibiting transcription of a target gene. Composite DNA binding domains and DNA sequences to which they bind are disclosed in Pomerantz et al, 1995, supra, the contents of which are incorporated herein by reference. Such composite DNA binding domains may be used as DNA binding domains in the practice of this invention, together with a target gene construct containing the cognate DNA sequences to which the composite DBD binds.

In embodiments involving indirect activation of transcription, the heterologous domains of the chimeras are effector domains of signaling proteins which upon aggregation or multimerization trigger the activation of transcription under the control of a responsive promoter. For example, the signaling domain may be the intracellular domain of the zeta subunit of the T cell receptor, which upon aggregation, triggers transcription of a gene linked to the IL-2 promoter or a derivative thereof (e.g. iterated NF-AT binding sites).

In another aspect of the invention, the heterologous domains are protein domains which upon mutual association are capable of triggering cell death. Examples of such domains are the intracellular domains of the Fas antigen or of the TNF R1. Chimeric proteins containing a Fas domain can be designed and prepared by analogy to the disclosure of PCT/US94/01617.

Engineered Receptor Domains

Figures 2A, 2B, 2C:
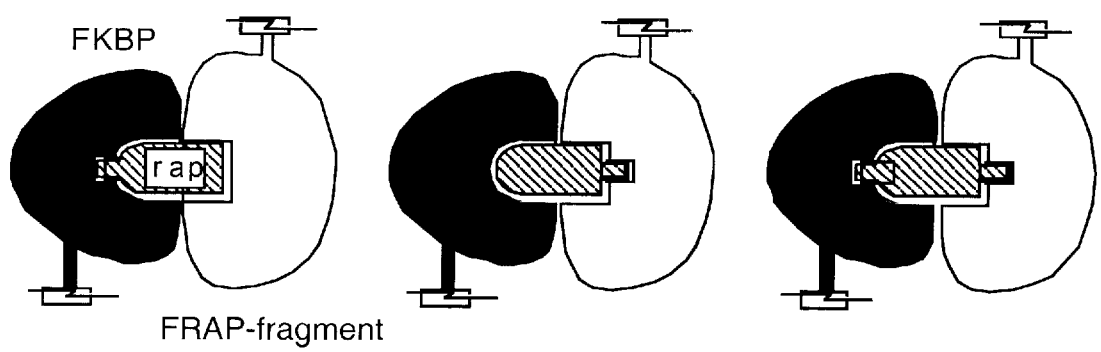
FIG. 2. (A–E) All panels depict various FRAP-derived and FKBP-derived domains of fusion proteins of the invention in schematic form, together with rapamycin and rapamycin analogs. Exemplary ligands with bumps and proteins with compensatory mutations are shown.
Figures 2D, 2E:
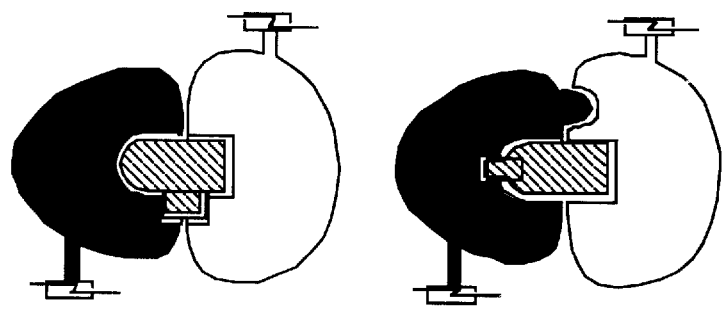

As noted previously, the FKBP and FRB domains may contain peptide sequence selected from the peptide sequences of naturally occurring FKBP and FRB domains. Naturally occurring sequences include those of human FKBP12 and the FRB domain of human FRAP. Alternatively, the peptide sequences may be derived from such naturally occurring peptide sequences but contain generally up to 10, and preferably 1–5, mutations in one or both such peptide sequences. As disclosed in greater detail herein, and as illustrated in FIG. 2, such mutations can confer a number of important features. For instance, an FKBP domain may be modified such that it is capable of binding a rapalog preferentially, i.e. at least one, preferably two, and even more preferably three or four or more orders of magnitude more effectively, with respect to the unmodified FKBP domain. An FRB domain may be modified such that it is capable of binding a (modified or unmodified) FKBP:rapalog complex preferentially, i.e. at least one, preferably two, and even more preferably three orders of magnitude more effectively, Wraith respect to the unmodified FRB domain. FKBP and FRB domains may be modified such that they are capable of forming a tripartite complex with a rapalog, or with rapamycin, preferentially, i.e. at least one, preferably two, and even more.preferably three orders of magnitude more effectively, with respect to unmodified FKBP and FRB domains. FIGS. 2A–E are presented for the purposes of illustration only; other related combinations of variously modified rapalogs and receptor domains bearing compensatory mutations are also encompassed by this invention and may be adapted to various applications.

(a) FKBP

Methods for identifying FKBP mutations that confer enhanced ability to bind derivatives of FK506 containing various substituents ("bumps") were disclosed in PCT/US94/01617. Similar strategies can be used to obtain modified FKBPs that preferentially bind bumped rapamycin derivatives, i.e., rapalogs. The structure of the complex between rapamycin and FKBP12 is known (see for example Van Duyne et al., J. Am. Chem. Soc. (1991) 113, 7433–7434). Such data can be used to reveal amino acid residues that would dash with various rapalog substituents. In this approach, molecular modelling is used to identify candidate amino acid substitutions in the FKBP domain that would accommodate the rapalog substituent(s), and site-directed mutagenesis may then be used to engineer the protein mutations so identified. The mutants are expressed by standard methods and their binding affinity for the rapalogs measured, for example by inhibition of rotamase activity, or by competition for binding with a molecule such as FK506, if the mutant retains appropriate activity/affinity.

More particularly, we contemplate that rapamycin derivatives with modifications at C-13 or C-14 (i.e., rapalogs in which Y is a substituent other than —OH and/or Z is other than =O) bind preferentially to FKBPs in which one or more of the residues, Tyr26, Phe36, Asp37, Tyr82 and Phe99, are substituted with amino acids that have smaller side chains (such as Gly, Ala, Val, Met and Ser). Examples of mutant FKBPs with modifications at positions 26 or 36 are noted in the "Illustrative Mutant FKBPs" table above. Similarly, we contemplate that rapalogs with modifications at C20 (i.e., rapalogs in which $R^4$ is other than —H) bind preferentially to FKBPs in which Tyr82 and/or Ile56 are replaced by other amino acids, especially those with smaller side chains. In a further example, we contemplate that rapalogs bearing modifications at C24 (i.e., in which W is other than =O) bind preferentially to FKBPs in which one or more of Phe46, Phe48 and Val55 are replaced by other amino acids, again especially those with smaller side chains. Moreover, we envisage that rapalogs with modifications at C28 and/or C30 (i.e., in which $R^3$ is other than H and/or V is other than =O) bind preferentially to FKBPs in which Glu54 is replaced by another amino acid, especially one with a smaller side chain. In all of the above examples, single or multiple amino acid substitutions may be made. Again, specific examples are noted in the previous table.

An alternative to iterative engineering and testing of single or multiple mutants is to co-randomize structurally-identified residues that are or would be in contact with or near one or more rapalog or rapamycin substituents. A collection of polypeptides containing FKBP domains randomized at the identified positions (such as are noted in the foregoing paragraph) is prepared e.g. using conventional synthetic or genetic methods. Such a collection represents a set of FKBP domains containing replacement amino acids at one or more of such positions. The collection is screened and FKBP variants are selected which possess the desired rapalog binding properties. In general, randomizing several residues simultaneously is expected to yield compensating mutants of higher affinity and specificity for a given bumped rapalog as it maximizes the likelihood of beneficial cooperative interactions between side chains. Techniques for preparing libraries randomized at discrete positions are known and include primer-directed mutagenesis using degenerate oligonucleotides, PCR with degenerate oligonucleotides, and cassette mutagenesis with degenerate oligonucleotides (see for example Lowman, H. B, and Wells, J. A. *Methods: Comp. Methods Enzymol.* 1991. 3, 205–216; Dennis, M. S. and Lazarus, R. A. 1994. J. Biol. Chem. 269, 22129–22136; and references therein).

We further contemplate that in many cases, randomization of only the few residues in or near direct contact with a given position in rapamycin may not completely explore all the possible variations in FKBP confirmation that could optimally accommodate a rapalog substituent (bump). Thus the construction is also envisaged of unbiased libraries containing random substitutions that are not based on structural considerations, to identify subtle mutations or combinations thereof that confer preferential binding to bumped rapalogs. Several suitable mutagenesis schemes have been described, including alanine-scanning mutagenesis (Cunningham and Wells (1989) Science 244, 1081–1085), PCR misincorporation mutagenesis (see e.g. Cadwell and Joyce,1992, PCR Meth. Applic. 2, 28–33), and 'DNA shuffling' (Stemmer, 1994, Nature 370, 389–391 and Crameri et al, 1996, Nature Medicine 2, 100–103). These techniques produce libraries of random mutants, or sets of single mutants, that are then searched by screening or selection approaches.

In many cases, an effective strategy to identify the best mutants for preferential binding of a given bump is a combination of structure-based and unbiased approaches. See Clackson and Wells, 1994, Trends Biotechnology 12, 173–184 (review). For example we contemplate the construction of libraries in which key contact residues are randomized by PCR with degenerate oligonucleotides, but with amplification performed using error-promoting conditions to introduce further mutations at random sites. A further example is the combination of component DNA fragments from structure-based and unbiased random libraries using DNA shuffling.

Screening of libraries for desirable mutations may be performed by use of a yeast 2-hybrid system (Fields and Song (1989) Nature 340, 245–246). For example, an FRB-VP16 fusion may be introduced into one vector, and a library of randomized FKBP sequences cloned into a separate GAL4 fusion vector. Yeast co-transformants are treated with bumped rapamycin (i.e., rapalog), and those harboring complementary FKBP mutants are identified by for example beta-galactosidase or luciferase production (a screen), or survival on plates lacking an essential nutrient (a selection), as appropriate for the vectors used. The requirement for bumped rapamycin to bridge the FKBP-FRAP interaction is a useful screen to eliminate false positives.

A further strategy for isolating modified ligand-binding domains from libraries of FKBP (or FRB) mutants utilizes a genetic selection for functional dimer formation described by Hu et. al. (Hu, J. C., et al. 1990. Science. 250:1400–1403; for review see Hu, J. C. 1995. Structure. 3:431–433). This strategy utilizes the fact that the bacteriophage lambda repressor cI binds to DNA as a homodimer and that binding of such homodimers to operator DNA prevents transcription of phage genes involved in the lytic pathway of the phage life cycle. Thus, bacterial cells expressing functional lambda repressor are immune to lysis by superinfecting phage lambda. Repressor protein comprises an amino terminal DNA binding domain (amino acids 1–92), joined by a 40 amino add flexible linker to a carboxy terminal dimerization domain. The isolated N-terminal domain binds to DNA with low affinity due to inefficient dimer formation. High affinity DNA binding can be restored with heterologous dimerization domains such as the GCN4 "leucine zipper". Hu et al have described a system in which phage immunity is used as a genetic selection to isolate GCN4 leucine zipper mutants capable of mediating lambda repressor dimer formation from a large population of sequences (Hu et al., 1990).

For example, to use the lambda repressor system to identify FRAP mutants complementary to bumped rapalogs, lambda repressor-FRAP libraries bearing mutant FRAP sequences are transformed into E. coli cells expressing wildtype lambda repressor-FKBP protein. Plasmids expressing FRAP mutants are isolated from those colonies that survive lysis on bacterial plates containing high titres of lambda phage and "bumped" rapamycin compounds. Alternatively, to isolate FKBP mutants, the above strategy is repeated with lambda repressor-FKBP libraries bearing mutant FKBP sequences transformed into E. coli cells expressing wildtype lambda repressor-FRAP protein.

A further alternative is to done the randomized FKBP sequences into a vector for phage display, allowing in vitro selection of the variants that bind best to the rapalog. Affinity selection in vitro may be performed in a number of ways. For example, rapalog is mixed with the library phage pool in solution in the presence of recombinant FRAP tagged with an affinity handle (for example a hexa-histidine tag, or GST), and the resultant complexes are captured on the appropriate affinity matrix to enrich for phage displaying FKBP harboring complementary mutations. Techniques for phage display have been described, and other in vitro selection selection systems can also be contemplated (for example display on lambda phage, display on plasmids, display on baculovirus). Furthermore, selection and screening strategies can also be used to improve other properties of benefit in the application of this invention, such as enhanced stability in vivo. For a review see Clackson, T. and Wells, J. A. 1994. Trends Biotechnol. 12, 173–184.

(b) FRAP

Similar considerations apply to the generation of mutant FRB domains which bind preferentially to rapalogs containing modifications (i.e., are 'bumped') relative to rapamycin in the FRAP-binding effector domain. For example, one may obtain preferential binding using rapalogs bearing substituents other than —OMe at the C7 position with FRBs based on the human FRAP FRB peptide sequence but bearing amino acid substitutions for one of more of the residues Tyr2038, Phe2039, Thr2098, Gln2099, Trp2101 and Asp2102. Exemplary mutations include Y2038H, Y2038L, Y2038V, Y2038A, F2039H, F2039L, F2039A, F2039V, D2102A, T2098A, T2098N, and T2098S. Rapalogs bearing substituents other than —OH at C28 and/or substituents other than =O at C30 may be used to obtain preferential binding to FRAP proteins bearing an amino acid substitution for Glu2032. Examplary mutations include E2032A and E2032S. Proteins comprising an FRB containing one or more amino acid replacements at the foregoing positions, libraries of proteins or peptides randomized at those positions (i.e., containing various substituted amino acids at those residues), libraries randomizing the entire protein domain, or combinations of these sets of mutants are made using the procedures described above to identify mutant FRAPs that bind preferentially to bumped rapalogs.

The affinity of candidate mutant FRBs for the complex of an FKBP protein complexed with a rapalog may be assayed by a number of techniques; for example binding of in vitro translated FRB mutants to GST-FKBP in the presence of drug (Chen et al. 1995. Proc. Natl. Acad. Sci. USA 92, 4947–4951); or ability to participate in a rapalog-dependent transcriptionally active complex with an appropriate FKBP fusion protein in a yeast two-hybrid assay.

FRB mutants with desired binding properties may be isolated from libraries displayed on phage using a variety of sorting strategies. For example, a rapalog is mixed with the library phage pool in solution in the presence of recombinant FKBP tagged with an affinity handle (for example a hexa-histidine tag, or GST), and the resultant complexes are captured on the appropriate affinity matrix to enrich for phage displaying FRAP harboring complementary mutations.

An additional feature of the FRB fusion protein that may vary in the various embodiments of this invention is the exact sequence of the FRB domain used. In some applications it may be preferred to use portions of an FRB which are larger than the minimal (89 amino acid) FRB domain. These include extensions N-terminal to residue Glu2025 (preferably extending to at least Arg2018 or Ile2021), as well as C-terminal extensions beyond position 2113, e.g. to position 2113, 2141 or 2174 or beyond), which may in some cases improve the stability of the folded FRB domain and/or the efficiency of expression. Other applications in which different FRB sequence termini may be used include those in which a long linker is desired for steric reasons on one or both sides of the FRB domain, for example to accommodate the distortions of the polypeptide chain required for FRB-mediated protein-protein association at the cell membrane or on DNA. Conversely, in other applications short linkers on one or both sides of the FRB domain may be preferred or required to present the heterologous action domain(s) appropriately for biological function In human gene therapy applications the use of naturally occurring human FRAP sequence for such linkers will generally be preferred to the introduction of heterologous sequences, or reduce the risk of provoking an immune response in the host organism.

Some rapalogs, especially rapalogs with modifications or substituents (relative to rapamycin) at positions believed to lie near the boundary between the FKBP binding domain and the FRAP binding domain, such as those on C28, C30, C7 and C24, possess reduced ability, relative to rapamycin, to form complexes with both mammalian FKBP and FRB domains, in particular, with those domains containing naturally occurring human peptide sequence. That reduced ability may be manifested as a reduced binding affinity as determined by any of the direct or indirect assay means mentioned herein or as reduced immunosuppressive activity as determined in an appropriate assay such as a T cell proliferation assay. In such cases, iterative procedures may be used to identify pairs of mutant FKBPs and mutant FRBs that are capable of complexing with the rapalog more effectively than the corresponding domains containing naturally occurring human peptide sequence. For example, one may first identify a complementary modified FKBP domain capable of binding to the rapalog, as discussed previously, and then using this mutant FKBP domain as an affinity matrix in complex with the rapalog, one may select a complementary modified FRB domain capable of associating with that complex. Several cycles of such mutagenesis and screening may be performed to optimize the protein pair.

For some embodiments, it will be desirable to use FRB and/or FKBP domains containing mutations that can affect the protein-protein interaction (see e.g. FIG. 2E). For instance, mutant FKBP domains which when bound to rapamycin or to a given rapalog are capable of complexing with an endogenous FRB measurably less effectively than to a mutant FRB are of particular interest. Also of interest are mutant FRB domains which are capable of associating with a complex of a mutant FKBP with rapamycin or a given rapalog measurable more effectively than with a complex of an endogenous FKBP with rapamycin. Similar selection and screening approaches to those delineated previously can be used (i) to identify amino acid substitutions, deletions or insertions to an FKBP domain which measurably diminish the domain's ability to form the tripartite complex with rapamycin or rapalog and the endogenous FRB; (ii) to identify amino acid substitutions, deletions or insertions. to an FRB domain which measurably diminish the domain's ability to form the tripartite complex with rapamycin or rapalog and the endogenous FKBP; and (iii) to select and/or otherwise identify compensating mutation(s) in the partner protein. As examples of suitable mutant FKBPs with diminished effectiveness in tripartite complex formation, we include mammalian, preferably human FKBP in which one or both of His87 and Ile90 are replaced with amino adds such as Arg, Trp, Phe, Tyr or Lys which contain bulky side chain groups; FRB domains, preferably containing mammalian, and more preferably of human, peptide sequence may then be mutated as described above to generate complementary variants which are capable of forming a tripartite complex with the mutant FKBP and rapamycin or a given rapalog. Illustrative FRB mutations which may be useful with H87W or H87R hFKBP12s include human FRBs in which Y2038 is replaced by V, S, A or L; F2039 is replaced by A; and/or R2042 is replaced by L, A or S. Illustrative FRB mutations which may be useful with I90W or I90R hFKBP12s include human FRBs in which K2095 is replaced with L, S, A or T.

Additionally, in optimizing the receptor domains of this invention, it should be appreciated that immunogenicity of a polypeptide sequence is thought to require the binding of peptides by MHC proteins and the recognition of the presented peptides as foreign by endogenous T-cell receptors. It may be preferable, at least in human gene therapy applications, to tailor a given foreign peptide sequence, including junction peptide sequences, to minimize the probability of its being immunologically presented in humans. For example, peptide binding to human MHC class I molecules has strict requirements for certain residues at key 'anchor' positions in the bound peptide: e.g. HLA-A2 requires leucine, methionine or isoleucine at position 2 and leucine or valine at the C-terminus (for review see Stern and Wiley (1994) Structure 2, 145–251). Thus in engineering proteins in the practice of this invention, this periodicity of these residues is preferably avoided, especially in human gene therapy applications. The foregoing applies to all protein engineering aspects of the invention, including without limitation the engineering of point mutations into receptor domains, and to the choice or design of boundaries between the various protein domains.

Other Components, Design Features and Applications

The chimeric proteins may contain as a heterologous domain a cellular localization domain such as a membrane retention domain. See e.g. PCT/US94/01617, especially pages 26–27. Briefly, a membrane retention domain can be isolated from any convenient membrane-bound protein, whether endogenous to the host cell or not. The membrane retention domain may be a transmembrane retention domain, i.e., an amino acid sequence which extends across the membrane as in the case of cell surface proteins, including many receptors. The transmembrane peptide sequence may be extended to span part or all of an extracellular and/or intracellular domain as well. Alternatively, the membrane retention domain may be a lipid membrane retention domain such as a myristoylation or palmitoylation site which permits association with the lipids of the cell surface membrane. Lipid membrane retention domains will usually be added at the 5' end of the coding sequence for N-terminal binding to the membrane, and, proximal to the 3'end for C-terminal binding. Peptide sequences involving post-translational processing to provide for lipid membrane binding are described by Carr, et al., *PNAS USA* (1988) 79, 6128; Aitken, et al., *FEBS Lett.* (1982) 150, 314; Henderson, et al., *PNAS USA* (1983) 80, 319; Schulz, et al., *Virology* (1984), 123, 2131; Dellman, et al., *Nature* (1985) 314, 374; and reviewed in *Ann. Rev. of Biochem.* (1988) 57, 69. An amino acid sequence of interest includes the sequence M-G-S-S-K-S-K-P-K-D-P-S-Q-R [SEQ ID NO: 1]. Various DNA sequences can be used to encode such sequences in the various chimeric proteins of this invention. Other localization domains include organelle-targeting domains and sequences such as -K-D-E-L [SEQ ID NO: 2] and -H-D-E-L [SEQ ID NO: 3] which target proteins bearing them to the endoplasmic reticulum, as well as nuclear localization sequences which are particularly useful for chimeric proteins designed for (direct) transcriptional regulation. Various cellular localization sequences and signals are well known in the art.

Further details which may be used in the practice of the subject invention relating to the design, assembly and use of constructs encoding chimeric proteins containing various action domains including cytoplasmic'signal initiation domains such as the CD3 zeta chain, nuclear transcription factor domains including among others VP16 and GAL4, domains capable of triggering apoptosis including the Fas cytoplasmic domain and others are disclosed in PCT/US94/01617 and PCT/US95/10591. The latter international application further disdoses additional features particularly applicable to the creation of genetically engineered animals which may be used as disease models in biopharmaceutical research. Those features include the use of tissue specific regulatory elements in the constructs for expression of the chimeric proteins and the application of regulated transcription to the expression of Cre recombinase as the target gene leading to the elimination of a gene of interest flanked by loxP sequences. Those features may be adapted to the subject invention.

In various cases, especially in embodiments involving whole animals containing cells engineered in accordance with this invention, it will often be preferred, and in some cases required, that the various domains of the chimeric proteins be derived from proteins of the same species as the host cell. Thus, for genetic engineering of human cells, it is often preferred that the heterologous domains (as well as the FKBP and FRB domains) be of human origin, rather than of bacterial, yeast or other non-human source.

We also note that epitope tags may also be incorporated into chimeric proteins of this invention to permit convenient detection.

Tissue-specific of Cell-type Specific Expression

It will be preferred in certain embodiments, that the chimeric proteins be expressed in a cell-specific or tissue-specific manner. Such specificity of expression may be achieved by operably liking one ore more of the DNA sequences encoding the chimeric protein(s) to a cell-type specific transcriptional regulatory sequence (e.g. promoter/enhancer). Numerous cell-type specific transcriptional regulatory sequences are known. Others may be obtained from genes which are expressed in a cell-specific manner. See e.g. PCT/US95/10591, especially pp. 36–37.

For example, constructs for expressing the chimeric proteins may contain regulatory sequences derived from known genes for specific expression in selected tissues. Representative examples are tabulated below:

| Tissue | Gene | Reference |
|---|---|---|
| lens | γ2-crystallin | Breitman, M.L, Clapoff, S., Rossant, J., Tsui, L. C., Golde, L. M., Maxwell, I. H., Bemstin, A. (1987) Genetic Ablation: targeted expression of a toxin gene causes microphthalmia in transgenic mice. Science 238: 1563–1565 |
| | αA-crystallin | Landel, C. P., Zhao, J., Bok, D., Evans, G. A. (1988) Lens-specific expression of a recombinant ricin induces developmental defects in the eyes of transgenic mice. Genes Dev. 2: 1168–1178 |
| | | Kaur, S., key, B., Stock, J., McNeish, J. D., Akeson, R., Potter, S. S. (1989) Targeted ablation of alpha-crystallin synthesizing cells produces lens-deficient eyes in transgenic-mice. Development 105: 613–619 |
| pituitary somatrophic cells | Growth hormone | Behringer, R. R., Mathews, L. S., Paimiter, R. D., Brinster, R. L. (1988) Dwarf mice produce: by genetic ablation of growth hormone-expressing cells. Genes Dev. 2: 453–461 |
| pancreas | Insulin- Elastase - acinar cell specific | Omitz, D. M., Palmiter, R. D., Hammer, R. E., Brinster, R. L., Swift, G. H., MacDonald, R. J. (1985) Specific expression of an elastastic human growth fusion in pancreatic acinar cells of transgeneic mice. Nature 131: 600–603 |
| | | Palmiter, R. D., Behringer, R. R., Quaife, C. J., Maxwell, F., Maxwell, I. H., Brinster, R. L. (1987) Cell lineage ablation in transgeneic mice by cell-specific expression of a toxin gene. Cell 50: 435–443 |
| T cells | lck promoter | Chaffin, K. E., Beais, C. R., Willde, T. M., Forbush, K. A., Simon, M. L., Perlmuller, R. M. (1990) PMBO journal 9: 3821–3829 |
| B cells | Immunoglobin kappa light chain | Borelli, E., Heyrnan, R., Hsi, M., Evans, R. M. (1988) Targeting of an indudble toxic phenotype in animal cells. Proc. Natl. Acad. sci. USA 85: 7572–7576 |
| | | Heyman, R. A., Borrelli, E., Lesley, J., Anderson, D., Richmond, D. .D., Baird, S. M., Hyrnan, R., Evans, R. M. (1989) Thymidine kinase obliteration: creation of transgenic mice with controlled immunodeficiencies. Proc. NatlI. Acad. Sci. USA 86: 2698–2702 |
| Schwann cells | $P_0$ promoter | Messing, A., Behringer, R. R., Hammang, J. P. Palmiter, R. D., Brinster, R.L., Lemke, G., $P_0$ promoter directs espression of reporter and toxin genes to Schwann cells of transgenic mice. Neuron 8: 507–520 1992 |
| | Myelin basic protein | Miskimins, R. Knapp, L., Dewey, M. J., Thang, X. Cell and tissue-specific expression of a heterologous gene under control |

-continued

| Tissue | Gene | Reference |
|---|---|---|
| | | of the myelin basic protein gene promoter in transgenic mice. Brain Res Dev Brain Res 1992 Vol 65: 217–21 |
| spermatids | protamine | Breitrnan, M. L., Rombola, H., Maxwell, L. H., Klintworth, G. K., Bernstein, A. (1990) Genetic ablation in transgenic mice with attenuated diphtheria toxin A gene. Mol. Cell. Biol. 10: 474–479 |
| lung | Lung surfacant gene | Omitz, D. M., Palmiter, R. D., Hammer, R. E., Brinster, R. L., Swift, G. H., MacDonald, R. J. (1985). Specific expression of an elastase-hunan growth fusion in pancreatic acinar cells of transgeneic mice. Nature 131: 600–603 |
| adipocyte $P_2$ | | Ross, S. R., Braves, R. A., Spiegelman, BM Targeted expression of a toxin gene to adipose tissue: transgenic mice resistant to obesity Genes and Dev 7: 1318–24 1993 |
| muscle | myosin light chain | Lee, K. J., Ross, R. S., Rockman, H. A., Harris, A. N., O'Brien, TX, van-Biken, M., Shubeita, HE, Kandoli, R., Brem, G., Prices et alJ. BIoI. Chem. 1992 Aug 5, 267: 15875–85 |
| | Alpha actin | Muscat, G. E., Perry, S., Prentice, H. Kedes, L. The human skeletal alpha-actin gene is regulated. by a muscle specific enhancer that binds theee nuclear factors. Gene Expression 2, 111–26, 1992 |
| neurons | neurofilament proteins | Reeben, M. Halmekyto, M. Alhonen, L. Sinervirta, R. Saarma, M. Janne, J. Tissue specific expression of rat light neurofilament promoter-driven reporter gene in transgerric mice. BBRC 1993: 192: 465–70 |
| liver | tyrosine aminotransferase, albumin, apolipoproteins | |

Target Gene Constructs

In embodiments of the invention in which the chimeric proteins are designed such that their multimerization activates transcription of a target gene, an appropriate target gene construct is also used in the engineered cells. Appropriate target gene constructs are those containing a target gene and a cognate transcriptional control element such as a promoter and/or enhancer which is responsive to the multimerization of the chimeric proteins. In embodiments involving direct activation of transcription, that responsiveness may be achieved by the presence in the target gene construct of one or more DNA sequences recognized by the DNA-binding domain of a chimeric protein of this invention (i.e., a DNA sequence to which the chimeric protein binds). In embodiments involving indirect activation of transcription, responsiveness may be achieved by the presence in the target gene construct of a promoter and/or enhancer sequence which is activated by an intracellular signal generated by multimerization of the chimeric proteins. For example, where the chimeric proteins contain the TCR zeta chain intracellular domain, the target gene is linked to and under the expression control of the IL-2 promoter region.

This invention also provides target DNA constructs containing (a) a cognate DNA sequence, e.g. to which a DNA-binding chimeric protein of this invention is capable of binding (or which is susceptible to indirect activation as discussed above), and (b) flanking DNA sequence from the locus of a desired target gene endogenous to the host cells. These constructs permit homologous recombination of the cognate DNA sequence into a host cell in association with an endogenous target gene. In other embodiments the construct contains a desired gene and flanking DNA sequence from a target locus permitting the homologous recombination of the target gene into the desired locus. Such a target construct may also contain the cognate DNA sequence, or the cognate DNA sequence may be provided by the locus.

The target gene in any of the foregoing embodiments may encode for example a surface membrane protein (such as a receptor protein), a secreted protein, a cytoplasmic protein, a nuclear protein, a recombinase such as Cre, a ribozyme or an antisense RNA. See PCT/US94/01617 for general design and construction details and for various applications including gene therapy and see PCT/US95/10591 regarding applications to animal models of disease.

This invention encompasses a variety of configurations for the chimeric proteins. In all cases involving the activation of target gene transcription, however, the chimeric proteins share an important characteristic: cells containing constructs encoding the chimeras and a target gene construct express the target gene at least one, preferably at least two, and more preferably at least three or four or more orders of magnitude more in the presence of the multimerizing ligand than in its absence. Optimally, expression of the selected gene is not observed unless the cells are or have been exposed to a multimerizing ligand.

To recap, the chimeric proteins are capable of initiating a detectable level of transcription of target genes within the engineered cells upon exposure of the cells to the rapamycin or rapalog ligand, i.e., following multimerization of the chimeras. Thus, transcription of target genes is activated in genetically engineered cells of this invention following exposure of the cells to a rapamycin or rapalog ligand capable of multimerizing the chimeric protein molecules. Said differently, genetically engineered cells of this invention contain chimeric proteins as described above and are responsive to the presence and/or concentration of a rapamycin or rapalog ligand which is capable of multimerizing those chimeric protein molecules. That responsiveness is manifested by the activation of transcription of a target gene. Such transcriptional activity can be readily detected by any conventional assays for transcription of the target gene. In other embodiments, the biological response to ligand-mediated multimerization of the chimeras is cell death or other biological events rather than direct activation of transcription of a target gene.

Introduction of Constructs into Cells

This invention is particularly useful for the engineering of animal cells and in applications involving the use of such engineered animal cells. The animal cells may be insect, worm or mammalian cells. While various mammalian cells may be used, including, by way of example, equine, bovine, ovine, canine, feline, murine, and non-human primate cells, human cells are of particular interest. Among the various species, various types of cells may be used, such as hematopoietic, neural, glial, mesenchymal, cutaneous, mucosal, stromal, muscle (including smooth muscle cells), spleen, reticuloendothelial, epithelial, endothelial, hepatic, kidney, gastrointestinal, pulmonary, fibroblast, and other cell types. Of particular interest are hematopoietic cells, which may include any of the nucleated cells which may be involved with the erythroid, lymphoid or myelomonocytic lineages, as well as myoblasts and fibroblasts.

Also of interest are stem and progenitor cells, such as hematopoietic, neural, stromal, muscle, hepatic, pulmonary, gastrointestinal and mesenchymal stem cells.

The cells may be autologous cells, syngeneic cells, allogeneic cells and even in some cases, xenogeneic cells with respect to an intended host organism. The cells may be modified by changing the major histocompatibility complex ("MHC") profile, by inactivating $\beta_2$-microglobulin to prevent the formation of functional Class I MHC molecules, inactivation of Class II molecules, providing for expression of one or more MHC molecules, enhancing or inactivating cytotoxic capabilities by enhancing or inhibiting the expression of genes associated with the cytotoxic activity, or the like.

In some instances specific clones or oligoclonal cells may be of interest, where the cells have a particular specificity, such as T cells and B cells having a specific antigen specificity or homing target site specificity.

Constructs encoding the chimeric proteins and target genes of this invention can be introduced into the cells as one or more DNA molecules or constructs, in many cases in association with one or more markers to allow for selection of host cells which contain the construct(s). The constructs can be prepared in conventional ways, where the coding sequences and regulatory regions may be isolated, as appropriate, ligated, cloned in an appropriate cloning host, analyzed by restriction or sequencing, or other convenient means. Particularly, using PCR, individual fragments including all or portions of a functional unit may be isolated, where one or more mutations may be introduced using "primer repair", ligation, in vitro mutagenesis, etc. as appropriate. The construct(s) once completed and demonstrated to have the appropriate sequences may then be introduced into a host cell by any convenient means.

The constructs may be incorporated into vectors capable of episomal replication (e.g. BPV or EBV vectors) or into vectors designed for integration into the host cells' chromosomes. The constructs may be integrated and packaged into non-replicating, defective viral genomes like Adenovirus, Adeno-associated virus (AAV), or Herpes simplex virus (HSV) or others, including retroviral vectors, for infection or transduction into cells. Alternatively, the construct may be introduced by protoplast fusion, electroporation, biolistics, calcium phosphate transfection, lipofection, microinjection of DNA or the like. The host cells will in some cases be grown and expanded in culture before introduction of the construct(s), followed by the appropriate treatment for introduction of the construct(s) and integration of the construct (s). The cells will then be expanded and screened by virtue of a marker present in the constructs. Various markers which may be used successfully include hprt, neomycin resistance, thynidine kinase, hygromycin resistance, etc., and various cell-surface markers such as Tac, CD8, CD3, Thy1 and the NGF receptor.

In some instances, one may have a target site for homologous recombination, where it is desired that a construct be integrated at a particular locus. For example, one can delete and/or replace an endogenous gene (at the same locus or elsewhere) with a recombinant target construct of this invention. For homologous recombination, one may generally use either Ω or O-vectors. See, for example, Thomas and Capecchi, *Cell* (1987) 51, 503–512; Mansour, et al., *Nature* (1988) 336, 348–352; and Joyner, et al., *Nature* (1989) 338, 153–156.

The constructs may be introduced as a single DNA molecule encoding all of the genes, or different DNA molecules having one or more genes. The constructs may be introduced simultaneously or consecutively, each with the same or different markers.

Vectors containing useful elements such as bacterial or yeast origins of replication, selectable and/or amplifiable markers, promoter/enhancer elements for expression in procaryotes or eucaryotes, and mammalian expression control elements, etc. which may be used to prepare stocks of construct DNAs and for carrying out transfections are well known in the art, and many are commercially available.

Introduction of Constructs into Animals

Cells which have been modified ex vivo with the DNA constructs may be grown in culture under selective conditions and cells which are selected as having the desired construct(s) may then be expanded and further analyzed, using, for example, the polymerase chain reaction for determining the presence of the construct in the host cells and/or assays for the production of the desired gene product(s). Once modified host cells have been identified, they may then be used as planned, e.g. grown in culture or introduced into a host organism.

Depending upon the nature of the cells, the cells may be introduced into a host organism, e.g. a mammal, in a wide variety of ways. Hematopoietic cells may be administered by injection into the vascular system, there being usually at least about $10^4$ cells and generally not more than about $10^{10}$ cells. The number of cells which are employed will depend upon a number of circumstances, the purpose for the introduction, the lifetime of the cells, the protocol to be used, for example, the number of administrations, the ability of the cells to multiply, the stability of the therapeutic agent, the physiologic need for the therapeutic agent, and the like. Generally, for myoblasts or fibroblasts for example, the number of cells will be at least about $10^4$ and not more than about $10^9$ and may be applied as a dispersion, generally being injected at or near the site of interest. The cells will usually be in a physiologically-acceptable medium.

Cells engineered in accordance with this invention may also be encapsulated, e.g. using conventional biocompatible materials and methods, prior to implantation into the host organism or patient for the production of a therapeutic protein. See e.g. Hguyen et al, Tissue Implant Systems and Methods for Sustaitning viable High Cell Densities within a Host, U.S. Pat. No. 5,314,471 (Baxter International, Inc.); Uludag and Sefton, 1993, J Biomed. Mater. Res. 27(10) :1213–24 (HepG2 cells/hydroxyethyl methacrylate-methyl methacrylate membranes); Chang et al, 1993, Hum Gene Ther 4(4):433–40 (mouse Ltk– cells expressing hGH/ inmmunoprotective perm-selective alginate microcapsules; Reddy et al, 1993, J Infect Dis 168(4):1082–3 (alginate); Tai and Sun, 1993, FASEB J 7(11):1061–9 (mouse fibroblasts expressing hGH/alginate-poly-L-lysine-alginate membrane); Ao et al, 1995, Transplanataion Proc. 27(6):3349, 3350 (alginate); Rajotte et al, 1995, Transplantation Proc. 27(6):3389 (alginate); Lakey et al, 1995, Transplantation Proc. 27(6):3266 (alginate); Korbutt et al, 1995, Transplantation Proc. 27(6):3212 (alginate); Dorian et al, U.S. Pat. No. 5,429,821 (alginate); Emerich et al, 1993, Exp Neurol 122(1):37–47 (polymer-encapsulated PC12 cells); Sagen et al, 1993, J Neurosci 13(6):241–523 (bovine chromaffin cells encapsulated in semipermeable polymer membrane and implanted into rat spinal subarachnoid space); Aebischer et al, 1994, Exp Neurol 126(2):151–8 (polymer-encapsulated rat PC12 cells implanted into monkeys; see also Aebischer, WO 92/19595); Savelkoul et al, 1994, J Immunol Methods 170(2):185–96 (encapsulated hybridomas producing antibodies; encapsulated transfected cell lines expressing various cytokines); Winn et al, 1994, PNAS USA 91(6):2324–8 (engineered BHK cells expressing human nerve growth factor encapsulated in an immunoisolation polymeric device and transplanted into rats); Emerich et al, 1994, Prog Neuropsychopharmacol Biol Psychiatry 18(5):935–46 (polymer-encapsulated PC12 cells implanted into rats); Kordower et al, 1994, PNAS USA 91(23):10898–902 (polymer-encapsulated engineered BHK cells expressing hNGF implanted into monkeys) and Butler et al WO 95/04521 (encapsulated device). The cells may then be introduced in encapsulated form into an animal host, preferably a mammal and more preferably a human subject in need thereof. Preferably the encapsulating material is semipermeable, permitting release into the host of secreted proteins produced by the encapsulated cells. In many embodiments the semipermeable encapsulation renders the encapsulated cells immunologically isolated from the host organism in which the encapsulated cells are introduced. In those embodiments the cells to be encapsulated may express one or more chimeric proteins containing component domains derived from proteins of the host species and/or from viral proteins or proteins from species other than the host species. For example in such cases the chimeras may contain elements derived from GAL4 and VP16. The cells may be derived from one or more individuals other than the recipient and may be derived from a species other than that of the recipient organism or patient.

Instead of ex vivo modification of the cells, in many situations one may wish to modify cells in vivo. For this purpose, various techniques have been developed for modification of target tissue and cells in vivo. A number of viral vectors have been developed, such as adenovirus, adeno-associated virus, and retroviruses, which allow for transfection and, in some cases, integration of the virus into the host. See, for example, Dubensky et al. (1984) Proc. Natl. Acad. Sci. USA 81, 7529–7533; Kaneda et al., (1989) Science 243,375–378; Hiebert et al. (1989) Proc. Natl. Acad. Sci. USA 86, 3594–3598; Hatzoglu et al. (1990) J. Biol. Chem. 265, 17285–17293 and Ferry, et al. (1991) Proc. Natl. Acad. Sci. USA 88, 8377–8381. The vector may be administered by injection, e.g. intravascularly or intramuscularly, inhalation, or other parenteral mode. Non-viral delivery methods such as administration of the DNA via complexes with liposomes or by injection, catheter or biolistics may also be used.

In accordance with in vivo genetic modification, the manner of the modification will depend on the nature of the tissue, the efficiency of cellular modification required, the number of opportunities to modify the particular cells, the accessibility of the tissue to the DNA composition to be introduced, and the like. By employing an attenuated or modified retrovirus carrying a target transcriptional initiation region, if desired, one can activate the virus using one of the subject transcription factor constructs, so that the virus may be produced and transfect adjacent cells.

The DNA introduction need not result in integration in every case. In some situations, transient maintenance of the DNA introduced may be sufficient. In this way, one could have a short term effect, where cells could be introduced into the host and then turned on after a predetermined time, for example, after the cells have been able to home to a particular site.

Multimerizing Agents

Ligands suitable for use in this invention include rapamycin and rapamycin analogs, derivatives and mimics (rapalogs) that are capable of binding to an FKBP chimera and a FRAP chimera to form a tripartitie complex. Rapalogs of this invention which contain one or more substituents ("bumps") that diminish, and preferably substantially preclude, their binding to FKBP and/or FRAP proteins endogenous to the engineered cells are preferred. Mutant FKBPs of this invention may be obtained and screened for binding to a given rapalog as described in PCT/US94/01617 and PCT/US94/08008. Some rapalogs possess optional substituents which diminish, and preferably substantially preclude, their binding as FKBP complexes to FRAP but which do bind, complexed to (mutant) FKBP chimeric proteins, to (mutant) FRAP chimeras (FIG. 2). Rapalogs containing such bumps permit more selective binding to mutant FKBP chimeras and/or mutant FRAP chimeras without interference by endogenous pools of FKBP12 or FRAP. This is desirable for a number of applications, especially uses in whole organisms. A further advantage of diminished binding to endogenous FRAP is that such multimerizing agents, alone or in conjunction with endogenous FKBP12 or chimeras containing FKBP domains, will possess correspondingly diminished immunosuppressive activity or mechanism-based toxicities relative to rapamycin. Also contemplated by this invention are chimeric proteins comprising mutant FKBP domains which due to surface residue mutation are substantially precluded from ligand-dependent binding to endogenous FRAP, but which can bind in a ligand-dependent manner to chimeric proteins containing one or more FRB domains with compensatory mutations (FIG. 2-E).

Monomeric monovalent ligands, such as those disclosed in PCT/US94/01617, as well as derivatized compounds described herein, which are capable of binding to one of the chimeric proteins but not effecting dimerization or higher order multimerization thereof (in view of the monovalent nature of the ligand) are multimerization antagonists.

Rapalogs of particular interest bind to human FKBP12 and/or inhibit its rotamase activity at least about an order of magnitude less potently than any of FK506, FK520 or rapamycin. Such assays are well known in the art. See e.g. Holt, et al., *J. Amer. Chem. Soc.,*1993, 115, 9925–9938. The diminution in inhibitory activity may be as great as about 2 orders of magnitude, and in some cases will exceed about three orders of magnitude. Useful rapalog substituents include among others, alkyl, aryl, —O-alkyl, —O-aryl, substituted or unsubstituted amine, amide, carbarnide and ureas, where alkyl and aryl are as defined elsewhere herein. See e.g. PCT/US94/01617 and PCT/US94/08008.

Multimerization ligands of this invention specifically include rapamycin and rapalogs of the formula

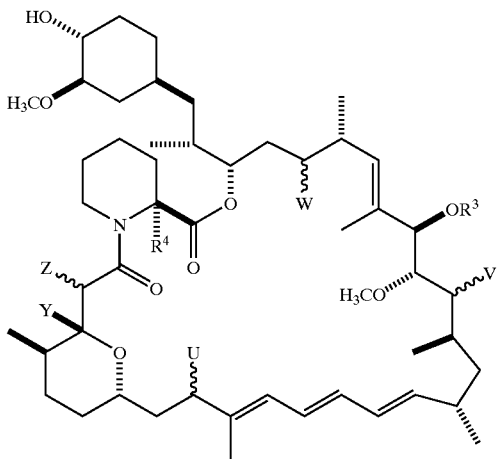

wherein U is —H, —OR¹, —SR¹, —OC(O)R¹ or —OC(O)NHR¹, —NHR¹, —NHC(O)R¹, —NH—SO₂—R¹ or —R², where R²=substituted aryl or allyl or alkylaryl (e.g. benzyl or substituted benzyl); V is —OR³ or (=O); W is =O, =NR⁴=NOR⁴ or =NNHR⁴, —NHOR⁴ or —NHNHR⁴, —OR⁴, —OC(O)R⁴ or —OC(O)NR⁴, or —H; Y is —OR⁵, —OC(O)R⁵ or —OC(O)NHR⁵; Z is =O, —OR⁶, —NR⁶, —H, —NC(O)R⁶, or —OC(O)R⁶ or —OC(O)NR⁶; R³ is H, —R⁷, —C(O)R⁷ or —C(O)NHR⁷ or C-28/C-30 cyclic carbonate; R⁴ is H or alkyl, where R¹, R⁴, R⁵, R⁶ and R⁷ are independently selected from H, alkyl, alkylaryl or aryl.

In rapamycin, U is —OMe, V is =O, W is =O, Y is —OH, Z is =O and R³ and R⁴ are H with the stereoisomerism as shown in Formula 1 on page 1. Rapalogs of this invention may contain substituents in any of the possible stereoisomeric orientations.

Alkyl, as the term is used herein, is intended to include saturated and unsaturated, linear (straight-chain), branched, cyclic, and polycyclic aliphatic hydrocarbons, generally containing 1–8 contiguous aliphatic carbon atoms (e.g. methyl, ethyl, n-propyl, iso-propyl, cyclopropyl, n-butyl, iso-butyl, sec-butyl, t-butyl, cyclobutyl, n-pentyl, iso-pentyl, sec-pentyl, cyclopentyl, and so on), which are optionally substituted with one or more functional groups selected from the group consisting of hydroxy, $C_1$–$C_8$ alkoxy, acyloxy, carbamoyl, amino, N-acylamino, keto, halo (chloro, bromo, fluoro or iodo), trihalomethyl, cyano, carboxyl, alkyl, cycloalkyl, aryl and heteroaryl, which functional groups may themselves (with the exception of hydroxy, halo and cyano groups) bear one or more of the foregoing functional groups. Preferably alkyl, alkoxy and acyl groups contain 1–6 contiguous aliphatic carbon atoms, and may bear substituents.

Aryl, as the term is used herein, is intended to include stable cyclic, heterocyclic, polycyclic, and polyheterocyclic unsaturated $C_3$–$C_{14}$ moieties (exemplified by but not limited to phenyl, biphenyl, naphthyl, pyridyl, furyl, thiophenyl, imidazoyl, pyrimidinyl, and oxazoyl) which may be substituted with one to five functional groups selected from the group consisting of hydroxy, $C_1$–$C_8$ alkoxy, $C_1$–$C_8$ branched or straight-chain alkyl, acyloxy, carbamoyl, amino, N-acylamino, nitro, halo, trifluoromethyl, cyano, and carboxyl, which functional groups may themselves (with the exception of hydroxy, halo, triflouromethyl and cyano groups) bear one or more of the foregoing functional groups.

Heteroalkyl and heteroaryl, as those terms are used herein, refer to alkyl and aryl moieties respectively, which contain one or more of oxygen, sulfur, or nitrogen in place of one or more carbon atoms.

In certain embodiments ligands of particular interest include a compound other than rapamycin itself, a reduced form of rapamycin bearing a hydroxyl group at position 14 or a rapamycin derivative in which U is a C2–C8 straightchain, branched or cyclic aliphatic or alkoxyl moiety; an aryl or heteroaryl substituted alkyl or alkoxyl moiety; or an aryl, aryloxy, heteroaryl or heteroaryloxy moiety, where the aryl and heteroaryl moeity may be substituted or unsubstituted.

Examples of a variety of such compounds, or related compounds incorporating such substituents are known in the art, as is their synthesis. For the sake of illustration, the following synthetic schemse are representative of transformations which can be employed to produce the desired rapalogs:

Preparation of C-7 Bumps

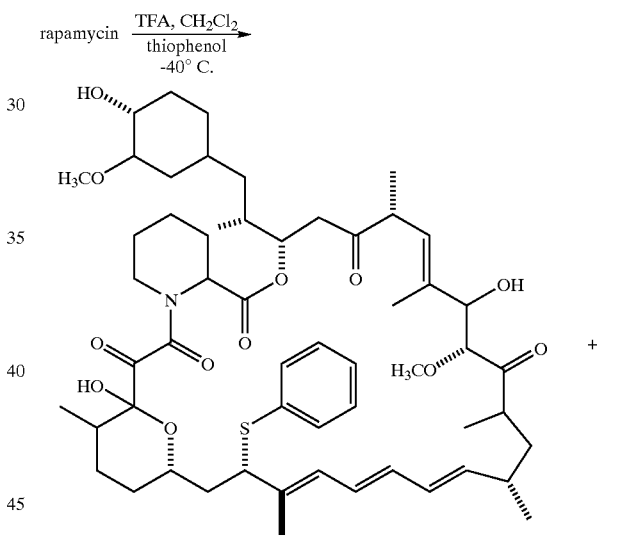

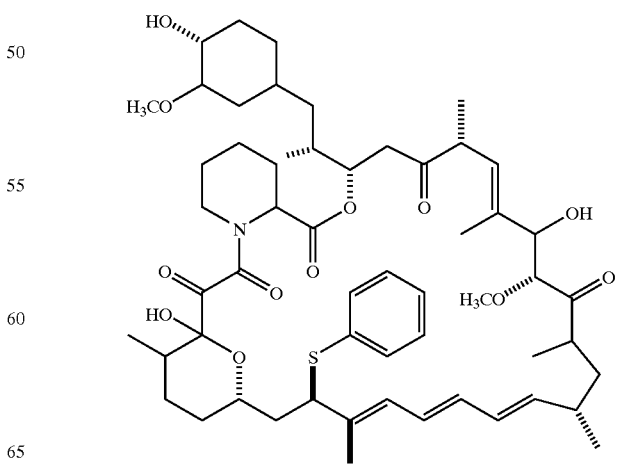

37
-continued
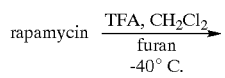
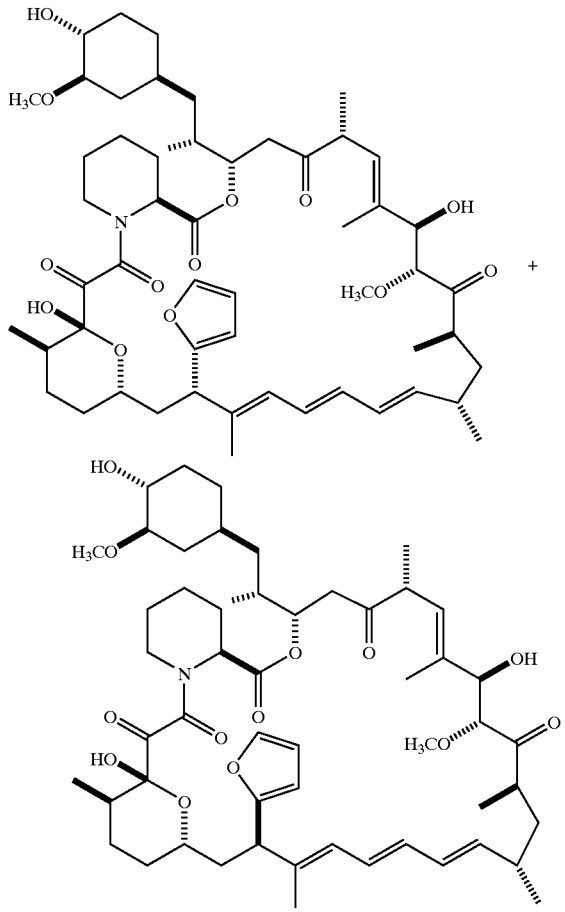
Literature Reference:
Luengo, et al. J. Org. Chem. 59, 6512 (1995).
Luengo, et al. Chem & Biol 2(7), 471-481 (1995)
Preparation of C-13 Bumps
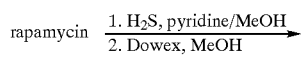
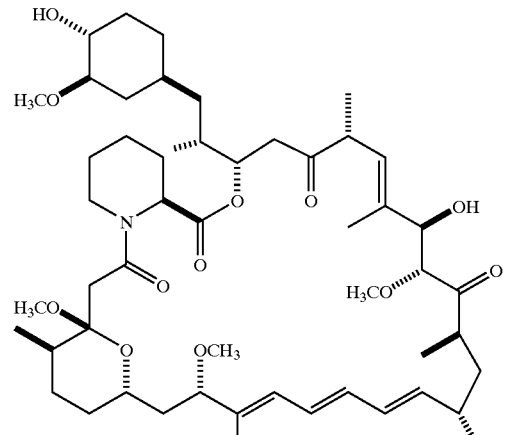
Literature Reference:
Luengo et al. Tet. Lett. 35, 6469 (1994).
38
-continued
Preparation of C-14 Bumps
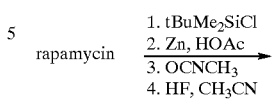
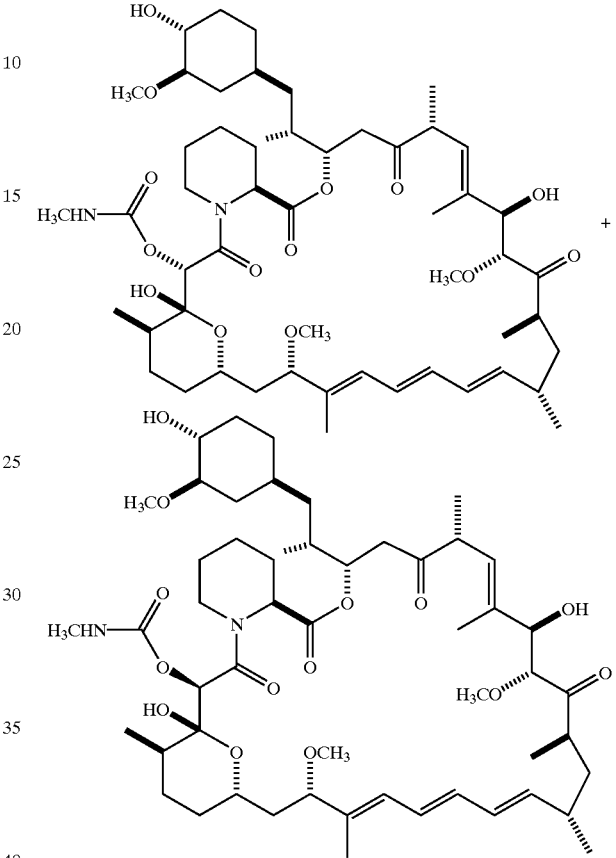
Literature Reference:
Schubert, et al. Angew Chem Int Ed Engl 23, 167 (1984).
Preparation of C-20 Bumps
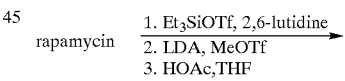
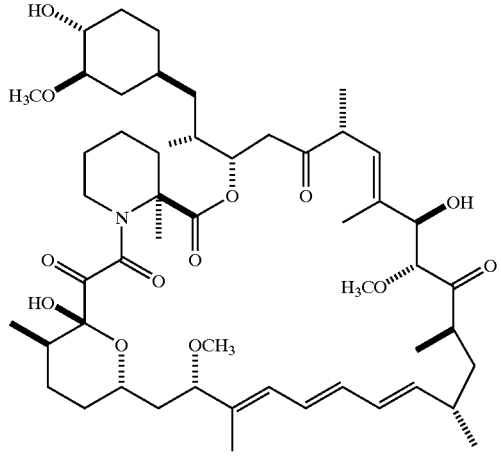
Literature Reference:
Nelson, U.S. Pat. No. 5,387,680

-continued

Preparation of C-24 Bumps rapamycin $\xrightarrow{\text{RNH}_2\cdot\text{HCl, NaOAc, MeOH}}$

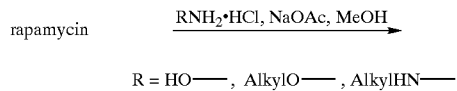

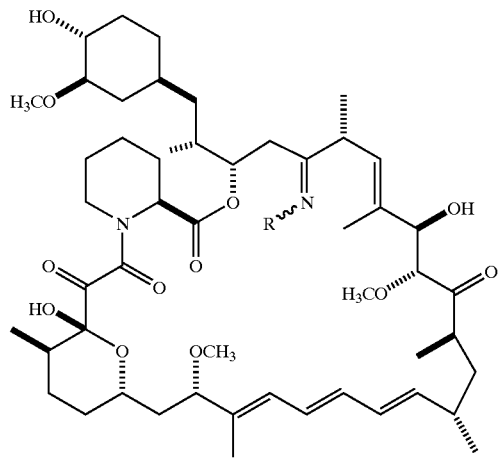

rapamycin $\xrightarrow[\text{2. NaBH}_3\text{CN, CeCl}_3]{\text{1. RNH}_2\cdot\text{HCl, NaOAc, MeOH}}$

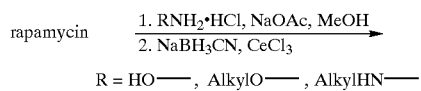

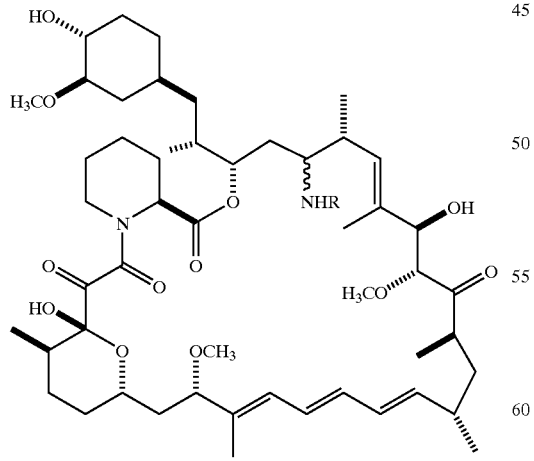

Literature References:
Failli, et al. U.S. Pat. No. 5,373,014
Kao, et al. U.S. Pat. No. 5,378,836
Lane, et al. Synthesis 1975, p136.

-continued

Preparation of C-28 Bumps rapamycin $\xrightarrow[\begin{array}{l}\text{2. RC(O)Cl, pyridine}\\\text{3. HF, CH}_3\text{CN}\end{array}]{\text{1. tBuMe}_2\text{SiOTf, 2,6-lutidine}}$

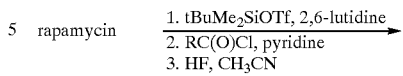

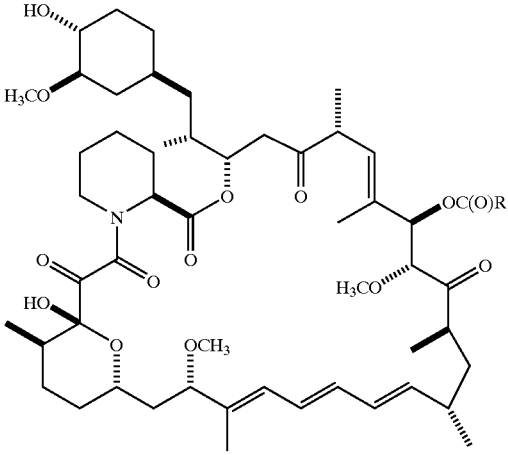

Preparation of C-30 Bumps rapamycin $\xrightarrow[\begin{array}{l}\text{2. NaBH}_3\text{CN, CeCl}_3\\\text{3. RC(O)Cl, pyridine}\\\text{4. HF, CH}_3\text{CN}\end{array}]{\text{1. tBuMe}_2\text{SiOTf, pyridine}}$

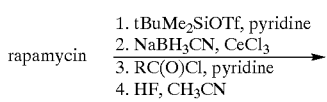

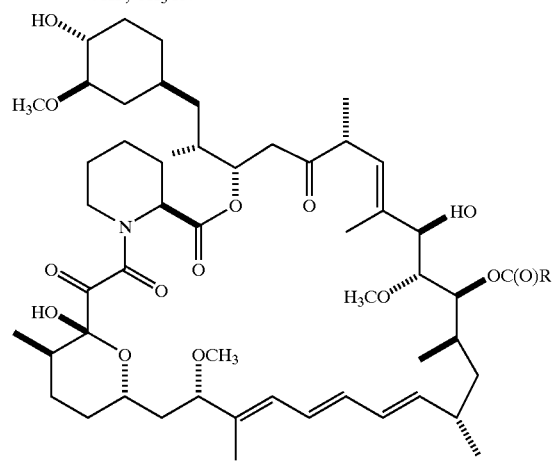

rapamycin $\xrightarrow[\text{2. COCl}_2\text{, pyridine}]{\text{1. NaBH}_3\text{CN, CeCl}_3}$

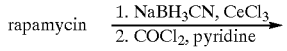

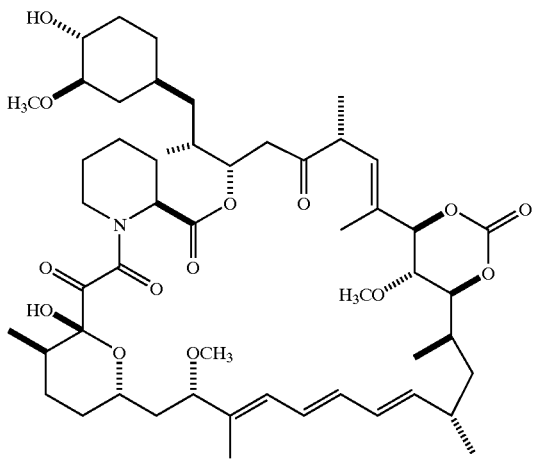

-continued

Literature Reference:
Luengo et al. Tet. Lett. 35, 6469 (1994).
Additional transformations include the following:

Modification at C-14 rapamycin $\xrightarrow{\text{Zinc}}$ acetic acid

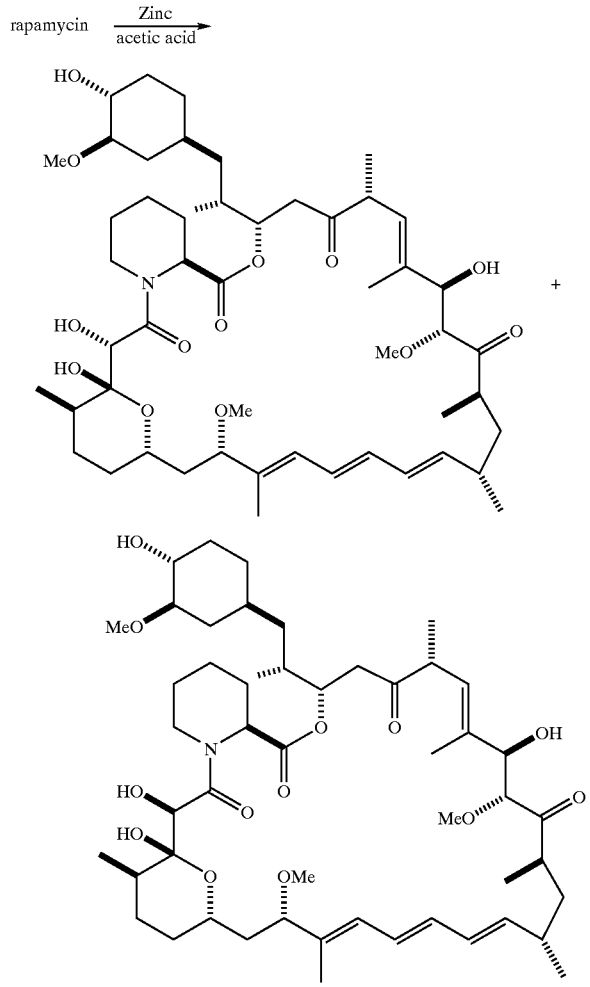

Literature reference:
Luengo, et al. Tetrahedron Letters 35:6469 (1994).

rapamycin $\xrightarrow{CH_2N_2}$

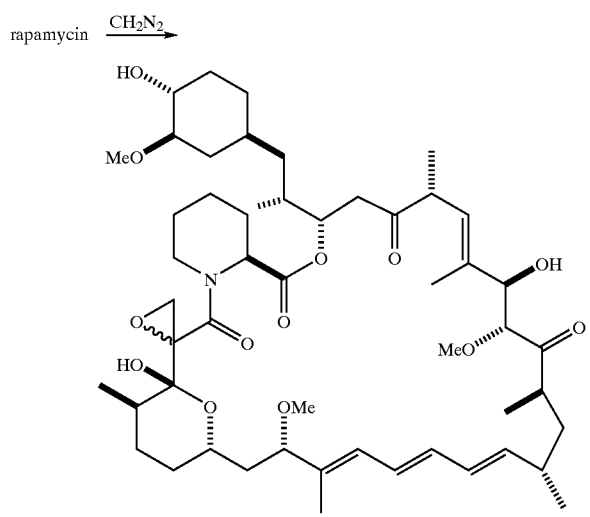

-continued

Literature reference:
Fisher, et al. J. Org. Chem. 56:2900 (1991).

rapamycin $\xrightarrow{HOCH_2CH_2NH_2}$

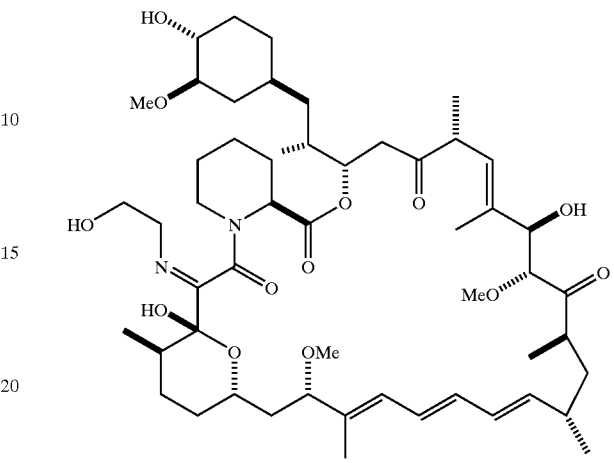

Literature reference:
Fisher, et al. J. Org. Chem. 56:2900 (1991).

rapamycin $\xrightarrow[\substack{\text{1. tBuMe}_2\text{SiCl} \\ \text{2. Zn, HOAc} \\ \text{3. Ph}_3\text{Bi(OAc)}_2 \\ \text{4. HF, CH}_3\text{CN}}]{}$

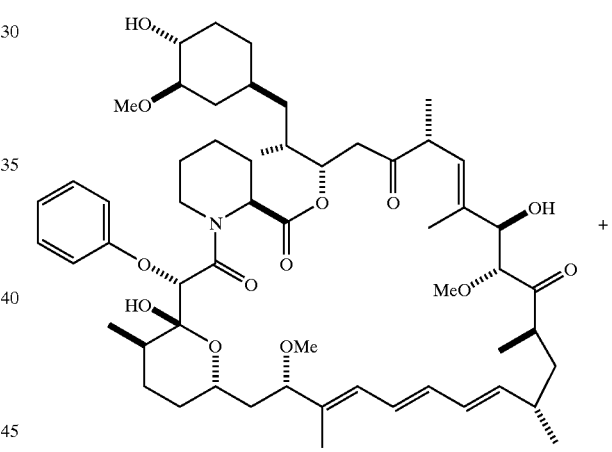

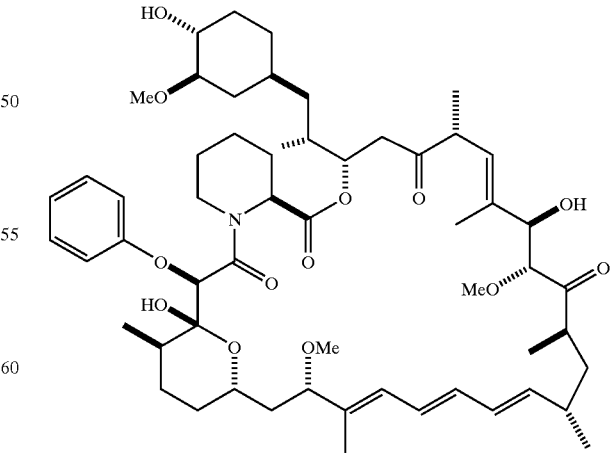

Literature reference:
Luengo, et al. Tetrahedron Letters 35:6469 (1994).
Finet Chemical Reviews 89:1487 (1989).

Modification at C-13 rapamycin
1. NH₃, MeOH
2. (MeCO)₂O

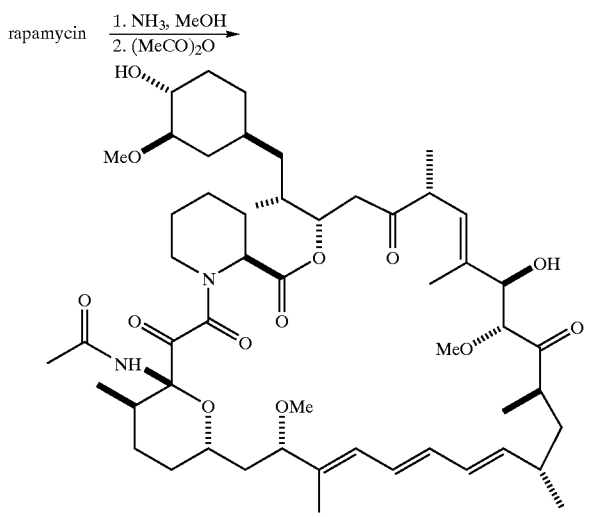

Literature reference:
Donald, et al. Tetrahedron Letters 1375 (1991).

Modification at C-24 rapamycin
1. tBuMe₂SiCl
2. NaBH₄
3. N,N'-disuccinimidyl carbonate 1. iPrNH₂
2. HF

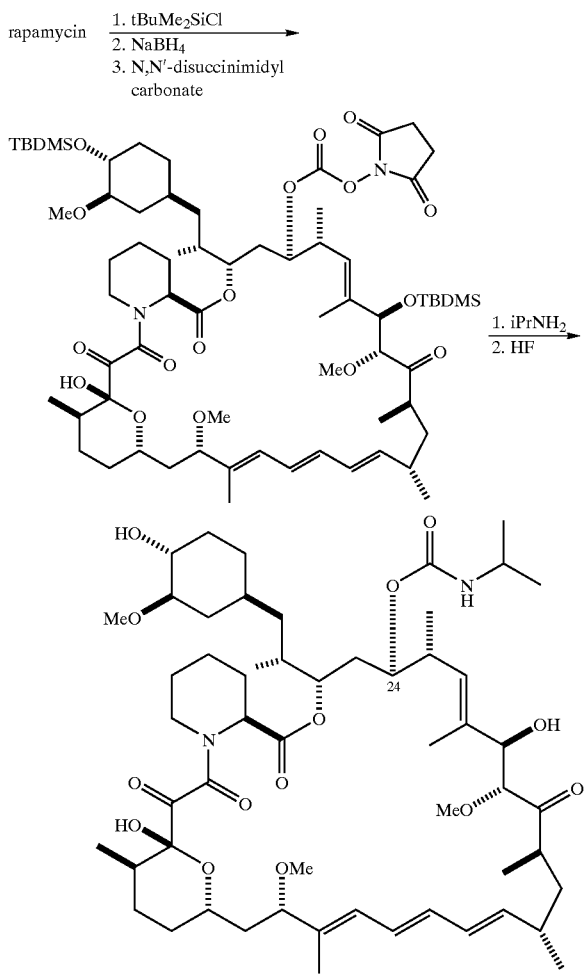

Literature reference:
Luengo, et al. Tetrahedron Letters 35:6469(1994).

Formulations, Dosage and Administration

By virtue of its capacity to promote protein-protein interactions, rapamycin or a rapalog of this invention may be used in pharmaceutical compositions and methods for promoting formation of tripartite complexes of chimeric proteins of this invention in a mammal containing genetically engineered cells of this invention.

The preferred method of such treatment or prevention is by administering to a mammal an effective amount of the compound to promote measurable formation of such complexes in the engineered cells, or preferably, to promote measurable actuation of the desired biological event triggered by such complexation, e.g. transcription of a target gene, apoptosis of engineered cells, etc.

Therapeutic/Prophylactic Administration & Pharmaceutical Compositions

Rapamycin and the various rapalogs can exist in free form or, where appropriate, in salt form. Pharmaceutically acceptable salts and their preparation are well-known to those of skill in the art. The pharmaceutically acceptable salts of such compounds include the conventional non-toxic salts or the quaternary ammonium salts of such compounds which are formed, for example, from inorganic or organic acids of bases.

The compounds of the invention may form hydrates or solvates. It is known to those of skill in the art that charged compounds form hydrated species when lyophilized with water, or form solvated species when concentrated in a solution with an appropriate organic solvent.

This invention also relates to pharmaceutical compositions comprising a therapeutically (or prophylactically) effective amount of the compound, and a pharmaceutically acceptable carrier or excipient. Carriers include e.g. saline, buffered saline, dextrose, water, glycerol, ethanol, and combinations thereof, and are discussed in greater detail below. The composition, if desired, can also contain minor amounts of wetting or emulsifying agents, or pH buffering agents. The composition can be a liquid solution, suspension, emulsion, tablet, pill, capsule, sustained release formulation, or powder. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Formulation may involve mixing, granulating and compressing or dissolving the ingredients as appropriate to the desired preparation.

The pharmaceutical carrier employed may be, for example, either a solid or liquid.

Illustrative solid carrier include lactose, terra alba, sucrose, talc, gelatin, agar, pectin, acacia, magnesium stearate, stearic acid and the like. A solid carrier can include one or more substances which may also act as flavoring agents, lubricants, solubilizers, suspending agents, fillers, glidants, compression aids, binders or tablet-disintegrating agents; it can also be an encapsulating material. In powders, the carrier is a finely divided solid which is in admixture with the finely divided active ingredient In tablets, the active ingredient is mixed with a carrier having the necessary compression properties in suitable proportions, and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Illustrative liquid carriers include syrup, peanut oil, olive oil, water, etc. Liquid carriers are used in preparing solutions, suspensions, emulsions, syrups, elixirs and pressurized compositions. The active ingredient can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (partially containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and arachis oil). For parenteral administration, the carrier can also be an oily ester such as ethyl oleate and isopropyl myristate. Sterile liquid carders are useful in sterile liquid form compositions for parenteral administration. The liquid carrier for pressurized compositions can be halogenated hydrocarbon or other pharmaceutically acceptable propellant. Liquid pharmaceutical compositions which are sterile solutions or suspensions can be utilized by, for example, intramuscular, intraperitoneal or subcutaneous injection. Sterile solutions can also be administered intravenously. The compound can also be administered orally either in liquid or solid composition form.

The carrier or excipient may include time delay material well known to the art, such as glyceryl monostearate or glyceryl distearate along or with a wax, ethylcellulose, hydroxypropylmethylcellulose, methylmethacrylate and the like. When formulated for oral administration, 0.01% Tween 80 in PHOSAL PG-50 (phospholipid concentrate with 1,2-propylene glycol, A. Nattermann & Cie. GmbH) has been recognized as providing an acceptable oral formulation for rapamycin, and may be adapted to formulations for various rapalogs.

A wide variety of pharmaceutical forms can be employed. If a solid carrier is used, the preparation can be tableted, placed in a hard gelatin capsule in powder or pellet form or in the form of a troche or lozenge. The amount of solid carrier will vary widely but preferably will be from about 25 mg to about 1 g. If a liquid carrier is used, the preparation will be in the form of a syrup, emulsion, soft gelatin capsule, sterile injectable solution or suspension in an ampule or vial or nonaqueous liquid suspension.

To obtain a stable water soluble dosage form, a pharmaceutically acceptable salt of rapamycin or a rapalog may be dissolved in an aqueous solution of an organic or inorganic acid, such as a 0.3M solution of succinic acid or citric acid. Alternatively, acidic derivatives can be dissolved in suitable basic solutions. If a soluble salt form is not available, the compound is dissolved in a suitable cosolvent or combinations thereof. Examples of such suitable cosolvents include, but are not limited to, alcohol, propylene glycol, polyethylene glycol 300, polysorbate 80, glycerin, polyoxyethylated fatty adds, fatty alcohols or glycerin hydroxy fatty acids esters and the like in concentrations ranging from 0–60% of the total volume.

Various delivery systems are known and can be used to administer the rapamycin or rapalog, or the various formulations thereof, including tablets, capsules, injectable solutions, encapsulation in liposomes, microparticles, microcapsules, etc. Methods of introduction include but are not limited to dermal, intradermal, intramuscular, intraperitoneal, intravenous, subcutaneous, intranasal, pulmonary, epidural, ocular and (as is usually preferred) oral routes. The compound may be administered by any convenient or otherwise appropriate route, for example by infusion or bolus injection, by absorption through epithelial or mucocutaneous linings (e.g., oral mucosa, rectal and intestinal mucosa, etc.) and may be administered together with other biologically active agents. Administration can be systemic or local. For treatment or prophylaxis of nasal, bronchial or pulmonary conditions, preferred routes of administration are oral, nasal or via a bronchial aerosol or nebulizer.

In certain embodiments, it may be desirable to administer the compound locally to an area in need of treatment; this may be achieved by, for example, and not by way of limitation, local infusion during surgery, topical application, by injection, by means of a catheter, by means of a suppository, or by means of a skin patch or implant, said implant being of a porous, non-porous, or gelatinous material, including membranes, such as sialastic membranes, or fibers.

In a specific embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic to ease pain at the side of the injection. Generally, the ingredients are supplied either separately or mixed together in unit dosage form, for example, as a lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

Administration to an individual of an effective amount of the compound can also be accomplished topically by administering the compound(s) directly to the affected area of the skin of the individual. For this purpose, the compound is administered or applied in a composition including a pharmacologically acceptable topical carrier, such as a gel, an ointment, a lotion, or a cream, which includes, without limitation, such carriers as water, glycerol, alcohol, propylene glycol, fatty alcohols, triglycerides, fatty acid esters, or mineral oils.

Other topical carriers include liquidpetroleum, isopropyl palmitate, polyethylene glycol, ethanol (95%), polyoxyethylene monolaurate (5%) in water, or sodium lauryl sulfate (5%) in water. Other materials such as anti-oxidants, humectants, viscosity stabilizers, and similar agents may be added as necessary. Percutaneous penetration enhancers such as Azone may also be included.

In addition, in certain instances, it is expected that the compound may be disposed within devices placed upon, in, or under the skin. Such devices include patches, implants, and injections which release the compound into the skin, by either passive or active release mechanisms.

Materials and methods for producing the various formulations are well known in the art and may be adapted for practicing the subject invention. See e.g. U.S. Pat. Nos. 5,182,293 and 4,837,311 (tablets, capsules and other oral formulations as well as intravenous formulations) and European Patent Application Publication Nos. 0 649 659 (published Apr. 26, 1995; rapamycin formulation for IV administration) and 0 648 494 (published Apr. 19, 1995; rapamycin formulation for oral administration).

The effective dose of the compound will typically be in the range of about 0.01 to about 50 mg/kgs, preferably about 0.1 to about 10 mg/kg of mammalian body weight, administered in single or multiple doses. Generally, the compound may be administered to patients in need of such treatment in a daily dose range of about 1 to about 2000 mg per patient. In embodiments in which the compound is rapamycin or is a rapalog with some residual immunosuppressive effects, it is preferred that the dose administered be below that associated with undue immunosuppressive effects.

The amount of compound which will be effective in the treatment or prevention of a particular disorder or condition will depend in part on the nature of the disorder or condition, and can be determined by standard clinical techniques. In addition, in vitro or in vivo assays may optionally be employed to help identify optimal dosage ranges. Effective doses may be extrapolated from dose-response curves derived from in vitro or animal model test systems. The precise dosage level should be determined by the attending physician or other health care provider and will depend upon well known factors, including route of administration, and the age, body weight, sex and general health of the individual; the nature, severity and clinical stage of the disease; the use (or not) of concomitant therapies; and the nature and extent of genetic engineering of cells in the patient.

The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceutical or biological products, which notice reflects approval by the agency of manufacture, use or sale for human administration.

Applications

This invention is applicable to any situation that calls for expression of an exogenously-introduced gene embedded within a large genome. The desired expression level could be preset very high or very low. Alternatively, the system may be further engineered to achieve regulated or titratable expression. See e.g. PCT/US93/01617. In most cases, the inadvertent activation of unrelated cellular genes is undesirable. The following are non-limiting examples of applications of the subject invention.

1. Regulated Gene Therapy

In many instances, the ability to switch a therapeutic gene on and off at will or the ability to titrate expression with precision are important for therapeutic efficacy. This invention is particularly well suited for achieving regulated expression of a therapeutic target gene in the context of human gene therapy. One example uses a pair of chimeric proteins (one containing a FRAP-derived receptor domain, the other containing an FKBP-derived receptor domain), a dimerizing agent capable of dimerizing the chimeras and a target gene construct to be expressed. One of the chimeric proteins comprises a composite DNA-binding domain as described in Pomerantz et al, supra, as the heterologous action domain. The second chimeric protein comprises a transcriptional activating domain as the heterologous action domain. The rapamycin or rapalog dimerizing reagent is capable of binding to both chimeras and thus of dimerizing or oligomerizing the chimeras. DNA molecules encoding and capable of directing the expression of these chimeric proteins are introduced into the cells to be engineered. Also introduced into the cells is a target gene linked to a DNA sequence to which the composite DNA-binding domain is capable of binding. Contacting the engineered cells or their progeny with the dimerizing reagent (by administering the agent to the animal or patient) leads to assembly of the transcription factor complex and hence to expression of the target gene. The design and use of similar components is disclosed in PCT/US93/01617. These may be adapted to the present invention by the use of a composite DNA-binding domain, and DNA sequence encoding it, in place of the alternative DNA-binding domains; a FRAP-derived receptor domain on one of the chimeras in place of an FKBP-derived receptor domain; and a monomeric rapamycin-type dimerizing agent in place of a dimeric dimerizing agent such as disclosed in the referenced patent document. In practice, the level of target gene expression should be a function of the number or concentration of chimeric transcription factor complexes, which should in turn be a function of the concentration of the dimerizing ligand. Experimental data discussed below evidences such dose (of dimerizing ligand)-responsive gene expression.

The dimerizing ligand may be administered to the patient as desired to activate transcription of the target gene. Depending upon the binding affinity of the ligand, the response desired, the manner of administration, the half-life, the number of cells present, various protocols may be employed. The ligand may be administered parenterally or orally. The number of administrations will depend upon the factors described above. The ligand may be taken orally as a pill, powder, or dispersion; bucally; sublingually; injected intravascularly, intraperitoneally, intramuscularly, subcutaneously; by inhalation, or the like. The ligand (and monomeric antagonist compound) may be formulated using conventional methods and materials well known in the art for the various routes of administration. The precise dose and particular method of administration will depend upon the above factors and be determined by the attending physician or human or animal healthcare provider. For the most part, the manner of administration will be determined empirically.

In the event that transcriptional activation by the ligand is to be reversed or terminated, a monomeric compound which can compete with the dimerizing ligand may be administered. Thus, in the case of an adverse reaction or the desire to terminate the therapeutic effect, an antagonist to the dimerizing agent can be administered in any convenient way, particularly intravascularly, if a rapid reversal is desired. Alternatively, one may provide for the presence of an inactivation domain (or transcriptional silencer) with a ligand binding domain. In another approach, cells may be eliminated through apoptosis via signalling through Fas or TNF receptor as described elsewhere. See International Patent Applications PCT/US94/01617 and PCT/US94/08008.

The particular dosage of the ligand for any application may be determined in accordance with the procedures used for therapeutic dosage monitoring, where maintenance of a particular level of expression is desired over an extended period of times, for example, greater than about two weeks, or where there is repetitive therapy, with individual or repeated doses of ligand over short periods of time, with extended intervals, for example, two weeks or more. A dose of the ligand within a predetermined range would be given and monitored for response, so as to obtain a time-expression level relationship, as well as observing therapeutic response. Depending on the levels observed during the time period and the therapeutic response, one could provide a larger or smaller dose the next time, following the response. This process would be iteratively repeated until one obtained a dosage within the therapeutic range. Where the ligand is chronically administered, once the maintenance dosage of the ligand is determined, one could then do assays at extended intervals to be assured that the cellular system is providing the appropriate response and level of the expression product.

It should be appreciated that the system is subject to many variables, such as the cellular response to the ligand, the efficiency of expression and, as appropriate, the level of secretion, the activity of the expression product, the particular need of the patient, which may vary with time and circumstances, the rate of loss of the cellular activity as a result of loss of cells or expression activity of individual cells, and the like.

2. Production of Recombinant Proteins and Viruses

Production of recombinant therapeutic proteins for commercial and investigational purposes is often achieved through the use of mammalian cell lines engineered to express the protein at high level. The use of mammalian cells, rather than bacteria or yeast, is indicated where the proper function of the protein requires post-translational modifications not generally performed by heterologous cells. Examples of proteins produced commercially this way include erythropoietin, tissue plasminogen activator, dotting factors such as Factor VIII:c, antibodies, etc. The cost of producing proteins in this fashion is directly related to the level of expression achieved in the engineered cells. A second limitation on the production of such proteins is toxicity to the host cell: Protein expression may prevent cells from growing to high density, sharply reducing production levels. Therefore, the ability to tightly control protein expression, as described for regulated gene therapy, permits cells to be grown to high density in the absence of protein production. Only after an optimum cell density is reached, is expression of the gene activated and the protein product subsequently harvested.

A similar problem is encountered in the construction and use of "packaging lines" for the production of recombinant viruses for commercial (e.g., gene therapy) and experimental use. These cell lines are engineered to produce viral proteins required for the assembly of infectious viral particles harboring defective recombinant genomes. Viral vectors that are dependent on such packaging lines include retrovirus, adenovirus, and adeno-associated virus. In the latter case, the titer of the virus stock obtained from a packaging line is directly related to the level of production of the viral rep and core proteins. But these proteins are highly toxic to the host cells. Therefore, it has proven difficult to generate high-titer recombinant AAV viruses. This invention provides a solution to this problem, by allowing the construction of packaging lines in which the rep and core genes are placed under the control of regulatable transcription factors of the design described here. The packaging cell line can be grown to high density, infected with helper virus, and transfected with the recombinant viral genome. Then, expression of the viral proteins encoded by the packaging cells is induced by the addition of dimnerizing agent to allow the production of virus at high titer.

3. Biological Research

This invention is applicable to a wide range of biological experiments in which precise control over a target gene is desired. These include: (1) expression of a protein or RNA of interest for biochemical purification; (2) regulated expression of a protein or RNA of interest in tissue culture cells (or in vivo, via engineered cells) for the purposes of evaluating its biological function; (3) regulated expression of a protein or RNA of interest in transgenic animals for the purposes of evaluating its biological function; (4) regulating the expression of a gene encoding another regulatory protein, ribozyme or antisense molecule that acts on an endogenous gene for the purposes of evaluating the biological function of that gene. Transgenic animal models and other applications in which the components of this invention may be adapted include those disclosed in PCT/US95/10591.

This invention further provides kits useful for the foregoing applications. Such kits contain DNA constructs encoding and capable of directing the expression of chimeric proteins of this invention (and may contain additional domains as discussed above) and, in embodiments involving regulated gene transcription, a target gene construct containing a target gene linked to one or more transcriptioal control elements which are activated by the multimerization of the chimeric proteins. Alternatively, the target gene construct may contain a cloning site for insertion of a desired target gene by the practitioner. Such kits may also contain a sample of a dimerizing agent capable of dimerizing the two recombinant proteins and activating transcription of the target gene.

EXAMPLES

Example 1

Constructs Encoding Chimeric Transcription Factors

A.

Unless otherwise stated, all DNA manipulations described in this and other examples were performed using standard procedures (See e.g., F. M. Ausubel et al., Eds., Current Protocols in Molecular Biology (John Wiley & Sons, New York, 1994).

B. Plasmids

Constructs encoding fusions of human FKBP12 (hereafter 'FKBP') with the yeast GAL4 DNA binding domain, the HSV VP16 activation domain, human T cell CD3 zeta chain intracellular domain or the intracellular domain of human FAS are disclosed in PCT/US94/01617.

Additional DNA vectors for directing the expression of fusion proteins relevant to this invention were derived from the mammalian expression vector pCGNN (Attar, R. M. and Gilman, M. Z. 1992. *MCB* 12: 2432–2443). Inserts cloned as XbaI-BamHI fragments into pCGNN are transcribed under the control of the human CMV promoter and enhancer sequences (nucleotides −522 to +72 relative to the cap site), and are expressed with an optional epitope tag (a 16 amino acid portion of the *H. influenzae* hemaglutinin gene that is recognized by the monoclonal antibody 12CA5) and, in the case of transcription factor domains, with an N-terminal nuclear localization sequence (NLS; from SV40 T antigen).

Except where stated, all fragments cloned into pCGNN were inserted as XbaI-BamHI fragments that included a SpeI site just upstream of the BamHI site. As XbaI and SpeI produce compatible ends, this allowed further XbaI-BamHI fragments to be inserted downstream of the initial insert and facilitated stepwise assembly of proteins comprising multiple components. A stop codon was interposed between the SpeI and BamHI sites. For initial constructs, the vector pCGNN-GAL4 was additionally used, in which codons 1–94 of the GAL4 DNA binding domain gene were cloned into the XbaI site of pCGNN such that a XbaI site is regenerated only at the 3' end of the fragment. Thus XbaI-BamHI fragments could be cloned into this vector to generate GAL4 fusions, and subsequently recovered.

(a) Constructs Encoding GAL4 DNA Binding Domain-FRAP Fusions

To obtain portions of the human FRAP gene, human thymus total RNA (Clontech #64028-1) was reverse transcribed using MMLV reverse transcriptase and random hexamer primer (Clontech 1st strand synthesis kit). This cDNA was used directly in a PCR reaction containing primers 1 and 2 and Pfu polymerase (Stratagene). The primers were designed to amplify the coding sequence for amino acids 2025–2113 inclusive of human FRAP: an 89 amino acid region essentially corresponding to the minimal 'FRB' domain identified by Chen et al. (*Proc. Natl. Acad. Sci. USA* (1995) 92, 4947–4951) as necessary and sufficient for FKBP-rapamycin binding (hereafter named FRB). The appropriately-sized band was purified, digested with XbaI and SpeI, and ligated into XbaI-SpeI digested pCGNN-GAL4. This construct was confirmed by restriction analysis (to verify the correct orientation) and DNA sequencing and designated pCGNN-GAL4-1FRB.

Constructs encoding FRB multimers were obtained by isolating the FRB XbaI-BamHI fragment, and then ligating it back into pCGNN-GAL4-1FRB digested with SpeI and BamHI to generate pCGNN-GAL4-2FRB, which was confirmed by restriction analysis. This procedure was repeated analogously on the new construct to yield pCGNN-GAL4-3FRB and pCGNN-GAL4-4FRB.

Vectors were also constructed that encode larger fragments of FRAP, encompassing the miniml FRB domain (amino adds 2025–2113) but extending beyond it. PCR primers were designed that amplify various regions of FRAP flanked by 5' XbaI and 3' SpeI sites as indicated below.

| Designation | amino acids | 5' primer | 3' primer |
|---|---|---|---|
| FRAP$_a$ | 2012–2127 | 6 | 7 |
| FRAP$_b$ | 1995–2141 | 5 | 8 |
| FRAP$_c$ | 1945–2113 | 3 | 2 |
| FRAP$_d$ | 1995–2113 | 5 | 2 |
| FRAP$_e$ | 2012–2113 | 6 | 2 |
| FRAP$_f$ | 2025–2127 | 1 | 7 |
| FRAP$_g$ | 2025–2141 | 1 | 8 |
| FRAP$_h$ | 2025–2174 | 1 | 4 |
| FRAP$_i$ | 1945–2174 | 3 | 4 |

Initially, fragment FRAP$_i$ was amplified by RT-PCR as described above, digested with XbaI and SpeI, and ligated into XbaI-SpeI digested pCGNN-GAL4. This construct, pCGNN-GAL4-FRAP$_i$, was analyzed by PCR to confirm insert orientation and verified by DNA sequencing. It was then used as a PCR substrate to amplify the other fragments using the primers listed. The new fragments were cloned as GAL4 fusions as described above to yield the constructs pCGNN-GAL4-FRAP$_a$, pCGNN-GAL4-FRAP$_b$ etc, which were confirmed by DNA sequencing.

Vectors encoding concatenates of two of the larger FRAP fragment of FRAP$_d$ and FRAP$_e$, were generated by analogous methods to those used earlier. XbaI-BamHI fragments encoding FRAP$_d$ and FRAP$_e$ were isolated from pCGNN-GAL4-FRAP$_d$ and pCGNN-GAL4-FRAP$_e$ and ligated back into the same vectors digested with SpeI and BamHI to generate pCGNN-GAL4-2FRAP$_d$ and pCGNN-GAL4-2FRAP$_e$. This procedure was repeated analogously on the new constructs to yield pCGNN-GAL4-3FRAP$_d$, pCGNN-GAL4-3FRAP$_e$, pCGNN-GAL4-4FRAP$_d$ and pCGNN-GAL4-4FRAP$_e$. All constructs were verified by restriction analysis.

(b) Constructs Encoding FRAP-VP16 Activation Domain Fusions

To generate N-terminal fusions of FRB domain(s) with the activation domain of the Herpes Simplex Virus protein VP16, the XbaI-BamHI fragments encoding 1, 2, 3 and 4 copies of FRB were recovered from the GAL4 fusion vectors and ligated into XbaI-BamHI digested pCGNN to yield pCGNN-1FRB, pCGNN-2FRB etc. These vectors were then digested with SpeI and BamHI. An XbaI-BamHI fragment encoding amino adds 414–490 of VP16 was isolated from plasmid pCG-Gal4-VP16 (Das, G., Hinkley, C. S. and Herr, W. (1995) *Nature* 374, 657–660) and ligated into the SpeI-BamHI digested vectors to generate pCGNN-1FRB-VP16, pCGNN-2FRB-VP16, etc. The constructs were verified by restriction analysis and/or DNA sequencing.

(c) Constructs Encoding ZFHD1 DNA Binding Domain-FRAP Fusions

An expression vector for directing the expression of ZFHD1 coding sequence in mammalian cells was prepared as follows. Zif268 sequences were amplified from a cDNA clone by PCR using primers 5'Xba/Zif and 3'Zif+G. Oct1 homeodomain sequences were amplified from a cDNA done by PCR using primers 5'Not Oct HD and Spe/Bam 3'Oct. The Zif268 PCR fragment was cut with XbaI and NotI. The OctI PCR fragment was cut with NotI and BamHI. Both fragments were ligated in a 3-way ligation between the XbaI and BamHI sites of pCGNN (Attar and Gilman, 1992) to make pCGNNZFHD1 in which the cDNA insert is under the transcriptional control of human CMV promoter and enhancer sequences and is linked to the nuclear localization sequence from SV40 T antigen. The plasmid pCGNN also contains a gene for ampicillin resistance which can serve as a selectable marker. (Derivatives, pCGNNZFHD1-FKBPx1 and pCGNNZFHD1-FKBPx3, were prepared containing one or three tandem repeats of human FKBP12 ligated as an XbaI-BamHI fragment between the SpeI and BamHI sites of pCGNNZFHD1. A sample of pCGNNZFHD1-FKBPx3 has been deposited with the American Type Culture Collection under ATCC Accession No. 97399.)

| Primers: | | |
|---|---|---|
| 5'Xba/Zif | 5'ATGCTCTAGAGAACGCCCATATGCTGGCCCT | [SEQ ID NO: 4] |
| 3'Zif + G | 5'ATGCGCGGCCGCCGCCTGTGTGGGTGCGGATGTG | [SEQ ID NO: 5] |
| 5'Not OctHD | 5'ATGCGCGGCCGCAGGAGGAAGAAACGCACCAGC | [SEQ ID NO: 6] |
| Spe/Bam 3'Oct | 5'GCATGGATCCGATTCAACTAGTGTTGATTCTTTTTTCTTTCTGGCGGCG | [SEQ ID NO: 7] |

To generate C-terminal fusions of FRB domain(s) with the chimeric DNA binding protein ZFHD1, the XbaI-BamHI fragments encoding 1, 2, 3 and 4 copies of FRB were recovered from the GAL4 fusion vectors and ligated into Spe-BamHI digested pCGNN-ZFHD1 to yield pCGNN-ZFHD1-1FRB, pCGNN-ZFHD1-2FRB etc. Constructs were verified by restriction analysis and/or DNA sequencing.

To examine the effect of introducing additional 'linker' polypeptide between ZFHD1 and a C-terminal FRB domain, FRAP fragments encoding extra sequence N-terminal to FRB were cloned as ZFHD1 fusions. XbaI-BamHI fragments encoding FRAP$_a$, FRAP$_b$, FRAP$_c$, FRAP$_d$ and FRAP$_e$ were excised from the vectors pCGNN-GAL4-FRAP$_a$, pCGNN-GAL4-FRAP$_b$ etc and ligated into SpeI-BamHI digested pCGNN-ZFHD1 to yield the vectors pCGNN-ZFHD1-FRAP$_a$, pCGNN-ZFHD1-FRAP$_b$, etc. Vectors encoding fusions of ZFHD1 to 2, 3 and 4 C-terminal copies of FRAP$_e$ were also constructed by isolating XbaI-BamHI fragments encoding 2FRAP$_e$, 3FRAP$_e$ and 4FRAP$_e$ from pCGNN-GAL4-2FRAP$_e$, pCGNN-GAL4-3FRAP$_e$ and pCGNN-GAL4-4FRAP$_e$ and ligating them into SpeI-BamHI digested pCGNN-ZFHD1 to yield the vectors pCGNN-ZFHD1-2FRAP$_e$, pCGNN-ZFHD1-3FRAP$_e$ and pCGNN-ZFHD1-4FRAP$_e$. All constructs were verified by restriction analysis.

Vectors were also constructed that encode N-terminal fusions of FRB domain(s) with ZFHD1. XbaI-BamHI fragments encoding 1, 2, 3 and 4 copies of FRAP$_e$ were isolated from pCGNN-GAL4-1FRAP$_e$, pCGNN-GAL4-2FRAP$_e$ etc and ligated into XbaI-BamHI digested pCGNN to yield the plasmids pCGNN-1FRAP$_e$, pCGNN-2FRAP$_e$ etc. These vectors were then digested with SpeI and BamHI, and an XbaI-BamHI fragment encoding ZFHD1 (isolated from pCGNN-ZFHD1) ligated in to yield the constructs pCGNN-1FRAP$_e$-ZFHD1, pCGNN-2FRAP$_e$-ZFHD1 etc, which were verified by restriction analysis.

(d) Constructs Encoding FRAP-p65 Activation Domain Fusions

To generate fusions of FRB domain(s) with the activation domain of the human NF-kB p65 subunit (hereafter designated p65), two fragments were amplified by PCR from the plasmid pCG-p65. Primers 9 (p65/5' Xba) and 11 (p65 3' Spe/Bam) amplify the coding sequence for amino acids 450–550, and primers 10 (p65/361 Xba) and 11 amplify the coding sequence for amino acids 361–550, both flanked by 5' XbaI and 3' SpeI/BamHI sites. PCR products were digested with XbaI and BamHI and cloned into XbaI-BamHI digested pCGNN to yield pCGNN-p65(450–550) and pCGNN-p65(361–550). The constructs were verified by restriction analysis and DNA sequencing.

The 100 amino acid P65 transcription activation sequence is encoded by the following linear sequence:

CTGGGGGCCTTGCTTGGAACAGCACA-
  GACCCAGCTGTGTTCACAGACCTG-
  GCATCCGTCGACAACTCCGAGTTTCA

GCAGCTGCTGAACCAGGGCCCAGAGGC-
  CCCCCACACAACTGAGCCCATGCTGATG-
  GAGTACCCTGAGGCTATAA

CTCGCCTAGTGACAGGGGCCCAGAGGC-
  CCCCCGACCCAGCTCCTGCTC-
  CACTGGGGGCCCCGGGGCTCCCCAATGGC

CTCCTTTCAGGAGATGAAGACTTCTC-
  CTCCATTGCGGACATGGACTTCTCAGC-
  CCTGCTGAGTCAGATCAGCTCC         [SEQ ID NO: 8]

The more extended p65 transcription activation domain (351–550) is encoded by the following linear sequence:

GATGAGTTTCCACCCATGGTGTTTCCT-
  TCTGGCAGATCAGCCAGGCCTCGGCCT-
  TGGCCCCGGCCCCTCCCCAAGT

CCTGCCCCAGGCTCCAGCCCCTGCCCCT-
  GCTCCAGCCATGGTATCAGCTCTGGC-
  CCAGGCCCCAGCCCCTGTCCCAG

TCCTAGCCCCAGGCCCTCCTCAGGCT-
  GTGGCCCCACCTGCCCCCAAGCCCAC-
  CCAGGCTGGGGAAGGAACGCTGTCA

GAGGCCCTGCTGCAGCTGCAGTTTGAT-
  GATGAAGACCTGGGGGCCTTGCTTG-
  GCAACAGCACAGACCCAGCTGTGTT

CACAGACCTGGCATCCGTCGACAACTC-
  CGAGTTTCAGCAGCTGCTGAAC-
  CAGGGCATACCTGTGGCCCCCCACACAA

CTGAGCCCATGCTGATGGAGTACCCT-
  GAGGCTATAACTCGCCTAGTGACAGC-
  CCAGAGGCCCCCCGACCCAGCTCCT

GCTCCACTGGGGGCCCCGGGGCTC-
  CCCAATGGCCTCCTTTCAGGAGATGAA-
  GACTTCTCCTCCATTGCGGACATGGA

CTTCTCAGCCCTGCTGAGTCAGATCAGC
  TCCTAA                          [SEQ ID NO: 9]

To generate N-terminal fusions of FRB domain(s) with portions of the p65 activation domain, plasmids pCGNN-1FRB, pCGNN-2FRB etc were digested with SpeI and BamHI. An XbaI-BamHI fragment encoding p65 (450–550) was isolated from pCGNN-p65(450–550) and ligated into the SpeI-BamHI digested vectors to yield the plasmids pCGNN-1FRB-p65(450–550), pCGNN-2FRB-p65 (450–550) etc. The construct pCGNN-1FRB-p65(361–550) was made similarly using an XbaI-BamHI fragment isolated from pCGNN-p65(361–550). These constructs were verified by restriction analysis.

To examine the effect of introducing additional 'linker' polypeptide between the p65 activation domain and an N-terminal FRB domain, FRAP fragments encoding extra sequence C-terminal to FRB were cloned as p65 fusions. XbaI-BamHI fragments encoding FRAP$_a$, FRAP$_b$, FRAP$_f$, FRAP$_g$ and FRAP$_h$ were excised from the vectors pCGNN-GAL4FRAP$_a$, pCGNN-GAL4-FRAP$_b$ etc and ligated into XbaI-BamHI digested pCGNN to yield the vectors pCGNN-FRAP$_a$, pCGNN-FRAP$_b$, etc. These plasmids were then digested with SpeI and BamHI, and a XbaI-BamHI fragment encoding p65 (amino acids 450–550) ligated in to yield the five vectors pCGNN-FRAP$_a$-p65, pCGNN-FRAP$_b$-p65, etc, which were verified by restriction analysis.

Vectors encoding fusions of p65 to 1 and 3 N-terminal copies of FRAP$_e$ were also prepared by digesting pCGNN-1FRAP$_e$ and pCGNN-3FRAP$_e$ with SpeI and BamHI. XbaI-BamHI fragments encoding p65(450–550) and p65 (361–550) (isolated from pCGNN-p65(450–550) and pCGNN-p65(361–550)) were then ligated in to yield the vectors pCGNN-1FRAP$_e$-p65(450–550), pCGNN-3FRAP$_e$-p65(450–550), pCGNN-1FRAP$_e$-p65(361–550) and pCGNN-3FRAP$_e$-p65(361–550). All constructs were verified by restriction analysis.

Vectors were also constructed that encode C-terminal fusions of FRB domain(s) with portions of the p65 activation domain. Plasmids pCGNN-p65(450–55b) and pCGNN-p65(361–550) were digested with SpeI and BamHI, and XbaI-BamHI fragments encoding 1 and 3 copies of FRAP$_e$ (isolated from pCGNN-GAL4-1FRAP$_e$ and pCGNN-GAL4-3FRAP$_e$) and 1 copy of FRB (isolated from pCGNN-GAL4-1FRB) ligated in to yield the plasmids pCGNN-p65 (450–550)-1FRAP$_e$, pCGNN-p65(450–550)-3FRAP$_e$, pCGNN-p65(361–550)-1FRAP$_e$, pCGNN-p65(361–550)-3FRAP$_e$, pCGNN-p65(450–550)-1FRB and pCGNN-p65(361–550)-1FRB. All constructs were verified by restriction analysis.

(e) Further Constructs

Other constructs can be made analogously with the above procedures, but using alternative portions of the FRAP sequence. For example, primers 12 and 13 are used to amplify the entire coding region of FRAP. Primers 1 and 13, 6 and 13, and 5 and 13, are used to amplify three fragments encompassing the FRB domain and extending through to the C-terminal end of the protein (including the lipid kinase homology domain). These fragments differ by encoding different portions of the protein N-terminal to the FRB domain. In each case, RT-PCR is used as described above to amplify the regions from human thymus RNA, the PCR products are purified, digested with XbaI and SpeI, ligated into XbaI-SpeI digested pCGNN, and verified by restriction analysis and DNA sequencing.

an NcoI site encompassing the ATG followed by SpeI and BamHI sites. To facilitate cloning, the sequence around the initiating ATG of pCGNN-ZFHD1-3FKBP was mutated to an NcoI site and the XbaI site was mutated to a NheI site using the oligonucleotides 5'-GAATTCCTAGAAGCGA<u>CCATGG</u>CTT
   CTAGC-3'  [SEQ ID NO: 29]

and

5'-GAAGAGAAAGGTG<u>GCTAGC</u>GAACGCC
   CATAT-3'  [SEQ ID NO: 30]

```
                      (f) Primer sequences 1 5'GCATGTCTAGAGAGATGTGGCATGAAGGCCTGGAAG         [SEQ ID NO: 10]
 2 5'GCATCACTAGTCTTTGAGATTCGTCGGAACACATG          [SEQ ID NO: 11]
 3 5'GCACATTCTAGAATTGATACGCCCAGACCCTTG            [SEQ ID NO: 12]
 4 5'CGATCAACTAGTAAGTGTCAATTTCCGGGGCCT            [SEQ ID NO: 13]
 5 5'GCACTATCTAGACTGAAGAACATGTGTGAGCACAGC         [SEQ ID NO: 14]
 6 5'GCACTATCTAGAGTGAGCGAGGAGCTGATCCGAGTG         [SEQ ID NO: 15]
 7 5'CGATCAACTAGTGGAAACATATTGCAGCTCTAAGGA         [SEQ ID NO: 16]
 8 5'CGATCAACTAGTTGGCACAGCCAATTCAAGGTCCCG         [SEQ ID NO: 17]
 9 5'ATGCTCTAGACTGGGGGCCTTGCTTGGCAAC              [SEQ ID NO: 18]
10 5'ATGCTCTAGAGATGAGTTTCCCACCATGGTG              [SEQ ID NO: 19]
11 5'GCATGGATCCGCTCAACTAGTGGAGCTGATCTGACTCAG      [SEQ ID NO: 20]
12 5'ATGCTCTAGACTTGGAACCGGACCTGCCGCC              [SEQ ID NO: 21]
13 5'GCATCACTAGTCCAGAAAGGGCACCAGCCAATAT           [SEQ ID NO: 22]
```

Restriction sites are underlined (XbaI=TCTAGA, SpeI= ACGAGT, BamHI=GGATCC).
(g) DNA Sequence of Representative Final Construct pCGNN-ZFHD1-1FRB respectively. An NcoI-BamHI fragment containing ZFHD1-3FKBP was then cloned downstream of pBS-IRES to create pBS-1RES-ZFHD1-3FKBP. The XbaI-BamHI fragment from this plasmid was next cloned into SpeI/BamHI-cut

```
                    12CA5 epitope
           M   A   S   S   Y   P   Y   D   V   P   D
5'gtagaagcgcgt ATG GCT TCT AGC TAT CCT TAT GAC GTG CCT GAC SV40 T NLS
  Y   A   S   L   G   G   P   S   S   P   K   K   K   R   K
 TAT GCC AGC CTG GGA GGA CCT TCT AGT CCT AAG AAG AAG AGA AAG
                             (X/S)

ZFHD1(5')
  V   S   R   E   R   P   Y   A   C   P   V   E   S   C   D...    [SEQ ID NO: 23]
 GTG TCT AGA GAA CGC CCA TAT GCT TGC CCT GTC GAG TCC TGC GA...
     XbaI

ZFHD1(3')          FRB(5')
 ...R   I   N   T   R   E   M   W   H   E   G   L   E   E...      [SEQ ID NO: 25]
 ...AGA ATC AAC ACT AGA GAG ATG TGG CAT GAA GGC CTG GAA GA...
                (S/X)

FRB (3')
  R   I   S   K   T   S   Y   *                                    [SEQ ID NO: 27]
 CGA ATC TCA AAG ACT AGT TAT TAG ggatcctgag
                SpeI           BamHI
```

Non-coding nucleotides are indicated in lower case (S/X) and (X/S) indicate the result of a ligation event between the compatible products of digestion with XbaI and SpeI, to produce a sequence that is cleavable by neither enzyme * indicates a stop codon
(h) Bicistronic Constructs The internal ribosome entry sequence (IRES) from the encephalomyocarditis virus was amplified by PCR from pWZL-Bleo. The resulting fragment, which was cloned into pBS-SK+ (Stratagene), contains an XbaI site and a stop codon upstream of the IRES sequence and downstream of it, pCGNN-1FRB-p65(361–550) to create pCGNN-1FRB-p65 (361–550)-IRES-ZFHD1-3FKBP.
C. Retroviral Vectors for the Expression of Chimeric Proteins Retroviral vectors used to express transcription factor fusion proteins from stably integrated, low copy genes were derived from pSRαMSVtkNeo (Muller et al., MCB 11:1785–92, 1991) and pSRαMSV(XbaI) (Sawyers et al., J. Exp. Med. 181:307–313, 1995). Unique BamHI sites in both vectors were removed by digesting with BamHI, filling in with Klenow and religating to produce pSMTN2 and pSMTX2, respectively. pSMTN2 expresses the Neo gene from an internal thymidine kinase promoter. A Zeocin gene (Invitrogen) will be cloned as a NheI fragment into a unique XbaI site downstream of an internal thymidine kinase promoter in pSMTX2 to yield pSNTZ. This Zeocin fragment was generated by mutagenizing pZeo/SV (Invitrogen) using the following primers to introduce NheI sites flanking the zeocin coding sequence.

Primer 1 5'-GCCATGGTGGCTAGCCTATA
    GTGAG                                        [SEQ ID NO: 31]

Primer 2 5'-GGCGGTGTTGGCTAGCGTC
    GGTCAG                                      [SEQ ID NO: 32]

pSMTN2 contains unique EcoRI and HindIII sites downstream of the LTR. To facilitate cloning of transcription factor fusion proteins synthesized as XbaI-BamHI fragments the following sequence was inserted between the EcoRI and HindIII sites to create pSMTN3:

```
                12CA5 epitope                                    [SEQ ID NO: 33]
                M   A   S   S   Y   P   Y   D   V   P   D
5'gaattccagaagcgcgt ATG GCT TCT AGC TAT CCT TAT GAC GTG CCT GAC SV40 T NLS
 Y   A   S   L   G   G   P   S   S   P   K   K   K   R   K
TAT GCC AGC CTG GGA GGA CCT TCT AGT CCT AAG AAG AAG AGA AAG V
GTG TCT AGA TAT CGA GGA TCC CAA GCT T
    XbaI            BamHI   HindIII
```

The equivalent fragment is inserted into a unique EcoRI site of pSMTZ to create pSMTZ3 with the only difference being that the 3' HindIII site is replaced by an EcoRI site.

pSMTN3 and pSMTZ3 permit chimeric transcription factors to be cloned downstream of the 5' viral LTR as XbaI-BamHI fragments and allow selection for stable integrants by virtue of their ability to confer resistance to the antibiotics G418 or Zeocin respectively.

To generate the retroviral vector SMTN-ZFHD1-3FKBP, pCGNN-ZFHD1-3FKBP was first mutated to add an EcoRI site upstream of the first amino acid of the fusion protein. An EcoRI-BamHI(blunted) fragment was then cloned into EcoRI-HindIII(blunted) pSRαMSVtkNeo (ref. 51) so that ZFHD1-31 KBP was expressed from the retroviral LTR.

Example 2
Rapamycin-dependent Transcriptional Activation

Figure 3A:
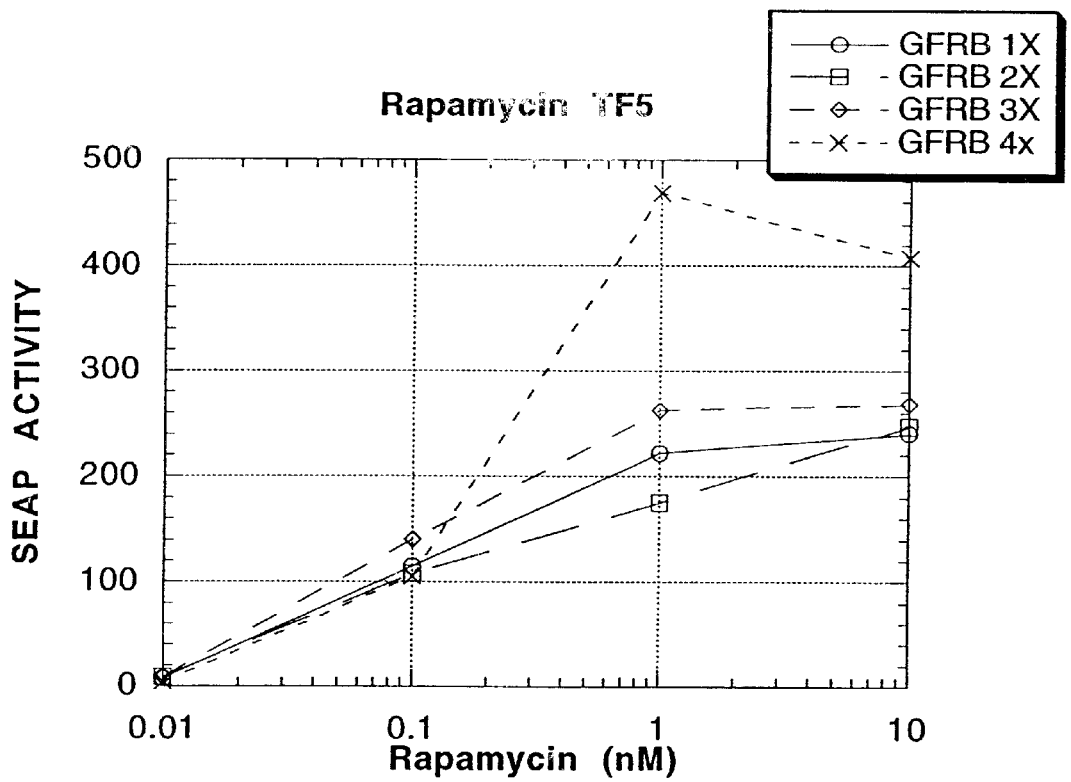
FIG. 3 compares results obtained in transcription assays using constructs with various multiples and configurations of FRAP and FKBP domains. (A) Indicates that.in this system, four copies of the FRB domain fused to the Gal4 DNA binding domain activated the stably integrated reporter gene more strongly than other corresponding fusion proteins with fewer FRB domains. (B) A single copy of FRB fused to p65 activation domain activated the reporter gene significantly more strongly than corresponding fusion proteins containing 2 or more copies of FR3.

Our previous experiments showed that three copies of FKBP fused either to a Gal4 DNA binding domain or a transcription activation domain activated both the stably integrated or transiently transfected reporter gene more strongly than corresponding fusion proteins containing only one or two FKBP domains. To evaluate this parameter with FRB fusion proteins, effector plasmids containing Gal4 DNA binding domain fused to one or more copies of an FRB domain were co-transfected with a plasmid encoding three FKBP domains and a p65 activation domain (3xFKBP-p65) by transient transfection. The data shown in FIG. 3A indicate that in this system, four copies of the FRB domain fused to the Gal4 DNA binding domain activated the stably integrated reporter gene more strongly than other corresponding fusion proteins with fewer FRB domains.
Method HT1080 B cells were grown in MEM supplemented with 10% Bovine Calf Serum. Approximately $4\times10^5$ cells/well in a 6 well plate (Falcon) were transiently transfected by Lipofection procedure as recommended by the supplier (GIBCO, BRL). The DNA: Lipofectamine ratio used in this experiment correspond to 1:6. Cells in each well recieved 500 ng of pCGNN F3-p6, 1.9 ug of PUC 118 plasmid as carrier and 100 ng of one of the following plasmids: pCGNN Gal4-1FRB, pCGNN Gal4-2FRB, pCGNN Gal4–3FRB or pCGNN Gal4-4FRB. Following transfection, 2 ml fresh media was added and supplemented with Rapamycin to the indicated concentration. After 24 hrs, 100 ul of the media was assayed for SEAP activity as described (Spencer et al, 1993).

Figure 3B:
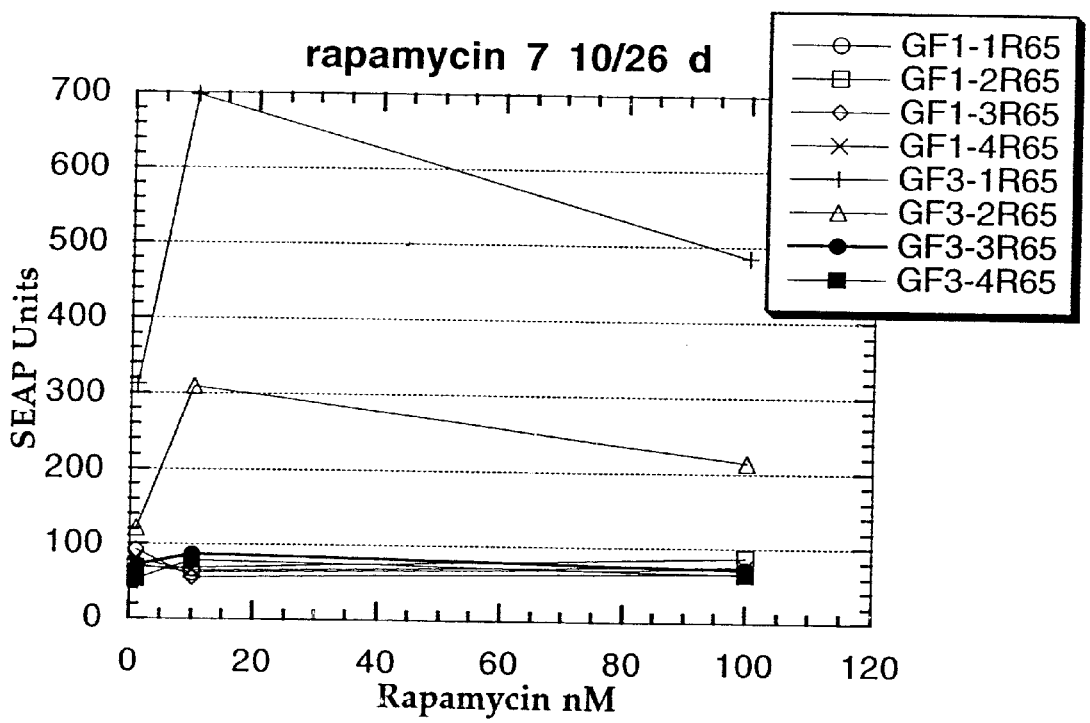

To test whether multiple FRB domains fused to a p65 activation domain results in increased transcriptional activation of the reporter gene, we co-transfected HT1080 B cells with plasmids expressing Gal4-3xFKBP and 1, 2, 3 or 4 copies of FRB fused to p65 activation domain. Surprisingly, unlike the DNA binding domain-FRB fusions, a single copy of FRB fused to p65 activation domain activated the reporter gene significantly more strongly than corresponding fusion proteins containing 2 or more copies of FRB. FIG. 3B.
Method HT1080 B cells were grown in MEM supplemented with 10% Bovine Calf Serum. Approximately $4\times10^5$ cells/well in a 6 well plate were transiently transfected by Lipofection procedure as recommended by GIBCO, BRL. The DNA:Lipofectamine ratio used correspond to 1:6. Cells in each well recieved 1.9 ug of PUC 118 plasmid as carrier, 100 ng of pCGNN-Gal4F3 and 500 ng one of the following plasmids :pCGNN1, 2, 3 or 4 FRB-p65. Following transfection, 2 ml fresh media was added and supplemented with Rapamycin to the indicated concentration. After 24 hrs, 100 ul of the media was assayed for SEAP activity as described (Spencer et al, 1993).

Similar experiments were also conducted using another stable cell line (HT1080 B14) containing the 5xGal4-IL2-SEAP reporter gene and DNA sequences encoding a fusion protein containing a Gal4 DNA binding domain and 3 copies of FKBP stably integrated. These cells were transiently transfected with effector plasmids expressing $p^65$ activation domain fused to 1 or more copies of an FRB domain. Similar to our observations with HT1080 B cells, effector plasmids expressing a single copy of FRB-p65 activation domain fusion protein activated the reporter gene more strongly than others with 2 or more copies of FRB.

Figure 4A:
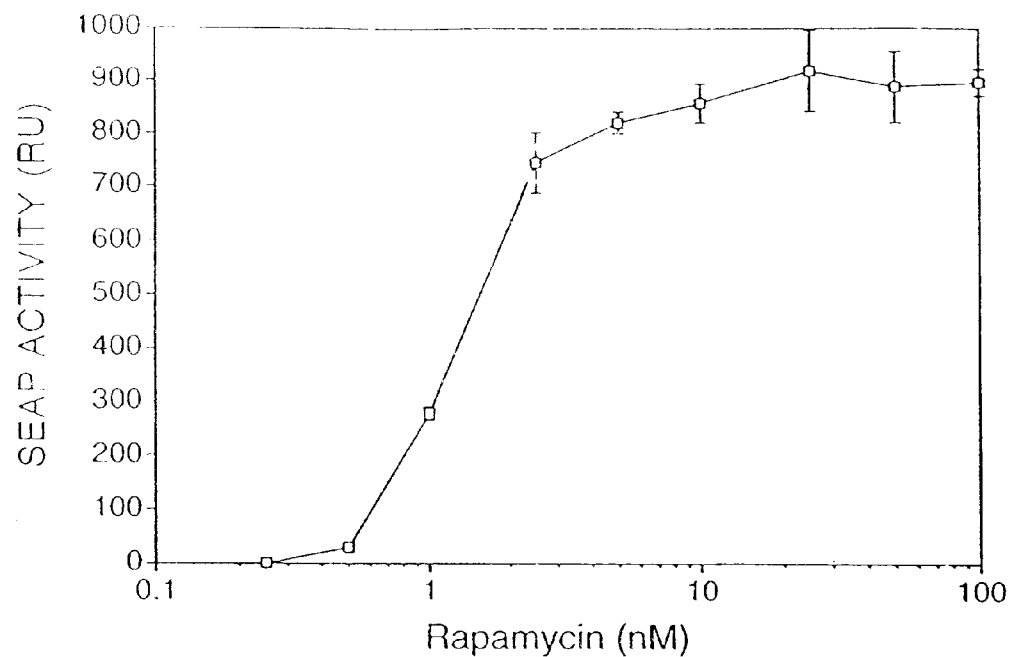
FIG. 4 depicts a dose-response curve for the rapamycin-dependent gene transcription as measured by production of secreted alkaline phosphatase activity at various rapamycin concentrations in transiently transfected cells (A, B) and in stably transfected cells (C, D). (A) Plasmids encoding ZFHD1-3FKBP and 1FRB-p65(361–450) were transfected into HT1080 cells with the pZHWTx12-CMV-SEAP reporter gene. SEAP activity secreted into the growth medium was measured following incubation with indicated concentration of rapamycin. (B) The indicated plasmids (–) were omitted and replaced with empty expression vector alone. SEAP activity was measured following incubation with or without 10 nM rapamycin as indicated. Transfections were performed in quadruplicate and mean values (in relative units)±standard deviation plotted. Rapamycin-regulated gene expression in stable cell lines. (C) The pLH-ZHWTx12-IL2-SEAP reporter gene, ZFHD1-3FKBP DNA binding domain and 1FRB-p65(361–550) activation domain were stably integrated into HT1080 cells in three steps to produce the clonal cell line HT20-6. SEAP activity secreted into the growth medium was measured following incubation of HT20-6 cells with the indicated concentration of rapamycin. Assays were performed in triplicate and mean values (in relative units)±standard deviation plotted. (D) Top: Schematic diagram of an IRES-containing plasmid used to express both 1FRB-p65(361–550) and ZFHD1-3FKBP from a single transcript. Bottom: pCGNN-1FRB-p65(361–550)-IRES-ZFHD1-3FKBP was transfected, along with a plasmid conferring resistance to zeocin, into HT1080 cells already containing the pLH-ZHWTx12-IL2-SEAP reporter gene stably integrated. Pools of zeocin-resistant clones, HT23 cells, were incubated with the indicated concentration of rapamycin and SEAP activity secreted into the growth medium measured.
Figure 4B:
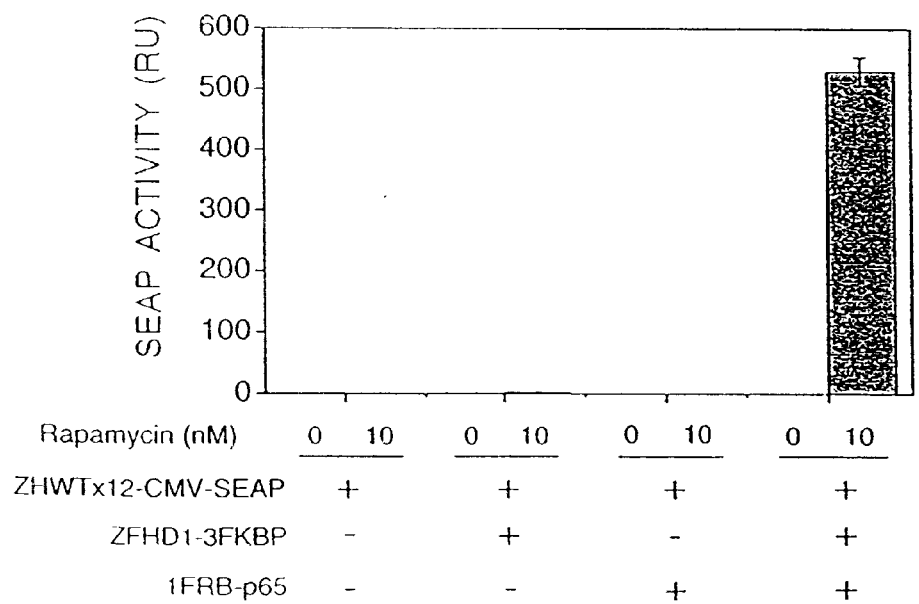

Example 3
A. Rapamycin-dependent Transcriptional Activation in Transiently Transfected Cells: ZFHD1 and p65 Fusions Human fibrosarcoma cells transiently transfected with a SEAP target gene and plasmids encoding representative ZFHD-FKBP- and FRB-p65-containing fusion proteins exhibited rapamycin-dependent and dose-responsive secretion of SEAP into the cell culture medium. See FIG. 4A. SEAP production was not detected in cells in which one or both of the transcription factor fusion plasmids was omitted, nor was it detected in the absence of added rapamycin (FIG. 4B). When all components were present, however, SEAP secretion was detectable at rapamycin concentrations as low as 0.5 nM (FIG. 4A). Peak SEAP secretion was observed at 5 nM. Similar results have been obtained when the same transcription factors were used to drive rapamycin-dependent activation of an hGH reporter gene or a stably integrated version of the SEAP reporter gene made by infection with a retroviral vector. It is difficult to determine the fold activation in response to rapamycin since levels of SEAP secretion in the absence of drug are undetectable, but it is clear that in this system there is at least a 1000-fold enhancement over background levels in the absence of rapamycin. Thus, this system exhibits undetectable background activity and high dynamic range.

Figure 5:
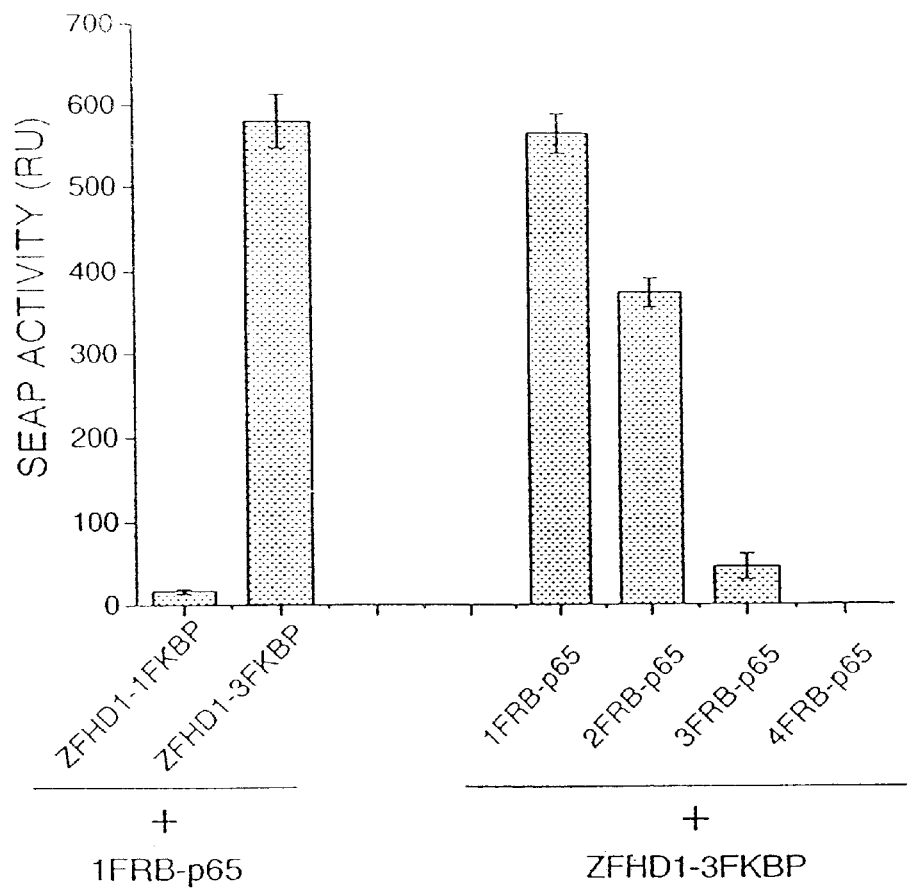
FIG. 5 depicts the results of rapamycin-dependent gene transcription experiments with various configurations of transcription factor fusion proteins. The experiments were aimed at determining an optimal configuration for rapamycin-binding domains in this system. HT1080 cells were transfected with plasmids encoding the indicated ZFHD1-FKBP and FRB-p65(450–550) fusion proteins. Transfected cells were incubated with medium containing 10 nM rapamycin and SEAP activity measured. Transfections were performed in triplicate and mean values (in relative units)±standard deviation are plotted. Immunoblot analysis showed that all fusions were expressed at similar levels with the exception of ZFHD1-1FKBP which was expressed at higher levels. Equivalent results were obtained when the amount of each plasmid transfected was varied across a wide range. Results are representative of 4 separate experiments.

Several different configurations for transcription factor fusion proteins were explored (FIG. 5). When FKBP domains were fused to ZFHD1 and FRBs to p65, optimal levels of rapamycin-induced activation ocurred when there were multiple FKBPs fused to ZFHD1 and fewer FRBs fused to p65. The preference for multiple drug-binding domains on the DNA-binding protein may reflect the capacity of these proteins to recruit multiple activation domains and therefore to elicit higher levels of promoter activity. The presence of only 1 drug-binding domain on the activation domain should allow each FKBP on ZFHD to recruit one p65. Any increase in the number of FRBs on p65 would increase the chance that fewer activation domains would be recruited to ZFHD, each one linked my multiple FRB-FKBP interactions.

Methods

HT1080 cells (ATCC CCL-121), derived from a human fibrosarcoma, were grown in MEM supplemented with non-essential amino acids and 10% Fetal Bovine Serum. Cells plated in 24-well dishes (Falcon, $6 \times 10^4$ cells/well) were transfected using Lipofectamine under conditions recommended by the manufacturer (GIBCO/BRL). A total of 300 ng of the following DNA was transfected into each well: 100 ng ZFHDx12-CMV-SEAP reporter gene, 2.5 ng pCGNN-ZFHD1-3FKBP or other DNA binding domain fusion, 5 ng pCGNN-1FRB-p65(361–550) or other activation domain fusion and 192.5 ng pUC118. In cases where the DNA binding domain or activation domain were omitted an equivalent amount of empty pCGNN expression vector was substituted. Following lipofection (for 5 hours) 500 µl medium containing the indicated amounts of rapamycin was added to each well. After 24 hours, medium was removed and assayed for SEAP activity as described (Spencer et al, Science 262:1019–24, 1993) using a Luminescence Spectrometer (Perkin Elmer) at 350 nm excitation and 450 nm emission. Background SEAP activity, measured from mock-transfected cells, was subtracted from each value.

To prepare transiently transfected HT1080 cells for injection into mice (See below), cells in 100 mm dishes ($2 \times 10^6$ cells/dish) were transfected by calcium phosphate precipitation for 16 hours (Gatz, C., Kaiser, A. & Wendenburg, R., 1991, Mol. Gen. Genet. 227, 229–237) with the following DNAs: 10 µg of ZHWTx12-CMV-hGH, 1 µg pCGNN-ZFHD1-3FKBP, 2 µg pCGNN-1FRB-p65(361–550) and 7 µg pUC118. Transfected cells were rinsed 2 times with phosphate buffered saline (PBS) and given fresh medium for 5 hours. To harvest for injection, cells were removed from the dish in Hepes Buffered Saline Solution containing 10 mM EDTA, washed with PBS/0.1% BSA/0.1% glucose and resuspended in the same at a concentration of $2 \times 10^7$ cells/ml.

Plasmids

Construction of the transcription factor fusion plasmids is described above.

pZHWTx12-CMV-SEAP

This reporter gene, containing 12 tandem copies of a ZFHD1 binding site (Pomerantz et al., 1995) and a basal promoter from the immediate early gene of human cytomegalovirus (Boshart et. al., 1985) driving expression of a gene encoding secreted alkaline phosphatase (SEAP), was prepared by replacing the NheI-HindIII fragment of pSEAP Promoter (Clontech) with the following NheI-XbaI fragment containing 12 ZFHD binding sites:

```
GCTAGCTAATGATGGGCGCTCGAGTAATGATGGGCGGTCGACTAATGATGGGCGCTCGAGTAATGATGGGCGTCTAG [SEQ ID NO: 35]

CTAATGATGGGCGCTCGAGTAATGATGGGCGGTCGACTAATGATGGGCGCTCGAGTAATGATGGGCGTCTAGCTAAT

GATGGGCGCTCGAGTAATGATGGGCGGTCGACTAATGATGGGCGCTCGAGTAATGATGGGCGTCTAGA
```

(the ZFHD1 binding sites are underlined), and the following XbaI-HindIII fragment containing a minimal CMV promoter (–54 to +45):

```
TCTAGAACGCGAATTCCGGTAGGCGTGTACGGTGGGAGGTCTATATAAGCAGAGCTCGTTTAGTGAACCGTCAGATC [SEQ ID NO: 36]

GCCTGGAGACGCCATCCACGCTGTTTTGACCTCCATAGAAGCTT
```

(the CMV minimal promoter is underlined).

pZHWTx12-CMV-hGH

Activation of this reporter gene leads to the production of hGH. It was constructed by replacing the HindIII-BamHI (blunted) fragment of pZHWTx12-CMV-SEAP (containing the SEAP coding sequence) with a HindIII (blunted)-EcoRI fragment from p0GH (containing an hGH genomnic clone; Selden et al., MCB 6:3171–3179, 1986; the BamHI and EcoRI sites were blunted together).

pZHWTx12-IL2-SEAP

This reporter gene is identical to pZHWTx12CMV-SEAP except the XbaI-HindIII fragment containing the minimal CMV promoter was replaced with the following XbaI-HindIII fragment containing a minimal IL2 gene promoter (–72 to +45 with respect to the start site; Siebenlist et al., MCB 6:3042–3049, 1986):

TCTAGAACGCGAATTC<u>AACATTTTGACACCCCCATAATATTTTTCCAGAATTAACAGTATAAATTGCATCTCTTGTT</u> [SEQ ID NO: 37]

<u>CAAGAGTTCCCTATCACTCTCTTTAATCACTACTCACAGTAACCTCAACTCCTGCCAC</u>AAGCTT (the IL2 minimal promoter is underlined).

pLH

To facilitate the stable integration of a single, or few, copies of reporter gene the following retroviral vector was constructed. pLH (LTR-hph), which contains the hygromycin B resistance gene driven by the Moloney murine leukemia virus LTR and a unique internal ClaI site, was constructed as follows: The hph gene was cloned as a HindIII-ClaI fragment from pBabe Hygro (Morganstern and Land, NAR 18:3587–96, 1990) into BamHI-ClaI cut pBabe Bleo (resulting in the loss of the bleo gene; the BamHI and HindIII sites were blunted together).

pLH-ZHWTx12-IL2-SEAP

To done a copy of the reporter gene containing 12 tandem copies of the ZFHD1 binding site and a basal promoter from the IU gene driving expression of the SEAP gene into the pLH retroviral vector, the MluI-ClaI fragment from pZHWTx12-IL2-SEAP (with ClaI linkers added) was cloned into the ClaI site of pLH. It was oriented such that the directions of transcription from the viral LTR and the internal ZFHD-IL2 promoters were the same.

pLH-G5-IL2-SEAP

To construct a retroviral vector containing 5 Gal4 sites embedded in a minimal IL2 promoter driving expression of the SEAP gene, a ClaI-BstBI fragment consisting of the following was inserted into the ClaI site of pLH such that the directions of transcription from the viral LTR and the internal Gal4-IL2 promoters were the same: A ClaI-HindIII fragment containing 5 Gal4 sites (underlined) and regions −324 to −294 (bold) and −72 to +45 of the IL2 gene (italics)

transiently transfected cells. In an attempt to rigorously quantitate background SEAP production and induction ratio in this clone, we performed a second set of assays in which the length of the SEAP assay was increased by a factor of approximately 50 to detect any SEAP activity in untreated cells. Under these conditions, mock transfected cells produced 47 arbitrary fluorescence units, while the transfected clone produced 54 units in the absence of rapamycin and over 90,000 units at 100 nM rapamycin. Thus, in this stable cell line, background gene expression was negligible and the induction ratio (7 units to 90,000 units) was greater than four orders of magnitude.

Figure 4C:
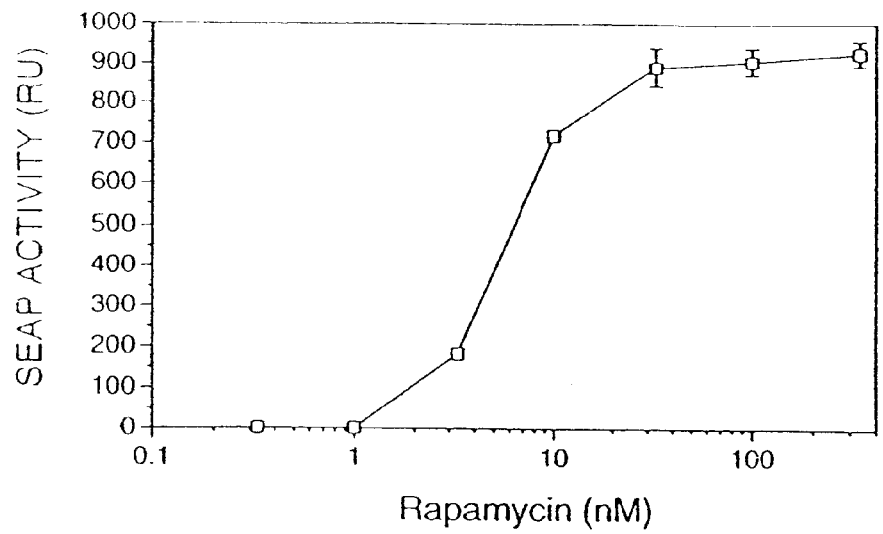
Figure 4D:
Figure 4D:
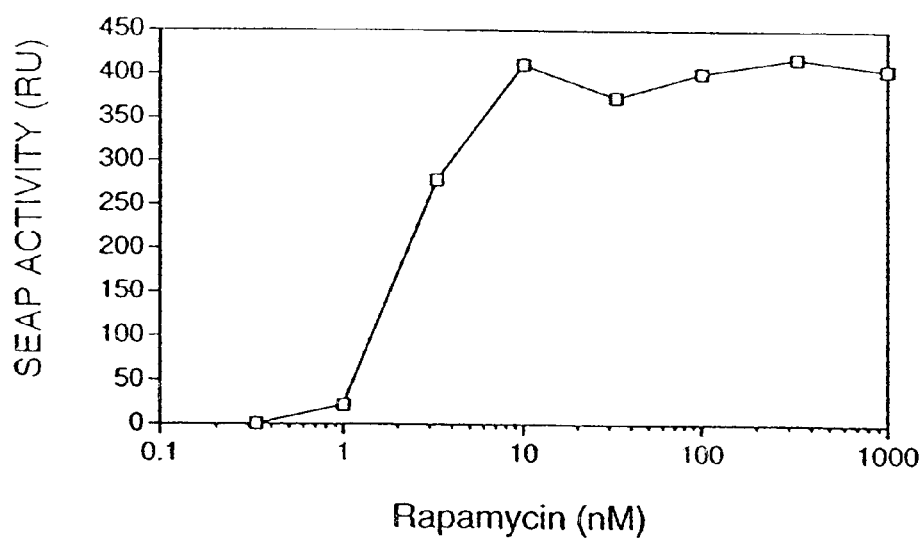

To simplify the task of stable transfection, we used a bicistronic expression vector that directs the production of both ZFHD1-3FKBP and 1FRB-p65 through the use of an internal ribosome entry sequence (IRES). This expression plasmid was cotransfected, together with a zeocin-resistance marker plasmid, into a cell line carrying a retrovirally-transduced SEAP reporter gene, and a pool of approximately fifty drug-resistant clones was selected and expanded. FIG. 4D shows that this pool of clones also exhibited rapamycin-dependent SEAP production with no detectable background and a very similar dose-response curve to that observed in transiently transfected cells. This pool would be expected to contain individual clones with performance similar to the clone studied in FIG. 4C. Thus, rapamycin-responsive gene expression can be readily obtained in both transiently and stably transfected cells. In both cases, regulation is characterized by very low background and high induction ratios.

Stable cell lines. Helper-free retroviruses containing the

5'ATCGATGTTTTCTGAGTTACTTTTGTATCCCCACCCCCCCTCGAGCTTGCATGCCTGCAGGT<u>CGGAGTAC</u> [SEQ ID NO: 38]

<u>TGTCCTCCGAGCGGAGTACTGTCCTCCGAGCGGAGTACTGTCCTCCGAGCGGAGTACT</u>

<u>GTCCTCCGAGCGCAGACTCTAGAGGATCCGAGAA</u>CATTTTGACACCCCCATAATATTTTTCCAGAATTAACAGTATA

AATTGCATCTCTTGTTCAAGAGTTCCCTATCACTCTCTTTAATCACTACTCACAGTAACCTCAACTCCTGCCACAAG

CTT, and a HindIII-BstBI fragment containing the SEAP gene coding sequence (Berger et al., Gene 66:1–10, 1988) mutagenized to add the following sequence (containing a BstB1 site) immediately after the stop codon:

5'-CCCGTGGTCCCGCGCGCCGAT [SEQ ID NO: 39]

B. Rapamycin-dependent Transcriptional Activation in Stably Transfected Cells

We conducted the following experiments to confirm that this system exhibits similar properties in stably transfected cells. We generated stable cell lines by sequential transfection of a SEAP target gene and expression vectors for ZFHD1-3FKBP and 1FRB-p65, respectively. A pool of several dozen stable clones resulting from the final transfection exhibited rapamycin-dependent SEAP production. From this pool, we characterized several individual clones, many of which produced high levels of SEAP in response to rapamycin. Results from one such done are shown in FIG. 4C. This clone produced SEAP at levels approximately forty times higher than the pool and significantly higher than reporter gene or DNA binding domain fusion were generated by transient co-transfection of 293T cells (Pear, W. S., Nolan, G. P., Scott, M. L. & Baltimore D., 1993, Production of high-titer helper-free retroviruses by transient transfection. Proc. Natl. Acad. Sci. USA 90, 8392–8396) with a Psi(−) amphotropic packaging vectorand the retroviral vectors pLH-ZHWTx12-IL2-SEAP or SMTN-ZFHD1-3FKBP, respectively. To generate a clonal cell line containing the reporter gene stably integrated, HT1080 cells infected with retroviral stock were diluted and selected in the presence of 300 µg/ml Hygromycin B. Individual clones from this and other cell lines described below were screened by transient transfection of the missing components followed by the addition of rapamycin as described above. All 12 clones analyzed were inducible and had little or no basal activity. The most responsive done, HT1080L, was selected for further study.

HT20-6 cells, which contain the pLH-ZHWTx12-IL2-SEAP reporter gene, ZFHD1-3FKBP DNA binding domain and 1FRB-p65(361–550) activation domain stably integrated, were generated by first infecting HT1080L cells with SMTN-ZFHD1-3FKBP-packaged retrovirus and selecting in medium containing 500 μg/ml G418. A strongly responsive clone, HT1080L3, was then transfected with linearized pCGNN-1FRB-p65(361–550) and pZeoSV (Invitrogen) and selected in medium containing 250 μg/ml Zeocin. Individual clones were first tested for the presence of 1FRB-p65(361–550) by western. Eight positive clones were analyzed by addition of rapamycin. All eight had low basal activity and in six of them, gene expression was induced by at least two orders of magnitude. The done that gave the strongest response, HT20-6, was selected for further analysis.

HT23 cells were generated by co-transfecting HT1080L cells with linearized pCGNN-1FRB-p65(361–550)-IRES-ZFHD1-3FKBP and pZeoSV and selecting in medium containing 250 μg/ml Zeocin. Approximately 50 clones were pooled for analysis.

For analysis, cells were plated in 96-well dishes ($1.5 \times 10^4$ cells/well) and 200 μl medium containing the indicated amounts of rapamycin (or vehicle) was added to each well. After 18 hours, medium was removed and assayed for SEAP activity. In some cases, medium was diluted before analysis and relative SEAP units obtained multiplied by the fold-dilution. Background SEAP activity, measured from untransfected HT1080 cells, was subtracted from each value.

Example 4
Rapamycin-dependent Production of hGH in Mice
In Vivo Methods: Animals, Husbandry, and General Procedures Male nu/nu mice were obtained from Charles River Laboratories (Wilmington, Mass.) and allowed to acclimate for five days prior to experimentation. They were housed under sterile conditions, were allowed free access to sterile food and sterile water throughout the entire experiment, and were handled with sterile techniques throughout. No immunocompromised animal demonstrated outward infection or appeared ill as a result of housing, husbandry techniques, or experimental techniques.

To transplant transiently transfected cells into mice, $2 \times 10^6$ transfected HT1080 cells, were suspended in 100 μl PBS/0.1% BSA/0.1% glucose buffer, and administered into four intramuscular sites (approximately 25 μl per site) on the haunches and flanks of the animals. Control mice received equivalent volume injections of buffer alone.

Rapamycin was formulated for in vivo administration by dissolution in equal parts of N,N-dimethylacetamide and a 9:1 (v:v) mixture of polyethylene glycol (average molecular weight of 400) and polyoxyethylene sorbitan monooleate. Concentrations of rapamycin, in the completed formulation, were sufficient to allow for in vivo administration of the appropriate dose in a 2.0 ml/kg injection volume. The accuracy of the dosing solutions was confirmed by HPLC analysis prior to intravenous administration into the tail veins. Some control mice, bearing no transfected HT1080 cells, received 10.0 mg/kg rapamycin. In addition, other control mice, bearing transfected cells, received only the rapamycin vehicle.

Blood was collected by either anesthetizing or sacrificing mice via $CO_2$ inhalation. Anesthetized mice were used to collect 100 μl of blood by cardiac puncture. The mice were revived and allowed to recover for subsequent blood collections. Sacrificed mice were immediately exsanguinated. Blood samples were allowed to clot for 24 hours, at 4° C., and sera were collected following centrifugation at 1000×g for 15 minutes. Serum hGH was measured by the Boehringer Mannheim non-isotopic sandwich ELISA (Cat No. 1 585 878). The assay had a lower detection limit of 0.0125 ng/ml and a dynamic range that extended to 0.4 ng/ml. Recommended assay instructions were followed. Absorbance was read at 405 nm with a 490 nm reference wavelength on a Molecular Devices microtiter plate reader. The antibody reagents in the ELISA demonstrate no cross reactivity with endogenous, murine hGH in diluent sera or native samples.

hGH Expression In Vivo

For the assessment of dose-dependent rapamycin-induced stimulation of hGH expression, rapamycin was administered to mice approximately one hour following injection of HT1080 cells. Rapamycin doses were either 0.01, 0.03, 0.1, 0.3, 1.0, 3.0, or 10.0 mg/kg. Seventeen hours following rapamycin administration, the mice were sacrificed for blood collection.

To address the time course of in vivo hGH expression, mice received 10.0 mg/kg of rapamycin one hour following injection of the cells. Mice were sacrificed at 4, 8, 17, 24, and 42 hours following rapamycin administration.

The ability of rapamycin to induce sustained expression of hGH from transplanted HT1080 cells was tested by repeatedly administering rapamycin. Mice were administered transfected HT1080 cells as described above. Approximately one hour following injection of the cells, mice received the first of five intravenous 10.0 mg/kg doses of rapamycin. The four remaining doses were given under anesthesia, immediately subsequent to blood collection, at 16, 32, 48, and 64 hours. Additional blood collections were also performed at 72, 80, 88, and 96 hours following the first rapamycin dose. Control mice were administered cells, but received only vehicle at the various times of administration of rapamycin. Experimental animals and their control counterparts were each assigned to one of two groups. Each of the two experimental groups and two control groups received identical drug or vehicle treatments, respectively. The groups differed in that blood collection times were alternated between the two groups to reduce the frequency of blood collection for each animal.

Results

Figure 6:
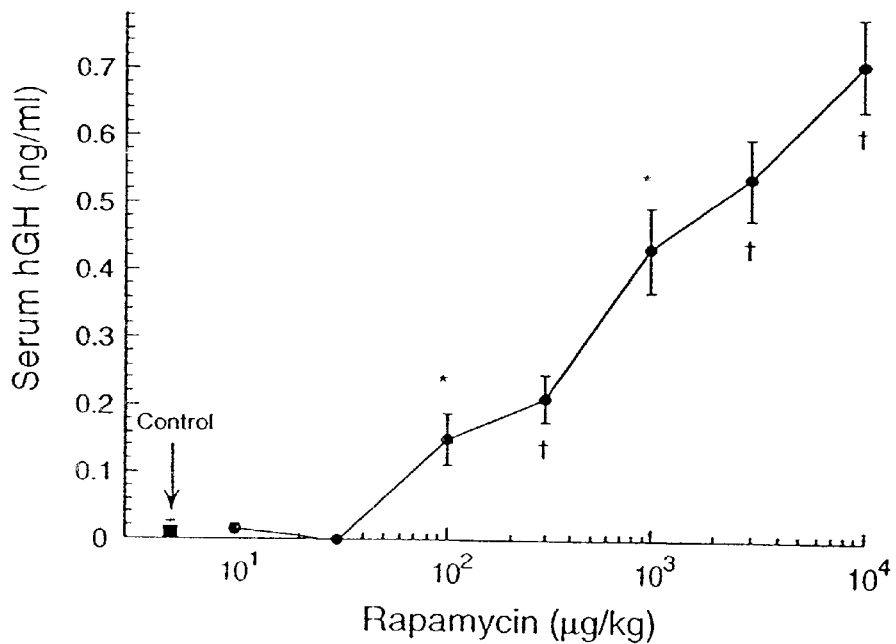
FIG. 6 demonstrates that in vivo administration of a dimerizing agent to animals into which engineered cells had been transplanted led to regulated gene expression and the production and secretion of the gene product. Transfected HT1080 cells ($2 \times 10^6$ total per animal, in four different sites) were injected intramuscularly into male nu/nu mice. Approximately one hour later, animals received the indicated concentration of intravenous rapamycin. Blood samples were collected 17 hours after rapamycin adminsitration and assayed for hGH concentration. Rapamycin treatment produced a dose-dependent increase in serum hGH (X±SEM; n=at least 5 at each dose). * represent statistical significance from each lower rapamycin dose and † represents statistical significance from rapamycin doses which are 10-fold and more lower ($p<0.05$, one-way analysis of variance and Tukey-Kramer multiple comparison testing).

Rapamycin elicited dose-responsive production of hGH in these animals (FIG. 6). hGH concentrations in the rapamycin-treated animals compared favorably with normal circulating levels in humans (0.2–0.3 ng/ml). No plateau in hGH production was observed in these experiments, suggesting that the maximal capacity of the transfected cells for hGH production was not reached. Control animals—those that received transfected cells but no rapamycin and those that received rapamycin but no cells—exhibited no detectable serum hGH. Thus, the production of hGH in these animals was absolutely dependent upon the presence of both engineered cells and rapamycin.

Figure 7:
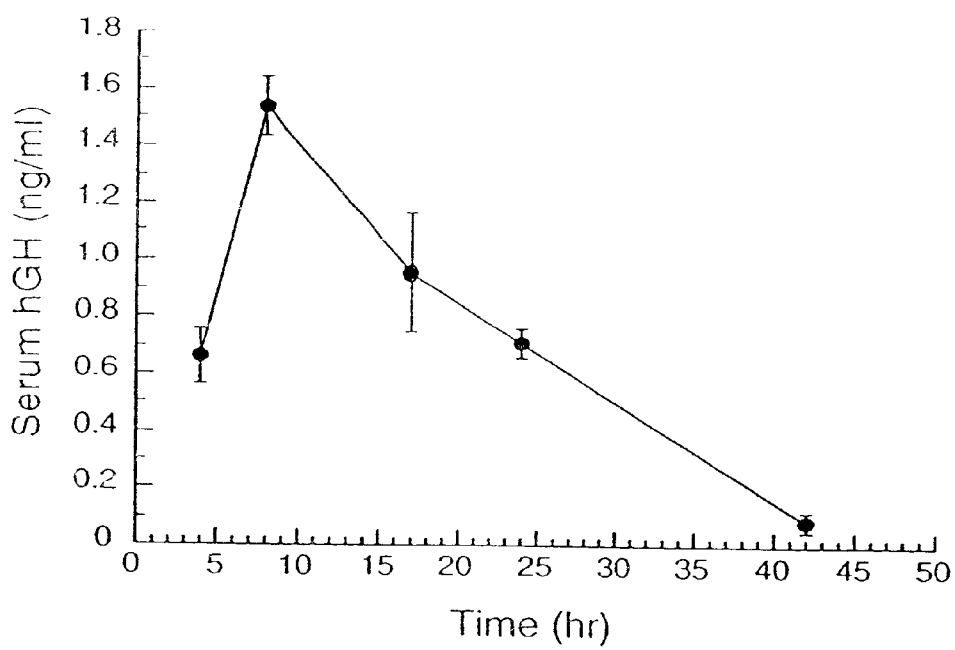
FIG. 7 demonstrates the ability of HT1080 cells, engineered as described in Example 4 (see also FIG. 6) and transplanted into mice, to produce hGH for prolonged periods of time following intravenous rapamycin administration. Mice were treated with 10.0 mg/kg rapamycin following transplantation of transfected HT1080 cells. Blood samples were collected at 4, 8, 17, 24, and 42 hours following rapamycin administration and serum hGH levels were measured (X±SEM, n=at least 4 per point). The terminal half-life of the hGH response was calculated to be 11.4 hours.

The presence of significant levels of hGH in the serum 17 hours after rapamycin administration was noteworthy, because hGH is cleared from the circulation with a half-life of less than four minutes in these animals. This observation suggested that the engineered cells continued to secrete hGH for many hours following rapamycin treatment. To examine the kinetics of rapamycin control of hGH production, we treated animals with a single dose of rapamycin and then measured hGH levels at different times thereafter. Serum hGH was observed within four hours of rapamycin treatment, peaked at eight hours (at over one hundred times the sensitivity limit of the hGH ELISA), and remained detectable 42 hours after treatment (FIG. 7). hGH concentration decayed from its peak with a half-life of approximately 11 hours. This half-life is several hundredfold longer than the half-life of hGH itself and approximately twice the half-life of rapamycin (4.6 hr) in these animals. The slower decay of serum hGH relative to rapamycin could reflect the presence of higher tissue concentrations of rapamycin in the vicinity of the implanted cells. Alternatively, persistence of hGH production from the engineered cells may be enhanced by the stability of hGH mRNA.

Figure 8:
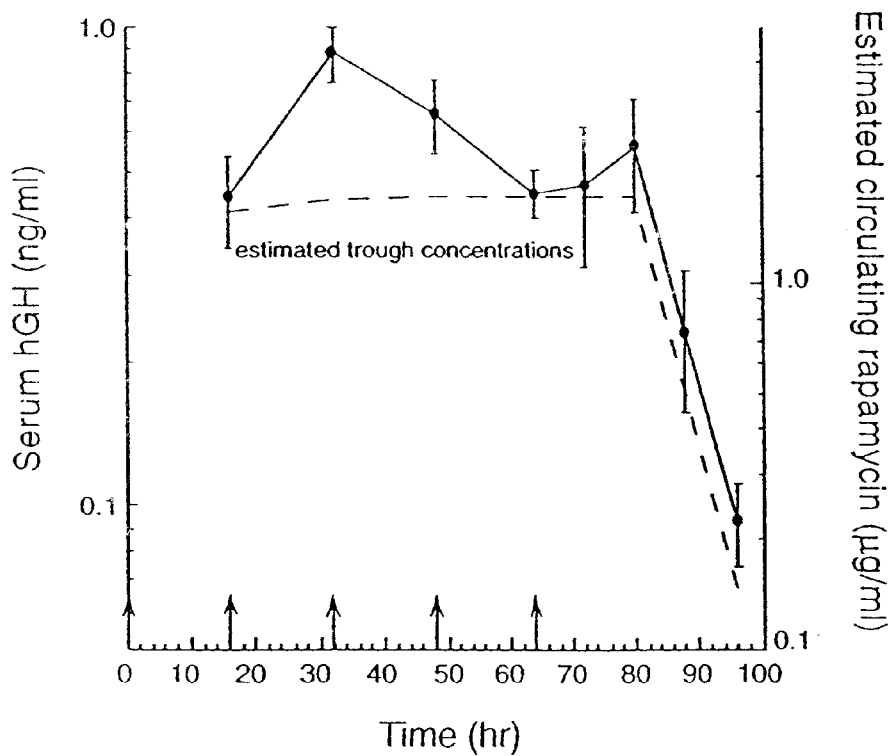
FIG. 8 demonstrates the ability of transplanted engineered cells to be restimulated by a second rapamycin administration after the effects of the first administration have dissipated. Rapamycin (10.0 mg/kg) was administered on multiple occasions (arrows). Data are plotted as X±SEM, n=4 to 9 mice per point (solid line). Concentrations of rapamycin estimated to be circulating throughout the experiment are also plotted (dashed line). The flat, horizontal line designated as "estimated trough rapamycin concentrations" represent the steady state trough concentrations of rapamycin that were calculated from the rapamycin pharmacokinetics and the 16 hour dosing interval used in the present study. The descending line, which begins at 80 hours, represents the estimated circulating rapamycin concentrations which show an elimination half-life of 4.6 hours.
Figure 9A:
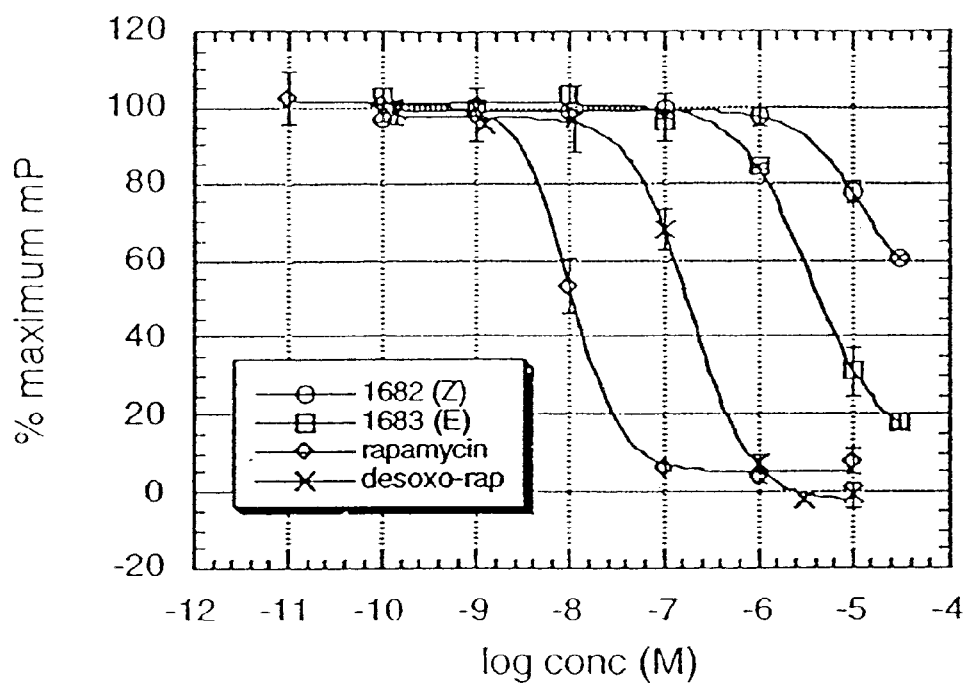
FIGS. 9A–9C shows the results of analysis of various rapamycin C24 oximes (prepared as described in Example 5) for FKBP binding affinity using the competitive FP assay described in Example 6. Results show the mean±SD of two independent experiments (the C24 methyl oxime plot shows a single experiment)
Figure 9A:
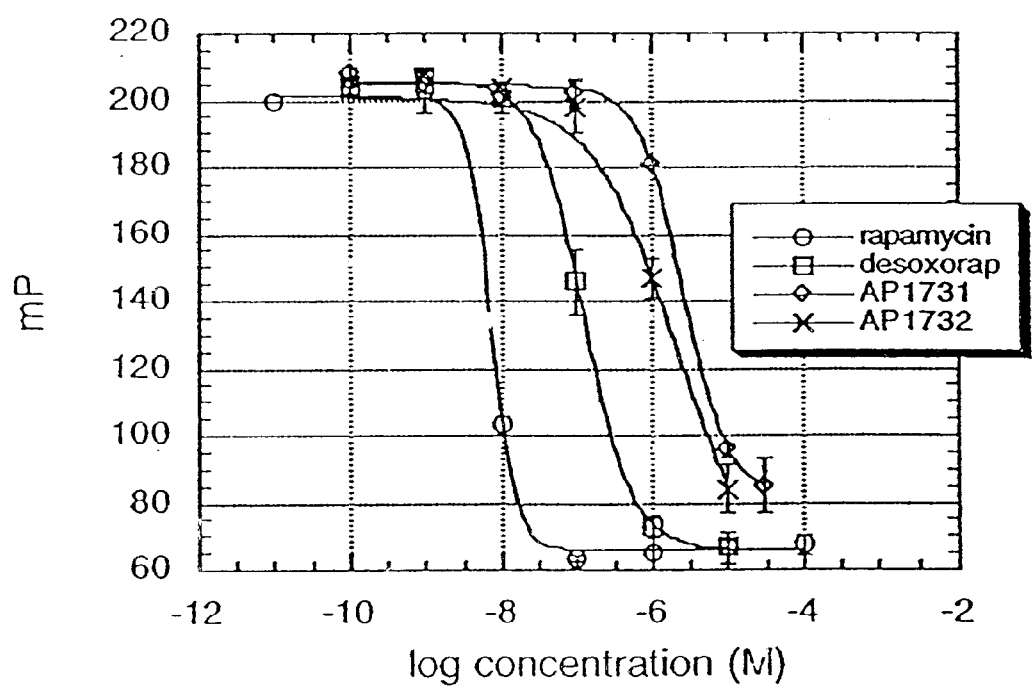
Figure 9B:
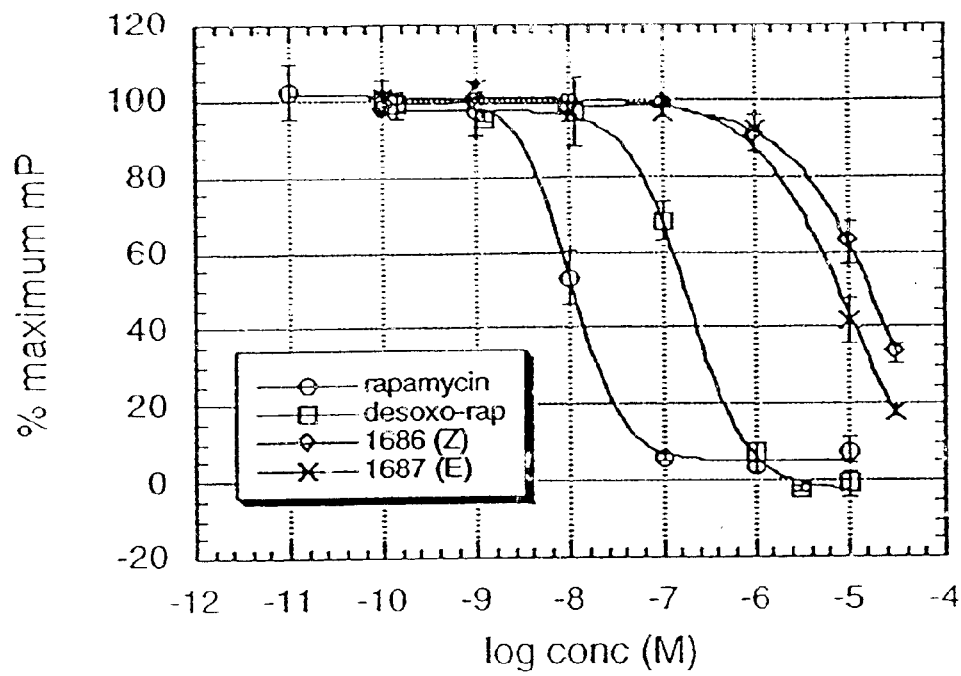
Figure 9B:
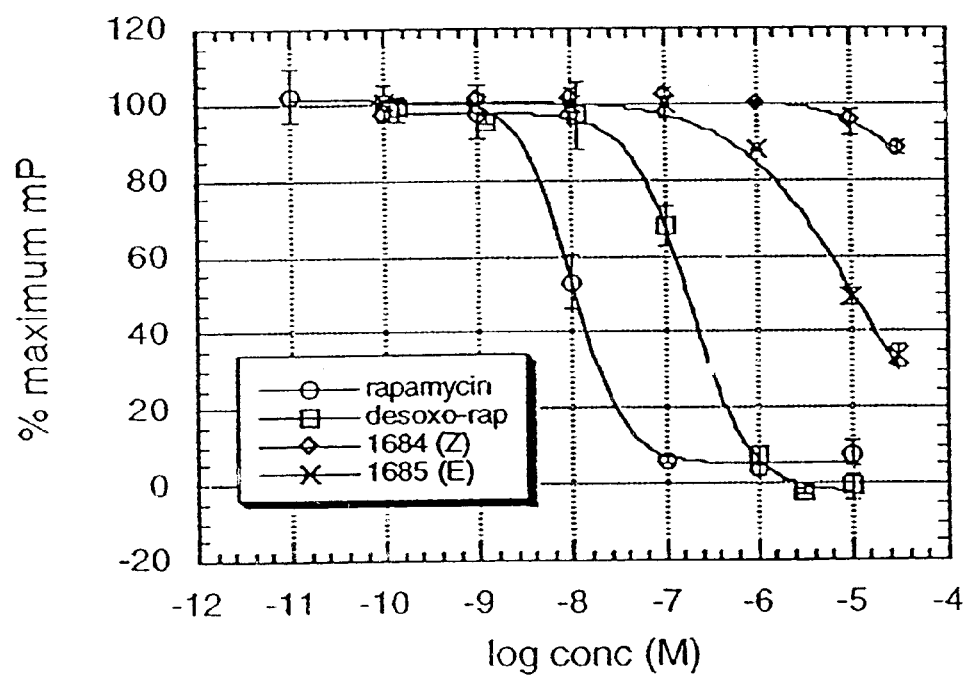
Figure 9C:
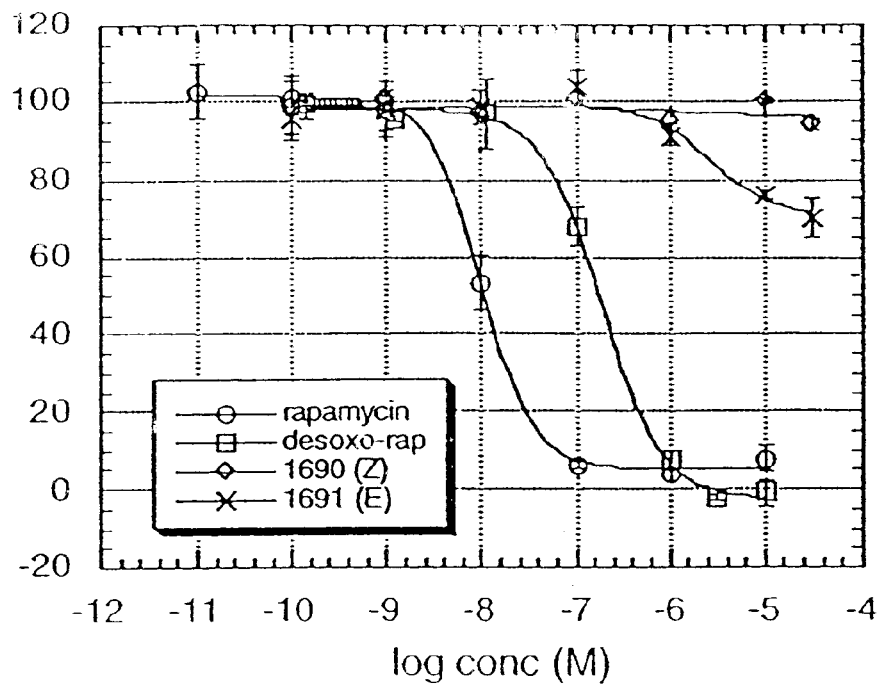
Figure 9C:
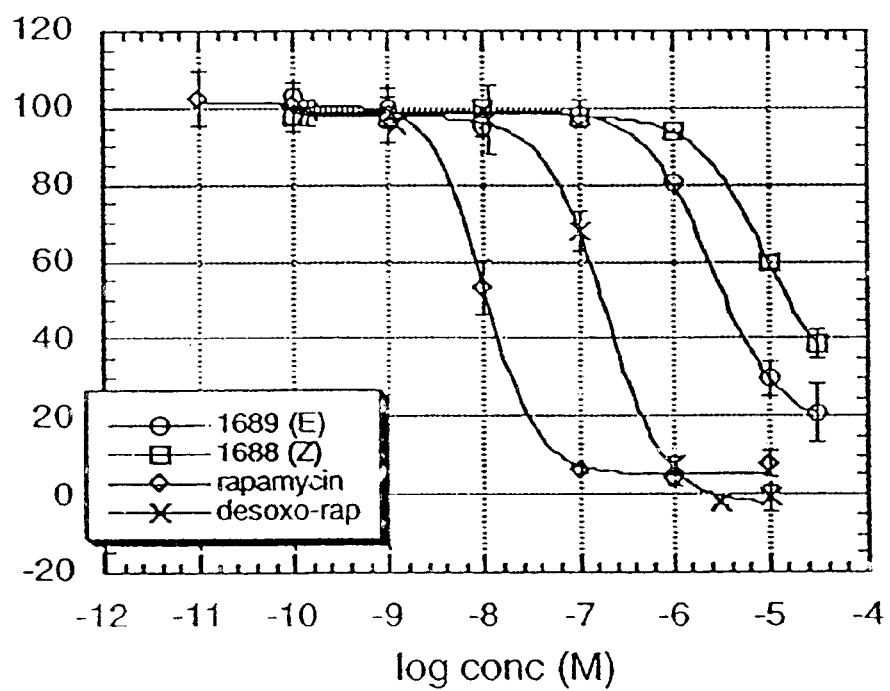
Figure 10:
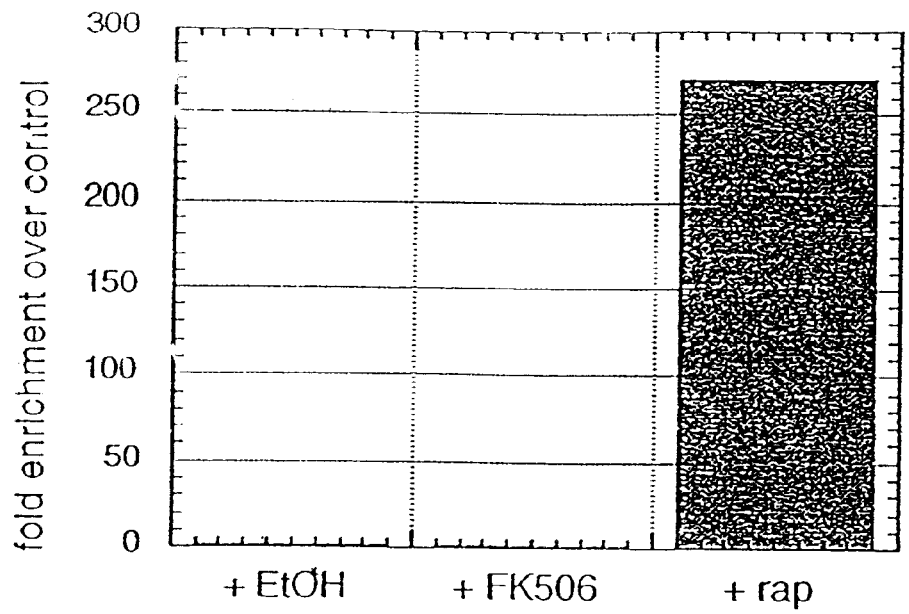
FIG. 10 shows the specific enrichment of phagemids displaying FRAP (amino acids 2015–2114) after incubating with His6-tagged FKBP in the presence of the indicated compounds, followed by capture on Ni-NTA agarose and elution. Results are expressed as the ratio of FRAP phagemids to a non-displaying control phagemid, where the ratio before sorting=1. Experimental details in Example 7.
Figure 11:
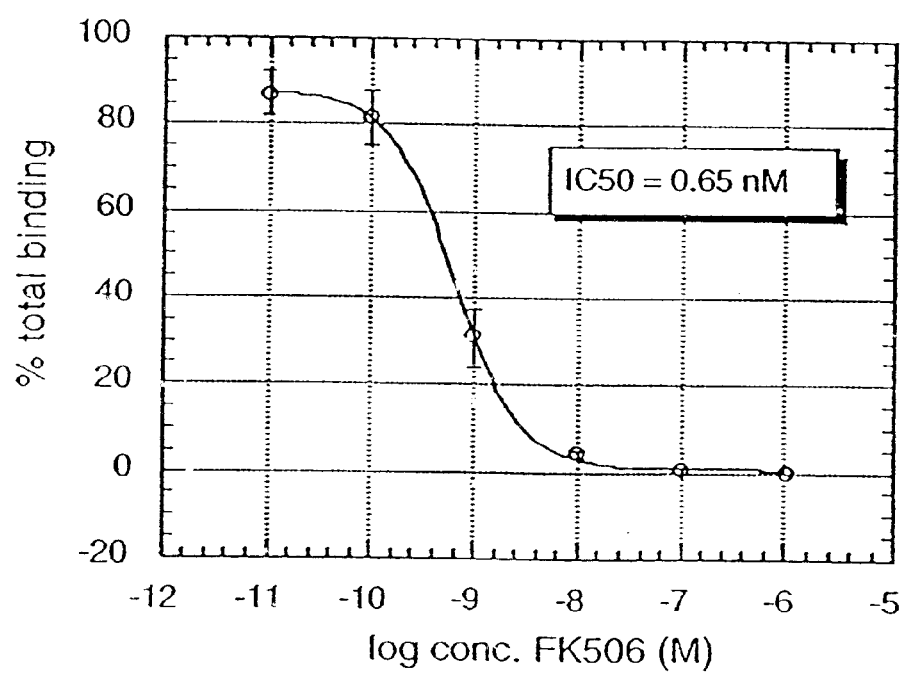
FIG. 11. FKBP display phage was prepared and its binding properties analyzed by ELISA as described in Example 7. Aliquots of FKBP phage particles were incubated with varying concentrations of FK506 and then applied to a well coated with biotinylated FK506 bound to streptavidin. Phage binding was visualized by anti-phage polyclonal antibody conjugated to HRP. Error bars represent the SD of triplicate determinations. The results show that FKBP displayed on phage interacts with FK506 with a value essentially identical to that of the soluble protein (IC50=0.65 nM).
Figure 12A:
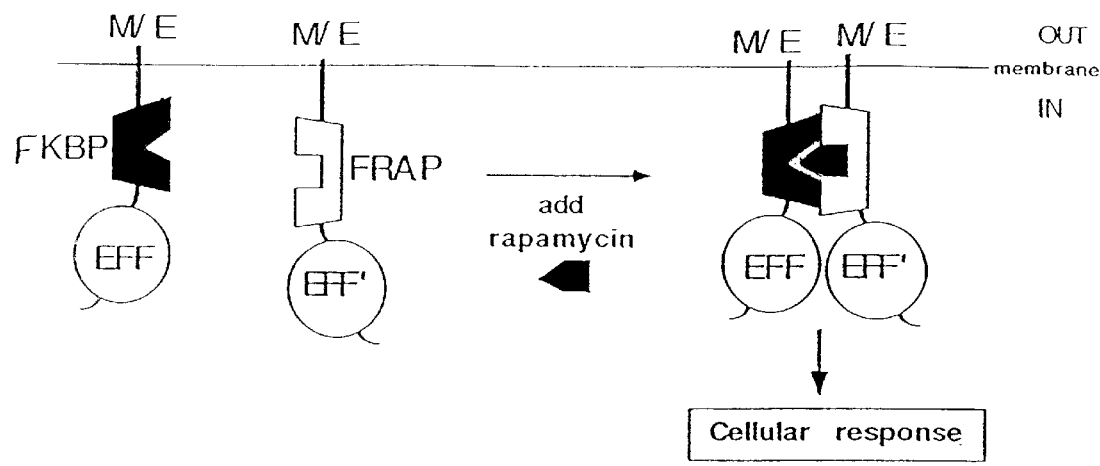
FIG. 12(A) depicts "two-component" oligomerization.
Figure 12B:
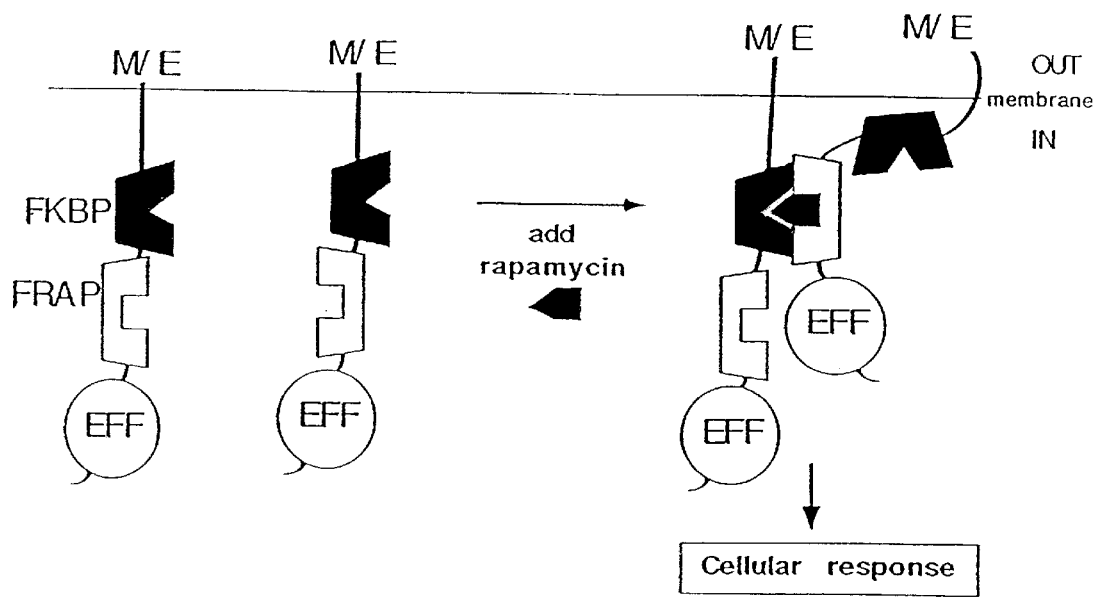
FIG. 12(B) depicts "one-component" oligomerization. M/E denotes a myristoylation motif or extracellular receptor domain(s) that locate the chimeric constructs in the membrane; EFF denotes effector domains that elicit a cellular response upon oligomerization (for example, a polypeptide including the death domain of FAS). Both configurations can be used to homodimerize or heterodimerize effector domains (heterodimerization is illustrated in (A) by the designations EFF and EFF'). Note that many other possible configurations can be envisaged: in particular, the order and number of each domain can be varied as appropriate.

Interestingly, administration of a second dose of rapamycin to these animals at 42 hr resulted in a second peak of serum hGH, which decayed with similar kinetics indicating that the engineered cells retained the ability to respond to rapamycin for at least two days. Therefore, to ascertain the ability of this system to elevate and maintain circulating hGH concentrations, we performed an experiment in which animals received multiple doses of rapamycin at 16-hour intervals. This interval corresponds to the time required for hGH levels to peak and then decline approximately halfway. According to this regimen, rapamycin concentration is predicted to approach a steady-state trough concentration of 1.7 µg/ml after two doses (shown as dotted line in FIG. 8). hGH levels should also approach a steady state trough concentration following the second dose. FIG. 8 shows that treated animals indeed held relatively stable levels of circulating hGH in response to repeated doses of rapamycin. After the final dose, hGH levels remained constant for 16 hours and then declined with a similar half-life as rapamycin (6.8 hours for hGH versus 4.6 hours for rapamycin). These data suggest that upon multiple dosing, circulating rapamycin imparts tight control over the secretion of hGH from transfected cells in vivo. In particular, it is apparent that protein production is rapidly terminated upon withdrawal of drug.

Discussion

These experiments demonstrate the feasibility of controlling the production of a secreted therapeutic protein from genetically engineered cells using a small-molecule drug. This system has many of the features required for use in human gene and cell therapy. It is characterized by very low background activity and high induction ratio. It functions independently of host physiology or any cell-type-specific factors. It is composed completely of human proteins. The controlling drug is well behaved in vivo and orally bioavailable.

With a system of this general design, it should be possible to provide stable and precisely titrated doses of secreted therapeutic proteins from engineered cells in vivo. Intermittent and pulsatile dosing should also be feasible. A considerable advantage of protein delivery from engineered cells under small-molecule control is that the rate of protein production at any given time is a function of the circulating concentration of the small-molecule drug. Therefore, the apparent pharmacokinetics of a therapeutic protein such as hGH can be dramatically altered. In our experiments, for example, the kinetics of circulating hGH delivered from engineered cells following a single administration of rapamycin are markedly different from those observed following a single administration of recombinant protein. hGH administered to mice intravenously is cleared with a half-time of a few minutes, whereas hGH levels from engineered cells induced with rapamycin decayed with a half-time of approximately eleven hours. Even in humans, where the half-time for hGH clearance is approximately twenty minutes, injections must be given every other day, and serum hGH levels fluctuate dramatically. It is likely that protein delivery from engineered cells under precise pharmacologic control will lead to more effective therapy, particularly for proteins with poor pharmacokinetics or low therapeutic index.

The use of a small-molecule drug to link a DNA-binding domain and activation domain is an effective strategy for regulating gene expression in vivo. One especially attractive feature is that the system is entirely modular, allowing each component to be optimized and engineered independently. In contrast to bacterial repressors, which rely on relatively subtle allosteric intramolecular interactions to control DNA-binding activity, the dimerization strategy can be adapted to virtually any DNA-binding and activation domain. We have used here a DNA-binding domain of defined structure which readily supports rational engineering of DNA-binding affinity and new recognition specificities. Similarly, activation domains can be engineered for maximal potency and other suitable properties. Indeed, the engineered transcription factors used in these experiments elicit very high levels of gene expression relative to conventional promoter/enhancer systems, and further enhancements in either domain can be readily incorporated. The ability to introduce engineered transcription factors dedicated to the transcription of a single target gene provides opportunities to achieve lower backgrounds and substantially higher levels of gene expression in vivo than conventional expression vectors.

We have also chosen to construct our regulated transcription factors from human proteins to minimize the potential for recognition by the immune system. It has been reported that autologous T cells expressing a fusion protein composed of bacterial hygromycin phosphotransferase and herpes virus thymidine kinase were effectively recognized and eliminated by host cytotoxic T cells, even in AIDS patients with debilitated immune systems (Riddell, S. R., et al. T-cell mediated rejection of gene-modified HIV-specific cytotoxic T lymphocytes in HIV-infected patients. *Nature Med.* 2, 216–223 (1996). This observation suggests that the risk of immune recognition of heterologous proteins in engineered cells is a real one and that, therefore, the use of human proteins for performing regulatory functions in human cells is prudent. Although each individual component of our transcription factor fusion proteins is human in sequence, each protein contains junction peptides which could potentially be recognized as foreign. These junctions may be designed or selected, however, to minimize their presentation to the immune system, as discussed previously.

The principal limitation of rapamycin-based systems is the native biological activity of rapamycin, which, through inhibition of FRAP activity blocks cell-cycle progression leading to immunosuppression in vivo. However, our experiments demonstrate that one can obtain physiologically relevant levels of therapeutic protein such as hCH at sub-immunosuppressive doses of rapamycin (less that 1 mg/kg). Moreover, the ability to introduce substituents onto the rapamycin molecule that abolish binding to either FKBP or FRAP provides easy access to rapamycin analogs completely devoid of immunosuppressive activity. Rapalogs devoid of native biological activity but retaining rapamycin's attractive pharmacological properties should prove widely useful for the regulation of engineered protein production in experimental animals and human gene therapy.

Example 5

Synthesis of Representative C-24 Modified Rapalosg

Rapamycin Purification

Rapamycin was obtained by fermentation. The rapamycin producing organism, *Streptomyces hygroscopicus* (ATCC# 29253), was cultivated on a complex media in 15 L or 30 L fed-batch fermentations. The biomass was harvested after 9–14 days by centrifugation. The supernatant was contacted for 1–2 hours with a nonionic, polymeric adsorbent resin, XAD-16 (Rohm and Haas). The adsorbent was recovered by centrifugation, combined with the biomass, and extracted repeatedly with methylene chloride. The solvent was removed in vacuo and the resulting reside extracted with acetonitrile which was then condensed in a similar manner. Chromatographic purification of the crude rapamycin was achieved by flash chromatography on silica gel (40% Acetone/Hexanes) followed by C-18 reversed-phase HPLC (70% $CH_3/H_2O$). Rapamycin obtained exhibited identical HPLC, spectroscopic, and biological charateristics as an authentic sample of rapamycin.

Rapamycin (E and Z)-24-(O-methloxime) (AP1731 and 1732) General Procedure

A solution of rapamycin (60 mg 65.6 mmol) in MeOH (2 mL) was treated with NaOAc (22 mg 262 mmol, 4.0 eq)

followed by methoxylamine hydrochloride (22 mg 262 mmol, 4.0 eq) and stirred at room temperature for 48 h. After this time the reaction mixture was quenched with $H_2O$ (10 mL) and extracted with EtOAc (3×10 ml). The combined organic extracts were washed with saturated NaCl solution (2×10 mL), dried over $Na_2SO_4$, filtered, and the solution concentrated in vacuo. The resulting residue was subjected to flash chromatography on silica gel (10% MeOH/ dichloromethane) to afford a mixture of isomers. The isomer mixture was separated by HPLC (35% AE 25% $H_2O$/MeCN through a Kromasil C-18 250×20 mm column, 12 mL/min) to provide 13 mg (21%) of the faster eluting Z isomer and 7.6 mg (12%) of the E isomer. Z isomer: high-resolution mass spectrum (FAB) m/z 965.5749 [$(M+Na)^+$, calcd for $C_{52}H_{82}N_2O_{13}Na$ 965.5710]. E isomer: high-resolution mass spectrum (FAB) m/z 965.5701 [$(M+Na)^+$, calcd for $C_{52}H_{82}N_2O_{13}Na$ 965.5710].

Rapamycin (E and Z)-24-(O-ethyloxime) (AP1688 and 1689)

Prepared in an analogous manner to Rapamycin (E and Z)-24O-methyloxime). The isomer mixture was separated by HPLC (30% $H_2O$/MeCN through a Kromasil C-18 250×20 mm column, 12 mL/min) to provide 7.7 mg (25%) of the faster eluting Z isomer and 0.5 mg (2%) of the E isomer. Z isomer: high-resolution mass spectrum.(FAB) m/z 979.5902 [$(M+Na)^+$, calcd for $C_{53}H_{84}N_2O_{13}Na$ 979.5871].

Rapamycin (E and Z)-24-(O-isobutyloxime) (AP1684 and 1685)

Prepared in an analogous manner to Rapamycin (E and Z)-24O-methyloxime). The isomer mixture was separated by HPLC (15% $H_2O$/MeCN through a Kromasil C-18 250×20 mm column, 12 mL/min) to provide 28 mg (65%) of the faster eluting Z isomer and 3.0 mg (7%) of the E isomer. Z isomer: high-resolution mass spectrum (FAB) m/z 1007.6146 [$(M+Na)^+$, calcd for $C_{55}H_{88}N_2O_{13}Na$ 1007.6184]. E isomer: high-resolution mass spectrum (FAB) m/z 1007.6157 [$(M+Na)^+$, calcd for $C_{55}H_{88}N_2O_{13}Na$ 1007.6184].

Rapamycin (E and Z)-24-(O-benzyloxime) (AP1682 and 1683)

Prepared in an analogous manner to Rapamycin (E and Z)-24O-methyloxime). The isomer mixture was separated by HPLC (15% $H_2O$/MeCN through a Kromasil C-18 250×20 mm column, 12 mL/min) to provide 19.6 mg (44%) of the faster eluting Z isomer and 6.1 mg (14%) of the E isomer. Z isomer: high-resolution mass spectrum (FAB) m/z 1041.6033 [$(M+Na)^+$, calcd for $C_{58}H_{86}N_2O_{13}Na$ 1041.6028]. E isomer: high-resolution mass spectrum (FAB) m/z 1041.5988 [$(M+Na)^+$, calcd for $C_{58}H_{86}N_2O_{13}Na$ 1041.6028].

Rapamycin (E and Z)-24-(O-carboxymethyloxime) (AP1686 and 1687)

Prepared in an analogous manner to Rapamycin (E and Z)-24-(O-methyloxime). The isomer mixture was separated by HPLC (45% $H_2O$/MeCN through a Kromasil C-18 250×20 mm column, 12 mL/min) to provide 4.6 mg (11%) of the faster eluting Z isomer and 1.0 mg (2%) of the E isomer. Z isomer: high-resolution mass spectrum (FAB) m/z 1009.5664 [$(M+Na)^+$, calcd for $C_{53}H_{82}N_2O_{15}Na$ 1009.5613]. E isomer: high-resolution mass spectrum (FAB) m/z 1009.5604 [$(M+Na)^+$, calcd for $C_{53}H_{82}N_2O_{15}Na$ 1009.5613].

Rapamycin (E and Z)-24-(O-carboxamidomethyloxime) (AP1729 and 1730)

Prepared in an analogous manner to Rapamycin (E and Z)-24(O-Methyloxime). The isomer mixture was separated by HPLC (35% $H_2O$/MeCN through a Kromasil C-18 250×20 mm column, 12 mL/min) to provide 6.2 mg (10%) of the faster eluting Z isomer and 1.4 mg (2%) of the E isomer. Z isomer: high-resolution mass spectrum (FAB) m/z 1008.5790 [$(M+Na)^+$, calcd for $C_{53}H_{83}N_3O_{14}Na$ 1008.5768]. E isomer: high-resolution mass spectrum (FAB) m/z 1008.5753 [$(M+Na)^+$, calcd for $C_{53}H_{83}N_3O_{14}Na$ 1008.5768].

Example 6

A. Assay of Binding of Rapamycin C24 'Bump' Analogs to FKBP

Affinities of rapamycin C24 analogs for FKBP were determined using a competitive assay based on fluorescence polarization (FP). A fluorescein-labelled FK506 probe (AP1491) was synthesized, and the increase in the polarization of its fluorescence used as a direct readout of % bound probe in an equilibrium binding experiment containing sub-saturating FKBP and variable amounts of rapamycin analog as competitor.

(i) Synthesis of fluoresceinated FK506 probe (AP1491)

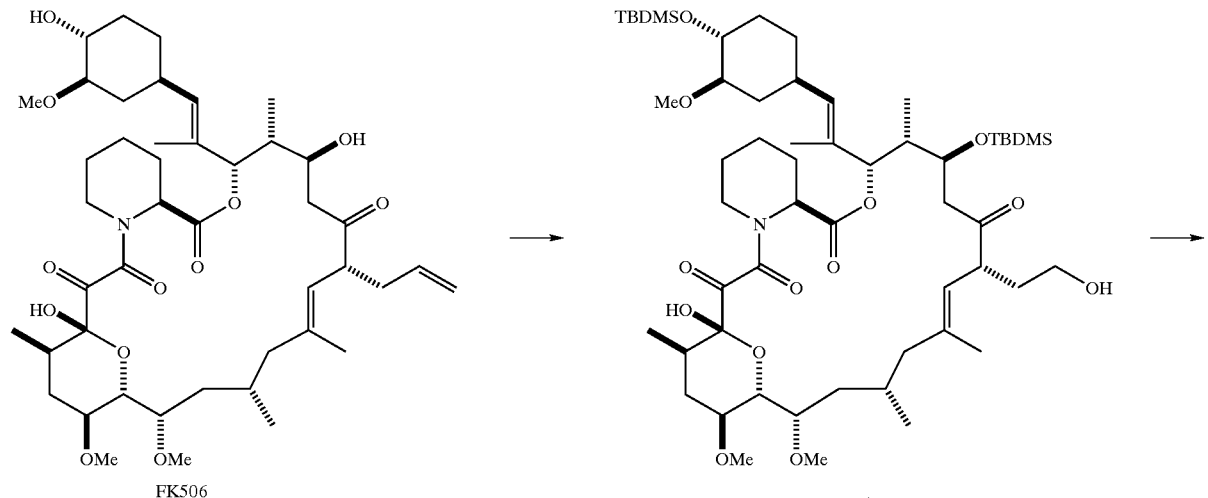

-continued

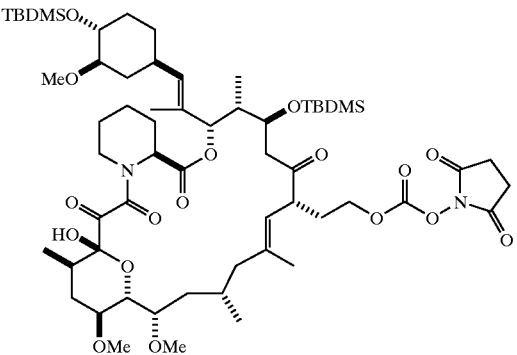

2

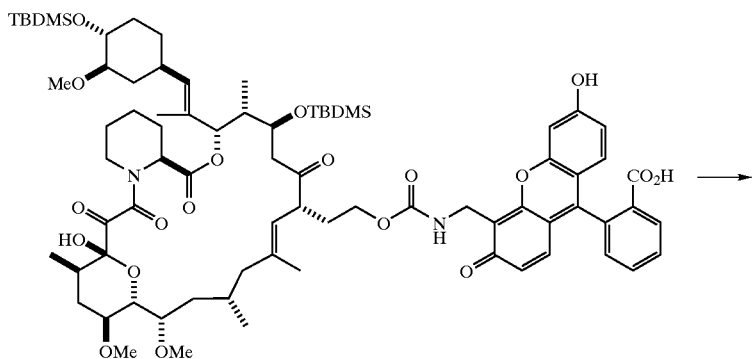

3

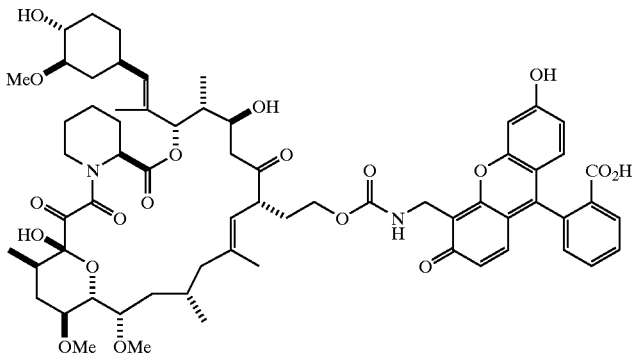

4

24,32-Bis(tert-Butyldimethylsilyl)ether of FK506 tert-Butyldimethylsilyl trifluoromethanesulfonate (108 μL, 470 μmol) was added dropwise to a stirred solution of FK506 (103 mg, 128 μmol) and 2,6-lutidine (89.5 μL, 768 μmol) in dichloromethane (3 mL) at 0° C. The resulting solution was stirred at 0° C. for 2 h, and then treated with MeOH (0.5 mL) and ether (15 mL). The mixture was washed with 10% aqueous NaHCO₃ (3 mL) and brine (3 mL). The organic layer was decanted, dried over anhydrous Na2SO₄, filtered, and concentrated to a yellow oil. Column chromatography (silica-gel, hexanes-EtOAc 3:1) gave the title compound as a colorless oil (104 mg).

Intermediate 1

To a solution of 24,32-bis(tert-butyldimethylsilyl)ether of FK506 (100 mg, 97 μmol) in THF (2.5 mL) was added morpholine N-oxide (68 mg, 580 μmol), followed by water (60 μL), and a 4% aqueous solution of osmium tetroxide (123 μL, 20 μmol). The resulting mixture was stirred at room temperature for 4.5 h. It was then treated with 50% aqueous MeOH (1.5 mL) and sodium periodate (207 mg, 970 μmol), and the suspension stirred for an additional 1 h. The mixture was diluted with ether (10 mL) and washed with saturated aqueous NaHCO₃ (2×4 mL). The organic layer was decanted, dried over anhydrous sodium sulfate containing a small amount of sodium sulfite, filtered, and concentrated. The residue was dissolved in anhydrous THF (2.8 mL), cooled to −78° C. under nitrogen, and treated with a 0.5 M solution of lithium tris[(3-ethyl-3pentyl)oxy]aluminum hydride in THF (282 μL). The resulting solution was stirred at −78° C. for 1.75 h, and then quenched by addition of ether (6 mL) and saturated ammonium chloride solution (250 μL). The mixture was allowed to warm up to room temperature and treated with anhydrous sodium sulfate. Filtration and concentration under reduced pressure afforded a pale yellow oil (97 mg), which was purified by column chromatography (silica-gel, hexanes-EtOAc 3:1) to afford 1 as a colorless oil.

Intermediate 2

A solution of the above alcohol (300 mg, 290 μmol) in acetonitrile (10 mL) was treated with 2,6-lutidine (338 μL, 2.9 mmol) and N,N'-disuccinimidylcarbonate (371 mg, 1.45 mmol). The resulting suspension was stirred at room temperature for 145 h, and then concentrated under reduced pressure. The residue was chromatographed (silica-gel, hexanes-EtOAc 2:1 to 100% EtOAc gradient) to afford the mixed carbonate 2 as a pale yellow oil (127 mg).
Intermediate 3

A solution of the above carbonate (30 mg, 26 μmol) and triethylamine (36 μL, 260 μmol) in acetonitrile (1 mL) was treated with 4'-(aminomethyl)fluorescein (13.5 mg, 34 μmol). The resulting bright orange suspension was stirred at room temperature for 1 h, and then concentrated under reduced pressure. The residue was chromatographed (silica-gel, hexanes-EtOAc 1:1 to 100% EtOAc to EtOAc-MeOH 1:1 gradient) to give 3 (20.5 mg) as a bright yellow solid.
Compound 4

A solution of bis-silyl ether 3 (35 mg, 25 μmol) in acetonitrile (2 mL) was treated with 48% (w/w) HF in water (250 μL). The resulting mixture was stirred at room temperature for 5.5 h. It was then diluted with dichloromethane (10 mL) and washed with water (2×2 mL). The organic layer was decanted, dried over anhydrous sodium sulfate, and concentrated under reduced pressure. The residue was chromatographed (silica-gel, 100% EtOAc) to afford 4 (13 mg) as a bright yellow solid.

(ii) Determination of Binding Affinities (IC50s) of Rapamycin Analogs Using FP

Serial 10-fold dilutions of each analog were prepared in 100% ethanol in glass vials and stored on ice. All other manipulations were performed at room temperature. A stock of recombinant pure FKBP (purified by standard methods, see e.g. Wiederrecht, G. et al. 1992. *J. Biol. Chem.* 267, 21753–21760) was diluted to 11.25 nM in 50 mM potassium phosphate pH 7.8/150 mM NaCl/100 μg/ml bovine gamma globulin ("FP buffer": prepared using only low-fluorescence reagents from Panvera) and 98 μl aliquots transferred to wells of a Dynatech micro-fluor black 96-well fluorescence plate. 2.0 μl samples of the rapamycin analogs were then transferred in duplicate to the wells with mixing. Finally, a probe solution was prepared containing 10 nM AP1491 in 0.1% ethanol/FP buffer, and 100 μl added to each well with mixing. Duplicate control wells contained ethanol instead of rapamycin analog (for 100% probe binding) or ethanol instead of rapamycin analog and FP buffer instead of FKBP (0% binding).

The plates was stored covered in the dark for approximately 30 min to permit equilibration and then the fluorescence polarization of the sample in each well read on a Jolley FPM-2 FP plate reader volley Consulting and Research, Inc., Grayslake, Ill.) in accordance with the manufacturer's recommendations. The mean polarization (mP units) for each competitor concentration was usually converted to % total binding by reference to the control values and plotted (y) vs. log molar final concentration of competitor (x). Non-linear least square analysis was used to fit the curve and extract the IC50 using the following equation:

$$y = M1 + (M4-M1)/(1+\exp(M2*(M3-x)))$$

where M3 is the IC50. For incomplete curves the IC50 was determined by interpolation. Rapamycin and C14-desoxo-rapamycin were included as controls in each case (C14-desoxo-rapamycin was prepared as described by Luengo, J. I. et al. 1994 *Tetrahedron Lett.* 35, 6469–6472).

(c) Results of Binding Analysis of Rapamycin C24 Oximes
Affinities are reported as IC50s and as fold loss in affinity (=IC50/IC50 of rapamycin).

|  | IC$_{50}$ |  | fold loss in affinity |
|---|---|---|---|
| Benzyl: |  |  |  |
| AP1682 (Z) | >30 | μM | >3000 |
| AP1683 (E) | 346 | μM | 346 |
| Isobutyl: |  |  |  |
| AP1684 (Z) | >30 | μM | >3000 |
| AP1685 (E) | 10.0 | μM | 1000 |
| Carboxymethyl: |  |  |  |
| AP1686 (Z) | 16.2 | μM | 1620 |
| AP1687 (E) | 8.13 | μM | 813 |
| Ethyl: |  |  |  |
| AP1688 (Z) | 16.6 | μM | 1660 |
| AP1689 (E) | 3.55 | μM | 355 |
| tert-butyl: |  |  |  |
| AP1690 (Z) | >30 | μM | >3000 |
| AP1691 (E) | >30 | μM | >3000 |
| Carboxamidomethyl: |  |  |  |
| AP1729 (Z) | 2.4 | μM | 304 |
| AP1730 (E) | 0.32 | μM | 40.5 |
| Methyl: |  |  |  |
| AP1731 (Z) | 3.2 | μM | 405 |
| AP1732 (E) | 1.6 | μM | 203 |
| rapamycin | 10.0 | nM | — |
| desoxo-rap | 186 | nM | 18.6 |

B. Assay of Binding of C7 Rapalog-FKBP Complexes to FRAP

A series of rapalogs with bulky substituents at C7 ("C7 rapalogs") was synthesized using chemistry broadly as described (Luengo et al. 1995. *Chemistry and Biology* 2, 471–481). The data here refer to the three rapalogs shown below:

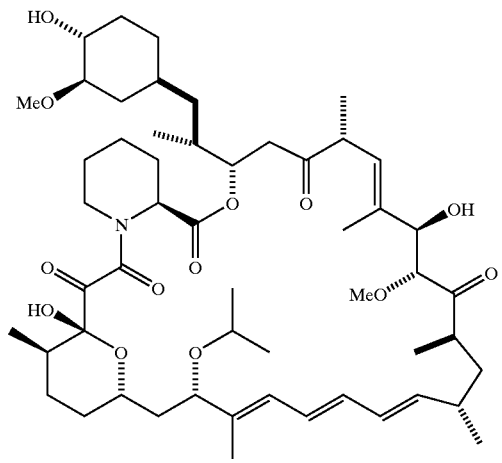

AP1700

-continued

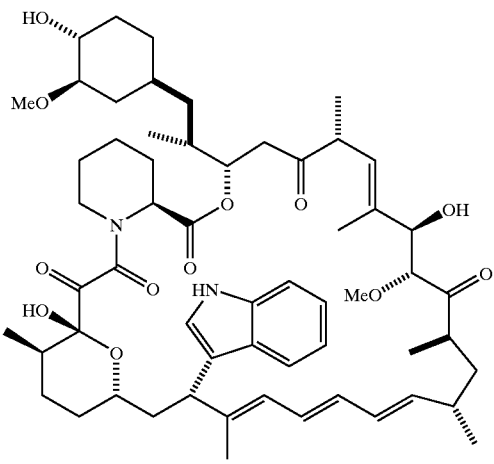
AP1701

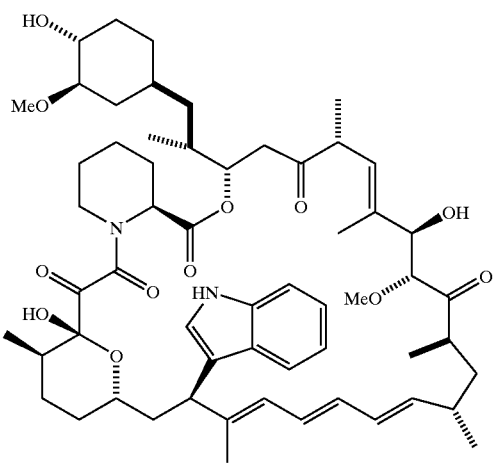
AP1702

(a) Synthesis

AP1700, 7S-isopropoxyrapamycin: A solution of rapamycin (60 mg, 0.066 mmol) in 3.0 mL of isopropanol was treated with solid p-toluenesulfonic acid (75 mg, 0.39 mmol). The reaction mixture was allowed to stir for 4 h at room temperature, then diluted with 30 mL of ethyl acetate and washed with saturated aqueous sodium bicarbonate (3×20 mL) and brine (2×20 mL). The organic phase was then dried over anydrous magnesium sulfate, filtered, and concentrated. Reverse phase HPLC (Rainin C-18 ODS 1" column, 35% acetonitile/water, 55° C.) afforded 25 mg (40%) of the desired product.

AP1701, 7R-(3-indolyl)rapamycin and AP1702, 7S-(3-indolyl)rapamycin: Trifluoroacetic acid (0.084 mL, 1.1 mmol) was added to a stirring solution of rapamycin (50 mg, 0.055 mmol) and indole (64 mg, 0.55 mmol) in 2 mL of dichloromethane at −40° C. The temperature was maintained between −40° C. and −45° C. for 3 h, then the reaction mixture was partitioned between ethyl acetate (10 mL) and brine (20 mL). The organic phase was then washed with additional brine (4×20 mL) and dried over anhydrous sodium sulfate. Reverse phase HPLC (Rainin C-18 ODS 1" column, 65% acetonitile/water, 55° C.) afforded the 11.8 mg of the 7S-indole and 7.6 mg of the 7R-indole (35%).

Compounds were characterized were by exact mass spec and NMR.

(b) FP Assay of FKBP Binding Affinity of C7 Rapalogs

The affinity of the rapalogs for FKBP was assayed as described for C24 rapalogs in section A above, using competitive FP. Rapamycin and C14-desoxo-rapamycin (prepared as described by Luengo et al. 1994. Tetrahedron Lett. 35, 6469–6472) were included as controls. Affinities are reported below as IC50s and fold loss in affinity (=IC50/IC50 of rapamycin):

|  | $IC_{50}$ (nM) | fold loss in affinity |
|---|---|---|
| rapamycin | 7.7 | (1) |
| desoxo-rapamycin | 162 | 20.8 |
| AP1700 | 17.8 | 2.5 |
| AP1701 | 33.1 | 4.6 |
| AP1702 | 24.5 | 3.0 |

These data indicate that these large C7 substituents do not cause large reductions in the affinity of the rapalogs for FKBP, in accordance with the location of the C7 position at the rapamycin-FRAP interface.

(c) FP Assay of FKBP Binding Affinity of C7 Rapalogs

To analyze the binding of rapalog-FKBP complexes to FRAP in cultured cells, we used HT20-6 cells (which contain a ZFHD1-responsive SEAP reporter and stably express ZFHD1-(3xFKBP) and FRB-p65: see Example 3(B)). HT206 cells were plated in 96-well dishes (1×10$^4$ cells/well) and 200 µl medium containing serial dilutions of rapalog was added to each well (in triplicate). After 22 hours, medium was removed and assayed for SEAP activity as described in example 2.

Figure 15:
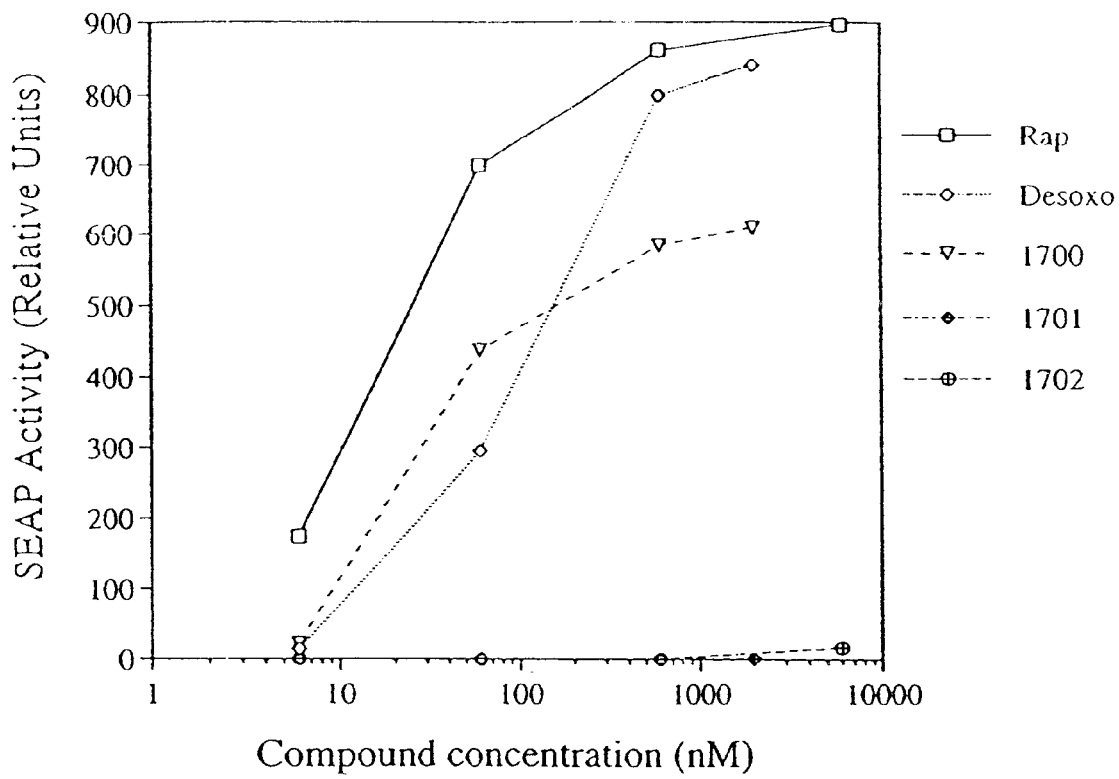
FIG. 15 shows that the isopropoxy C7 substituent of AP1700 leads to a modest reduction in FRAP affinity (as indicated by the reduction in SEAP production). However, the larger indolyl substituents of AP1701 and AP1702 almost completely abolish SEAP expression, showing that the modifications are acting as bumps to prevent binding of the rapalog-FKBP complex to FRAP.

The results are presented in FIG. 15 and show that the isopropoxy C7 substituent of AP1700 leads to a modest reduction in FRAP affinity (as indicated by the reduction in SEAP production). However, the larger indolyl substituents of AP1701 and AP1702 almost completely abolish SEAP expression, showing that the modifications are acting as bumps to prevent binding of the rapalog-FKBP complex to FRAP.

C7 rapalogs are also assayed for their ability to reduce the proliferation of activated human T cells or murine splenocytes as a measure of their reduced ability to binding FRAP. Suitable assays are well known in the art for example, inhibition of $^3$H-thymidine uptake (Luengo et al. 1995. Chemistry and Biology 2, 471–481).

Example 7

Mutagenesis and Phage Display to Generate Modified Ligand-Binding Domains Complementary to Various Rapalogs A. Engineered FKBP and FRB Domains We have designed and prepared recombinant DNA constructs encoding the fusion proteins tabulated below which bear illustrative modified ligand-binding domains. Except a otherwise stated, mutants were generated using oligonudeotide-mediated site-directed mutagenesis according to standard methods (Kunkel, T. A., Bebenek, K. and McClary, J. 1991. Meth Enzymol. 204, 235–139), and confirmed by dideoxy sequencing.

Fusion Proteins containing modified FKBP domains (F36V hFKBP12)---p65
(F36V hFKBP12)---(F36V hFKBP12)-p65
(F36V hFKBP12)---(F36V hFKBP12)---(F36V hFKBP12)--p65
(F36M hFKBP12)---p65
(F36M hFKBP12)---(F36M hFKBP12)-p65
(F36M hFKBP12)---(F36M hpKBP12)-(P36M hFKBP12)--p65

-continued

Fusion Proteins containing modified FKBP domains (F36V hFKBP12)--ZFHD1
(F36V hFKBP12)---(P36V hFKBP12)---ZFHD1
(F36V hFKBP12)---(F36V hFKBP12)---(P36V hFKBP12)-ZFHD1
(F36M hFKBP12)---ZFHD1
(F36M hPKBP12)---(P36M hPKBP12)---ZFHD1
(F36M hPKBP12)---(F36M hFKBP12)---(F36M hFKBP12)---ZFHD1
myr-(F36V hPKBP12)---(F36V hPKBP12)---Fas
myr-(F36M hPKBP12)---(F36M hFKBP12)--Fas
myr-(F36A hFKBP12)---(F36A hFKBP12)---Fas
myr-(F36S/F99A hFKBP12)---(P36S/F99A hpKBP12)---Fas 1. "hPKBP12" indicates amino acids 1–107 of human FKBP12 referred to previously
2. "p65" indicates residues 361–550 of p65
3. "Fas" indicates residues 175 304 of human Fas
4. "ZFHD1" is as described elsewhere
5. "myr" indicates the src myristoylation sequence
6. mutations are indicated usin the previously described convention We have also prepared constructs encoding the following FRB fusion proteins:

Fusion Proteins containing modified (hFRAP) FRB domains

| | |
|---|---|
| (T2098A FRB)---p65 | (F2039H FRB)---p65 |
| (T2098N FRB)---p65 | (F2039L FRB)---p65 |
| (D2102A FRB)---p65 | (F2039A FRB)---p65 |
| (Y2038H FRB)---p65 | (K2095S/D2096N/T2098N FRB)---p65 |
| (Y2038L FRB)---p65 | (TOR2 FRB)---p65 |
| (Y2038A FRB)--p65 | |

1. "p65" indicates p65 residues 361–550, as above
2. "FRB" indicates the 89 amino acid FRB of human FRAP
3. "TOR2 FRB" indicates amino acids 1961–2052 of S. cerevisiae TOR2

Yeast and Candida FRBs, modified by analogy to the modified hFRAP FRB domains discussed herein, may also be prepared by substitution of a codon for a different amino acid in place of one or more of the two conserved Phe residues and the conserved Asp and Asn residues within each of their FRB domains. Illustrative modified FRB domains derived from TOR1 and TOR$^2$, include the following:

Modified TOR1 and TOR2 FRB Domains

| TOR1 | TOR2 |
|---|---|
| F1975H | F1978H |
| F1975L | F1978L |
| F1975A | F1978A |
| F1975S | F1978S |
| F1975V | F1978V |
| F1976H | F1979H |
| F1976L | F1979L |
| F1976A | F1979A |
| F1976S | F1979S |
| F1976V | F1979V |
| D2039A | D2042A |
| N2035A | N2038A |
| N2035S | N2038S |

These modified TOR1 and TOR2 FRBs are designed for use with rapalogs containing C7 substituents

B. Testing Rationally Designed FKBP Mutants for Binding to Rapalogs

An expression vector based on pET20b (Novagen) was constructed using standard procedures that expresses FKBP preceded by a hexahistidine tag and a portion of the *H. influenza* hemaglutinin protein that is an epitope for the monoclonal antibody 12CA5. The sequence of the protein encoded by this vector is as follows:

```
        His6     HA tag         FKBP->                                    [SEQ ID NO: 40]
        MHHHHHHYPYDVPDYAAMAHMGVQVETISPGDGRTFPKRGQTCVVHYTGMLEDGKKFDSSR

DRNKPFKFMLGKQEVIRGWEEGVAQMSVGQRAKLTISPDYAYGATGHPGIIPPHATLVFDV

ELLKLE
```

To generate expression vectors for FKBPs mutated at rapamycin contact residues, oligonucleotide-mediated site-directed mutagenesis was performed on the single-stranded form of the vector prepared from *E.coli* CJ236, as described (Kunkel, T. A., Bebenek, K. and McClary, J. 1991. *Meth Enzymol.* 204, 235–139). Mutants were confirmed by dideoxy sequencing. Mutant proteins were expressed in *E.coli* BL21(DE3) (Novagen) as described (Wiederrecht, G. et al. 1992. *J. Biol. Chem.* 267, 21753–21760), and purified to homogeneity as described (Cardenas, M. E. et al. 1994. *EMBO J.* 13, 5944–5957).

Using this protocol the following mutant human FKBP12 proteins were generated, using the indicated oligonudeotide primers (mutated bases in upper case; 5'→3'):

Mutants designed for binding to C24 rapalogs:

| | | |
|---|---|---|
| Phe46His | agcataaacttaTGgggcttgtttctg | [SEQ ID NO: 41] (1) |
| Phe46Leu | agcataaacttTaagggcttgtttctg | [SEQ ID NO: 42] (2) |
| Phe46Ala | agcataaacttaGCgggcttgtttctg | [SEQ ID NO: 43] (3) |
| Phe48His | ttgcctagcataTGcttaaagggcttg | [SEQ ID NO: 44] (4) |
| Phe48Leu | ttgcctagcatTaacttaaagggcttg | [SEQ ID NO: 45] (5) |
| Phe48Ala | ttgcctagcataGCcttaaagggcttg | [SEQ ID NO: 46] (6) |

-continued

| | | [SEQ ID NO: 47] | |
|---|---|---|---|
| Glu54Ala | cctcggatcaccGCctgcttgcctag | | (7) |

| | | [SEQ ID NO: 48] | |
|---|---|---|---|
| Val55Ala | cagcctcggatcGCctcctgcttgcc | | (8) |

Mutants designed for binding to C13/C14 rapalogs:

| | | |
|---|---|---|
| Phe36Ala | ccgggaggaatcGGCtttctttccatcttc [SEQ ID NO: 49] | (9) |
| Phe36Val | ccgggaggaatcGACtttctttccatcttc [SEQ ID NO: 50] | (10) |
| Phe36Ser | ccgggaggaatcAGAtttctttccatcttc [SEQ ID NO: 51] | (11) |
| Phe36Met | ccgggaggaatcCATtttctttccatcttc [SEQ ID NO: 52] | (12) |
| (Phe36Met + Phe99Ala) | aagctccacatcGGCgacgagagtggc + primer 12 [SEQ ID NO: 53] | (13) |
| (Phe36Met + Phe99Gly) | aagctccacatcGCCgacgagagtggc + primer 12 [SEQ ID NO: 54] | (14) |
| (Phe36Ala + Phe99Ala) | primer 9 + primer 13 | |
| (Phe36Ala + Phe99Gly) | primer 9 + primer 14 | |
| Tyr26Ala | caagcatcccggtgGCgtgcaccacgcag [SEQ ID NO: 55] | (15) |
| Asp37Ala | tcccgggaggaaGCaaatttctttccatc [SEQ ID NO: 56] | (16) |

Mutant designed for binding to C28/C30 rapalogs:

| | | |
|---|---|---|
| Glu54Ala | cctcggatcaccGCctgcttgcctag [SEQ ID NO: 57] | (17) |

To assay the relative binding affinity of rapamycin and rapalogs to FKBP mutants, a competitive fluorescence polarization (FP) assay is used that relies on the retention of FK506 (and hence probe) binding affinity by the mutants. The procedure is identical to that described in example 6 except that a direct binding assay is first performed to determine the dilution (concentration) of mutant FKBP to use in the competition reactions in order to obtain sub-saturation. Serial dilutions of mutant FKBP are made in FP buffer (example 6) in 100 $\mu$l volumes in Dynatech microfluor plates, and then 100 $\mu$l of 10 nM AP1491 (probe) in [FP buffer+2% ethanol] added to each well. Equilibration and plate reading are as in example 6. A plot of mP units vs concentration of FKBP mutant is fit to following equation:

$$y=M3+(((x+M1+M2)-\text{SQRT}(((x+M1+M2)^2)-(4*x*M1)))/(2*(M1)))*(M4-M3)$$

and the final mutant concentration/dilution at which 90% of probe is specifically bound is determined by interpolation. This final concentration is then used in a competition FP assay carried out as in example 6, with 2× the final concentration of mutant replacing 11.25 nM FKBP in the protocol. Instead of 90% saturation, 75% can be selected to impart greater sensitivity to the competition assay. Serial dilutions of rapamycin analogs are used as competitor and the results are expressed as IC50 for each rapalog binding to each mutant.

C. Testing Rationally Designed FRB Mutants for Binding to FKBP-rapalog Complexes A NcoI-BamHI fragment encoding residues 2021–2113 (inclusive) of human FRAP was generated by PCR with primers 28 and 29 (below),and cloned into a derivative of pET20b(+) (Novagen) in which the NdeI site is mutated to NcoI, to create pET-FRAP(2021–2113). Single-stranded DNA of this vector was used as a template in site-directed mutagenesis procedures, as described above, to generate vectors encoding FRAPs mutated at rapamycin contact residues. Mutants were confirmed by dideoxy sequencing. Mutants were then amplified by PCR using primers (30 and 31) that append XbaI and SpeI sites, and cloned into XbaI-SpeI digested pCGNN-FRB-p65(361–550) (example 1) to generate a series of constructs directing mammalian expression of chimeric proteins of the form E-N-mutant FRAP(2021–2113)-p65(361–550), where E indicates HA epitope tag and N indicates nuclear localization sequence. Constructs were verified by restriction digestion and dideoxy sequencing.

Using this procedure the following constructs encoding mutant FRAPs that potentially bind to C7 rapalogs, each fused to the p65(361–550) activation domain, were generated using the indicated oligonucleotide primers (mutated bases in upper case; 5'3'):

| | | | |
|---|---|---|---|
| Tyr2038His | cctttccccaaagtGcaaacgagatgc | (18) | [SEQ ID NO: 58] |
| Tyr2038Leu | cctttccccaaaAGcaaacgagatgc | (19) | [SEQ ID NO: 59] |
| Tyr2038Ala | cctttccccaaaGCcaaacgagatgc | (20) | [SEQ ID NO: 60] |
| Phe2039His | gttcctttccccAtGgtacaaacgagatg | (21) | [SEQ ID NO: 61] |
| Phe2039Leu | gttcctttccccTaagtacaaacgagatg | (22) | [SEQ ID NO: 62] |
| Phe2039Ala | gttcctttccccaGCgtacaaacgagatg | (23) | [SEQ ID NO: 63] |
| Thr2098Ala | gtcccaggcttggGCgaggtccttgac | (24) | [SEQ ID NO: 64] |
| (Lys2095Ser + Asp2096Asn + Thr2098Asn) | gtcccaggcttggTTgaggTTcGAgacattccctgatttc | (25) | [SEQ ID NO: 65] |
| Thr2098Asn | gtcccaggcttggTTgaggtccttgac | (26) | [SEQ ID NO: 66] |
| Asp2102Ala | catgataatagaggGCccaggcttgggtg | (27) | [SEQ ID NO: 67] |

To assay the relative binding affinity of these mutants for complexes of FKBP with rapamycin and various rapalogs, each construct is transiently co-transfected into human HT1080B14 cells, as described in example 2. Following transfection, serial dilutions of rapamycin or rapalog are added to the culture medium. After 24 hours, SEAP activity is measured as described in example 2; the potency of SEAP activation at various rapalog concentrations is proportional to the affinity of the FRAP mutant for the complex between FKBP and the rapalog.

```
PCR primers (restriction sites upper case; 5'-> 3'):
gcatcCCATGGcaatcctctggcatgagatgtggcatgaaggcctggaag   (28 [SEQ ID NO: 68]

cgtgaGGATCCtactttgagattcgtcggaacac                  (29 [SEQ ID NO: 69]

gcatcTCTAGAatcctctggcatgagatgtggcatgaaggcctggaag    (30 [SEQ ID NO: 70]

ggtctGGATCCctaataACTAGTctttgagattcgtcggaacacatg     (31 [SEQ ID NO: 71]
```

D. Functional Display of the FRB Domain of FRAP on Filamentous Bacteriophage: One Approach to Selection as an Alternative to Rational Design of Modified Domains
(a) Vector Construction A derivative of pCANTAB-5E, a carbenicillin-resistant phagemid display vector (Pharmacia), was constructed by site-directed mutagenesis with primer 1 in which Cys202 of fd geneIII is replaced with Tyr. Cys202 can disrupt display of proteins fused at Asp198 due to the formation of mixed disulfides, a problem alleviated by the Tyr substitution (Cunningham, B. C. et al. 1994. *EMBO J.* 13, 2508). The construct was verified by DNA sequencing and then digested with NcoI and BamHI. A pair of oligonucleotides (2 and 3) was ligated in to yield the plasmid pCANTAB-AP-poly, which contains a NcoI-SpeI-BamHI polylinker between the NcoI site in the geneIII signal sequence and the BamHI site at codon 198 in geneIII. This vector can accept in frame NcoI-BamHI fragments to give constructs directing the N-terminal display of the encoded protein on pIII residues 198–406, the fusion configuration described by Cunningham et al. (1994: *EMBO J.* 13, 2508).

A fragment of FRAP encoding residues 2015–2114 inclusive was amplified from pCGNN-FRAP$_i$ by PCR with Pfu polymerase (Stratagene) and the primers 4 and 5. The fragment was purified, digested with NcoI and BamHI, and ligated into NcoI-BamHI digested pCANTAB-AP-poly to yield the vector p-CANTAB-FRAP(2015–2114), which was verified by DNA sequencing.
(b) Preparation of His6-flag-FKBP To provide tagged FKBP protein for affinity enrichments of phagemids displaying FRAP, an expression vector based on pET20b (Novagen) was constructed using standard procedures that expressed FKBP preceded by a hexahistidine tag (for affinity purification) and 'flag' sequence (Kodak IBI) (for immunological detection). The protein was expressed in *E.coli* BL21(DE3) (Novagen) as described (Wiederrecht, G. et al. 1992. *J. Biol. Chem.* 267, 21753–21760) and purified to homogeneity using Ni-NTA agarose (Qiagen) as described (Cardenas, M. E. et al. 1994. *EMBO J.* 13, 5944–5957).

The sequence of the expressed protein was as follows:

(c) Binding Enrichments p-CANTAB-AP-FRAP(2015–2114) was transformed into *E.coli* XL-1 (Stratagene) and display phage prepared by rescue with helper phage K07 essentially as described (Lowman, H. B, and Wells, J. A. *Methods: Comp. Methods Enzymol.* 1991. 3, 205–216) except that the overnight culture used to innoculate the phagemid growth was grown in medium containing 2% glucose, and the phage growth was carried out at 25° C. after an initial 1 hour incubation at 37° C. to allow K07 infection. To provide a reference reagent, phagemid particles were also prepared from cells transformed with the chloramphenicol-resistant vector pBC (Stratagene). Phagemid titers (colony-forming units, cfu) in each case were determined as described (Lowman, H. B, and Wells, J. A. *Methods: Comp. Methods Enzymol.* 1991. 3, 205–216).

To demonstrate specific binding enrichment of FRAP display phage on FKBP-rapamycin, approximately $10^8$ cfu were mixed with approximately $10^{10}$ cfu of pBC phagemids in a volume of 250 µl of PBS/3%BSA/0.05% tween-20 ('PBSBT'). 1 µM (final) His6-flag-FKBP protein was added followed by 2.5 µl of 100 µM rapamycin or FK506 in 100% ethanol, or ethanol alone. The mixture was incubated for 1 hour at room temperature, and then 100 µl of a 1:1 slurry of Ni-NTA agarose beads equilibrated in PBSBT added (to capture the His6-tagged FKBP and any associated phagemids). The mixture was tumbled gently on a end-over-end mixer for 15 min, after which the beads were pelleted by spinning at 8000 rpm for 30 seconds in a microfuge. The beads were then washed 5 times in 1 ml PBS/0.05% tween-20 and 5 times in 1 ml PBS/0.05% tween-20/1M NaCl. Bound phagemids were eluted from the beads by adding 200 µl 0.2 M glycine pH 2.0 and incubating for 10 min. The beads were pelleted and the supernatant (containing eluted phagemids) collected and neutralized with 26 µl 1 M Tris base. Carbenicillin (carb) and chloramphenicol (chlor)-resistant cfu titers were determined as described above, and the carb/chlor ratio used as a measure of the specific enrichment of (carbenicillin-resistant) FRAP phagemids.

The results showed a dramatic enrichment (271-fold) of FRAP phage compared to the starting mixture after affinity enrichment on the rapamycin-FKBP matrix, but not on the

```
His6    Flag       FKBP->                                                  [SEQ ID NO: 72]
MHHHHHHDYKDDDDKAMAHMGVQVETISPGDGRTFPKRGQTCVVHYTGMLEDGKKFDSSRD

RNKPFKFMLGKQEVIRGWEEGVAQMSVGQRAKLTISPDYAYGATGHPGIIPPHATLVFDVE

LLKLE
```

FK506-FKBP matrix (2.4-fold) or FKBP alone (1.5-fold). This experiment demonstrates the procedure that is used to purify from a library mutant FRAPs that bind rapamycin analogs bearing bumps on the FRAP binding side of the molecule (for example at the C7 position).

(d) Primers

```
1 5'CCTTGATATTCATAAACGAATGGATC
  [SEQ ID NO: 73]

2 5'CATGGCGACTAGTTAAGCACGTAG
  [SEQ ID NO: 74]

3 5'GATCCTACGTGCTTAACTAGTCGC
  [SEQ ID NO: 75]

4 5'GCATCCATGGCCGCTGAGCTGATCCGAGTGGCCATC
  [SEQ ID NO: 76]

5 5'CTGAGGATCCTACTGCTTTGAGATTCGTCGGAACAC
  [SEQ ID NO: 77]
```

Restriction sites are underlined (NcoI=CCATGG; BamHI= GGATCC)

(e) Sequence of pCANTAB-AP-FRAP(2015–2114)

ng of plasmid pCGNN-F1 (U.S. patent application Ser. No. 08/581,713 (filed Dec. 29, 1995)). The PCR product was purified, digested with NcoI and BamHI and ligated into NcoI-BamHI digested pCANTAB-AP-poly to yield the vector pCANTAB-AP-FKBP which was verified by restriction analysis and DNA sequencing. This construct directs the N-terminal display of FKBP on pIII residues 198–406 where Cys202 has been mutated to Tyr: the configuration described by Cunningham et al. (1994. *EMBO J.* 13. 2508).

(b) Synthesis of Biotinylated FK506 for Affinity Enrichment Studies

To provide an immobilized ligand to allow demonstration of functional display of FKBP on phage, a variant of FK506 was synthesized that has a biotin moiety attached through a linker to the allyl group of the effector domain (see scheme below). To a solution of N-(6-aminohexyl)FK506 (35 mg, 36.8 mmol) in 2 mL of $CH_2Cl_2$ was added biotin-Su (25.1 mg, 73.5 mmol), followed by addition of $NEt_3$ (51.4 mL, 368 mmol). DMF was added to the suspension until the reaction mixture became clear. The reaction was complete after 10 min. The mixture was diluted with $CH_2Cl_2$ (25 mL),

```
geneIII leader->                                                                      [SEQ ID NO: 78]
M   K   K   L   L   F   A   I   P   L   V   V   P   F   Y   A   A   Q   P   A
GTG AAA AAA TAA TTA TTC GCA ATT CCT TTA GTT GTT CCT TCC TAT GCG GCC CAG CCG GCC FRAP(2015-)->
M   A   A‡  E   L   I   R   V   A   I   L   W   H   E   M   W   H   E   G   L
ATG GCC ACT GAG CTG ATC CGA GTG GCC ATC CTC TGG CAT GAG ATG TGG CAT GAA GGC CTG
NcoI E   E   A   S   R   L   Y   F   G   E   R   N   V   K   G   M   F   E   V   L
GAA GAG GCA TCT CGT TTG TAC TTT GGG GAA AGG AAC GTG AAA GGC ATG TTT GAG GTG CTG E   P   L   H   A   M   M   E   R   G   P   Q   T   L   K   E   T   S   F   N
GAG CCC TTG CAT GCT ATG ATG GAA CGG GGC CCC CAG ACT CTG AAG GAA ACA TCC TTT AAT Q   A   Y   G   R   D   L   M   E   A   Q   E   W   C   R   K   Y   M   K   S
CAG GCC TAT GGT CGA GAT TTA ATG GAG GCC CAA GAG TGG TGC AGG AAG TAC ATG AAA TCA G   N   V   K   D   L   T   Q   A   W   D   L   Y   Y   H   V   F   R   R   I
GGG AAT GTC AAG GAC CTC ACC CAA GCC TGG GAC CTC TAT TAT CAT GTG TTC CGA CGA ATC geneIII (198-)->
S   K   Q   *   D   P   F   V   Y†
TCA AAG CAG tag GAT CCA TTC GTT TAT G......
            BamHI
notes on the preceding sequence:
*indicates an amber stop codon that is suppressed as Gln in supE E. coli strains such as XL-1
(Lowman, H.B. and Wells, J.A. 1993, J. Mol. Biol. 234, 564-578)
†indicates the position of the engineered Cys202->Tyr mutation
‡indicates the first amino acid (Ala) of the mature polypeptide after signal peptide cleavage
```

E. Functional Display of FKBP on Filamentous Bacteriophage (a) Vector Construction The coding sequence of FKBP (amino acids 1–107) was amplified by PCR with primers 1 and 2, using as template 5 washed with $H_2O$ (15 mL), brine (15 mL), and dried over $Na_2SO_4$. Flash chromatography with 10% $MeOH/CH_2Cl_2$ as the eluent gave 13 mg (30%) of the desired product as a white solid. The structure was confirmed by NMR and MS.

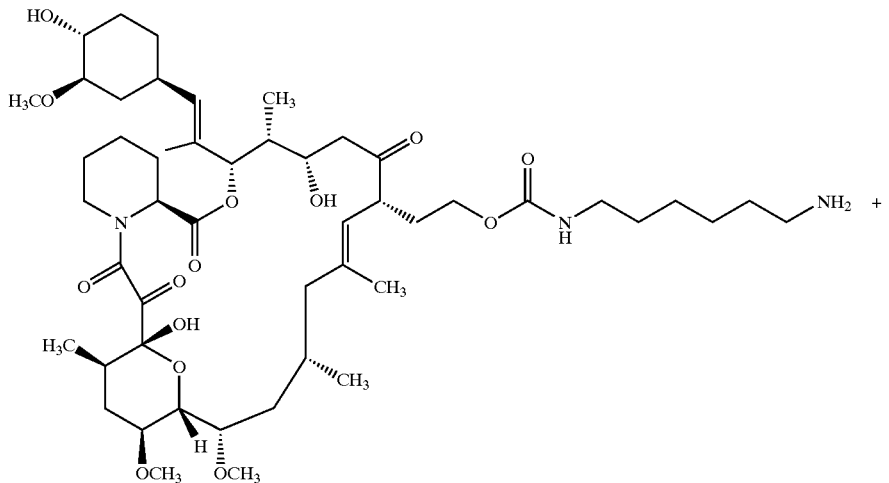

N-(6-aminohexyl) FK506 carbarnate
(for the preparation of this compound, see ariad 317 PCT)

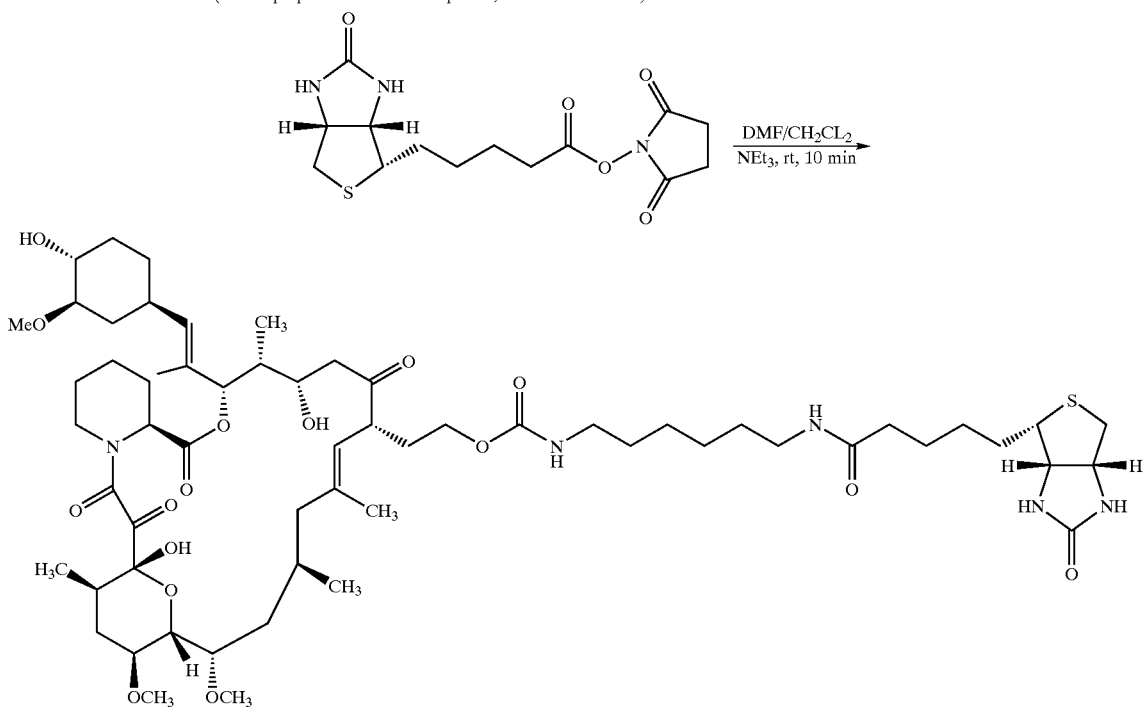

(c) Growth of FKBP Display Phage pCANTAB-AP-FKBP was transformed into *E.coli* XL-1 (Stratagene) and display phage prepared by rescue with helper phage K07, essentially as described (Lowman, H. B. and Wells, J. A. *Methods: Comp. Methods Enzymol.* 1991, 3, 205–216) except that the overnight culture used to innoculate phagemid growth was grown in medium containing 2% glucose. Phagemid titers (colony-forming units, cfu) were determined as described (Lowman, H. B. and Wells, J. A. *Methods: Comp. Methods Enzymol.* 1991, 3, 205–216).

(d) Demonstration of Functional FKBP Display by Competitive ELISA Using Biotinylated FK506

Wells of a 96-well maxisorp plate (Nunc) were coated with 100 μl per well of 1 μg/ml streptavidin (Pierce) in PBS, covered and incubated overnight at 4° C. After blocking with 1% tween-20/PBS for one hour at room temperature, the blocking solution was removed, 10 nM biotinylated FK506 was added in PBS/1% ethanol and incubation continued for a further 10 minutes. Meanwhile, 100 μl incubations were set up in separate tubes containing FKBP phage (approximately $5 \times 10^5$ cfu) and serial dilutions of FK506 in PBS/0.02% BSA/1% ethanol. These incubations were left one hour ar room temperature to equilibrate, after which the coated wells were washed five times with PBS/0.05% tween-20 and the phage-FK506 mixtures added to the wells. The plate was incubated 1 hour at room temperature and then washed fifteen times with PBS/0.05% tween-20. To detect bound phage, 100 μl of a 1/5000 dilution of anti-M13 antibody-HRP conjugate (Pharmacia) was added to each well and incubated for one hour at room temperature, after which the plates were washed ten times as before and then HRP activity quantitated using TMB substrate (Boehringer) in accordance with the manufacturer's instructions. Values were calculated as % total phage binding with reference to control wells that received no biotinylated FK506 coat (0% binding) or no FK506 competitor (100% binding).

As shown in the figure, this experiment demonstrated specific, high-affinity binding of the displayed FKBP for FK506. The IC50 for the interaction in this assay was 0.65 nM, in excellent agreement with the published $K_d$ of FKBP for FK506 of 0.4–1 nM. This experiment established that display of FKBP on phage could be used as a means to affinity select, from a library of mutants, FKBPs that have affinity for bumped ligands.

(e) Generation of a Library of Mutant FKBPs on Phage Targetted to the C13 and C14 Positions of Rapamycin To generate a library of mutant FKBPs for obtaining variants that bind rapamycin analogs bumped at the C13 or C14 positions, the de generate primers 3 and 4 were used to reamplify a portion of the FKBP gene and introduce the degenerate codon NNS (where N is any base and S is G or C) in place of the codons for Tyr26, Phe36, Asp37, Arg42 and Phe99. The side chains of these residues were observed using computer graphics to be contact with the C14 carbonyl and/or C13 hydroxyl, or to abut residues that are in contact, and were therefore candidates for mutation to generate mutants that might have good affinity for analogs with bumps introduced at these positions. Convenient ApaLI and BamHI sites that flank the randomized region and are unique in pCANTAB-AP-FKBP were used.

A portion of FKBP was amplified from pCGNN-F1 using primers 3 and 4 and Pfu polymerase. The PCR product was purified using the QIAEX II kit (Qiagen), digested extensively with ApaLI and BamHI, and ligated into ApaLI-BamHI digested pCANTAB-AP-FKBP. Ligation products are purified by phenol extraction, concentrated by ethanol precipitation and electroporated by standard techniques (Dower, W. J. et al. 1988. *Nucleic Acids Res.* 16, 6127) into *E.coli* XL-1 cells. Phage are-rescued and titered as described previously (Lowman, H. B. and Wells, J. A. *Methods: Comp. Methods Enzymol.* 1991, 3, 205–216).

(f) Library Sorting

Approximately $10^{10}$–$10^{11}$ cfu phagemid particles are prepared in 250 µl PBS/3% BSA/0.05% tween-20 (PBSBT). Recombinant GST-FRAP fusion protein (expressed in *E.coli* and purified as described by Chen et al. 1995. *Proc. Natl. Acad. Sci. USA*. 92, 4947–4951) is added to a final concentration of 1 µM, followed by 2.5 µl of a 10 µM stock of bumped rapamycin 100% ethanol. The mixture is incubated for 1 hour at room temperature, and then 100 µl of a 1:1 slurry of glutathione-agarose beads (Pharmacia) equilibrated in PBSBT added (to capture the GST-tagged FRAP and any associated phagemids). The mixture is tumbled gently on a end-over-end mixer for 15 min, after which the beads are pelleted by spinning at 8000 rpm for 30 seconds in a microfuge. The beads are then washed 5 times in 1 ml PBS/0,05% tween-20 and 5 times in 1 ml PBS/0.05% tween-20/1M NaCl. Bound phagemids are eluted from the beads by adding 200 µl 0.2 M glycine pH 2.0 and incubating for 10 min. The beads are pelleted and the supernatant (containing eluted phagemids) collected and neutralized with 26 µl 1 M Tris base. Carbenicillin (carb) and chloramphenicol (chlor)-resistant cfu titers are determined as described above, and the carb/chlor ratio used as a measure of the specific enrichment of (carbenicillin-resistant) FRAP phagemids. 100 µl of the eluted phage stock is used to infect log phase. *E.coli* XL-1 cells to prepare phagemids for the next round of selection, as described (Lowman, H. B. and Wells, J. A. *Methods: Comp. Methods Enzymol.* 1991, 3, 205–216).

Titers of phage are monitored over several rounds of selection, and when specific enrichment over background is detected, individual FKBP phage clones can be isolated and sequenced by standard techniques. Binding of the clones to bumped rapamycins is measured by competitive ELISA or fluorescence polarization assay.

(g) Primer Sequences 1. 5' CCATA<u>CCATGG</u>AGTGCAGGTGGAGACT [SEQ ID NO: 80]

2. 5' GCAT<u>GGATCC</u>TATTCCAGTTTAGAAGC [SEQ ID NO: 81]

3. 5' GCCCTGAAT<u>GTGCAC</u>NNSACCGGGATGCTTGAAGA
   TGGAAAGAANNSNNSTCCTCCCGG-
   GACNNSAACAAGCCCTTTAAGTTTATG
   CTAGGC [SEQ ID NO: 82]

4. 5' GCGAACTAC<u>GGATCC</u>TAAATTCCAGTTTTAGAAGC
   TCCACATCSNNGACGAGAGTGGCATG
   TGGTGGGATGAT [SEQ ID NO: 83]

Restriction sites are underlined (NcoI=CCATGG; BamHI= GGATCC; ApaLI=GTGCAC)

(h) Sequence of pCANTAB-AP-FKBP

[SEQ ID NO: 84]

```
geneIII leader->
V   K   K   L   L   F   A   I   P   L   V   V   P   F   Y   A   A   Q   P   A
GTG AAA AAA TTA TTA TTC GCA ATT CCT TTA GTT GTT CCT TTC TAT GCG GCC CAG CCG GCC
                                                                            ―

FKBP-->
M   A   A⁺  G   V   Q   V   E   T   I   S   P   G   D   G   R   T   F   P   K
ATG GCC GCA GGA GTG CAG GTG GAG ACT ATC TCC CCA GGA GAC GGG CGC ACC TTC CCC AAG
―――   ―
NcoI

R   G   Q   T   C   V   V   H   Y   T   G   M   L   E   D   G   K   K   F   D
CGC GGC CAG ACC TGC GTG GTG CAC TAC ACC GGG ATG CTT GAA GAT GGA AAG AAA TTT GAT
                        ―――――――
                        ApaLI

S   S   R   D   R   N   K   P   F   K   F   M   L   G   K   Q   E   V   I   R
TCC TCC CGG GAC AGA AAC AAG CCC TTT AAG TTT ATG CTA GGC AAG CAG GAG GTG ATC CGA

G   W   E   E   G   V   A   Q   M   S   V   G   Q   R   A   K   L   T   I   S
GGC TGG GAA GAA GGG GTT GCC CAG ATG AGT GTG GGT CAG AGA GCC AAA CTG ACT ATA TCT

P   D   Y   A   Y   G   A   T   G   H   P   G   I   I   P   P   H   A   T   L
CCA GAT TAT GCC TAT GGT GCC ACT GGG CAC CCA GGC ATC ATC CCA CCA CAT GCC ACT CTC
```

-continued

```
                                                geneIII(198-)->
 V   F   D   V   E   L   L   K   L   E   *   D   P   F   V   Y†  E
GTC TTC GAT GTG GAG CTT CTA AAA CTG GAA tag GAT CCA TTC GTT TAT GAA . . .
                                                BamHI
*indicates an amber stop codon that is suppressed as Gln in supE E. coli strains such as XL-1
(Lowman, H.B. and Wells, J.A. 1993. J. Mol. Biol. 234, 564–578)
†indicates the position of the engineered Cys202->Tyr mutation
‡indicates the first amino acid (Ala) of the mature polypeptide after signal peptide cleavage
```

Example 8
Rapamycin-Dependent Activation of Signal Transduction

Many cellular receptors can be activated by aggregation, either by their physiological ligand or by anti-receptor antibodies. Additionally, the aggregation of two different proteins can often trigger an intracellular signal. Rapamycin and its analogs may be used to trigger activation of a receptor effector domain by oligomerizing chimeric proteins, one of which contains one or more FKBPs and an effector domain and the other of which contains one or more FRAP domains and an effector domain. This scheme is illustrated in FIG. T1(a). While both proteins are shown anchored to the membrane, a single one could be membrane anchored, and addition of rapamycin or analog would recruit the second protein to the membrane via dimerization. Membrane anchoring may be effected through a transmembrane protein anchor or through lipid modification of the protein (s), such as myristoylation. The same effector domain may be present on both proteins, or different protein domains that interact functionally may be used, such as a protein kinase and a protein kinase substrate. Alternatively, a second effector may serve to inhibit the activity of the first effector.

We note that in some embodiments, the chimeric proteins are mixed chimeras, discussed previously, and contain FKBP and FRAP domains together with the heterologous efector domain. Oligomerization of a single mixed chimera may also be used to activate signal transduction, as shown in FIG. T1(b). Here rapamycin is shown to dimerize two identical copies of the protein. Reiteration of the FKBP and FRAP domains permits higher multiples to occur, subject to geometric constraints.

Two examples of the use of rapamycin in signal transduction are to trigger receptor tyrosine kinase activation and to trigger apoptosis via Fas activation, both-of which are discussed below. Unless otherwise mentioned all DNA manipulations were performed following standard procedures (F. M. Ausubel et al., Eds., Current Protocols in Molecular Biology, John Wiley & Sons, New York, 1994) and all protein protocols were performed following standard procedures (Harlow, E. and Lane, D. 1988. Antibodies, a Laboratory Manual. Cold Spring Harbor Laboratory, Cold Spring Harbor.). All PCR products used to make constructs were confirmed by sequencing.

A. Rapamycin-inducible Receptor Tyrosine Kinase Activation

1. Construction of pCM, an Expression Vector Containing a Myristylation Signal

A XbaI-Myr-BamHI cassette, obtained by annealing oligonucleotides 1 and 2, was digested with XbaI/BamHI and cloned into the XbaI/BamHI site of the pCG expression vector (Tanaka, M. and Herr, W. 1990. Cell 60: 375–386) to create pCGM. (For oligonucleotide sequences, see (7) below). This oligonucleotide cassette consists of an inframe XbaI site followed by sequence encoding for the first 15 amino acids residues of c-Src tyrosine kinase that has been shown to allow myristoylation and target protein to the plasma membrane (Cross et al., 1984. MCB. 4:1834–1842). The myristoylation domain is followed by an inframe SpeI site and stop codons. The XbaI site in the pCG vector is placed such that it adds two amino acids between the initiating Met and the sequence cloned. Since the spacing between the initiating Met and the myristylated Gly is crucial for membrane localization of c-Src (Pellman et al. 1985. PNAS. 82: 1623–1627) the XbaI site following the ATG in pCGM was deleted by site directed mutagenesis following manufacturers protocol (Muta-Gene, BioRad). To facilitate future cloning steps the SpeI site in the myristylation cassette was mutated to a XbaI site. Single stranded uracil-DNA of pCGM was prepared and the mutagenesis was carried out using both oligonucleotide 3 (to delete the XbaI site following ATG and add an EcoRl site 5' to ATG) and oligonucleotide 4 (to change the SpeI site following the myristylation domain to a XbaI site). The resulting sequence surrounding the ATG of the pCM vector was confirmed by sequencing using oligonucleotide 5 (see sequence 1, (8) below).

2. Addition of FKBPs and an Epitope Tag to pCM Generates pCMF1/2/3.HA

A SpeI-HA-BamHI cassette was prepared by annealing complementary oligonucleotides (oligonucleotides 6 and 7). This cassette has an inframe SpeI site followed by nine amino acids of H. influenzae hemaglutinin gene that is recognized by the monoclonal antibody 12CA5, stop codons and a BamHI site. The SpeI-HA-BamHI cassette was sub cloned into the SpeI/BamHI site of pCGNNF1, pCGNNF2 and pCGNNF3. Subsequently, the 1/2/3 copies of FKBP fused with HA epitope was sub cloned as an XbaI/BamHI fragment into pCM. The resulting plasmid (pCMF1/2/3.HA) has the following features: myristylation domain; an inframe XbaI site; one/two/three copies of FKBP; an inframe SpeI site; a HA epitope tag; and stop codons.

3. Addition of FRBs and an Epitope Tag to pCM Generates pCMFR1/2/3.Flag

A SpeI-Flag-BamHI cassette can be prepared by annealing complementary oligonucleotides (oligonucleotides 8 and 9). This cassette has the same features as the SpeI-HA-BamHI cassette described above with the exception that the inframe SpeI site is followed by sequence that codes for eight amino acids (DYKDDDDY) [SEQ ID NO: 86] (Hopp et al., 1988. Biotech. 6: 1205–1210) that is recognized by a monoclonal antibody anti-FLAG.M2 (Kodak Scientific Imaging Systems). The SpeI-Flag-BamHI cassette is sub cloned into the SpeI/BamHI site in pCGNN-1FRB, pCGNN-2FRB and, pCGNN-3FRB. Subsequently 1/2/3 copies of FRB domain-Flag epitope fusions are sub cloned as a XbaI/BamHI fragment into pCM. The resulting plasmid (pCMFR$^{1/2/3}$·Flag) has the following features: myristylation domain; an inframe XbaI site; one/two/three copies of FRB; an inframe SpeI site; a Flag epitope tag; and stop codons.

4. Fusion of FKBP and FRB Constructs to Receptor Tyrosine Kinase Cytoplasmic Domain The cytoplasmic domain of receptor tyrosine kinase of choice (e.g., EGFR, erbB-2, PDGFR, KDR/Flk-1, Flt-1) is PCR amplified with inframe 5'XbaI and 3'SpeI sites. The PCR product may be subcloned either into the inframe XbaI site such that the XbaI site is restored, or into the inframe SpeI site such that the SpeI site is. restored in pCMFR series or pCMFseries vectors (see above). As a result, the FKBP/FRB domain(s) can be placed either C-terminal or NH2-terminal to the cytoplasmic domain of the receptor tyrosine kinase. The vectors are constructed such that (i) the cytoplasmic domain of a given receptor is fused to both FKBP and FRB (for e.g., EGFR cytoplasmic domain fused to either FKBP or FRB) or (ii) can be constructed such that cytoplasmic domains of two different receptors are fused to FKBP and FRB (for e.g., EGFR cytoplasmic domain fused to FKBP and erbB-2 cytoplasmic domain fused to FRB). In the former case (i) addition of the drug, rapamycin, will induce the formation of homodimers (e.g., EGFR/EGFR) while, in the latter (ii) addition of the drug will induce heterodimer (e.g., EGFR/erbB-2) and result in activation of the signal transduction cascade.

5. Testing the Constructs

To test the ability of rapamycin or analog to induce dimerization of FKBP- and FRB-receptor cytoplasmic domain fusions, the constructs of choice (e.g., pCMEGFR-FR$^1$ and pCMEGFR-F1) are cotransfected into Cos-1 cells by lipofection (Gibco BRL). Three days after transfection the cells are induced with rapamycin and lysed in lysis buffer (1% Triton X-100; 50 mM Tris.cl pH$_{8.0;\ 150}$ mM NaCl; 5 mM NaF; 1 mM sodium ortho vanadate; 10 ug/ml aprotinin; 10 ug/ml leupeptin). The fusion proteins from rapamycin-treated and untreated cell lysates are immunoprecipitated with anti-Flag and 12CA5 antibodies and immunoblotted with anti-phosphotyrosine antibody. The choice of cell type; the amount of DNA transfected; the concentration of rapamycin used and the duration of drug treatment are varied to achieve optimal results.

6. Rapamycin-inducible Cell Growth

A selected mammalian cell line (e.g., NIH3T3) is cotransfected with constructs encoding for FRB and FKBP fusion proteins (e.g., pCMEGFR-FR1 and pCMEGFR-F1) and stable cell lines expressing the fusion proteins are established. To determine whether rapamycin-inducible activation of receptor cytoplasmic domain will induce cell proliferation, stable cell lines expressing the fusion proteins are grown either in the presence or absence of rapamycin and the changes in cell growth rate are determined by routine procedures (e.g., by monitoring cell number; by determining the $^3$H thymidine incorporation rate, etc.). The choice of receptor tyrosine kinase; the type of receptor activation (homodimer vs. heterodimer) may be chosen to obtain optimal results.

7. Oligonucleotide sequences

| | | |
|---|---|---|
| 1: | CATGTCTAGAGGGAGTAGCAAGAGCAAGCCTAAGGACCCCAGCCAGCGCACTAGTTAAGAATTCTGATGAT CAGCGGATCCTAGC | [SEQ ID NO: 87] |
| 2: | GCTAGGATCCGCTGATCATCAGAATTCTTAACTAGTGCGCTGGCTGGGGTCCTTAGGCTTGCTCTTGCTAC TCCCTCTAGACATG | [SEQ ID NO: 88] |
| 3: | CGCCTTGTAGAATTCGCGCGTATGGGGAGTAGCAAGA | [SEQ ID NO: 89] |
| 4: | CCCAGCCAGCGCTCTAGATAAGAATTCTGA | [SEQ ID NO: 90] |
| 5: | AAGGGTCCCCAAACTCAC | [SEQ ID NO: 91] |
| 6: | GCATGACTAGTTATCCGTACGACGTACCAGACTACGCATAAGAAAAGTGAGGATCCTACGG | [SEQ ID NO: 92] |
| 7: | CCGTAGGATCCTCACTTTTCTTATGCGTAGTCTGGTACGTCGTACGGATAACTAGTCATGC | [SEQ ID NO: 93] |
| 8: | CCGTAGGATCCTCACTTTTCTTAATAATCGTCATCGTCTTTGTAGTCACTAGTCATGC | [SEQ ID NO: 94] |
| 9: | GCATGACTAGTGACTACAAAGACGATGACGATTATTAAGAAAAGTGAGGATCCTACGG | [SEQ ID NO: 95] |

8. Sequence 1:

[SEQ ID NO: 96]

```
                              M   G   S   S   K   S
CGC CTT GTA GAA ttc GCG CGT ATG ggg agt agc aag K   P   K   D   P   S   Q   R   S   R  stop
agc aag cct aag gac ccc agc cag cgc tct aga taa stop
gaa ttc tga tga tca gcG GAT CCT GAG AAC T
```

The modified sequences are in lowercase bold and the intitiating ATG is underlined. Sequences in uppercase are from the parental pCG backbone.

B. Constructs Encoding Chimeric Proteins that Include Domain(s) of Fas

The ability to control Fas activation and trigger apoptosis via a small molecule has applications both in gene therapy, where it may be used to selectively eliminate engineered cells, and in experimental systems. The proteins described here are anchored to the membrane via the low affinity NGF receptor, also called p75. It should be appreciated, however, that another protein anchor could be readily substituted. p75 is useful experimentally because of the availability of antibodies to its extracellular domain, and its lack of high affinity interaction with any identified ligand (Bothwell, M. 1995. Annu. Rev. Neurosci. 18:223–253).

1. 2-Protein Rapamycin-Regulated Fas Activation (a) Construction of the p75 Vector Vectors to direct the expression of FRAP-Fas fusion proteins containing the extracellular and transmembrane domain of the low affinity NGF receptor (also known as p75) were derived from the mammalian expression vector pJ7W (Morgenstern, J. P. and Land, H. 1990. Nucleic Acids Res. 18:1068), modified by substitution of a. pUC backbone for the original pBR backbone using standard methods. We call this vector pA7W. Inserts cloned into the polylinker sites of this plasmid are transcribed under the control of the simian CMV promoter and enhancer sequences. The polylinker follows the CMV sequence with HindIII-SalI-XbaI-BamHI-SstI-EcoRI-ClaI-KpnI-BglII. Any mammalian expression vector with suitable cloning sites and promoter could be substituted.

A restriction fragment encoding a fragment of p75 flanked by HindIII and XbaI sites was generated by PCR using primers J1 (5') and J2 (3'), based on the sequence of p75 (Johnson, D., Lanahan, A., Buck, C. R., Shegal, A., Morgan, C., Mercer, E., Bothwell, M., Chao, M. 1986. Cell 47:545–554). The original source of the PCR template was a clone derived from a human brain library, using primers similar to J1 and J2 but with different restriction sites. The 5' end of the resulting fragment contains a HindIII site followed by an EcoRI site, a Kozak sequence and the initiation of p75 coding sequence (amino acid 1). The 3' end generated encodes the receptor sequence up to and including amino acid 274, 2 amino acids past the predicted membrane spanning sequence, followed by an XbaI site. Analogous portions of other transmembrane receptors can be substituted for this fragment. The PCR product was subcloned as a HindIII-XbaI fragment into HindIII-XbaI cut pA7W, generating pA7Wp75. The construct was verified by restriction analysis and DNA sequencing.

(b) Addition of Fas to pA7Wp75

XbaI-SpeI fragments encoding Fas amino acids 206–304 (FasS) and Fas amino acids 206–319 (FaSL) were made by PCR and subcloned into pA7Wp75 cut with the same enzymes. The primers used were J3 (5') and J4 or J5 (3'). J5 generates a fragment of Fas that ends beyond its termination codon; when cut with SpeI, the nucleotides encoding the terminal 15 aa of Fas are removed to give a truncated form of intracellular Fas we call $Fas_S$. Removal of these 15 aa increases the activity of Fas in some cell types (Itoh, N., and Nagata, S. 1993. J. Biol. Chem 268:10932). Primer J4 replaces the natural termination codon of Fas with a SpeI site, and also mutates the original SpeI site contained in Fas, generating $Fas_L$. The plasmids generated from subcloning these fragments are pA7Wp75-$Fas_S$ and pA7Wp75-$Fas_L$, respectively. These construct were verified by restriction analysis and DNA sequencing. To attach an epitope tag to these inserts, the XbaI-SpeI Fas fragments were isolated and ligated into the XbaI-SpeI cut backbone of pCMF1/2/3.HA, plasmids described above which encode an epitope tag of 9 amino acids from the *H. influenza* haemagglutinin protein (E) 3' to the SpeI site, followed by a BamHI site. Cutting the resultant plasmid with XbaI and BamHI generated fragments encoding Fas followed by the epitope tag (designated E for these constructs).

(c) p75FRAP-Fas-epitope Fusion Proteins: Addition of FRAP-containing Fragments to pA7Wp75-$Fas_S$E and pA7Wp75-$Fas_L$E to Generate p75-$FRAP_x$-$Fas_{SorL}$E and p75-$Fas_{SorL}$-$FRAP_x$E The XbaI-SpeI fragments containing a portion of FRAP are described previously in this document. These XbaI-SpeI fragments were inserted into either the XbaI site directly after the p75 coding sequence to generate p75-$FRAP_x$-$Fas_{SorL}$E or into the SpeI site directly after the Fas fragment to generate p75-$Fas_{SorL}$-$FRAP_x$E. Alternatively, more than one FRAP fragment is subcloned in, either as a FRAPn fragment, or by sequential subcloning of XbaI-SpeI fragments into the Spe I site available after subcloning the first FRAP into either XbaI or SpeI. Thus the final series of vectors encodes (from the N to the C terminus) p75 extracellular and transmembrane sequence, one or more FRAP-derived domains fused N- or C-terminally to one or more Fas intracellular domains, and an epitope tag.

(d) p75-FKBP-Fas Fusion Proteins: Addition of FKBP-containing Fragments to pA7Wp75-$Fas_S$E and pA7Wp75-$Fas_L$E to Generate p75-$FKBP_n$-$Fas_{SorL}$ or p75-$Fas_{SorL}$-$FKBP_n$ The XbaI-SpeI fragments containing one or more FKBPs have been described elsewhere in this document. These fragments were inserted into either the XbaI site directly after the p75 coding sequence to generate p75-$FKBP_n$-$Fas_{SorL}$ or into the SpeI site directly after the Fas fragment to generate p75-$Fas_{SorL}$-$FKBP_n$. Thus the final series of vectors encodes (from the N- to the C-terminus) p75 extracellular and transmembrane sequence, one or more FKBPs fused N- or C-terminally to one or more Fas intracellular domains, and an epitope tag.

(e) Assay of Rapamycin-Mediated Fas Activation

The ability of expression of a protein containing Fas and FRAP domains and a protein containing Fas and FKBP domains to activate Fas and trigger cell death upon addition of rapamycin can be tested in either transiently or stably transfected cells.

For transient transfections, the two plasmids to be tested are cotransfected into a cell line such as HT1080 by a standard method such as lipofection, calcium phosphate precipitation or electroporation. One or more days after transfection, cells are treated with no addition or one or more concentrations of rapamycin or one or more concentrations of a dimerizing agent such as FK1012. The FK1012 serves as a positive control that the FKBP-Fas construct is functional. Several hours to 1 day later, the cells are monitored for response by one of several methods. Cell lysates were prepared by conventional means and used to generate Western blots that are probed with antibody directed against HA or against the extracellular domain of p75. Alternatively, cells can be assayed by collection in isotonic solution plus 10 mM EDTA, stained with anti-p75 monoclonal antibody and labeled secondary antibody, and the positive cells measured by FACS. A decrease in either Western blot signal or FACS signal upon treatment indicates sucessful induction of cell death (or decrease in protein expression). In addition, commercially available kits can be used to monitor apoptosis.

To stably transfect cells, a vector encoding a selectable marker such as neomycin resistance is cotransfected along with the plasmids described. Two to three days after transfection, cells are plated into G418 and the resistant population or clones are isolated by standard means. These populations can then be monitored directly for induction of apoptosis by treatment with dimerizer followed by cell counting or other measure of cell viability.

An alternative means of generating stable cell lines expressing the constructs of interest is to subclone the inserts into a retroviral vector. The inserts are excisable with Eco RI to facilitate this subcloning. The vector is then used to make transducing supernatants by a packaging cell using conventional methods.

2. Single Protein Rapamycin-Regulated Fas Activation (a). Construction of FKBP-FRAP Chimeric Fragments FKBP-FRAP Fusion Constructs for Rapamycin-dependent Homodimerization of Fas Intracellular Domain i. Structure-assisted Design In order to design molecules containing both FRAP and FKBP domains that are capable of rapamycin-dependent homodimerization, the three dimensional structure of the ternary complex between human FKBP12, rapamycin, and a portion of human FRAP encompassing the minimal FRB domain may be considered. Requirements for homodimerization of two molecules of fusion proteins containing FRAP, FKBP and Fas moieties include (i) sufficient length and flexibility of the polypeptide to accomodate the distortions necessary for the FRAP-FKBP interaction to occur between molecules tethered at the membrane, while preserving the ability of aggregated Fas to transduce a signal; and (ii) prevention or minimization of intramolecular dimerization by rapamycin, an event expected to be highly entropically favored due to the chelate effect, and therefore to prevent the desired intermolecular molecular dimerization.

Structural considerations led us to the following design preferences for the fusion constructs:

(i) FRB and FKBP should be joined with a polypeptide linker sufficiently short that intramolecular dimerization is sterically prevented. The currently preferred configuration is FRAP-FKBP as the C-terminus of FRAP and the N-terminus of FKBP are distant, allowing a long linker (>ten amino acids) that should still prevent intramolecular dimerization yet afford flexibility.

(ii) This FRAP-FKBP 'cassette' can be present membrane-proximally (i.e. with Fas domain(s) added to the C-terminus), or membrane distal (with the Fas domain membrane-proximal and the FRAP-FKBP cassette appended C-terminally).

(iii) A long linker should be present N-terminal to the FRAP-FKBP domains, to allow for the structural distortions implied by dimerization at the membrane or if the domains are added C-terminally. Again a N-terminal location of FRAP is preferred as this long linker can then comprise natural FRAP sequence from the region N-terminal to the FRB domain, minimizing the imnmunogenicity of the chimeric protein.

(iv) Optimal linker lengths and fusion positions for a given protein should be confirmed empirically.

A series of 12 fusions of FKBP and FRAP, designated T1–T12, was designed. Nine were N-FRAP-FKBPC fusions including between 13, 23 or 33 amino acids N-terminal to Arg2018 (the N-terminal linker), and 4, 7 or 10 residues separating the two proteins. The remaining three were N-FKBP-FRAP-C fusions interposing 3, 0 or −4 residues of FRAP sequence between FKBP Glu107 and FRAP Arg2018.

(ii) Construction

The twelve fusions were made as XbaI-BamHI cassettes that could be cloned directly as a single fragment, using the three-primer PCR splicing method (Yon, J. and Fried, M. 1989. *Nucleic Acids Res.* 17, 4895). Cloning in this way avoided the introduction of restriction sites between the genes that would encode foreign sequence and alter the length of the linker. A mixture of 1 ng each of pCGNN-1FRAP$_i$ and pCANTAB-AP-FKBP was amplified using Pfu polymerase with 1 µM each of two outer primers (A and C), in the presence of 0.01 µM of a single 'splice' oligo (B) complementary to both genes that directs the desired fusion. The primers used are tabulated below:

| # | construct | oligos A | B | C | N-term* (aa) | linker† (aa) |
|---|---|---|---|---|---|---|
| T1 | FRAP(1985–2116)-FKBP | 100 | 102 | 105 | 33 | 4 |
| T2 | FRAP(1995–2116)-FKBP | 93 | 102 | 105 | 23 | 4 |

-continued

| # | construct | oligos A | B | C | N-term* (aa) | linker† (aa) |
|---|---|---|---|---|---|---|
| T3 | FRAP(2005–2116)-FKBF | 101 | 102 | 105 | 13 | 4 |
| T4 | FRAF(1985–2119)-FKBP | 100 | 103 | 105 | 33 | 7 |
| T5 | FRAP(1995–2119)-FKBP | 93 | 103 | 105 | 23 | 7 |
| T6 | FRAP(2005–2119)-FKBP | 101 | 103 | 105 | 13 | 7 |
| T7 | FRAP(1985–2122)-FKBP | 100 | 104 | 105 | 33 | 10 |
| T8 | FRAP(1995–122)-FKBP | 93 | 104 | 105 | 23 | 10 |
| T9 | FRAP(2005–2122)-FKBP | 101 | 104 | 105 | 13 | 10 |
| T10 | FKBP-FRAP(2014–2114) | 106 | 107 | 110 | — | 3 |
| T11 | FKBP-FRAP(2018–2114) | 106 | 108 | 110 | — | 0 |
| T12 | FKBP-FRAP(2021–2114) | 106 | 109 | 110 | — | −4 |

*Number of amino acids between the Arg encoded by the 5' XbaI site and FRAP Arg2018 (for fusions T1–T9)
†Number of amino acids between FRAP Ser2112 and FKBP Gly1 (for fusions T1–T9); or between FKBP Glu107 and FRAP Arg 2018 (for fusions T10–T12)

PCR products were purified, digested with XbaI and BamHI, and ligated into XbaI-BamHI digested pCM. The constructs were verified by restriction analysis and DNA sequencing.

Primer Sequences 93 5' GCACTA<u>TCTAGA</u>CTGAAGAACATGTG
    TGAGCACAGC     [SEQ ID NO: 98]

100 5' GCAT<u>TCTAGA</u>AGACCCGGCACAATG
    CAGCCAAC     [SEQ ID NO: 99]

101 5' GCAT<u>TCTAGA</u>CTGGTCCAGCAGGC
    CATGATGGTG     [SEQ ID NO: 100]

102 5' CGAATCTCAAAGCAGCTGCCTGGAGTG-
    CAGGTGGAGACTATC     [SEQ ID NO: 101]

103 5' AAGCAGCTGCCTCAGCTCACAGGAGTG-
    CAGGTGGAGACTATC     [SEQ ID NO: 102]

104 5' CCTCAGCTCACATCCTTAGAGGGAGTG-
    CAGGTGGAGACTATC     [SEQ ID NO: 103]

105 5' GCCAA<u>GGATCCC</u>TAATA
    <u>ACTAGTT</u>TCCAGTTTTAGAAGCTCCAC [SEQ ID NO: 104]

106 5' GCAT<u>TCTAGA</u>GGAGTGCAGGTGG
    AGACTATC     [SEQ ID NO: 105]

107 5' GTGGAGCTTCTAAAACTGGAAGAG-
    GAGCTGATCCGAGTGGCC     [SEQ ID NO: 106]

108 5' GTGGAGCTTCTAAAACTGGAACGAGTG-
    GCCATCCTCTGGCAT     [SEQ ID NO: 107]

109 5' GTGGAGCTTCTAAAACTGGAAATC-
    CTCTGGCATGAGATGTGG     [SEQ ID NO: 108]

110 5' CGTCA<u>GGATCCC</u>TAATA
    <u>ACTAGTT</u>CTGCTTTGAGATTCGT
    CGGA     [SEQ ID NO: 109]

Restriction sites are underlined (XbaI=TCTAGA, SpeI=ACGAGT, BamHI=GGATCC).

```
Sequence of representative construct: fusion T6
xbaI      FRAP(2005-)->
TCT AGA ctg gtc cag cag gcc atg atg gtg agc gag gag ctg atc cga gtg gcc atc ctc    [SEQ ID NO: 110]
 S   R   L   V   Q   Q   A   M   M   V   S   E   E   L   I   R   V   A   I   L tgg cat gag atg tgg cat gaa ggc ctg gaa gag gca tct cgt ttg tac ttt ggg gaa agg
 W   H   E   M   W   H   E   G   L   E   E   A   S   R   L   Y   F   G   E   R aac gtg aaa ggc atg ttt gag gtg ctg gag ccc ttg cat gct atg atg gaa cgg ggc ccc
 N   V   K   G   M   F   E   V   L   E   P   L   H   A   M   M   E   R   G   P cag act ctg aag gaa aca tcc ttt aat cag gcc tat ggt cga gat tta atg gag gcc caa
 Q   T   L   K   E   T   S   F   N   Q   A   Y   G   R   D   L   M   E   A   Q gag tgg tgc agg aag tac atg aaa tca ggg aat gtc aag gac ctc acc caa gcc tgg gac
 E   W   C   R   K   Y   M   K   S   G   N   V   K   D   L   T   Q   A   W   D FKBP(1)->
ctc tat tat cat gtg ttc cga cga atc tca aag cag ctg cct cag ctc aca GGA GTG CAG
 L   Y   Y   H   V   F   R   R   I   S   K   Q   L   P   Q   L   T   G   V   Q GTG GAG ACT ATC TCC CCA GGA GAC GGG CGC ACC TTC CCC AAG CGC GGC CAG ACC TGC GTG
 V   E   T   I   S   P   G   D   G   R   T   F   P   K   R   G   Q   T   C   V GTG CAC TAC ACC GGG ATG CTT GAA GAT GGA AAG AAA TTT GAT TCC TCC CGG GAC AGA AAC
 V   H   Y   T   G   M   L   E   D   G   K   K   F   D   S   S   R   D   R   N AAG CCC TTT AAG TTT ATG CTA GGC AAG CAG GAG GTG ATC CGA GGC TGG GAA GAA GGG GTT
 K   P   F   K   F   M   L   G   K   Q   E   V   I   R   G   W   E   E   G   V GCC CAG ATG AGT GTG GGT CAG AGA GCC AAA CTG ACT ATA TCT CCA GAT TAT GCC TAT GGT
 A   Q   M   S   V   G   Q   R   A   K   L   T   I   S   P   D   Y   A   Y   G GCC ACT GGG CAC CCA GGC ATC ATC CCA CCA CAT GCC ACT CTC GTC TTC GAT GTG GAG CTT
 A   T   G   H   P   G   I   I   P   P   H   A   T   L   V   F   D   V   E   L SpeI             BamHI
CTA AAA CTG GAA ACT AGT TAT TAG GGA TCC
 L   K   L   E   T   S   Y   *   G   S
```

(b) Addition of FRAP-FKBP Chimeric Inserts to pA7Wp75-Fas$_S$E and pA7Wp75-Fas$_L$E Subcloning of T1 through T12 as XbaI-SpeI fragments into pA7Wp75-Fas$_S$E and pA7Wp75-Fas$_L$E linearized with XbaI generates p75TFas$_{SorL}$E. Subcloning into pA7Wp75-FaS$_L$E linearized with SpeI generated p75-Fas$_{SorL}$T-E. These constructs are listed in Table 1 ((d) below).

(c) Alternative FRAP-Fas-FKBP Constructs

Instead of the format of the chimeric fragments T1–T12, the single chain strategy could require a different orientation of domains for optimal activity. To this end, another series of constructs was made in which FKBP and FRB are separated by a Fas fragment. The starting points for these constructs are pCMF1HA, pCMF2HA, and PCMF3HA. Similar to the strategy described above for the construction of chimeric transcription factors, FKBP and FRB fragments (described elsewhere in this document) were cloned into the pCM backbones as XbaI-BamHI fragments that included a SpeI site just upstream of the BamHI site. As XbaI and SpeI produce compatible ends, this allowed further XbaI-BamHI fragments to be inserted downstream of the initial insert. Additionally, cloning of an XbaI-SpeI fragment results in the addition of the fragment at the 5' end of the construct. The final p75-anchored construct was made by subcloning the XbaI-SpeI fragments shown in Table 1 ((d) below) into pA7Wp75-Fas$_S$E. A similar series is made by subcloning into pA7Wp75-Fas$_L$E. Insertion into vector cut with XbaI resulted in addition of the insert 3' to the p75 fragment. Insertion into this vector cut with SpeI resulted in addition of the insert 3' to the Fas fragment. Insertion into this vector cut with XbaI and SpeI resulted in addition 3' to the p75 fragment, and elimination of the Fas fragment originally in the vector. By using these three subcloning strategies, the following series of constructs was generated. Numerical subscripts define the number of times the domain is reiterated.

TABLE 1

| NAME | xba I-Spe I FRAGMENT SUBCLONED | VECTOR SITE(S) USED TO SUBCLONE INSERT INTO pA7W p75-Fas$_S$E | CONSTRUCT |
|---|---|---|---|
| A1 | K$_2$Fas$_L$ | Spe I + Xba I | NKf$_2$Fas$_L$E |
| A2 | R | Spe I | NFas$_S$RE |
| A3 | R | Xba I | NRFas$_S$E |
| A4 | R$_2$ | Spe I | NFas$_S$R$_2$E |
| A5 | R$_2$ | Xba I | NR$_2$Fas$_S$E |
| A6 | K$_2$Fas$_S$R | Spe I | NFas$_S$K$_2$Fas$_S$RE |
| A7 | KFas$_S$R | Spe I | NFas$_S$KFas$_S$RE |
| A8 | K$_2$Fas$_S$R$_2$ | Spe I | NFas$_S$NK$_2$Fas$_S$R$_2$E |
| A9 | KFas$_S$R$_2$ | Spe I | NFas$_S$NK$_2$Fas$_S$R$_2$E |
| A10 | T1 | Spe I | NFas$_S$T1E |
| A11 | T2 | Spe I | NFas$_S$T2E |
| A12 | T3 | Spe I | NFas$_S$T3E |
| A13 | T4 | Spe I | NFas$_S$T4E |
| A14 | T5 | Spe I | NFas$_S$T5E |
| A15 | T6 | Spe I | NFas$_S$T6E |
| A16 | T7 | Spe I | NFas$_S$T7E |
| A17 | T8 | Spe I | NFas$_S$T8E |
| A18 | T9 | Spe I | NFas$_S$T9E |
| A19 | T10 | Spe I | NFas$_S$T10E |
| A20 | T11 | Spe I | NFas$_S$T11E |
| A21 | T12 | Spe I | NFas$_S$T12E |
| A22 | K$_2$Fas$_S$R | Xba I | NK$_2$Fas$_S$RFas$_S$E |
| A23 | KFas$_S$R | Xba I | NKFas$_S$RFas$_S$E |

TABLE 1-continued

| NAME | xba I-Spe I FRAGMENT SUBCLONED | VECTOR SITE(S) USED TO SUBCLONE INSERT INTO pA7W p75-Fas$_S$E | CONSTRUCT |
|---|---|---|---|
| A24 | K$_2$Fas$_S$R$_2$ | Xba I | NK$_2$FaSSR$_2$Fas$_S$E |
| A25 | KFas$_S$R$_2$ | Xba I | NKFas$_S$R$_2$Fas$_S$E |
| A26 | T1 | Xba I | NT1Fas$_S$E |
| A27 | T2 | Xba I | NT2Fas$_S$E |
| A28 | T3 | Xba I | NT3Fas$_S$E |
| A29 | T4 | Xba I | NT4Fas$_S$E |
| A30 | T5 | Xba I | NT5Fas$_S$E |
| A31 | T6 | Xba I | NT6Fas$_S$E |
| A32 | T7 | Xba I | NT7Fas$_S$E |
| A33 | T8 | Xba I | NT8Fas$_S$E |
| A34 | T9 | Xba I | NT9Fas$_S$E |
| A35 | T10 | Xba I | NT10Fas$_S$E |
| A36 | T11 | Xba I | NT11Fas$_S$E |
| A37 | T12 | Xba I | NT12Fas$_S$E |
| A38 | K$_2$Fas$_S$R | Spe I + Xba I | NK$_2$Fas$_S$RE |
| A39 | KFas$_S$R | Spe I + Xba I | NKFas$_S$RE |
| A40 | K$_2$Fas$_S$R$_2$ | Spe I + Xba I | NK$_2$Fas$_S$R$_2$E |
| A41 | KFas$_S$R$_2$ | Spe I + Xba I | NKFas$_S$R$_2$E |

Code:
N = p75 NGF receptor aa 1–274
Fas$_S$ = Fas aa 206–304
Fas$_L$ = Fas aa 206–319
K = FKBP aa 2–108
R = FRAP 2012–2113, but other boundaries can be substituted
E = HA epitope followed by termination codons as described in pCMF1/2/3.HA (e) Termini of Fragments Used (FKBP and FRB Fragments are Described Elsewhere in this Document)

i. p75 extracellular and transmembrane fragment
5'end:
    HindIII-EcoRI_Kozak_p75 coding sequence
                      M   G   A   G   A........
5'GGCCCAAGCTTGAATTCCGGGCGATGGGGGCAGGTGCC3'......    [SEQ ID NO: 112]

3'end:
                    transmembrane      XbaI
..................A   Y   I   A   F   K   R   S   R
...............5'GCCTACATAGCCTTCAAGAGGTCTAGACCG3'    [SEQ ID NO: 114]

ii. Intracellular domain of Fas:
5'end:
    Xba I    intracellular Fas
     S   R   K   R   K   E   V   Q   K.......
5'GGCTCTAGAAAGAGAAAGGAAGTACAGAAA3'......    [SEQ ID NO: 116]

3'end of Fas$_L$ construct:
    mutation of SpeI                                SpeI
..T  S  D  S  E  N  S  N  F  R  N  E  I  Q  S  L  V  T  S    [SEQ ID NO: 118]
5'ACTAGCGACTCAGAAAATTCAAACTTCAGAAATGAAATCCAAAGCTTGGTCACTAGT3'

3'end of Fas$_S$ construct:
                                  SpeI
..... I  I  L  K  D  I  T  S
....5'ATCATCCTCAAGGACATTACTAGT3'    [SEQ ID NO: 120]

(f) Oligos Used

J1. ggcccaagcttgaattccgggcgatgggggcaggtgcc    [SEQ ID NO: 122]

J2. cggtctagacctcttgaaggctatgtaggc    [SEQ ID NO: 123]

J3. ggctctagaaagagaaaggaagtacagaaa    [SEQ ID NO: 124]

J4. gcactagtgaccaagctttggatttcatttctgaagtttgaattttctgagtcgctagta    [SEQ ID NO: 125]

J5. ttagccctcgagctagaccaagctttggatttc    [SEQ ID NO: 126]

For constructs in which a myristoylation sequence is used to anchor protein to the membrane, pCM (described elsewhere in this application) was used, and inserts were cloned in 3' to the myristoylation signal sequence as XbaI-BamHI or XbaI-SpeI fragments.

(g) Rapamycin-regulated Apoptosis of Stable Transfected Human HT1080 Cells in Culture XbaI-BamHI fragments from constructs A30 and A31 (d, table 1) were cloned into pCM to generate M30 and M31, constructs that direct the expression of MT5Fas$_S$E and MT6Fas$_S$E, where M denotes a myristoylation domain (see this example sections A.1. and A.8.) and other abbreviations are as described in d, table 1.-EcoRI-BamHI fragments containing these expression cassettes were then cloned into the retroviral vector pSMTN3 (Example 1). Helper-free retroviruses containing this DNA were generated by transient co-transfection of 293T cells (Pear, W. S. et al. 1993. Proc. Natl. Acad. Sci. USA, 90, 8392–8396) with the constructs and a Psi(−) amphotropic packaging vector. HT1080 cells were infected with viral stock and selected with G418.

To assay apoptosis of the stably transfected pools of cells in response to rapamycin, cells were plated in a 96-well culture plates at 10000 cells/well. After an overnight incubation, serial dilutions of rapamycin were added, together with 50 ng/ml (final) actinomycin D, and incubation continued at 37° C. and 5% $CO_2$ for approximately 20 hours. The media was removed and replaced with 100 μl of media containing 10% alamar blue dye. Plates were incubated as before, and the extent of cell viability assessed periodically by spectrophotometric determination of OD at 570 nm and 600 nm on a microtiter plate reader. Typically reading was continued until control (untreated) wells are at OD 0.2–0.4 after subtraction of blank.

Figure 13:
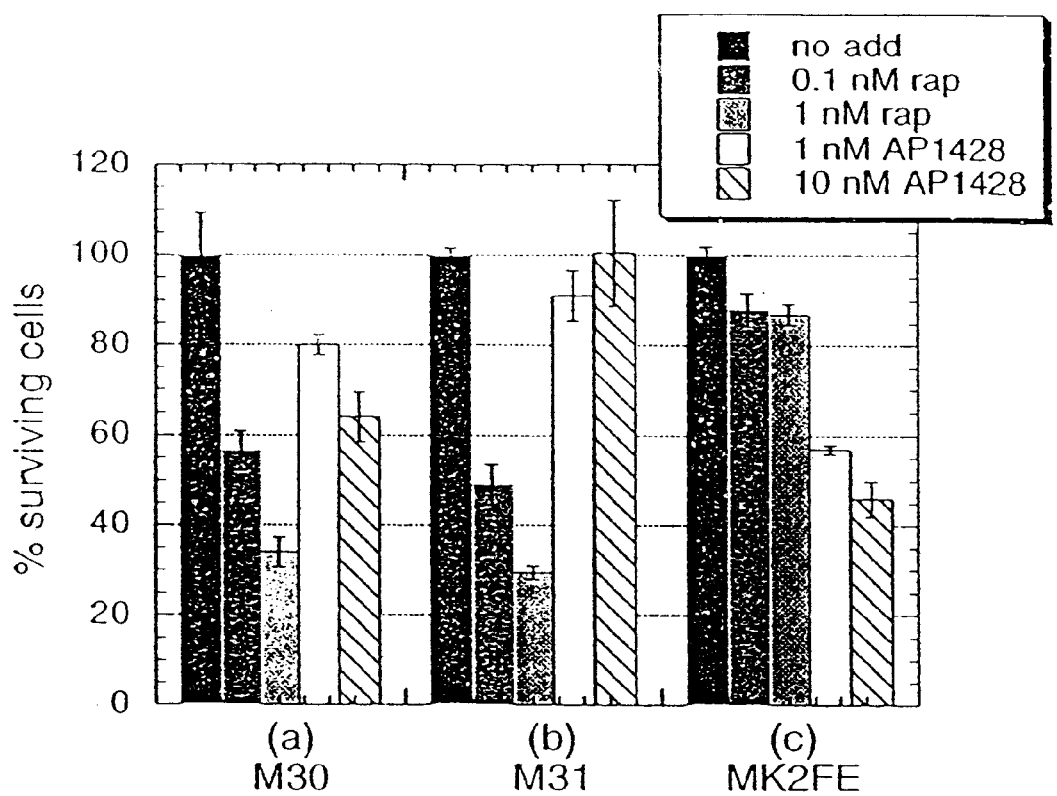
FIG. 13 shows reduction in survival of cells expressing mixed chimeric proteins (A, B) comprising a myristoylation domain, an FRB domain from human FRAP, an FKBP domain from hFKBP12, and a portion of the intracellular domain of Fas, as described in Example 8. (C) illustrates control experiments using a chimera containing a myristoylation domain, two FKBP domains and a Fas intracellular domain, designed to dimerize in the presence of AP1428 but not in the presence of rapamcyin.

FIG. 13 shows that the survival of cells stably transfected with (a) M30 and (b) M31-expressing constructs is potently reduced in the presence of rapamycin, in a dose-dependent manner. As evident from FIG. 13(c), the extent of cell death is comparable to that of cells expressing a myristoylated (FKBPx2)-Fas construct (as disclosed in PCT/US94/08008) treated with a synthetic FKBP homodimerizer AP1428:

molecule control of therapeutic gene expression. One approach to creating a transcription factor that is dependent upon rapamycin for DNA binding is to exploit the fact that many transcription factors bind to their cognate sequences as dimers. The DNA binding domains of such transcription factors can often be subdivided into a region involved in directly contacting DNA and a region involved in mediating dimer formation. Thus by replacing a natural transcription factor dimerization domain with FKBP or FRAP the chimeric transcription factor should display rapamycin-dependent DNA binding.

Any human dimeric transcription factor may be amenable to such an approach. Examples include HNF-1, SRF or other MADS box containing proteins, any member of the helix-loop-helix transcription factor family e.g. MyoD, myogenin, any member of the bZIP transcription factor family e.g. FOS, TN, ATF, CREB.

To avoid undesired activation of therapuetic genes by endogenous transcription factors, one may engineer the DNA binding specificities of chimeric transcription factors away from that of the "parental" proteins. This may be achieved by altering half site spacing of the palindromic target DNA sequences such that rapamycin mediated chimeric protein dimers can bind but naturally occuring parental dimers cannot.

Figure 14:
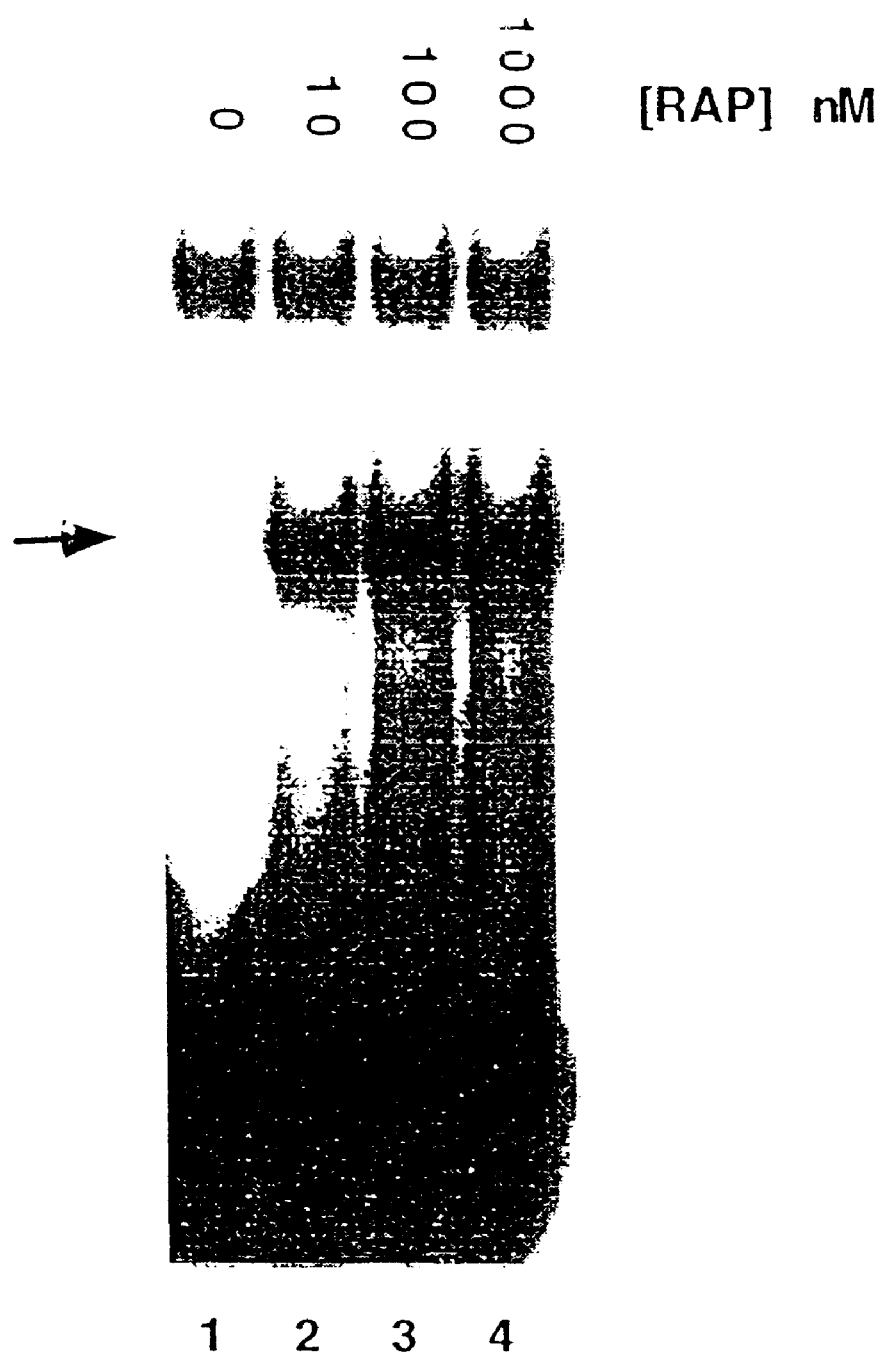
FIG. 14 shows a gel mobility shift assay of binding reactions containing approximately equal amounts of Lex-FKBP and Lex-FRAP proteins incubated with DNA containing a Lex binding site. In the absence of Rapamycin no specific binding is detectable (FIG. 14, Lane 1). The inclusion of increasing amounts of Rapamycin in the binding reaction results in the concomitant appearance of a specific complex in the mobility shift gel (FIG. 14, Lanes 2–4). These results support the conclusion that rapamycin promotes formation of a Lex-FKBP/Lex-FRAP heterodimer that is capable of binding to DNA containing a LexA target sequence. See Example 9 for additional details.

Rapamycin-dependent DNA Binding in vitro has been Demonstrated with Derivatives of the Bacterial Repressor Protein LexA LexA binds to its target operator as a dimer and is comprised of an amino terminal domain that interacts directly with DNA and a carboxy terminal domain that mediates dimerization. Chimeric proteins have been constructed in which the LexA dimerization domain is replaced by FKBP or FRAP. FIG. 14 shows a gel mobility shift assay of binding reactions containing approximately equal amounts of Lex-FKBP and Lex-FRAP proteins incubated with DNA containing a Lex binding site. In the absence of Rapamycin no specific binding is detectable (FIG. 14, Lane 1). The inclusion of increasing amounts of Rapamycin in the binding reaction results in the concomitant appearance of a

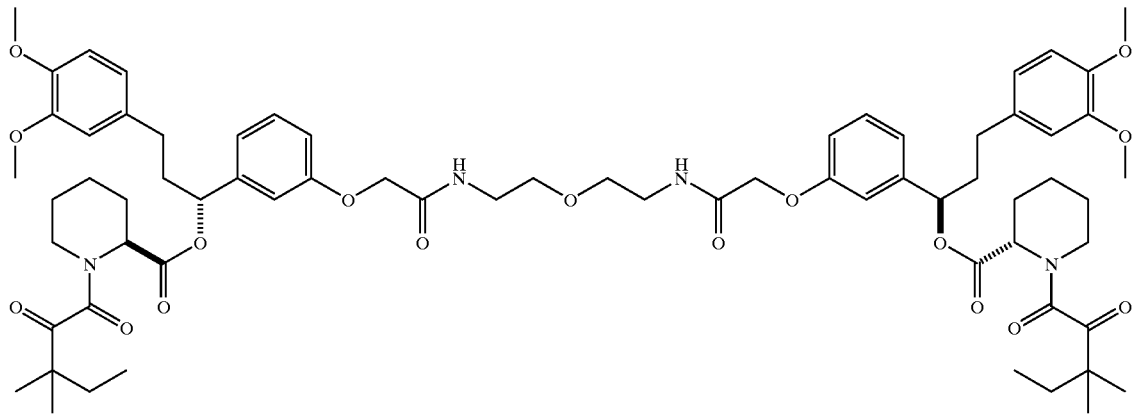

AP1428 is compound 49 disclosed in PCT/US95/10559. Note that rapamycin has minimal effects on survival of cells not expressing mixed chimeric proteins (FIG. 13(c)).

Example 9
Rapamycin-dependent DNA Binding

The ability to regulate transcription factor function at the level of DNA binding is an alternative approach to small specific complex in the mobility shift gel (FIG. 14, Lanes 2–4). These results support the conclusion that rapamycin promotes formation of a Lex-FKBP/Lex-FRAP heterodimer that is capable of binding to DNA containing a LexA target sequence.

FIG. 14
Rapamycin-dependent DNA binding by Lex-FKBP/Lex-FRAP heterodimers Lex-FKBP and Lex-FRAP proteins were translated in vitro and mixed together in a binding reaction with radiolabeled LexCon oligonucleotide. Rapamycin was included in binding reactions at the concentrations shown (Lanes 1–4).

The arrow indicates the position of rapamycin dependent protein-DNA complexes. The sequence of the LexCon probe is shown below, the LexA binding site is underlined:

LexCon.Top 5'-GATCCTCTAGA
TACTGTATATATATACAGTAAG
ATCTC-3'  [SEQ ID NO: 127]

LexCon.Bot 3'-GAGATCTATGACATATATATATGTCATTCTAG
AGAGCT-5'  [SEQ ID NO: 128]

Plasmid Constructions

Plasmids p19BL87, p19BL87G6FKBP and p19BL87FRB are constructed in pET-19BHA, a pET-19B based vector modified such that all expressed proteins contain an amino-terminal His.Tag followed by a Haemaglutinin epitope Tag.

p19BL87 encodes the LexA DNA binding domain (aa 1–87). LexA coding sequence was amplified by PCR from pCGNNLex202 with primers LexA Xba and LexA87 Spe/Bam. The PCR product was digested with XbaI and BamHI and ligated between the XbaI and BamHI sites of p19BHA.

p19BL87G6FKBP encodes LexA (aa 1–87) fused in frame to FKBP (aa2–108) via a six Glycine flexible linker. FKBP coding sequence was amplified by PCR from pCGNNF1 with primers 5'XG6FKBP and FKBP 3'Spe/Bam. pCGNNZFHD1-FKBPx3 (ATCC Accession No. 97399) may also be used as a source for FKBP-encoding DNA. See U.S. Ser. No. 08/581,713, filed Dec. 29, 1995. The PCR product was digested with XbaI and BamHI and ligated between the SpeI and BamHI sites of p19BL87.

p19BL87FRB encodes LexA (aa 1–87) fused in frame to FRAP (aa2025–2113). FRAP coding sequence was isolated as an XbaI-BamHI fragment from pCGNN-CAL4-1FRB and ligated between the SpeI and BamHI sites of p19BL87.

PCR Primers

LexA Xba 5'-ATGCTCTAGAAAAGCGTTAACGGCCAGGCAA-
3'  [SEQ ID NO: 129]

LexA 87 Spe/Bam 5'-CGTAGGATCCTTACTAACTAGTTGGT-
TCACCGGCAGCCACACG-3'  [SEQ ID NO: 130]

5'XG6FKBP 5'-TCAGTCTAGAGGAGGCGGTGCAGGTG-
GAGCTAGCGGAGTGCAGGTGGAAAC
CAT-3'  [SEQ ID NO: 131]

FKBP 3 'Spe/Bam 5 '-TCAGGGATCCTCAATAACTAGTTTC-
CAGTTTTAGAAGCTC-3'  [SEQ ID NO: 132]

Binding Reactions p19BL87G6FKBP and p19BL87FRB plasmids were translated in vitro using a TNT coupled reticulocyte lysate system (Promega) according to manufacturer's instructions.

Binding reactions contained 15 ml of binding buffer (10 mM Tris pH 7.5, 1 mM DTT, 0.1 mM EDTA, 10% v/v glycerol, 5 mM MgCl$_2$, 60 mM NaCl), 50 mg/ml Bovine Serum Albumin (NEB); 200 ng Poly(dIdC)-Poly(dIdC) (Pharmacia); 1 ml each of L87G6FKBP and L87FRB programmed reticulocyte lysate and 0.2 ng g-$^{32}$P-dATP labeled LexCon probe in a total volume of 20 ml. Rapamycin was added to the appropriate concentration and reactions were incubated at room temperature for 30 min.

Gel Mobility Shift Assay

Complexes were resolved on 4% 40:1 crosslinked polyacrylamide gels in 0.5×TBE buffer, run at 10–15 V/cm for 2 hours. The gel was dried, unfixed, onto 3MM paper and autoradiographed for 8 hours.

What is claimed is:

1. A method of expressing a selected gene in muscle cells present in a mammalian subject, said method comprising:
   (a) providing recombinant adeno-associated virus (AAV) particles which comprise a recombinant DNA construct comprising said selected gene operably linked to elements for controlling the expression of said selected gene; and
   (b) delivering said recombinant AAV particles intramuscularly to permit expression of said selected gene at a level which provides a therapeutic effect in the mammalian subject
   wherein the recombinant AAV particles also contain additional recombinant DNA constructs which encodes and directs the expression in said muscle cells of:
      (a) a first fusion protein containing one or more FK506-binding protein (FKBP) domains and a transcription activation domain, and
      (b) a second fusion protein containing an FKBP-rapamycin-binding (FRB) domain and a DNA binding domain which binds to a control element operably linked to said selected gene,
      wherein said fusion proteins permit rapamycin-dependent expression of the selected gene.

2. The method of claim 1, wherein said muscle cells are derived from smooth muscle.

3. The method of claim 1, wherein said muscle cells are myoblasts.

4. The method of claim 1, wherein said selected gene encodes a therapeutic protein.

5. The method of claim 4, wherein said protein is a secreted protein.

6. A method of treating disease in a mammalian subject, said method comprising administering a recombinant AAV virus which comprises a selected gene operably linked to control elements that direct the expression of said selected gene in cells in said subject, whereby said virus transduces muscle cells in said subject permitting expression of the selected gene by said transduced cells at a level sufficient to treat the disease,
   wherein the recombinant AAV virus also contains additional recombinant DNA constructs which encodes and directs the expression in said muscle cell of:
      (a) a first fusion protein containing one or more FKBP domains and a transcription activation domain, and
      (b) a second fusion protein containing an FRB domain and a DNA binding domain which binds to a control element operably linked to said selected gene, wherein said fusion proteins permit rapamycin-dependent expression of the selected gene.

7. A method of treating disease in a mammalian subject, said method comprising:
  (a) introducing recombinant AAV virus into muscle cells in vitro to produce a population of transduced muscle cells, wherein said recombinant AAV particles comprise a recombinant DNA construct comprising a selected gene operably linked to elements for controlling the expression of said selected gene; and
  (b) administering to muscle of said subject a therapeutically effective amount of a the transduced muscle cells from step (a), permitting expression of the selected gene by said transduced cells at a level sufficient to treat the disease
  wherein the recombinant AAV virus also contains additional recombinant DNA constructs which encodes and directs the expression in cells of:
    (a) a first fusion protein containing one or more FKBP domains and a transcription activation domain, and
    (b) a second fusion protein containing an FRB domain and a DNA binding domain which binds to a control element operably linked to said selected gene,
  wherein said fusion proteins permit rapamycin-dependent expression of the selected gene.

8. A method for delivering a therapeutically effective amount of a protein systemically to a mammalian subject, said method comprising:
  administering intramusclularly to said subject recombinant AAV particles which comprise a recombinant DNA construct comprising said selected gene operably linked to elements for controlling the expression of said selected gene, permitting the particles to transduce muscle cells in said subject, and permitting said transduced cells to express the selected gene to produce a systemic level of the protein which provides for a therapeutic effect in said subject,
  wherein the recombinant AAV virus also contains additional recombinant DNA constructs which encodes and directs the expression in said muscle cells of:
    (a) a first fusion protein containing one or more FKBP domains and a transcription activation domain, and
    (b) a second fusion protein containing an FRB domain and a DNA binding domain which binds to a control element operably linked to said selected gene,
    wherein said fusion proteins permit rapamycin-dependent expression of the selected gene.

9. A method for delivering a therapeutically effective amount of a protein systemically to a mammalian subject, said method comprising:
  (a) introducing recombinant AAV virus into muscle cells in vitro to produce a population of transduced muscle cells, wherein said recombinant AAV particles comprise a recombinant DNA construct comprising a selected gene operably linked to elements for controlling the expression of said selected gene; and
  (b) administering to muscle of said subject a therapeutically effective amount of a the transduced muscle cells from step (a), permitting expression of the selected gene by said transduced cells at a level sufficient to provide a therapeutic effect in said subject wherein the recombinant AAV virus also contains additional recombinant DNA constructs which encodes and directs the expression in said muscles cells of:
    (a) a first fusion protein containing one or more FKBP domains and a transcription activation domain, and
    (b) a second fusion protein containing an FRB domain and a DNA binding domain which binds to a control element operably linked to said selected gene,
    wherein said fusion proteins permit rapamycin-dependent expression of the selected gene.

10. A method of secreting protein from muscle cells present in a mammalian subject, said method comprising:
  (a) providing recombinant adeno-associated virus (AAV) particles which comprise a recombinant DNA construct comprising a selected gene encoding a secreted protein operably linked to elements for controlling the expression of said selected gene; and
  (b) delivering the recombinant AAV particle by intramuscular administration, whereby said secreted protein is expressed and secreted from said muscle cells at a level which provides a therapeutic effect in the mammalian subject wherein the recombinant AAV virus also contains additional recombinant DNA constructs which encodes and directs the expression in said muscles cells of:
    (a) a first fusion protein containing one or more FKBP domains and a transcription activation domain, and
    (b) a second fusion protein containing an FRB domain and a DNA binding domain which binds to a control element operably linked to said selected gene,
    wherein said fusion proteins permit rapamycin-dependent expression of the selected gene.

* * * * *